US012661342B2

(12) United States Patent
García Collazo et al.

(10) Patent No.: US 12,661,342 B2
(45) Date of Patent: Jun. 23, 2026

(54) HETEROARYL COMPOUNDS AND THERAPEUTIC USES THEREOF IN CONDITIONS ASSOCIATED WITH THE ALTERATION OF THE ACTIVITY OF BETA-GLUCOCEREBROSIDASE

(71) Applicant: GT GAIN THERAPEUTICS SA, Lugano (CH)

(72) Inventors: Ana Maria García Collazo, Esplugues de Llobregat (ES); Elena Cubero Jordà, Barcelona (ES); Manolo Bellotto, Lugano (CH); Enrique Fernández Inglesias, Hospitalet de Llobregat (ES)

(73) Assignee: GT GAIN THERAPEUTICS SA, Lugano (CH)

( * ) Notice: Subject to any disclaimer, the term of this patent is extended or adjusted under 35 U.S.C. 154(b) by 942 days.

(21) Appl. No.: 17/779,482

(22) PCT Filed: Nov. 25, 2020

(86) PCT No.: PCT/IB2020/061158
§ 371 (c)(1),
(2) Date: May 24, 2022

(87) PCT Pub. No.: WO2021/105908
PCT Pub. Date: Jun. 3, 2021

(65) Prior Publication Data

US 2023/0107499 A1 Apr. 6, 2023

(30) Foreign Application Priority Data

Nov. 25, 2019 (EP) .................................... 19383037

(51) Int. Cl.
*A61K 31/44* (2006.01)
*A61K 31/137* (2006.01)
(Continued)

(52) U.S. Cl.
CPC ............ *A61K 31/44* (2013.01); *A61K 31/137* (2013.01); *A61K 31/443* (2013.01);
(Continued)

(58) Field of Classification Search
CPC .... A61K 31/137; A61K 31/44; A61K 31/443; A61K 31/4433; A61K 31/4439;
(Continued)

(56) References Cited

U.S. PATENT DOCUMENTS 3,271,393 A 9/1966 Takeo et al.
11,174,242 B2 11/2021 Garcia Collazo et al.
(Continued)

FOREIGN PATENT DOCUMENTS

WO WO-2004039796 A1 5/2004
WO WO-2005066171 A1 7/2005
(Continued)

OTHER PUBLICATIONS

Hoglinger et. al., "GBA-associated PD: chances and obstacles for targeted treatment strategies", Journal of Neural Transmisson (Year: 2022).*
Sun, "Lysosomal storage disease overview", Ann Transl Med (Year: 2018).*
Behl et. al., "Cross-talks among GBA mutations, glucocerebrosidase and a-synuclein in GBA-associated Parkinson's disease and their targeted therapeutic approaches: a comprehensive review," Transl. Neurodegener. (Year: 2021).*
Sardi et. al., "Gaucher-related synucleinopathies: The examination of sporadic neurodegeneration from a rare (disease) angle," Progress in Neurobiology (Year: 2015).*
(Continued)

*Primary Examiner* — Jeffrey H Murray
*Assistant Examiner* — Daniel John Burkett
(74) *Attorney, Agent, or Firm* — STERNE, KESSLER, GOLDSTEIN & FOX P.L.L.C.

(57) ABSTRACT

The application is directed to compounds of formulae (IA) and (IB) and their salts and solvates, wherein $R^{1a}$, $R^{2a}$, $R^{3a}$, $A^1$, $A^2$, $A^3$, $R^{1b}$, $R^{2b}$, $R^{3b}$, $B^1$, and $B^2$ are as set forth in the specification, as well as to methods for their preparation, pharmaceutical compositions comprising the same, and use thereof for the treatment and/or prevention of, e.g., lysosomal storage diseases, such as Gaucher's disease, and α-synucleinopathies, such as Parkinson's disease.

(IA)

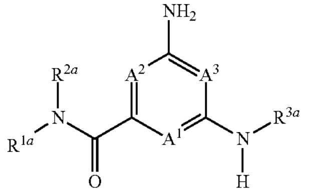

(IB)

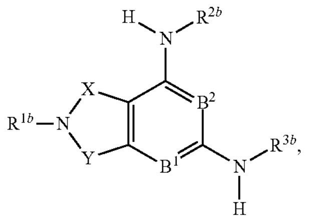

31 Claims, No Drawings

(51) Int. Cl.

| | |
|---|---|
| ***A61K 31/443*** | (2006.01) |
| ***A61K 31/4433*** | (2006.01) |
| ***A61K 31/4439*** | (2006.01) |
| ***A61K 31/444*** | (2006.01) |
| ***A61K 31/445*** | (2006.01) |
| ***A61K 31/4725*** | (2006.01) |
| ***A61K 31/496*** | (2006.01) |
| ***A61K 31/505*** | (2006.01) |
| ***A61K 31/506*** | (2006.01) |
| ***A61K 31/519*** | (2006.01) |
| ***A61K 31/53*** | (2006.01) |
| ***A61K 38/47*** | (2006.01) |
| ***A61P 3/00*** | (2006.01) |
| ***C07D 213/81*** | (2006.01) |
| ***C07D 239/48*** | (2006.01) |
| ***C07D 251/18*** | (2006.01) |
| ***C07D 295/195*** | (2006.01) |
| ***C07D 401/06*** | (2006.01) |
| ***C07D 403/06*** | (2006.01) |
| ***C07D 405/12*** | (2006.01) |
| ***C07D 405/14*** | (2006.01) |
| ***C07D 471/04*** | (2006.01) |

(52) U.S. Cl.

CPC ...... *A61K 31/4433* (2013.01); *A61K 31/4439* (2013.01); *A61K 31/444* (2013.01); *A61K 31/445* (2013.01); *A61K 31/4725* (2013.01); *A61K 31/496* (2013.01); *A61K 31/505* (2013.01); *A61K 31/506* (2013.01); *A61K 31/519* (2013.01); *A61K 31/53* (2013.01); *A61K 38/47* (2013.01); *A61P 3/00* (2018.01); *C07D 213/81* (2013.01); *C07D 239/48* (2013.01); *C07D 251/18* (2013.01); *C07D 295/195* (2013.01); *C07D 401/06* (2013.01); *C07D 403/06* (2013.01); *C07D 405/12* (2013.01); *C07D 405/14* (2013.01); *C07D 471/04* (2013.01)

(58) Field of Classification Search

CPC ................ A61K 31/444; A61K 31/445; A61K 31/4725; A61K 31/496; A61K 31/505; A61K 31/506; A61K 31/519; A61K 31/53; A61K 38/47; A61P 25/00; A61P 3/00; C07D 213/81; C07D 239/48; C07D 251/18; C07D 295/195; C07D 401/06; C07D 401/12; C07D 403/06; C07D 405/12; C07D 405/14; C07D 471/04

See application file for complete search history.

(56) References Cited

U.S. PATENT DOCUMENTS

| | | | |
|---|---|---|---|
| 2006/0173050 | A1 | 8/2006 | Liu et al. |
| 2016/0207933 | A1 | 7/2016 | Bourque et al. |
| 2022/0135535 | A1 | 5/2022 | Garcia Collazo et al. |

FOREIGN PATENT DOCUMENTS

| | | | |
|---|---|---|---|
| WO | WO-2011049737 | A1 | 4/2011 |
| WO | WO-2016168420 | A1 | 10/2016 |
| WO | WO-2018122775 | A1 | 7/2018 |
| WO | WO-2019241787 | A9 | 12/2019 |

OTHER PUBLICATIONS

Choi et. al., "Lysosomal Enzyme Glucocerebrosidase Protects against AB1-42 Oligomer-Induced Nuerotoxicity," PLoS One (Year: 2015).*

Roberts et. al., "Synucleinopathy in Amyotrophic Lateral Sclerosis: A Potential Avenue for Antisense Therapeutics?", Int. J. Mol. Sci. (Year: 2022).*

Zheng, W., et al., "Three classes of glucocerebrosidase inhibitors identified by quantitative high-throughput screening are chaperone leads for Gaucher disease," Proceedings of the National Academy of Sciences of the United States of America 104(32):13192-13197, National Academy of Sciences, United States (Aug. 2007).

Wermuth, C.G., "Molecular Variations Based on Isoteric Replacements," in *The Practice of Medicinal Chemistry* , Japanese translation by Nagase, H., Chapter 13, pp. 235-271, Wermuth, C.G., ed., Technomic Co., Ltd, Japan (Aug. 1998).

English language translation of Office Action for Japanese Patent Application No. 2022-530662, mailed on Sep. 27, 2024, Japan Patent Office, Japan, 8 pages.

Beutler, E., et al., "Glucocerebrosidase Mutations in Gaucher disease," Mol. Med. 1(1):82-92, Springer Science+Business Media, Germany (1994).

Boyd, R.E., et al., "Pharmacological Chaperones as Therapeutics for Lysosomal Storage Diseases," J. Med. Chem. 56(7):2705-2725, American Chemical Society, United States (2013).

Coutinho M.F., et al., "Less Is More: Substrate Reduction Therapy for Lysosomal Storage Disorders," Int. J. Mol. Sci. 17:1065, MDPI, Switzerland (2016).

Eisa, H.M. et al., "Synthesis and antimicrobial testing of 2-amino-4-(p-fluoro-m-nitroanilino)-6-substituted-s-triazines," Pakistan Journal of Scientific and Industrial Research 31(7):474-476, Scientific Information Centre, Pakistan (1988).

Eisa, H.M., et al., "Synthesis of certain 2-aminoadamantane derivatives as potential antimicrobial agents," Pharmazie 46(3):182-184, Govi-Verlag Pharmazauticher Verlag, Germany (1991).

Goda, F., et al., "Synthesis and Antiviral Activity of 1, 3, 5-Triazine Derivatives," Mansoura Journal of Pharmaceutical Science 20(2):1-10, Faculty of Pharmacy, Mansoura University, Egypt (2004).

Goda, F., et al., "Synthesis, biological evaluation and molecular modeling investigation of some new benzimidazole analogs as antiviral agents," Saudi Pharmaceutical Journal 16(2):103-111, Elsevier, Netherlands (2008).

International Search Report and Written Opinion for International Application No. PCT/IB2020/061158, European Patent Office, Netherlands, mailed on May 4, 2021, 18 pages.

Jung, O., et al., "Progress and potential of non-inhibitory small molecule chaperones for the treatment of Gaucher disease and its potential implications for Parkinson disease," Expert Rev. Proteomics 13(5):471-479, Taylor & Francis, United Kingdom (2016).

Khanna, R., et al., "The pharmacological chaperone isofagomine increases the activity of the Gaucher disease L444P mutant form of beta-glucosidase," FEBS J. 277(7):1618-1638, Federation of European Biochemical Societies, United Kingdom (2010).

Kothayer, H., et al., "Design, synthesis and in vitro anticancer evaluation of 4,6-diamino-1,3,5-triazine-2-carbohydrazides and -carboxamides," Bioorg. Med. Chem. Lett. 23(24):6886-6889, Elsevier, Netherlands (2013).

Maegawa, G.H.B., et al., "Identification and Characterization of Ambroxol as an Enzyme Enhancement Agent for Gaucher Disease," J. Biol. Chem. 284(35):23502-23516, American Society for Biochemistry and Molecular Biology, United States (2009).

Mazzulli, J.R., et al., "Activation of ß-Glucocerebrosidase Reduces Pathological α-Synuclein and Restores Lysosomal Function in Parkinson's Patient Midbrain Neurons," J. Neurosci. 36(29):7693-7706, Society for Neuroscience, United States (2016).

Parenti, G., et al., "Pharmacological Chaperone Therapy: Preclinical Development, Clinical Translation, and Prospects for the Treatment of Lysosomal Storage Disorders," Mol. Ther. 23(7):1138-1148, Cell Press, United Kingdom (2015).

Patnaik, S., et al., "Discovery, structure-activity relationship, and biological evaluation of noninhibitory small molecule chaperones of glucocerebrosidase," J. Med. Chem. 55(12):5734-5748, American Chemical Society, United States (2012).

Siebert, M., et al., "Glucocerebrosidase is shaking up the synucleinopathies," Brain 137(Pt 5):1304-1322, Oxford University Press, United Kingdom (2014).

(56) References Cited

OTHER PUBLICATIONS

Sun, Y., et al., "Ex Vivo and in Vivo Effects of Isofagomine on Acid β-Glucosidase Variants and Substrate Levels in Gaucher Disease," J. Biol. Chem. 287(6):4275-4287, American Society for Biochemistry and Molecular Biology, United States (2012).
Behl, T., et al., "Cross-talks among GBA mutations, glucocerebrosidase, and α-synuclein in GBA-associated Parkinson's disease and their targeted therapeutic approaches: a comprehensive review," Translational Neurodegeneration 10(1):4, pp. 1-13, BioMed Central, United Kingdom (Jan. 2021).
Canosa, A., et al., "GBA variants influence cognitive status in amyotrophic lateral sclerosis," Journal of Neurology, Neurosurgery, and Psychiatry 93(4):453-455 and supplementary methods, BMJ Publishing Group, United Kingdom (Sep. 2021).
Choi, S., et al., "Lysosomal Enzyme Glucocerebrosidase Protects against Aβ1-42 Oligomer-Induced Neurotoxicity," PLoS One 10(12):e0143854, pp. 1-18, Public Library of Science, United States (Dec. 2015).
Dhanve, P., et al., "Ambroxol: A potential therapeutics against neurodegeneration," Health Sciences Review 7:100096, pp. 1-6, Elsevier, Netherlands (Jun. 2023).
Luikinga, S., et al., "Profound lipid dysregulation in mutant TDP-43 mice is ameliorated by the glucocerebrosidase 2 inhibitor ambroxol," bioRxiv, preprint article posted Sep. 2, 2022, https://doi.org/10.1101/2022.08.30.505901, 28 pages, Cold Spring Harbor Laboratory, United States (Sep. 2022).
Roberts, B., et al., "Synucleinopathy in Amyotrophic Lateral Sclerosis: A Potential Avenue for Antisense Therapeutics?" International Journal of Molecular Sciences 23(16):9364, pp. 1-24, MDPI, Switzerland (Aug. 2022).
Sardi, S.P., et al., "Gaucher-related synucleinopathies: The examination of sporadic neurodegeneration from a rare (disease) angle," Progress in Neurobiology 125:47-62, Elsevier, United Kingdom (Feb. 2015).
Yang, S.Y., et al., "Ambroxol reverses tau and α-synuclein accumulation in a cholinergic N370S GBA1 mutation model," Human Molecular Genetics 31(14):2396-2405, Oxford University Press, United Kingdom (Feb. 2022).

* cited by examiner

HETEROARYL COMPOUNDS AND THERAPEUTIC USES THEREOF IN CONDITIONS ASSOCIATED WITH THE ALTERATION OF THE ACTIVITY OF BETA-GLUCOCEREBROSIDASE

CROSS-REFERENCE TO RELATED APPLICATION

This application claims priority to European Patent Application No. EP19383037.9, filed on Nov. 25, 2019, the entirety of which is incorporated by reference herein.

FIELD OF THE DISCLOSURE

The present disclosure is related to heteroaryl compounds, and especially pyridyl, pyrimidinyl, and triazinyl compounds, new processes for their preparation, and the use of the heteroaryl compounds in the treatment and/or prevention of conditions associated with the alteration of the activity of β-glucocerebrosidase in a patient, such as, for example, lysosomal storage diseases and α-synucleinopathies. The present disclosure is also related to the use of the heteroaryl compounds described herein in the treatment and/or prevention of medical disorders in a patient, such as, for example, Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, or unimpaired aging.

BACKGROUND OF THE DISCLOSURE

Gaucher's disease, suggested to arise from β-glucocerebrosidase enzyme deficiency, is very rare lysosomal storage disease. The condition associated with β-glucocerebrosidase is known to be caused by a deficiency of the enzyme β-glucocerebrosidase due to mutations in the gene.

β-Glucocerebrosidase cleaves β-glucocerebroside from different substrates, and deficiencies in its activity cause the substrates (i.e., gangliosides, and oligosaccharides carrying terminal β-linked glucocerebroside) to accumulate in patients suffering from conditions associated with β-glucocerebrosidase activity, such as Gaucher's disease. Beutler et al. (*Mol Med.* 1(1):82-92 (1994)) reported that deficiency of glucocerebrosidase leads to accumulation of insoluble glucocerebrosides in the tissues, resulting in the clinical manifestations of Gaucher's disease.

In many lysosomal disorders, like Gaucher's disease, the mutant enzymes often retain catalytic activity but fold improperly in the endoplasmic reticulum ("ER"). This triggers ER accumulation of the mutant protein, which is eventually tagged for proteasome degradation by ubiquitination, avoiding the transport of the enzyme to the lysosome. See, e.g., Patniak et al., *Journal of Medicinal Chemistry* 55(12):5734-5748 (2012).

Gaucher's (or Gaucher) disease is a heterogenous disorder having three subtypes. The majority of patients, those without neurologic manifestations of the disease, are classified as type I. In type I, clinical manifestations include enlarged spleen and liver, platelet deficiency, anemia, and bone disease. Types II and III are neuronopathic forms, classified with respect to severity and to the time of onset of neurologic disease. Type II is most severe with symptoms at or near the time of birth. Patients with type II have a median life span of 9 months. Type III has a later onset. See, e.g., Patniak et al., *Journal of Medicinal Chemistry* 55(12):5734-5748 (2012). Patients with Gaucher's disease exhibit hematological manifestations, such as anemia and thrombocytopenia, as well as hepatosplenomegaly, skeletal deformities, and in some cases, neurological impairment. See, e.g., Boyd et al., *Journal of Medicinal Chemistry* 56 (7):2705-2725 (2013).

Enzyme replacement therapy ("ERT") and substrate inhibition therapy ("SRT") are two current therapies for type I Gaucher's disease. ERT involves longterm treatment via injection of a recombinant enzyme (imiglucerase) into patients. While ERT may be effective in reducing and reversing the clinical symptoms of the disease, it is very costly. SRT is generally indicated for the treatment of adult patients with mild to moderate type I Gaucher's disease for whom ERT is not a therapeutic option. The prescribed drug, an iminosugar miglustat, inhibits glucosylceramide synthetase, reducing the production of glucocerebrosides in the lysosome. While SRT may be effective for some patients, it is associated with side effects, including weight loss, diarrhea, tremors, and peripheral nerve damage. Neither ERT nor SRT are effective against the neuronopathic types II and III of Gaucher's disease. See, e.g., Patniak et al., *Journal of Medicinal Chemistry* 55(12):5734-5748 (2012).

Mutations in the gene encoding glucocerebrosidase are also a risk factor for α-synucleinopathies, such as Parkinson's disease and diffuse Lewy Body disease. Parkinson's disease is a degenerative disorder of the central nervous system associated with death of dopamine-containing cells in a region of the midbrain. Diffuse Lewy Body disease is a dementia that is sometimes confused with Alzheimer's disease.

Small molecules capable of binding allosterically or competitively to mutated β-glucocerebrosidase enzyme, thereby stabilizing the enzyme against degradation (chaperones), constitute an important therapeutic target in conditions associated with the alteration of the activity of β-glucocerebrosidase. By binding and stabilizing mutant proteins, these chemical chaperones facilitate protein folding and eventually increase their transport to the lysosome. Improved trafficking of the mutant protein from the ER to the lysosome results in the reduction of lysosome size and correction of the storage. These chaperones may also increase the stability of mutant enzymes toward degradation in the lysosome. See, e.g., Patniak et al., *Journal of Medicinal Chemistry* 55(12):5734-5748 (2012).

It has been surprisingly found that compounds of formulae (IA) and (IB) are capable of binding to β-glucocerebrosidase thereby stabilizing the enzyme against denaturation.

BRIEF SUMMARY OF THE DISCLOSURE

The present disclosure is related to the discovery that heteroaryl compounds represented by formulae (IA) and (IB) are capable of binding to β-glucocerebrosidase (mutated or not) and are thus useful in the treatment or prevention of, e.g., a lysosomal storage disease, such as Gaucher's disease, or α-synucleinopathies, such as Parkinson's disease, or other conditions associated with the alteration of the activity of β-glucocerebrosidase.

In one aspect, the present disclosure provides compounds represented by formulae (IA) and (IB) below, and pharmaceutically acceptable salts and solvates thereof, collectively referred to herein as "Compounds of the Disclosure" (each is individually referred to hereinafter as a "Compound of the Disclosure").

In another aspect, the present disclosure provides a method of treating or preventing a condition associated with the alteration of the activity of β-glucocerebrosidase in a patient in need thereof. The method comprises administering to the patient in need thereof an effective amount of a Compound of the Disclosure.

In another aspect, the present disclosure provides a method of treating or preventing a lysosomal storage disease, such as Gaucher's disease, in a patient in need thereof by administering an effective amount of a Compound of the Disclosure.

In another aspect, the present disclosure provides a method of treating or preventing an α-synucleinopathy, such as Parkinson's disease, in a patient in need thereof by administering an effective amount of a Compound of the Disclosure.

In another aspect, the present disclosure is directed to a method of treating or preventing a disease or disorder selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging.

In another aspect, the methods described herein further comprise administering to the patient at least one other therapeutic agent. In another aspect, the therapeutic agent is an effective amount of an enzyme for enzyme replacement therapy. In another aspect, the enzyme is β-glucocerebrosidase or an analog thereof. In another aspect, the enzyme is imiglucerase. In another aspect, the therapeutic agent is an effective amount of a small molecule chaperone. In another aspect, the small molecule chaperone binds competitively to an enzyme. In another aspect, the small molecule chaperone is selected from the group consisting of iminoalditols, iminosugars, aminosugars, thiophenylglycosides, glycosidase, sulfatase, glycosyl transferase, phosphatase, and peptidase inhibitors. In another aspect, the small molecule chaperone is selected from the group consisting of isofagomine, N-nonyl-1-deoxynojirimycin (NN-DNJ), ambroxol, and miglustat. In another aspect, the small molecule chaperone is selected from the group consisting of isofagomine, N-nonyl-1-deoxynojirimycin (NN-DNJ), and ambroxol. In another aspect, the small molecule chaperone is miglustat.

In another aspect, the therapeutic agent is an effective amount of substrate reduction agent for substrate reduction therapy. In another aspect, the substrate reduction agent is miglustat.

In another aspect, the present disclosure provides a Compound of the Disclosure, as described herein, for use in the prevention or treatment of a condition associated with the alteration of the activity of β-glucocerebrosidase in a patient in need thereof.

In another aspect, the present disclosure provides a Compound of the Disclosure, as described herein, for use in the prevention or treatment of a lysosomal storage disease, such as Gaucher's disease.

In another aspect, the present disclosure provides a Compound of the Disclosure, as described herein, for use in the prevention or treatment of an α-synucleinopathy, such as Parkinson's disease.

In another aspect, the present disclosure provides a Compound of the Disclosure, as described herein, for use in the prevention or treatment of a disease or disorder selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging.

In another aspect, the present disclosure is also directed to the use of a Compound of the Disclosure, as described herein, for the treatment or prevention of a condition associated with the alteration of the activity of β-glucocerebrosidase in a patient in need thereof, such as lysosomal storage diseases and α-synucleinopathies described herein.

In another aspect, the present disclosure provides a pharmaceutical composition comprising a Compound of the Disclosure, as described herein, and at least one pharmaceutically acceptable excipient.

In another aspect, the present disclosure provides a Compound of the Disclosure, as described herein, for use as a medicament.

In another aspect, the present disclosure provides use of a Compound of the Disclosure, as described herein, in the preparation of a medicament for the prevention or treatment of a condition associated with the alteration of the activity of β-glucocerebrosidase in a patient in need thereof, such as lysosomal storage diseases and α-synucleinopathies described herein.

In another aspect, the present disclosure provides a pharmaceutical composition comprising a Compound of the Disclosure, as described herein, and at least one pharmaceutically acceptable excipient, for use in the treatment or prevention of a condition associated with the alteration of the activity of β-glucocerebrosidase in a patient in need thereof, such as lysosomal storage diseases and α-synucleinopathies described herein.

Other aspects and advantages of the disclosure will be readily apparent from the following detailed description of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the disclosure as claimed.

DETAILED DESCRIPTION OF THE DISCLOSURE

One aspect of the disclosure is based on the use of Compounds of the Disclosure for binding to β-glucocerebrosidase. In view of this property, Compounds of the Disclosure are expected to be useful for treating or preventing, e.g., Gaucher's disease and other diseases or conditions described herein.

Compounds of the Disclosure useful in this aspect of the disclosure are compounds of formula (IA) and formula (IB):

(IA)

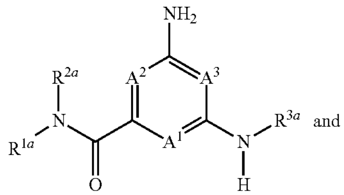

and (IB)

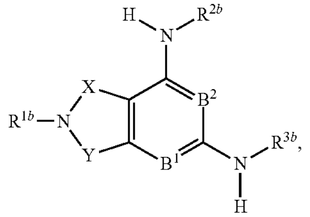

and the pharmaceutically acceptable salts and solvates thereof, wherein $A^1$, $A^2$, $A^3$, $R^{1a}$, $R^{2a}$, $R^{3a}$, $B^1$, $B^2$, $R^{1b}$, $R^{2b}$, and $R^{3b}$ are as defined below.

In another aspect, Compounds of the Disclosure are compounds of formula (IA):

(IA)

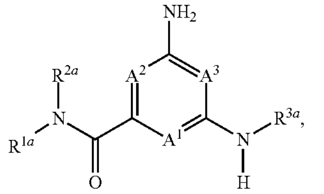

and the pharmaceutically acceptable salts and solvates thereof, wherein $A^1$, $A^2$, and $A^3$ are each independently selected from the group consisting of N, CH and $C(R^{4a})$, provided that at least one of $A^1$, $A^2$, or $A^3$ is N;

each $R^{4a}$ is independently selected from the group consisting of halogen, —$C_{1-4}$ alkyl, —$C_{1-4}$ alkoxy, and —CN;

$R^{1a}$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(═O)$Ra^a$, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, -(5- to 10-membered)-$C_{2-9}$ heterocyclyl, and optionally substituted —O—($C_{6-10}$ aryl); and wherein said cycloalkyl, alkylcycloalkyl, aryl, alkylaryl, heteroaryl, alkylheteroaryl, heterocyclyl and alkylheterocyclyl is optionally fused to a further (second) ring; and $R^{2a}$ is selected from the group consisting of hydrogen, —$C_{1-4}$ alkyl, and $C_{3-6}$ cycloalkyl, wherein said —$C_{1-4}$ alkyl is optionally substituted; or $R^{1a}$ and $R^{2a}$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

$Ra^a$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each $Rb^a$ is independently hydrogen, —$C_{1-4}$ alkyl, —$C_{3-10}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms; and $R^{3a}$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$alkyl optionally substituted with 1, 2, or 3 substituents each independently selected from the group consisting of halogen, —CN, —$ORb^a$, and —$N(Rb^a)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl; and wherein said —$C_{6-10}$ aryl is optionally fused to a 5- or 6-membered heterocyclic ring.

In some aspects, Compounds of the Disclosure are compounds of formula (IA) and the pharmaceutically acceptable salts and solvates thereof, wherein $A^1$, $A^2$, and $A^3$ are each independently selected from the group consisting of N, CH and $C(R^{4a})$, provided that at least one of $A^1$, $A^2$, or $A^3$ is N;

each $R^{4a}$ is independently selected from the group consisting of halogen, —$C_{1-4}$ alkyl, —$C_{1-4}$ alkoxy, and —CN;

$R^{1a}$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(=O)$Ra^a$, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, -(5- to 10-membered)-$C_{2-9}$ heterocyclyl, and optionally substituted —O—($C_{6-10}$ aryl); and wherein said cycloalkyl, alkylcycloalkyl, aryl, alkylaryl, heteroaryl, alkylheteroaryl, heterocyclyl and alkylheterocyclyl is optionally fused to a further (second) ring; and $R^{2a}$ is selected from the group consisting of hydrogen, —$C_{1-4}$ alkyl, and $C_{3-6}$ cycloalkyl, wherein said —$C_{1-4}$ alkyl is optionally substituted; or $R^{1a}$ and $R^{2a}$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

$Ra^a$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each $Rb^a$ is independently hydrogen, —$C_{1-4}$ alkyl, —$C_{3-10}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms; and $R^{3a}$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$alkyl optionally substituted with 1, 2, or 3 substituents each independently selected from the group consisting of halogen, —CN, —$ORb^a$, and —$N(Rb^a)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another aspect, Compounds of the Disclosure are compounds of formula (IA), and the pharmaceutically acceptable salts and solvates thereof, wherein one of $A^1$, $A^2$ and $A^3$ is N.

In another aspect, Compounds of the Disclosure are compounds of formula (IA), and the pharmaceutically acceptable salts and solvates thereof, wherein two of $A^1$, $A^2$ and $A^3$ are N.

In another aspect, Compounds of the Disclosure are compounds of formula (IA), and the pharmaceutically acceptable salts and solvates thereof, wherein $A^1$, $A^2$ and $A^3$ are N. In some embodiments of this aspect, the compound of formula (IA) is not

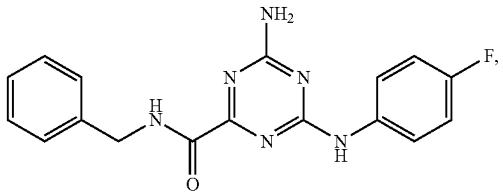

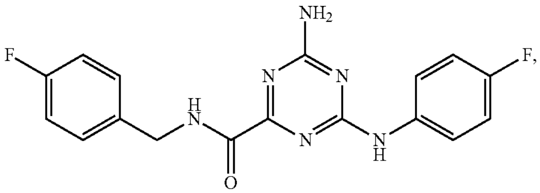

or

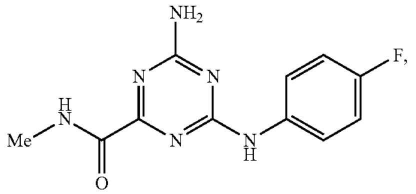

pharmaceutically acceptable salt thereof.

In some aspects, Compounds of the Disclosure are compounds of formula (IA), and the pharmaceutically acceptable salts thereof, wherein no more than two of $A^1$, $A^2$, and $A^3$ are N.

In another aspect, Compounds of the Disclosure are compounds of formula (IA), and the pharmaceutically acceptable salts and solvates thereof, wherein $A^1$ is N and $A^2$ and $A^3$ are each independently selected from the group consisting of CH and $C(R^{4a})$. In another embodiment, $A^2$ and $A^3$ are both CH.

In another aspect, Compounds of the Disclosure are compounds of formula (IA), and their pharmaceutically acceptable salts and solvates thereof, wherein $A^2$ is N and $A^1$ and $A^3$ are each independently selected from the group consisting of CH and $C(R^{4a})$. In another embodiment, $A^1$ and $A^3$ are both CH.

In another aspect, Compounds of the Disclosure are compounds of formula (IA), and the pharmaceutically acceptable salts and solvates thereof, wherein $A^3$ is N and $A^1$ and $A^2$ are each independently selected from the group consisting of CH and $C(R^{4a})$. In another embodiment, $A^1$ and $A^2$ are both CH.

In another aspect, Compounds of the Disclosure are compounds of formula (IA), and the pharmaceutically acceptable salts and solvates thereof, wherein $A^1$ and $A^2$ are both N and $A^3$ is CH or $C(R^{4a})$. In another embodiment, $A^3$ is CH.

In another aspect, Compounds of the Disclosure are compounds of formula (IA), and the pharmaceutically acceptable salts and solvates thereof, wherein $A^1$ and $A^3$ are both N and $A^2$ is CH or $C(R^{4a})$. In another embodiment, $A^2$ is CH.

In another aspect, Compounds of the Disclosure are compounds of formula (IA), and the pharmaceutically acceptable salts and solvates thereof, wherein $A^2$ and $A^3$ are both N and $A^1$ is CH or $C(R^{4a})$. In another embodiment, $A^1$ is CH. In another aspect, Compounds of the Disclosure are compounds of formula (IA), and the pharmaceutically acceptable salts and solvates thereof, wherein $R^{3a}$ is —$C_{6-10}$ aryl optionally substituted with 1, 2 or 3 substituents each independently selected from the group consisting of halogen, hydroxy, —CN, —$ORb^a$, —$SRb^a$, —$N(Rb^a)_2$, —$C_{1-4}$alkyl optionally substituted with 1, 2, or 3 substituents each independently selected from the group consisting of halogen, —CN, —$ORb^a$, and —$N(Rb^a)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another embodiment, $R^{3a}$ is unsubstituted —$C_{6-10}$ aryl or —$C_{6-10}$ aryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, CN, —$O(C_{1-4})$alkyl, —$N(C_{1-4}$ alkyl$)_2$, and —$NH(C_{1-4}$ alkyl). In another aspect, $R^{3a}$ is unsubstituted —$C_{6-10}$ aryl, and preferably unsubstituted phenyl. In another aspect, $R^{3a}$ is —$C_{6-10}$ aryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, —CN, —$O(C_{1-4})$alkyl, —$N(C_{1-4}$ alkyl$)_2$, and —$NH(C_{1-4}$ alkyl). In another aspect, $R^{3a}$ is —$C_{6-10}$ aryl, and preferably phenyl, substituted with 1 or 2 substituents each independently selected from the group consisting of halogen, hydroxy, —CN, methoxy, ethoxy, methylthio, ethylthio, dimethylamino, diethylamino, methylamino, ethylamino, halomethyl (such as fluoromethyl), di(halo)methyl (such as difluoromethyl), tri(halo) methyl (such as trifluoromethyl), cyanomethyl, methoxymethyl, methoxyethyl, dimethylaminomethyl, dimethylaminoethyl, methylaminomethyl, and methylaminoethyl. In another aspect, $R^{3a}$ is phenyl substituted with halogen, hydroxy, —CN, methyl, ethyl, methoxy, or ethoxy. In another aspect, the substituent is attached to the meta-position of the phenyl group. In another aspect, the substituent is attached to the ortho-position of the phenyl group. In another aspect, the substituent is attached to the para-position of the phenyl group.

In some aspects, Compounds of the Disclosure are compounds of formula (IA), and the pharmaceutically acceptable salts and solvates thereof, wherein $R^{3a}$ is phenyl substituted with 1 or 2 substituents each independently selected from the group consisting of F, Cl, Br, I, hydroxy, methyl, methoxy, and —CN. In some aspects, $R^{3a}$ is phenyl substituted with F or hydroxy at the ortho- or meta-position of the phenyl group. In some aspects, $R^{3a}$ is phenyl substituted with F or hydroxy at the ortho-position of the phenyl group. In some aspects, $R^{3a}$ is phenyl substituted with F or hydroxy at the meta-position of the phenyl group.

In some aspects, Compounds of the Disclosure are compounds of formula (IA), and the pharmaceutically acceptable salts and solvates thereof, wherein $R^{3a}$ is unsubstituted —$C_{6-10}$ aryl fused to a 5- or 6-membered heterocyclic ring. In some aspects, $R^{3a}$ is unsubstituted phenyl fused to a 5- or 6-membered heterocyclic ring. In some aspects, the 5- or 6-membered heterocyclic ring contains 1, 2, or 3 heteroatoms selected from the group consisting of N, S, and O, and the remaining atoms are carbon atoms. In some aspects, the fused heterocyclic ring is a 5-membered ring having 1 or 2 oxygen atoms. In some aspects, the fused heterocyclic ring is a 6-membered ring having 1 or 2 oxygen atoms. In some aspects, $R^{3a}$ is

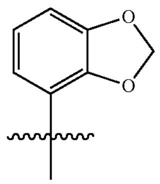

or

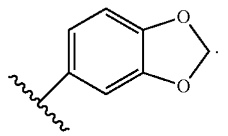

In another aspect, Compounds of the Disclosure are compounds of formula (IA), and the pharmaceutically acceptable salts and solvates thereof, wherein $R^{3a}$ is -(5- or 10-membered)-$C_{1-9}$ heteroaryl optionally substituted with 1, 2 or 3 substituents each independently selected from the group consisting of halogen, hydroxy, —CN, —$ORb^a$, —$SRb^a$, —$N(Rb^a)_2$, —$C_{1-4}$alkyl optionally substituted with 1, 2, or 3 substituents each independently selected from the group consisting of halogen, —CN, —$ORb^a$, and —$N(Rb^a)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another aspect, $R^{3a}$ is unsubstituted -(5- to 10-membered)-$C_{1-9}$ heteroaryl or -(5- to 10-membered)-$C_{1-9}$ heteroaryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, —CN, —$O(C_{1-4})$alkyl, —$N(C_{1-4}$ alkyl$)_2$, and —$NH(C_{1-4}$ alkyl). In another aspect, $R^{3a}$ is unsubstituted -(5- to 10-membered)-$C_{1-9}$ heteroaryl. In another aspect, $R^{3a}$ is -(5- to 10-membered)-$C_{1-9}$ heteroaryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, —CN, —$O(C_{1-4})$alkyl, —$N(C_{1-4}$ alkyl$)_2$, and —$NH(C_{1-4}$ alkyl). In some aspects, the -(5- to 10-membered)-$C_{1-9}$ heteroaryl is pyridin-2-yl, pyridin-3-yl, or pyridin-4-yl.

In another aspect, $R^{3a}$ is —$C_{3-10}$ cycloalkyl optionally substituted with 1, 2 or 3 substituents each independently selected from the group consisting of halogen, hydroxy, —CN, —$ORb^a$, —$SRb^a$, —$N(Rb^a)_2$, —$C_{1-4}$alkyl optionally substituted with 1, 2, or 3 substituents each independently selected from the group consisting of halogen, —CN, —$ORb^a$, and —$N(Rb^a)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another aspect, $R^{3a}$ is unsubstituted —$C_{3-10}$ cycloalkyl or —$C_{3-10}$ cycloalkyl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another aspect, $R^{3a}$ is $C_{4-6}$ cyclohexyl optionally substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH ($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another aspect, $R^{3a}$ is cyclohexyl optionally substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl).

In another aspect, $R^{3a}$ is -(5- to 10-membered)-$C_{2-9}$ heterocyclyl optionally substituted with 1, 2 or 3 substituents each independently selected from the group consisting of halogen, hydroxy, —CN, —ORb$^a$, —SRb$^a$, —N(Rb$^a$)$_2$, —$C_{1-4}$ alkyl optionally substituted with 1, 2, or 3 substituents each independently selected from the group consisting of halogen, —CN, —ORb$^a$, and —N(Rb$^a$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another aspect, Compounds of the Disclosure are compounds of formula (IA), and the pharmaceutically acceptable salts and solvates thereof, wherein $R^{2a}$ is H and $R^{1a}$ is as defined above.

In another aspect, Compounds of the Disclosure are compounds of formula (IA), and the pharmaceutically acceptable salts and solvates thereof, wherein $R^{2a}$ is —$C_{1-4}$ alkyl and $R^{1a}$ is as defined above. In another aspect, $R^{2a}$ is methyl or ethyl. In another aspect, $R^{2a}$ is methyl.

In another aspect, Compounds of the Disclosure are compounds of formula (IA), and the pharmaceutically acceptable salts and solvates thereof, wherein $R^{1a}$ is —$C_{6-10}$ aryl or —$C_{1-4}$ alkyl-$C_{6-10}$ aryl, wherein said aryl or alkylaryl is optionally substituted with 1, 2 or 3 substituents each independently selected from the group consisting of halogen, hydroxy, —CN, —ORb$^a$, —SRb$^a$, —N(Rb$^a$)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein Rb$^a$ is as defined above, and wherein said aryl is optionally fused to a further (second) ring.

In another aspect, $R^{1a}$ is unsubstituted $C_{6-10}$ aryl or $C_{6-10}$ aryl substituted with 1, 2 or 3 substituents each independently selected from the group consisting of halogen, hydroxy, —CN, —ORb$^a$, —SRb$^a$, —N(Rb$^a$)$_2$, —$C_{1-4}$ alkyl optionally substituted with 1, 2, or 3 substituents each independently selected from the group consisting of halogen, —CN, —ORb$^a$, and —N(Rb$^a$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl, wherein Rb$^a$ is as defined above; and wherein said aryl is optionally fused to a further (second) ring. In another aspect, $R^{1a}$ is unsubstituted —$C_{6-10}$ aryl or —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH ($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another aspect, $R^{1a}$ is unsubstituted —$C_{6-10}$ aryl. In another aspect, $R^{1a}$ is unsubstituted phenyl. In another aspect, $R^{1a}$ is —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In some aspects, $R^{1a}$ is unsubstituted $C_{6-10}$ aryl fused to a 5- or 6-membered heterocyclic ring. In some aspects, the 5- or 6-membered heterocyclic ring contains 1, 2, or 3 heteroatoms selected from the group consisting of N, S, and O, and the remaining atoms are carbon atoms. In some aspects, the fused heterocyclic ring is a 5-membered ring having 1 or 2 oxygen atoms. In some aspects, the fused heterocyclic ring is a 6-membered ring having 1 or 2 oxygen atoms. In some aspects, $R^{1a}$ is

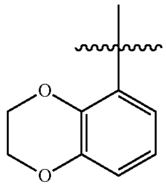
or
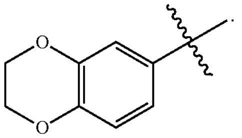
.

In another aspect, $R^{1a}$ is unsubstituted —$C_{1-4}$ alkyl-$C_{6-10}$ aryl or —$C_{1-4}$ alkyl-$C_{6-10}$ aryl optionally substituted with 1, 2 or 3 substituents each independently selected from the group consisting of halogen, hydroxy, —CN, —ORb$^a$, —SRb$^a$, —N(Rb$^a$)$_2$, —$C_{1-4}$alkyl optionally substituted with 1, 2, or 3 substituents each independently selected from the group consisting of halogen, —CN, —ORb$^a$, and —N(Rb$^a$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl, wherein Rb$^a$ is as defined above; and wherein said aryl is optionally fused to a further (second) ring. In another aspect, $R^{1a}$ is unsubstituted —$C_{1-4}$ alkyl-$C_{6-10}$ aryl or —$C_{1-4}$ alkyl-$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another aspect, $R^{1a}$ is unsubstituted —$C_{1-4}$ alkyl-$C_{6-10}$ aryl. In another aspect, $R^{1a}$ is unsubstituted benzyl or phenethyl. In another aspect, $R^{1a}$ is —$C_{1-4}$ alkyl-$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, CN, —O($C_{1-4}$)alkyl, —N($C_{1-4}$ alkyl)$_2$, and —NH($C_{1-4}$ alkyl).

In another aspect, Compounds of the Disclosure are compounds of formula (IA), and the pharmaceutically acceptable salts and solvates thereof, wherein $R^{1a}$ is —$C_{3-10}$ cycloalkyl or —$C_{1-4}$ alkyl-$C_{3-10}$ cycloalkyl, wherein said cycloalkyl or alkylcycloalkyl is optionally substituted with 1, 2 or 3 substituents each independently selected from the group consisting of halogen, hydroxy, —CN, —ORb$^a$, —SRb$^a$, —N(Rb$^a$)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein Rb$^a$ is as defined above; and wherein said cycloalkyl is optionally fused to a further (second) ring. In another aspect, $R^{1a}$ is an unsubstituted —$C_{3-10}$ cycloalkyl fused to a phenyl ring. In another aspect, $R^{1a}$ is —$C_{4-7}$ cycloalkyl fused to a phenyl ring.

In another aspect, $R^{1a}$ is an unsubstituted pentyl or hexyl ring fused to a phenyl ring.

In another aspect, Compounds of the Disclosure are compounds of formula (IA), and the pharmaceutically acceptable salts and solvates thereof, wherein Rb$^a$ is hydrogen or —$C_{1-4}$ alkyl.

In another aspect, Compounds of the Disclosure are compounds of formula (IA), and the pharmaceutically acceptable salts and solvates thereof, wherein $R^{1a}$ and $R^{2a}$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring. In another aspect, $R^{1a}$ and $R^{2a}$ together with the nitrogen atom form a piperazinyl ring optionally substituted at the nitrogen with —$C_{1-4}$ alkyl (such as methyl or ethyl), —$C_{6-10}$ aryl (such as phenyl) optionally substituted with $C_{1-4}$ alkyl or —O($C_{1-4}$ alkyl), or —C(═O)O($C_{1-4}$ alkyl).

In another aspect, Compounds of the Disclosure are compounds of formula (IA), and the pharmaceutically acceptable salts and solvates thereof, wherein $R^{1a}$ and $R^{2a}$ together with the nitrogen atom to which they are attached form a 5- or 6-membered ring optionally fused to a phenyl ring. In another aspect, $R^{1a}$ and $R^{2a}$ together with the nitrogen atom to which they are attached form a 5- or 6-membered ring fused to a phenyl ring. In some aspects, $R^{1a}$ and $R^{2a}$ together with the nitrogen atom to which they are attached form

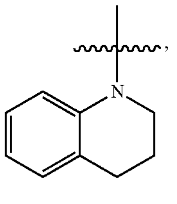,
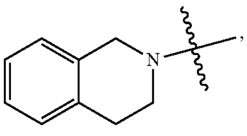,
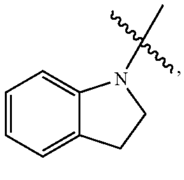, or
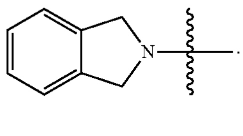.

In another aspect, the present disclosure provides a Compound of the Disclosure of formula (IA) selected from the group consisting of

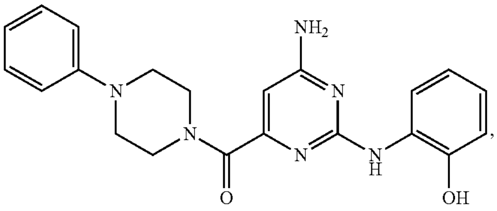,
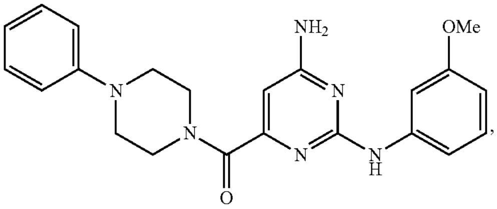,
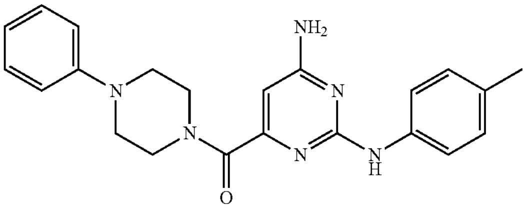,
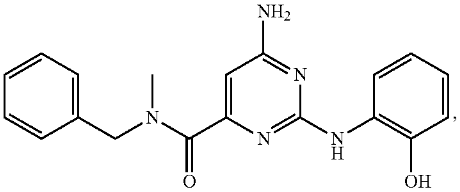,
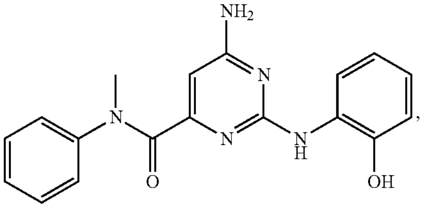,
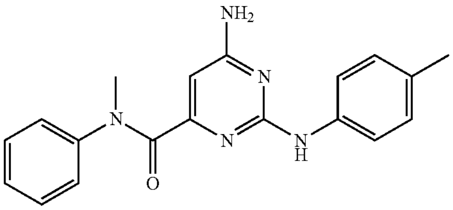,
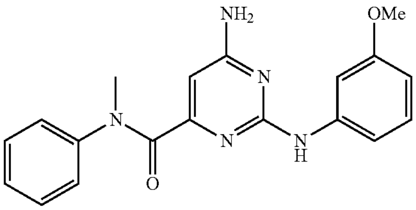,
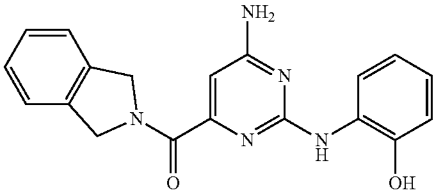, -continued
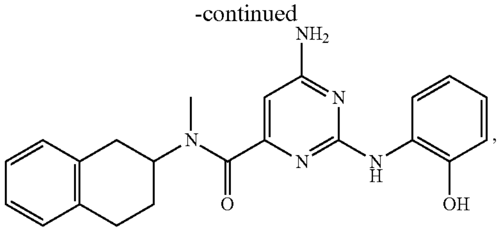
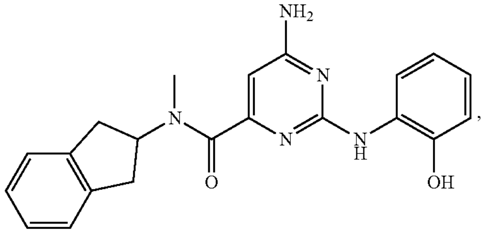
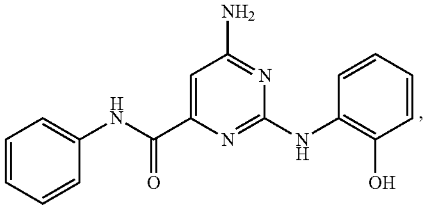
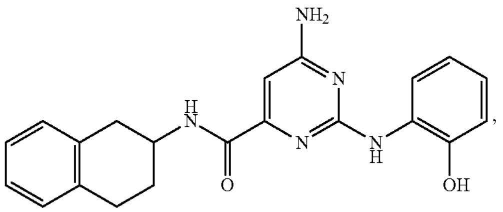
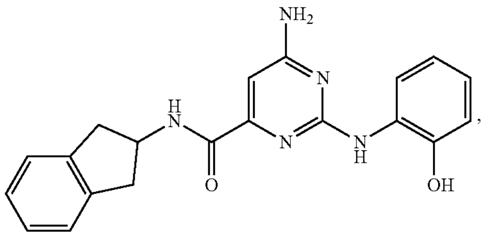
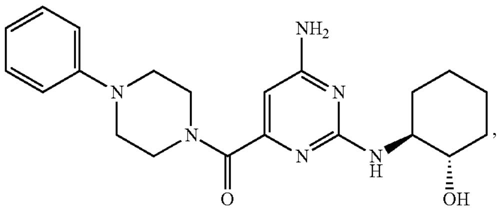
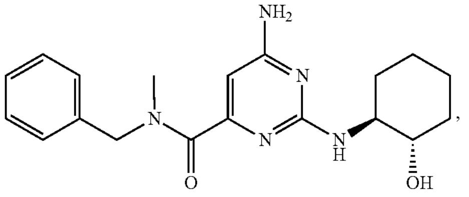
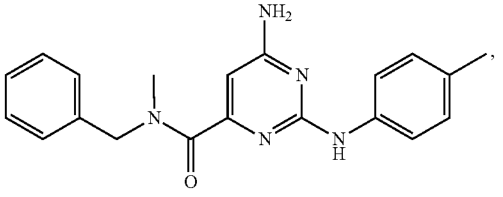
and
-continued
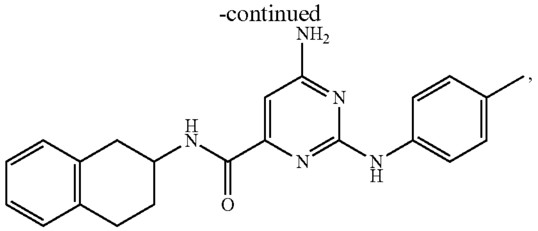
and the pharmaceutically acceptable salts and solvates thereof.
In another aspect, the present disclosure provides a Compound of the Disclosure of formula (IA) selected from the group consisting of
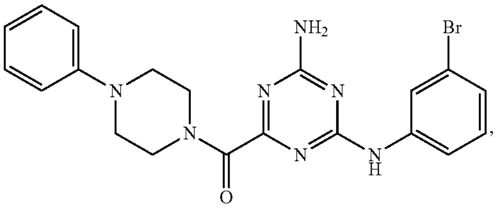
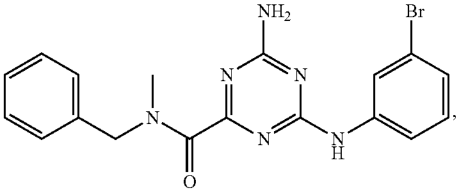
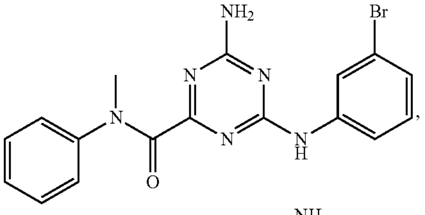
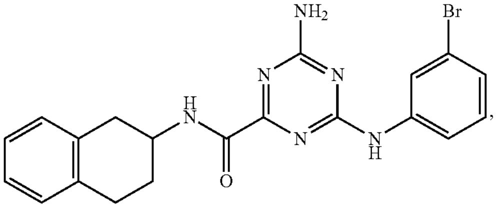
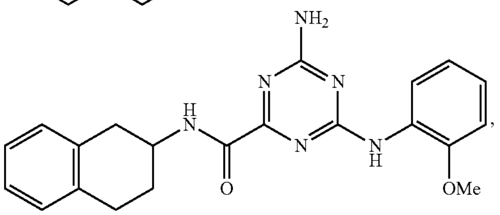
and
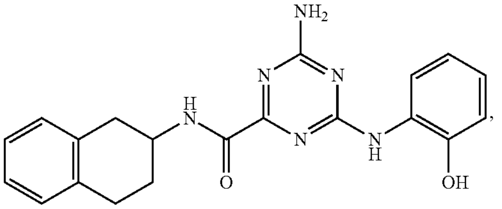
and the pharmaceutically acceptable salts thereof.

In another aspect, the present disclosure provides a Compound of the Disclosure of formula (IA) selected from the group consisting of
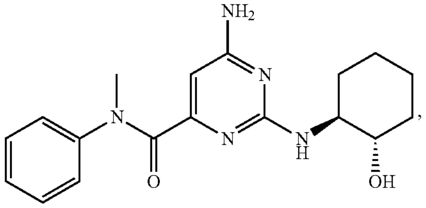
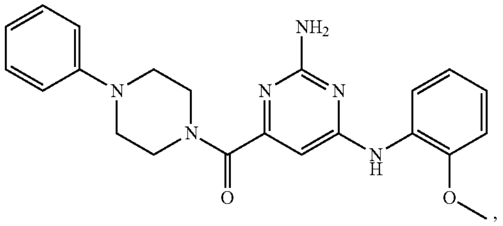
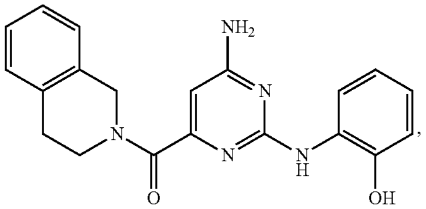
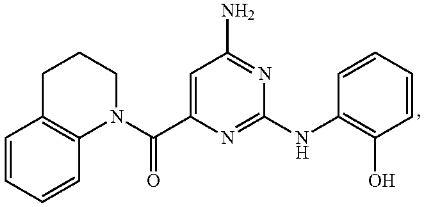
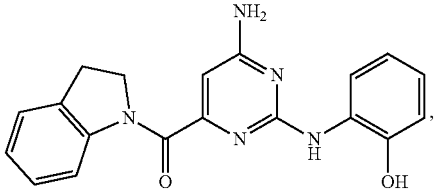
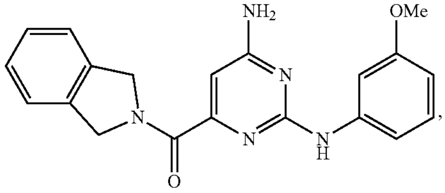
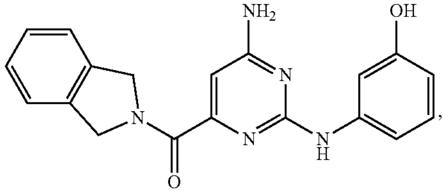
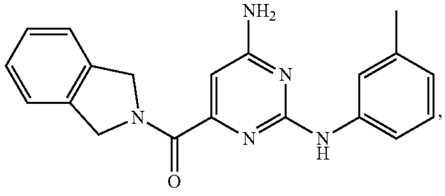
-continued
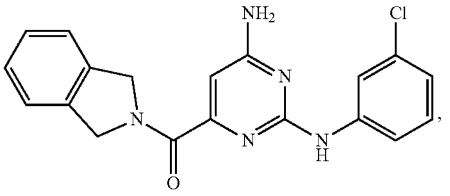
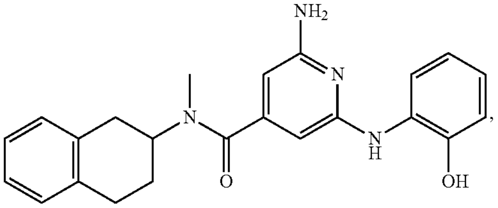
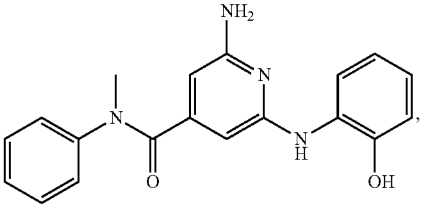
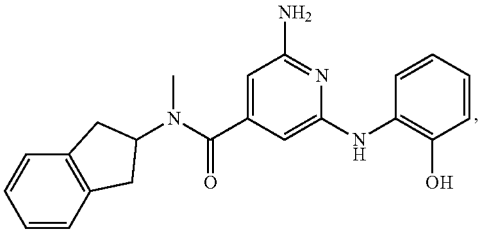
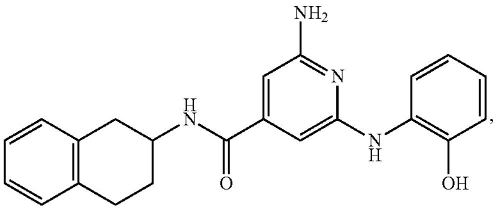
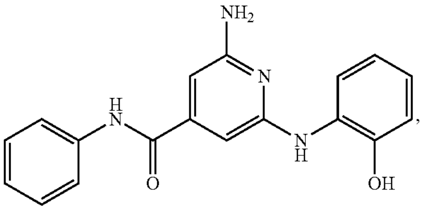
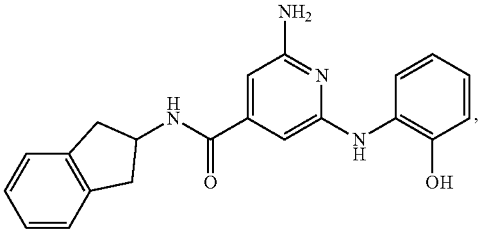
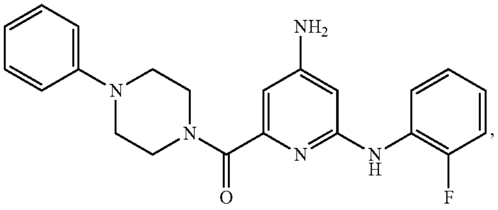

-continued
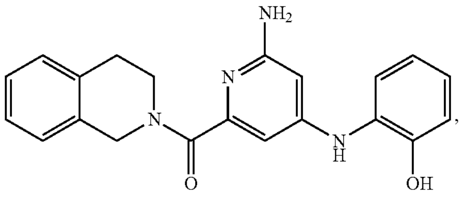
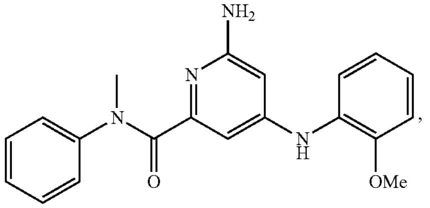
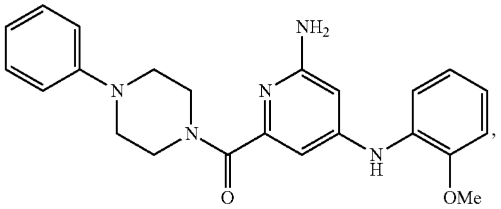
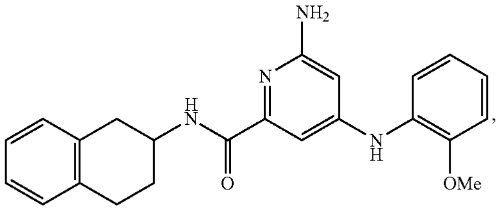
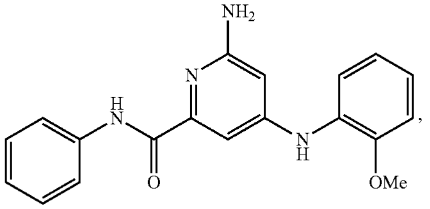
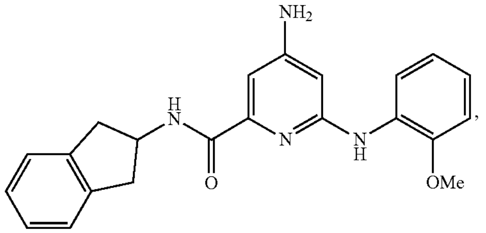
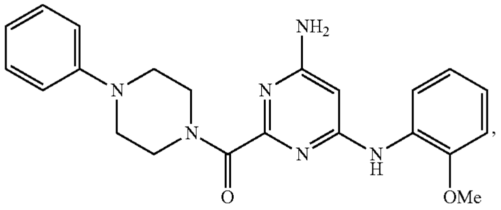
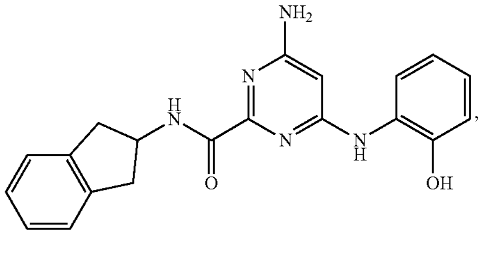
-continued
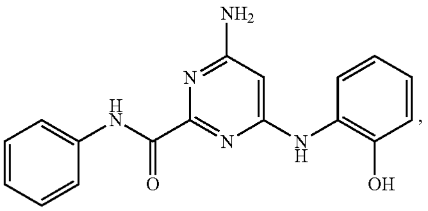
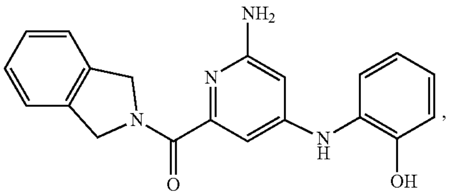
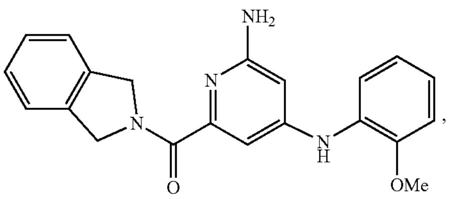
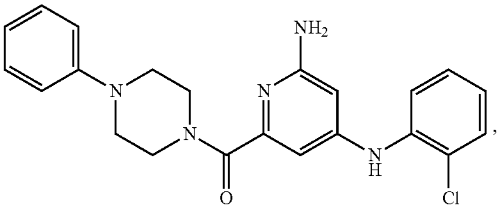
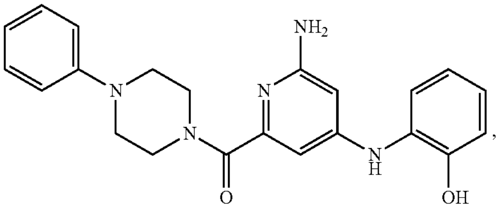
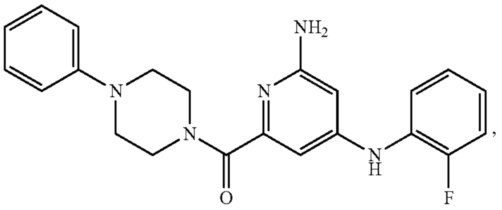
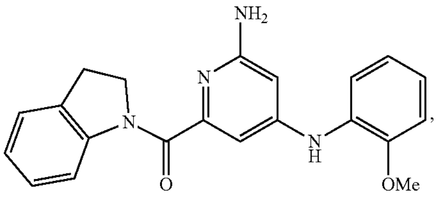
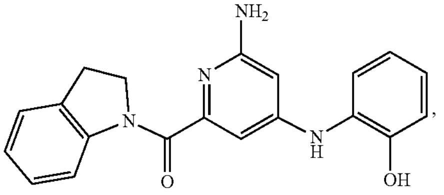

-continued
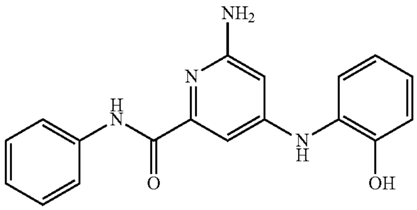,
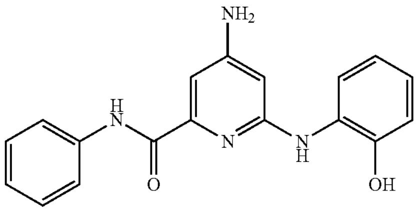,
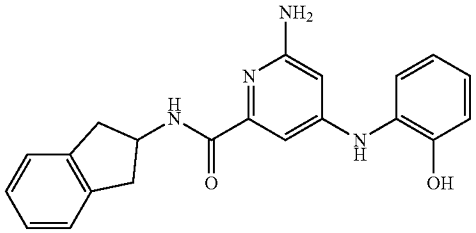,
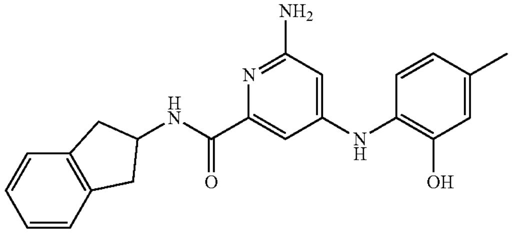,
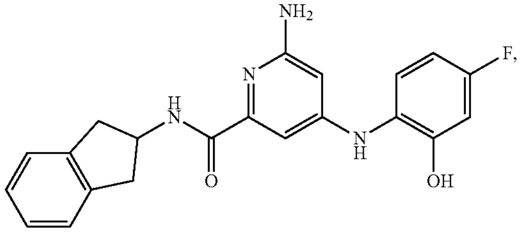,
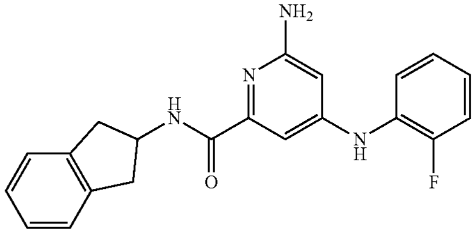,
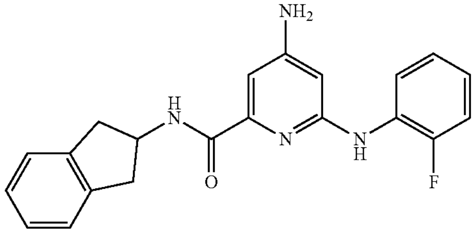,
-continued
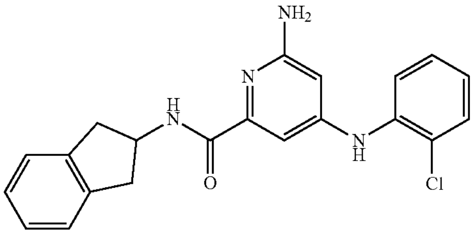,
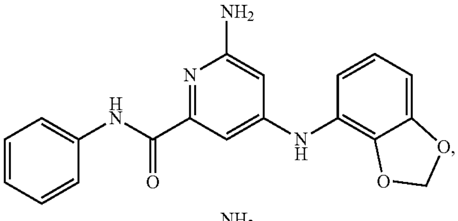,
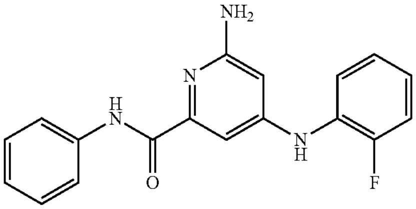,
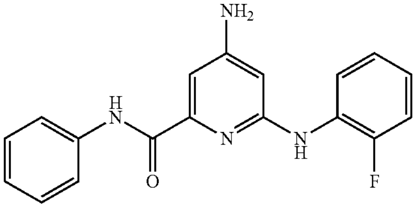,
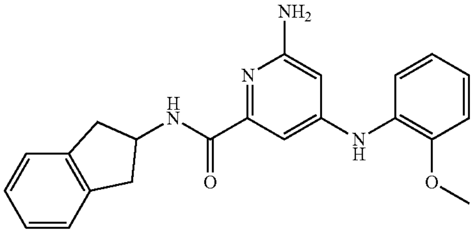,
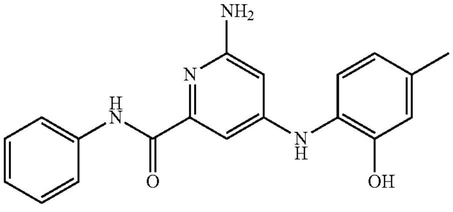,
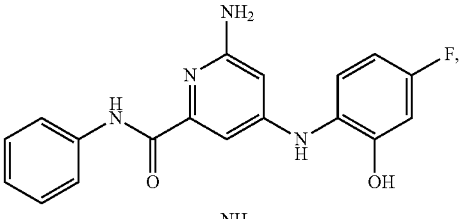,
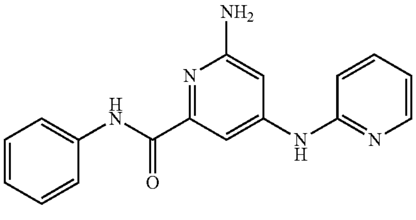, -continued
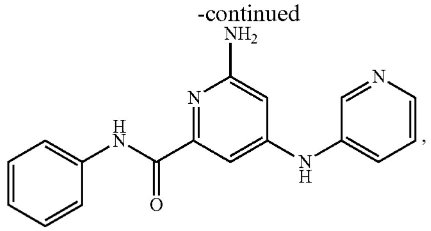
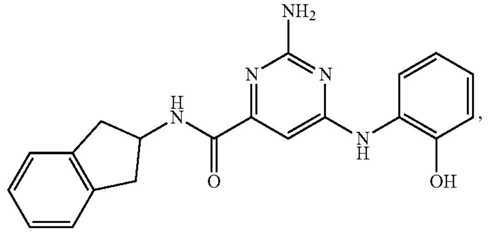
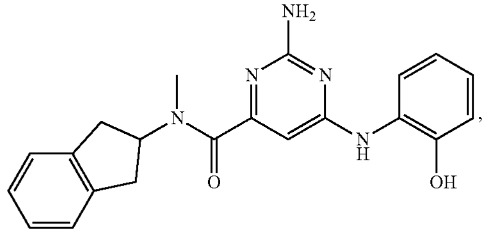
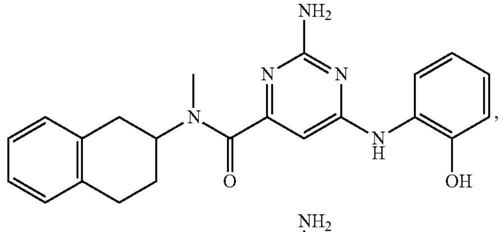
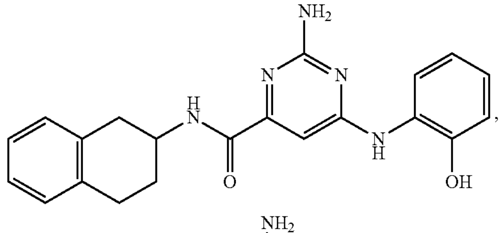
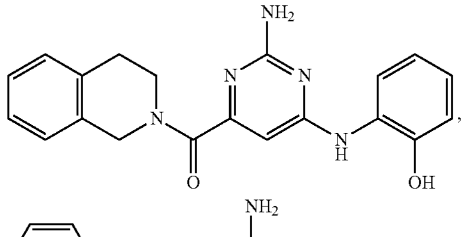
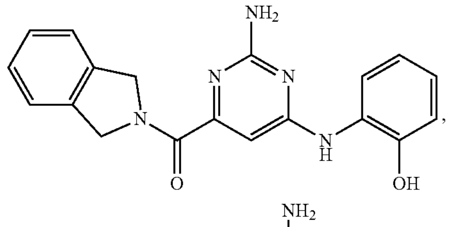
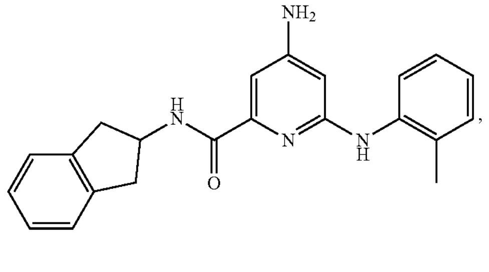
-continued
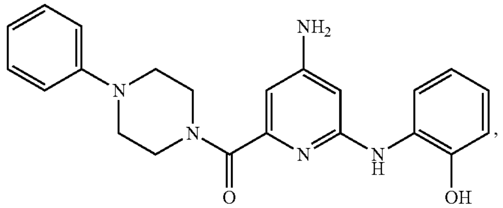
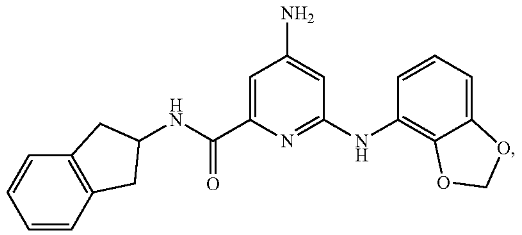
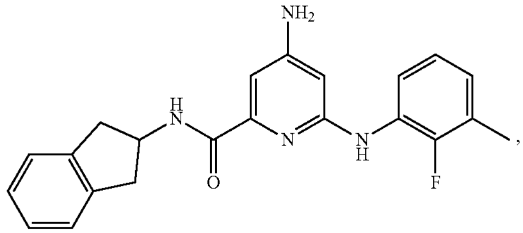
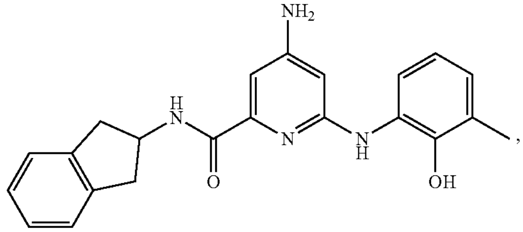
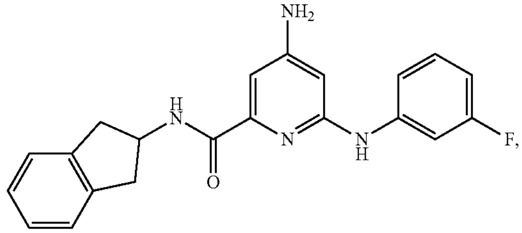
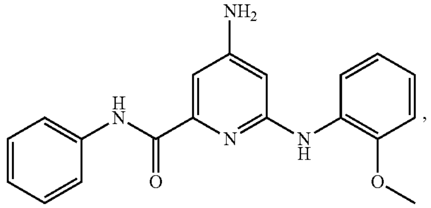
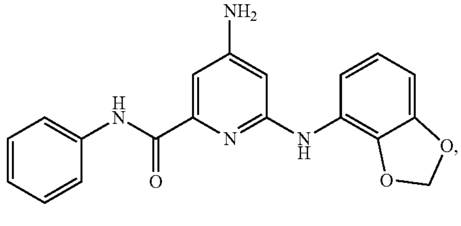

-continued
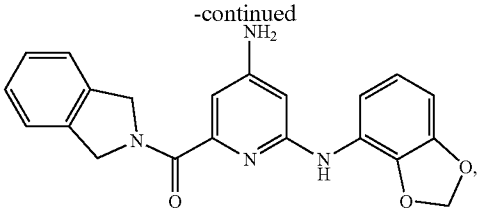
,
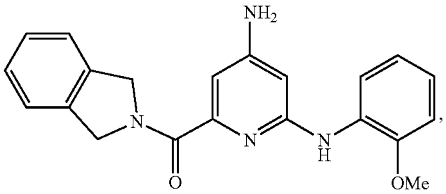
,
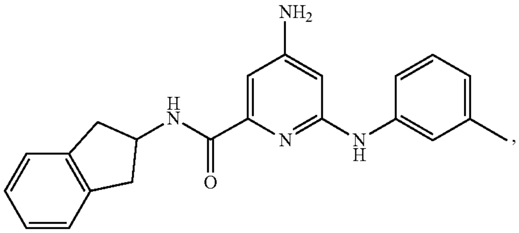
,
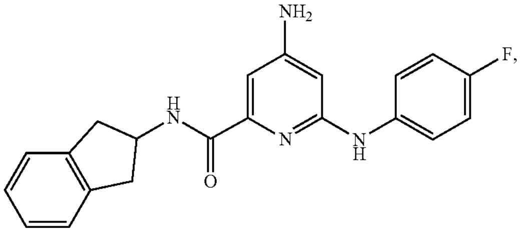
,
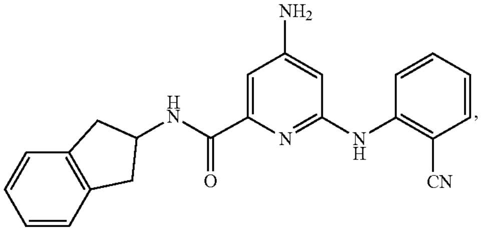
,
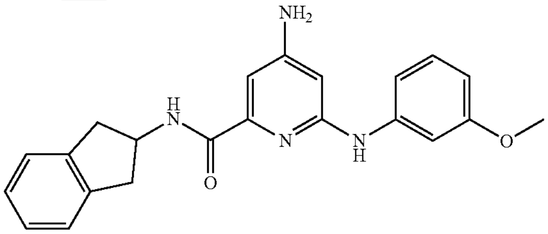
,
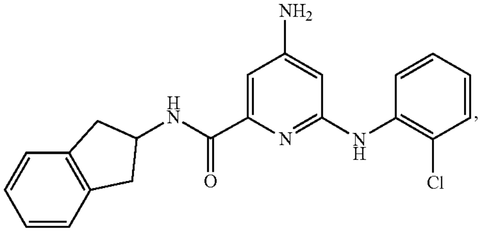
,
-continued
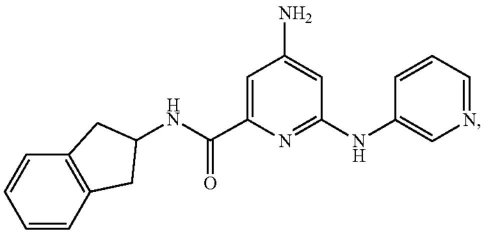
,
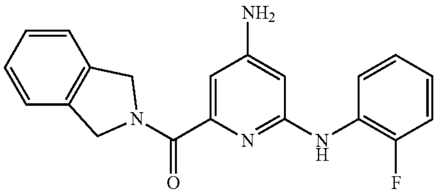
,
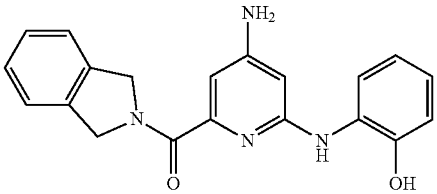
,
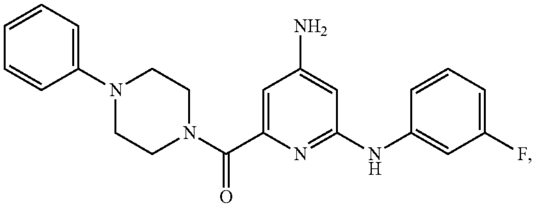
,
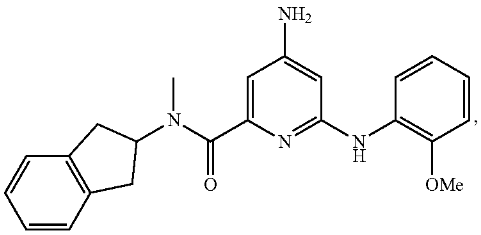
,
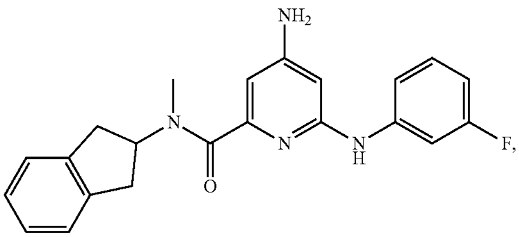
,
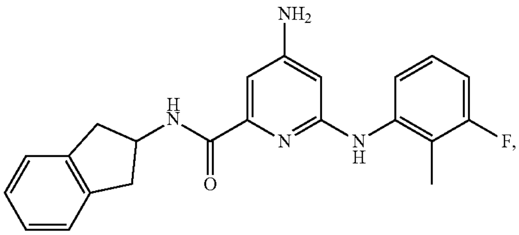
, -continued
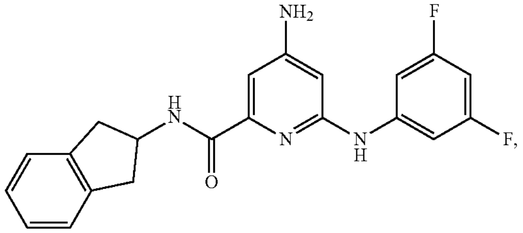
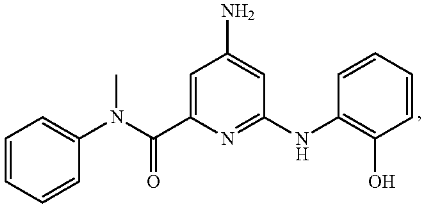
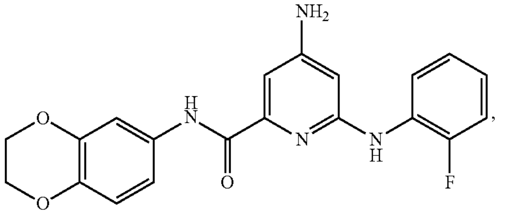
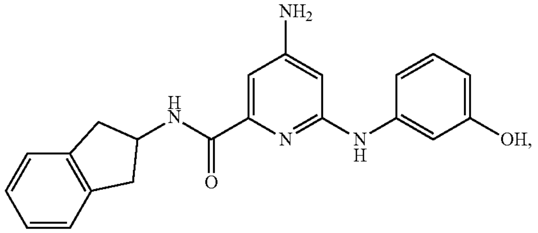
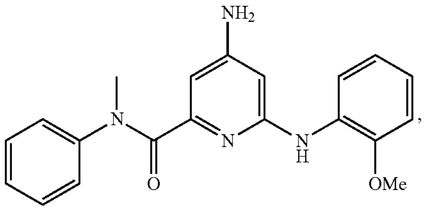
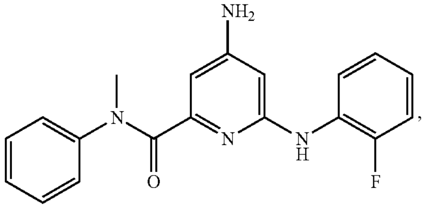
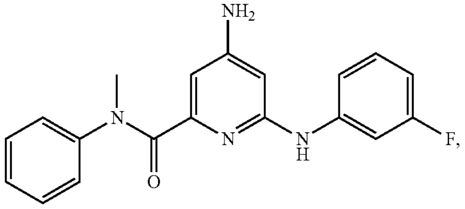
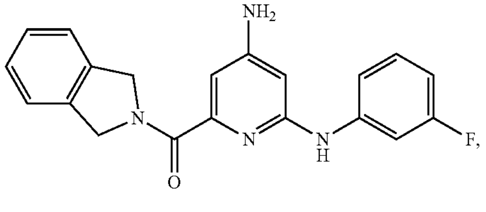
-continued
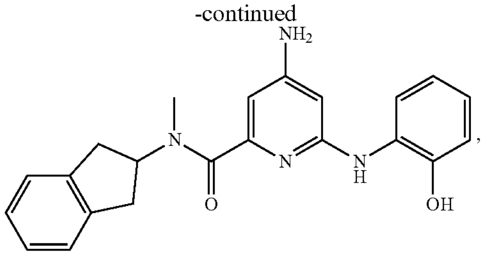
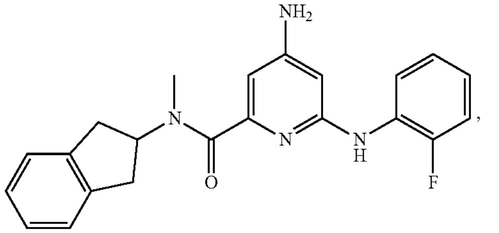
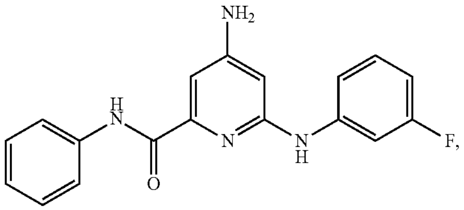
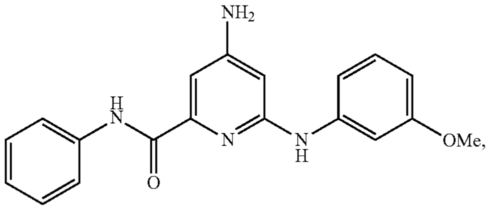
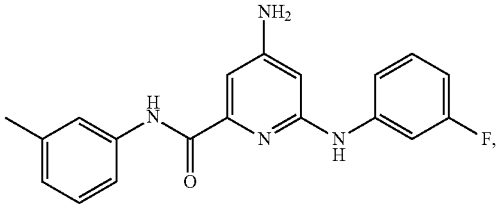
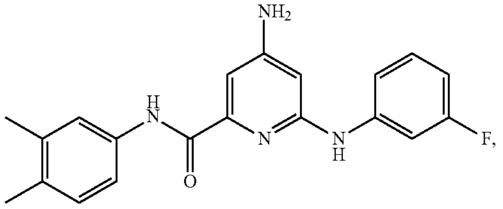
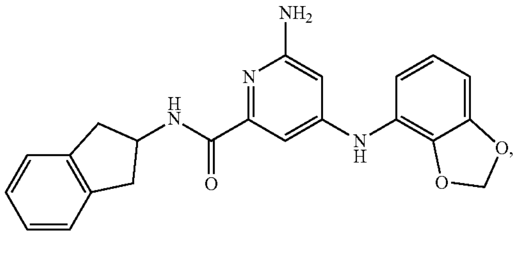

-continued
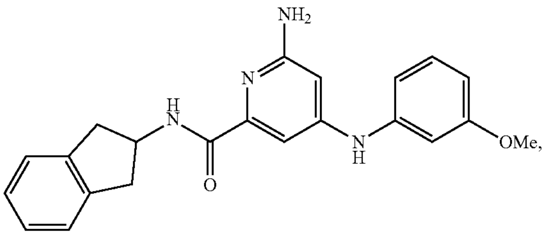
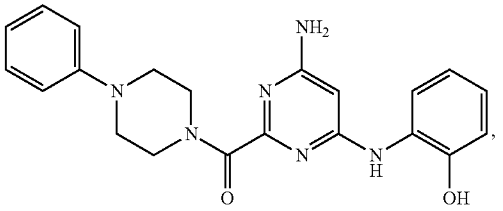
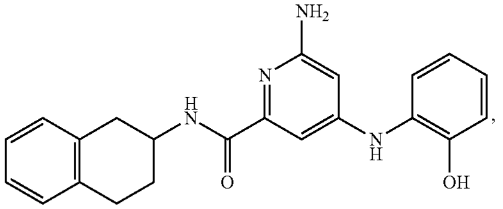
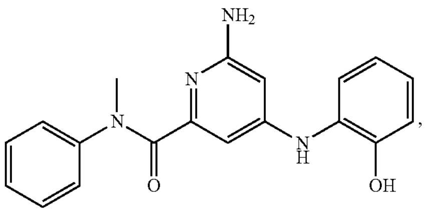
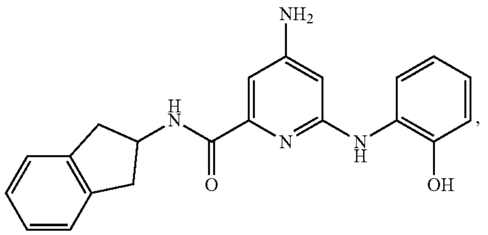
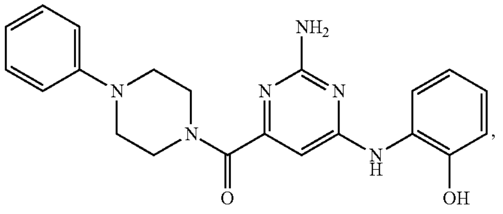
and
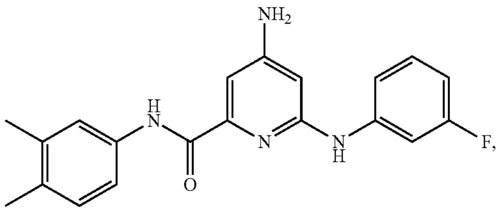
and pharmaceutically acceptable salts thereof. In some embodiments, the pharmaceutically acceptable salt is a hydrochloride salt (a HCl-salt).
In another aspect, the present disclosure provides a Compound of the Disclosure of formula (IA) selected from the group consisting of
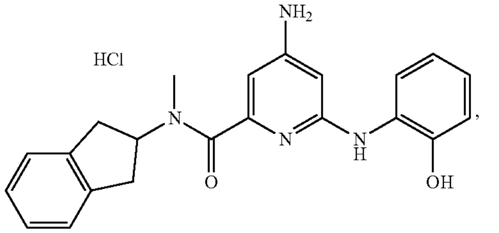
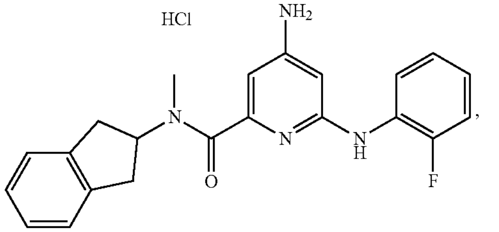
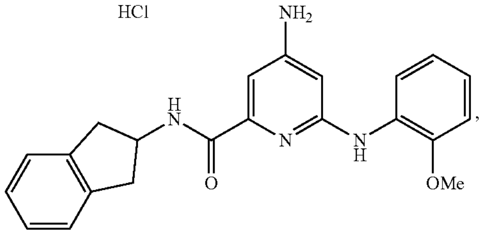
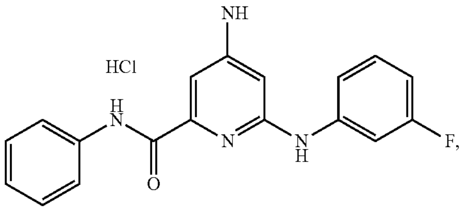
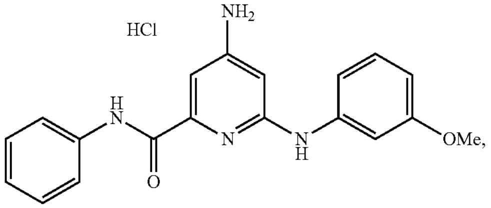
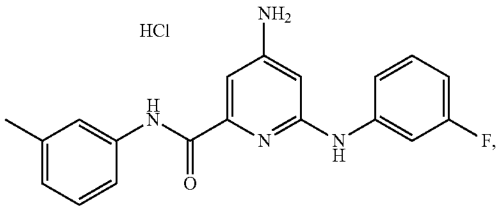
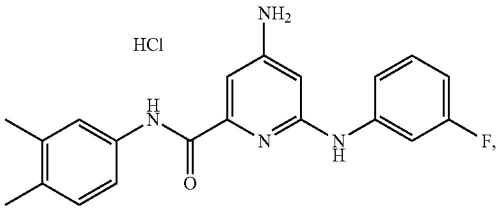

-continued

HCl

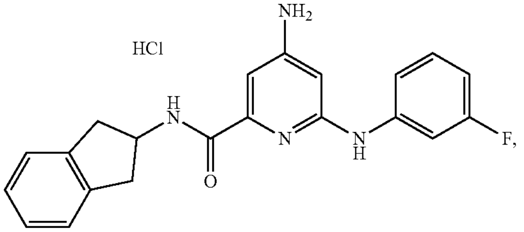

,

HCl

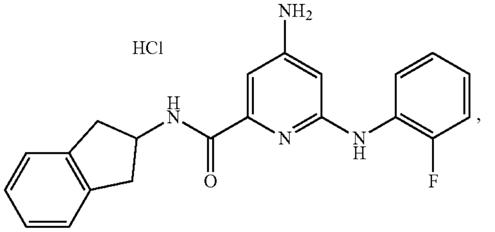

HCl

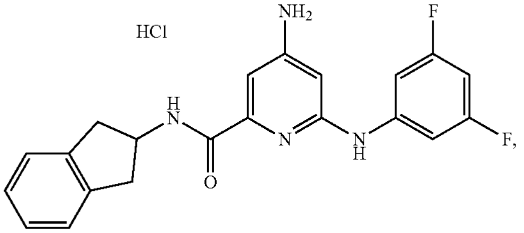

and

HCl

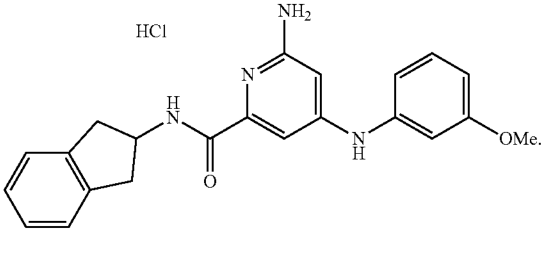

In another aspect, Compounds of the Disclosure are compounds of formula (IB):

(IB)

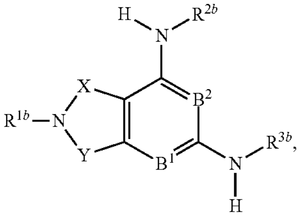

and the pharmaceutically acceptable salts and solvates thereof, wherein $B^1$ and $B^2$ are each independently selected from the group consisting of N, CH and C($R^{4b}$), provided that at least one of $B^1$ or $B^2$ is N;

each $R^{4b}$ is independently selected from the group consisting of halogen, —$C_{1-4}$ alkyl, —$C_{1-4}$ alkoxy, and —CN;

X and Y are independently selected from the group consisting of a bond (i.e. is absent), $C_{1-4}$ alkylene, C(═O), C(═O)—$C_{1-2}$ alkylene, and $C_{1-2}$ alkylene-C(═O);

$R^{1b}$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(═O)$Ra^b$, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^b$, —$SRb^b$, —N($Rb^b$)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, -(5- to 10-membered)-$C_{2-9}$ heterocyclyl, and optionally substituted —O—($C_{6-10}$ aryl); and wherein said cycloalkyl, alkylcycloalkyl, aryl, alkylaryl, heteroaryl, alkylheteroaryl, heterocyclyl and alkylheterocyclyl is optionally fused to a further (second) ring; and $Ra^b$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^b$, —$SRb^b$, —N($Rb^b$)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each $Rb^b$ is independently hydrogen, —$C_{1-4}$ alkyl, —$C_{3-10}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms; and $R^{2b}$ and $R^{3b}$ are each independently selected from the group consisting of hydrogen, —$C_{1-4}$ alkyl, —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —$ORb^b$, —$SRb^b$, —N($Rb^b$)$_2$, —$C_{1-4}$alkyl optionally substituted with 1 or 2 substituents each independently selected from the group consisting of halogen, —CN, —$ORb^b$, and —N($Rb^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another aspect, Compounds of the Disclosure are compounds of formula (IB), and the pharmaceutically acceptable salts and solvates thereof, wherein $B^1$ and $B^2$ are N.

In another aspect, Compounds of the Disclosure are compounds of formula (IB), and the pharmaceutically acceptable salts and solvates thereof, wherein $B^1$ is N and $B^2$ is selected from the group consisting of CH and C($R^{4b}$). In another aspect, $B^2$ is CH.

In another aspect, Compounds of the Disclosure are compounds of formula (IB), and their pharmaceutically acceptable salts and solvates thereof, wherein $B^2$ is N and $B^1$ is selected from the group consisting of CH and $C(R^{4b})$. In another aspect, $B^1$ is CH.

In another aspect, Compounds of the Disclosure are compounds of formula (IB), and the pharmaceutically acceptable salts and solvates thereof, wherein $R^{2b}$ hydrogen or —$C_{1-4}$ alkyl and $R^{3b}$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —$ORb^b$, —$SRb^b$, —$N(Rb^b)_2$, —$C_{1-4}$alkyl optionally substituted with 1 or 2 substituents each independently selected from the group consisting of halogen, —CN, —$ORb^b$, and —$N(Rb^b)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another aspect, Compounds of the Disclosure are compounds of formula (IB), and the pharmaceutically acceptable salts and solvates thereof, wherein $R^{3b}$ hydrogen or —$C_{1-4}$ alkyl and $R^{2b}$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —$ORb^b$, —$SRb^b$, —$N(Rb^b)_2$, —$C_{1-4}$alkyl optionally substituted with 1 or 2 substituents each independently selected from the group consisting of halogen, —CN, —$ORb^b$, and —$N(Rb^b)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another aspect, Compounds of the Disclosure are compounds of formula (IB), and the pharmaceutically acceptable salts and solvates thereof, wherein $R^{2b}$ is hydrogen or —$C_{1-4}$ alkyl and $R^{3b}$ is —$C_{6-10}$ aryl optionally substituted with 1, 2 or 3 substituents each independently selected from the group consisting of halogen, hydroxy, —CN, —$ORb^b$, —$SRb^b$, —$N(Rb^b)_2$, —$C_{1-4}$alkyl optionally substituted with 1 or 2 substituents each independently selected from the group consisting of halogen, —CN, —$ORb^b$, and —$N(Rb^b)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another aspect, $R^{3b}$ is unsubstituted —$C_{6-10}$ aryl or —$C_{6-10}$ aryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1 or 2 substituents each independently selected from the group consisting of halogen, CN, —$O(C_{1-4}$ alkyl), —$N(C_{1-4}$ alkyl$)_2$, and —$NH(C_{1-4}$ alkyl). In another aspect, $R^{3b}$ is unsubstituted —$C_{6-10}$ aryl, and preferably unsubstituted phenyl. In another aspect, $R^{3b}$ is —$C_{6-10}$ aryl substituted with 1 or 2 substituents each independently selected from the group consisting of halogen, hydroxy, —CN, —$O(C_{1-4}$ alkyl), —$S(C_{1-4})$alkyl, —$N(C_{1-4}$ alkyl$)_2$, —NH ($C_{1-4}$ alkyl), and —$C_{1-4}$ alkyl optionally substituted with 1 or 2 substituents each independently selected from the group consisting of halogen, —CN, —$O(C_{1-4}$ alkyl), —$N(C_{1-4}$ alkyl$)_2$, and —$NH(C_{1-4}$ alkyl). In another aspect, $R^{3b}$ is —$C_{6-10}$ aryl, and preferably phenyl, substituted with 1 or 2 substituents each independently selected from the group consisting of halogen, hydroxy, —CN, methoxy, ethoxy, methylthio, ethylthio, dimethylamino, diethylamino, methylamino, ethylamino, halomethyl (such as fluoromethyl), di(halo)methyl (such as difluoromethyl), cyanomethyl, methoxymethyl, methoxyethyl, dimethylaminomethyl, dimethylaminoethyl, methylaminomethyl, and methylaminoethyl. In another aspect, $R^{3b}$ is phenyl substituted with halogen, hydroxy, —CN, methyl, ethyl, methoxy, or ethoxy. In another aspect, the substituent is attached to the meta-position of the phenyl group. In another aspect, the substituent is attached to the ortho-position of the phenyl group. In another aspect, the substituent is attached to the para-position of the phenyl group.

In another aspect, Compounds of the Disclosure are compounds of formula (IB), and the pharmaceutically acceptable salts and solvates thereof, wherein $R^{2b}$ is hydrogen or —$C_{1-4}$ alkyl and $R^{3b}$ is -(5- to 10-membered)-$C_{1-9}$ heteroaryl optionally substituted with 1, 2 or 3 substituents each independently selected from the group consisting of halogen, hydroxy, —CN, —$ORb^b$, —$SRb^b$, —$N(Rb^b)_2$, —$C_{1-4}$alkyl optionally substituted with 1 or 2 substituents each independently selected from the group consisting of halogen, —CN, —$ORb^b$, and —$N(Rb^b)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another aspect, $R^{3b}$ is unsubstituted -(5- to 10-membered)-$C_{1-9}$ heteroaryl or -(5- to 10-membered)-$C_{1-9}$ heteroaryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1 or 2 substituents each independently selected from the group consisting of halogen, —CN, —$O(C_{1-4})$ alkyl, —$N(C_{1-4}$ alkyl$)_2$, and —$NH(C_{1-4}$ alkyl). In another aspect, $R^{3b}$ is unsubstituted -(5- or 10-membered)-$C_{1-9}$ heteroaryl. In another aspect, $R^{3b}$ is -(5- or 10-membered)-$C_{1-9}$ heteroaryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1 or 2 substituents each independently selected from the group consisting of halogen, —CN, —$O(C_{1-4})$ alkyl, —$N(C_{1-4}$ alkyl$)_2$, and —$NH(C_{1-4}$ alkyl).

In another aspect, Compounds of the Disclosure are compounds of formula (IB), and the pharmaceutically acceptable salts and solvates thereof, wherein $R^{2b}$ is hydrogen or —$C_{1-4}$ alkyl and $R^{3b}$ is —$C_{3-10}$ cycloalkyl or -(5- to 10-membered)-$C_{2-9}$ heterocyclyl, wherein said cycloalkyl and heterocyclyl groups are optionally substituted with 1, 2 or 3 substituents each independently selected from the group consisting of halogen, hydroxy, —CN, —$ORb^b$, —$SRb^b$, —$N(Rb^b)_2$, —$C_{1-4}$alkyl optionally substituted with 1 or 2 substituents each independently selected from the group consisting of halogen, —CN, —$ORb^b$, and —$N(Rb^b)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another aspect, Compounds of the Disclosure are compounds of formula (IB), and the pharmaceutically acceptable salts and solvates thereof, wherein $R^{3b}$ is hydrogen or —$C_{1-4}$ alkyl and $R^{2b}$ is —$C_{6-10}$ aryl optionally substituted with 1, 2 or 3 substituents each independently selected from the group consisting of halogen, hydroxy, —CN, —$ORb^b$, —$SRb^b$, —$N(Rb^b)_2$, —$C_{1-4}$alkyl optionally substituted with 1 or 2 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another aspect, $R^{2b}$ is unsubstituted —$C_{6-10}$ aryl or —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1 or 2 substituents each independently selected from the group consisting of halogen, CN, —O($C_{1-4}$ alkyl), —N($C_{1-4}$ alkyl)$_2$, and —NH($C_{1-4}$ alkyl). In another aspect, $R^{2b}$ is unsubstituted —$C_{6-10}$ aryl, and preferably unsubstituted phenyl. In another aspect, $R^{2b}$ is —$C_{6-10}$ aryl substituted with 1 or 2 substituents each independently selected from the group consisting of halogen, hydroxy, —CN, —O($C_{1-4}$ alkyl), —S($C_{1-4}$)alkyl, —N($C_{1-4}$ alkyl)$_2$, —NH ($C_{1-4}$ alkyl), and —$C_{1-4}$ alkyl optionally substituted with 1 or 2 substituents each independently selected from the group consisting of halogen, —CN, —O($C_{1-4}$ alkyl), —N($C_{1-4}$ alkyl)$_2$, and —NH($C_{1-4}$ alkyl). In another aspect, $R^{2b}$ is —$C_{6-10}$ aryl, and preferably phenyl, substituted with 1 or 2 substituents each independently selected from the group consisting of halogen, hydroxy, —CN, methoxy, ethoxy, methylthio, ethylthio, dimethylamino, diethylamino, methylamino, ethylamino, halomethyl (such as fluoromethyl), di(halo)methyl (such as difluoromethyl), cyanomethyl, methoxymethyl, methoxyethyl, dimethylaminomethyl, dimethylaminoethyl, methylaminomethyl, and methylaminoethyl. In another aspect, $R^{2b}$ is phenyl substituted with halogen, hydroxy, —CN, methyl, ethyl, methoxy, or ethoxy. In another aspect, the substituent is attached to the meta-position of the phenyl group. In another aspect, the substituent is attached to the ortho-position of the phenyl group. In another aspect, the substituent is attached to the para-position of the phenyl group.

In another aspect, Compounds of the Disclosure are compounds of formula (IB), and the pharmaceutically acceptable salts and solvates thereof, wherein $R^{3b}$ is hydrogen or —$C_{1-4}$ alkyl and $R^{2b}$ is -(5- to 10-membered)-$C_{1-9}$ heteroaryl optionally substituted with 1, 2 or 3 substituents each independently selected from the group consisting of halogen, hydroxy, —CN, —ORb$^b$, —SRb$^b$, —N(Rb$^b$)$_2$, —$C_{1-4}$ alkyl optionally substituted with 1 or 2 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another aspect, $R^{2b}$ is unsubstituted -(5- or 10-membered)-$C_{1-9}$ heteroaryl or -(5- to 10-membered)-$C_{1-9}$ heteroaryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1 or 2 substituents each independently selected from the group consisting of halogen, —CN, —O($C_{1-4}$) alkyl, —N($C_{1-4}$ alkyl)$_2$, and —NH($C_{1-4}$ alkyl). In another aspect, $R^{3b}$ is unsubstituted -(5- to 10-membered)-$C_{1-9}$ heteroaryl. In another aspect, $R^{2b}$ is -(5- or 10-membered)-$C_{1-9}$ heteroaryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1 or 2 substituents each independently selected from the group consisting of halogen, —CN, —O($C_{1-4}$) alkyl, —N($C_{1-4}$ alkyl)$_2$, and —NH($C_{1-4}$ alkyl).

In another aspect, Compounds of the Disclosure are compounds of formula (IB), and the pharmaceutically acceptable salts and solvates thereof, wherein $R^{3b}$ is hydrogen or —$C_{1-4}$ alkyl and $R^{2b}$ is —$C_{3-10}$ cycloalkyl or -(5- to 10-membered)-$C_{2-9}$ heterocyclyl, wherein said cycloalkyl and heterocyclyl groups are optionally substituted with 1, 2 or 3 substituents each independently selected from the group consisting of halogen, hydroxy, —CN, —ORb$^b$, —SRb$^b$, —N(Rb$^b$)$_2$, —$C_{1-4}$ alkyl optionally substituted with 1 or 2 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

In another aspect, Compounds of the Disclosure are compounds of formula (IB), and the pharmaceutically acceptable salts and solvates thereof, wherein $R^{2b}$ is hydrogen and $R^{3b}$ is as defined above.

In another aspect, Compounds of the Disclosure are compounds of formula (IB), and the pharmaceutically acceptable salts and solvates thereof, wherein $R^{3b}$ is hydrogen and $R^{2b}$ is as defined above.

In another aspect, Compounds of the Disclosure are compounds of formula (IB), and the pharmaceutically acceptable salts and solvates thereof, wherein $R^{1b}$ is —$C_{6-10}$ aryl or —$C_{1-4}$ alkyl-$C_{6-10}$ aryl, wherein said aryl or alkylaryl is optionally substituted with 1, 2 or 3 substituents each independently selected from the group consisting of halogen, hydroxy, —CN, —ORb$^b$, —SRb$^b$, —N(Rb$^b$)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein Rb$^b$ is as defined above.

In another aspect, $R^{1b}$ is unsubstituted $C_{6-10}$ aryl or $C_{6-10}$ aryl substituted with 1, 2 or 3 substituents each independently selected from the group consisting of halogen, hydroxy, —CN, —ORb$^b$, —SRb$^b$, —N(Rb$^b$)$_2$, —$C_{1-4}$ alkyl optionally substituted with 1, 2, or 3 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another aspect, $R^{1b}$ is unsubstituted —$C_{6-10}$ aryl or —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another aspect, $R^{1b}$ is unsubstituted —$C_{6-10}$ aryl. In another aspect, $R^{1b}$ unsubstituted phenyl. In another aspect, $R^{1b}$ is —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl).

In another aspect, $R^{1b}$ is unsubstituted —$C_{1-4}$ alkyl-$C_{6-10}$ aryl or —$C_{1-4}$ alkyl-$C_{6-10}$ aryl optionally substituted with 1, 2 or 3 substituents each independently selected from the group consisting of halogen, hydroxy, —CN, —ORb$^b$, —SRb$^b$, —N(Rb$^b$)$_2$, —$C_{1-4}$alkyl optionally substituted with 1, 2, or 3 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl. In another aspect, $R^{1b}$ is unsubstituted —$C_{1-4}$ alkyl-$C_{6-10}$ aryl or —$C_{1-4}$ alkyl-$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH($C_{1-4}$ alkyl). In another aspect, $R^1$ is unsubstituted —$C_{1-4}$ alkyl-$C_{6-10}$ aryl. In another aspect, $R^{1b}$ is unsubstituted benzyl or unsubstituted phenethyl. In another aspect, $R^{1b}$ is —$C_{1-4}$ alkyl-$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, CN, —O($C_{1-4}$)alkyl, —N($C_{1-4}$ alkyl)$_2$, and —NH($C_{1-4}$ alkyl).

In another embodiment, Compounds of the Disclosure are compounds of formula (IB), and the pharmaceutically acceptable salts and solvates thereof, wherein $Rb^b$ is hydrogen or —$C_{1-4}$ alkyl.

In another aspect, Compounds of the Disclosure are compounds of formula (IB), and the pharmaceutically acceptable salts and solvates thereof, wherein X is absent and Y is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein X is $C_{1-4}$ alkylene and Y is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein X is C(═O) and Y is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein X is C(═O)—$C_{1-2}$ alkylene and Y is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein X is $C_{1-2}$ alkylene-C(═O) and Y is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein Y is absent and X is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein Y is $C_{1-4}$ alkylene and X is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein Y is C(═O) and X is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein Y is C(═O)—$C_{1-2}$ alkylene and X is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts and solvates thereof, wherein Y is $C_{1-2}$ alkylene-C(═O) and X is selected from the group consisting of a bond (i.e. is absent), $C_{1-4}$ alkylene, C(═O), C(═O)—$C_{1-2}$ alkylene, and $C_{1-2}$ alkylene-C(═O).

In another aspect, Compounds of the Disclosure are compounds of formula (IB), and the pharmaceutically acceptable salts thereof, wherein X and Y are each independently $C_{1-4}$ alkylene. In another aspect, X is a methylene group and Y is an ethylene group. In another aspect, X is an ethylene group and Y is a methylene group.

In another embodiment, the present disclosure provides a Compound of the Disclosure of formula (IB) selected from the group consisting of

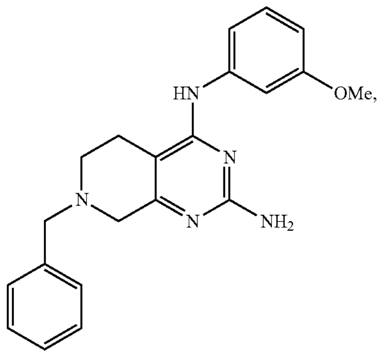

,

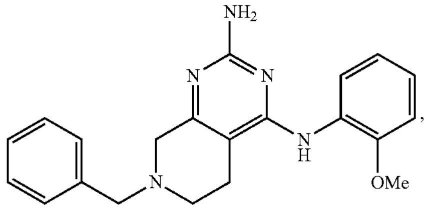

,

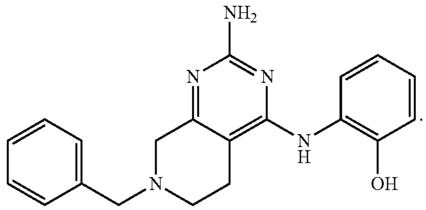

.

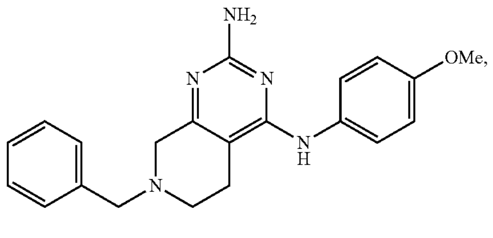

,

-continued

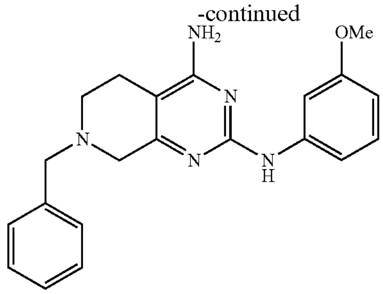

,

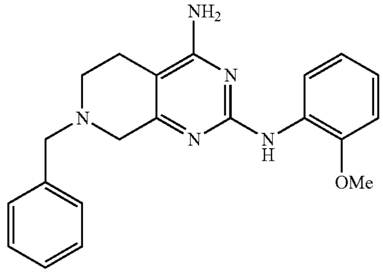

,

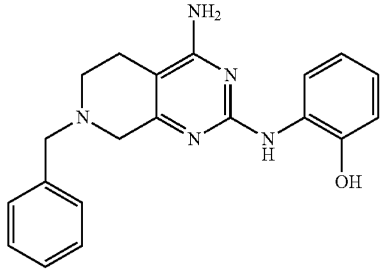

,

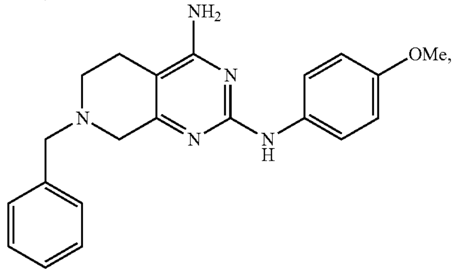

,

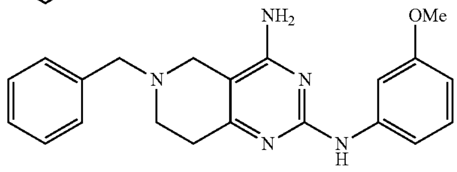

, and

HCl

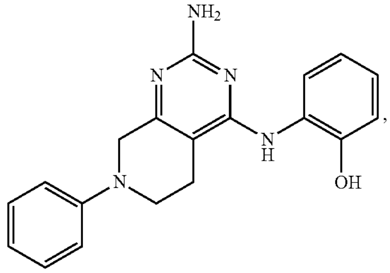

, and the pharmaceutically acceptable salts and solvates thereof.

As used herein, the terms "halogen" or "halo" refer to —F, —Cl, —Br, or —I.

As used herein, the term "hydroxy" or "hydroxyl" refers to the group —OH.

As used herein, the term "alkyl" refers to a linear or branched hydrocarbon chain radical consisting of carbon and hydrogen atoms, containing no unsaturation, which is attached to the rest of the molecule by a single bond and, unless otherwise specified, an alkyl radical typically has from 1 to 4 carbon atoms, i.e., $C_{1-4}$ alkyl. Exemplary $C_{1-4}$ alkyl groups can be methyl, ethyl, n-propyl, i-propyl, n-butyl, tert-butyl, i-butyl and sec-butyl. In another embodiment, the alkyl is $C_{1-2}$ alkyl (methyl or ethyl).

As used herein, the term "$C_{1-4}$ alkoxy" refers to oxygen substituted by one of the $C_{1-4}$ alkyl groups mentioned above (e.g., methoxy, ethoxy, propoxy, iso-propoxy, butoxy, tert-butoxy, iso-butoxy, and sec-butoxy), for example by one of the $C_{1-2}$ alkyl groups.

As used herein, the term "cycloalkyl" embraces saturated carbocyclic radicals and, unless otherwise specified, a cycloalkyl radical typically has from 3 to 6 carbon atoms. Examples of cycloalkyl groups include cyclopropyl, cyclobutyl, cyclopentyl, cyclohexyl and cycloheptyl. It is, for example, cyclopropyl, cyclopentyl and cyclohexyl. In another embodiment, the cycloalkyl group is $C_{3-10}$ cycloalkyl.

As used herein, the term "alkylcycloalkyl" when employed in the definition of a substituent refers to a cycloalkyl group as defined above which is linked through an alkylene radical, such as $C_{1-4}$ alkylene, with the core structure which it substitutes. As an example, a cyclopentylethyl substituent is a substituent consisting of a cyclopentyl group linked through an ethylene group to the core structure which it substitutes.

As used herein, the terms "heterocyclyl" or "heterocyclic group" embrace typically a monocyclic or polycyclic, non-aromatic, saturated or unsaturated $C_{2-10}$ carbocyclic ring, such as a 5- to 10-membered radical, in which one or more, for example 1, 2, 3 or 4 of the carbon atoms, for example, 1 or 2 of the carbon atoms are replaced by a heteroatom selected from N, O and S. In one embodiment, the heterocyclyl is a $C_{3-7}$ heterocyclyl, i.e., a heterocycle having 3-7 carbon atoms and at least one heteroatom. In another embodiment, a heterocyclyl is a (5- to 10-membered)-$C_{2-9}$ heterocyclyl, i.e., a heterocycle having 5- to 10-members, of which 2-9 members are carbon. In another embodiment, the heteroatom is N. In another embodiment, the heteroatom is O.

In another embodiment, the heterocyclyl radicals are saturated. A heterocyclic radical can be a single ring or two or more fused rings wherein at least one ring contains a heteroatom. When a heterocyclyl radical carries one or more substituents, the substituents can be the same or different.

A said optionally substituted heterocyclyl is typically unsubstituted or substituted with 1, 2 or 3 substituents which can be the same or different. Examples of heterocyclic radicals include piperidyl, pyrrolidyl, pyrrolinyl, piperazinyl, morpholinyl, thiomorpholinyl, pyrazolinyl, pyrazolidinyl, quinuclidinyl, tetrazolyl, cromanyl, isocromanyl, imidazolidinyl, oxiranyl, azaridinyl, 4,5-dihydro-oxazolyl and 3-aza-tetrahydrofuranyl. The substituents are, for example, selected from halogen atoms, for example, fluorine or chlorine atoms, hydroxy groups, alkoxycarbonyl groups in which the alkyl moiety has from 1 to 4 carbon atoms, hydroxycarbonyl groups, carbamoyl groups, nitro groups, cyano groups, $C_{1-4}$ alkyl groups optionally substituted by one or more halogen atoms, $C_{1-4}$ alkoxy groups, optionally substituted by one or more halogen atoms and $C_{1-4}$ hydroxyalkyl groups.

As used herein, the term "alkylheterocyclyl" when employed in the definition of a substituent refers to a heterocyclyl group as defined above which is linked through an alkylene radical with the core structure which it substitutes. In one embodiment, the alkylheterocyclyl is a —$C_{1-4}$ alkyl-(5- to 10-membered)-$C_{2-9}$ heterocyclyl.

As used herein, the term "aryl" designates typically a $C_{6-10}$ monocyclic or polycyclic aryl radical such as phenyl and naphthyl. In another embodiment, the aryl is phenyl. A said optionally substituted aryl radical is typically unsubstituted or substituted with 1, 2 or 3 substituents which can be the same or different. The substituents are, for example, selected from halogen atoms, for example, fluorine or chlorine atoms, hydroxy groups, alkoxycarbonyl groups in which the alkyl moiety has from 1 to 4 carbon atoms, hydroxycarbonyl groups, carbamoyl groups, nitro groups, cyano groups, $C_{1-4}$ alkyl groups optionally substituted by one or more halogen atoms, $C_{1-4}$ alkoxy groups, optionally substituted by one or more halogen atoms and $C_{1-4}$ hydroxyalkyl groups. When an aryl radical carries 2 or more substituents, the substituents can be the same or different. Unless otherwise specified, the substituents on an aryl group are typically themselves unsubstituted.

As used herein, the term "alkylaryl" when employed in the definition of a substituent refers to an aryl group as defined above which is linked through an alkylene radical, such as $C_{1-4}$ alkylene, with the core structure which it substitutes.

As used herein, the term "heteroaryl" designates typically a 5- to 10-membered ring system, comprising at least one heteroaromatic ring and containing at least one heteroatom selected from O, S and N, typically 1, 2, 3, or 4 heteroatoms.

A heteroaryl group can comprise a single ring or two or more fused rings wherein at least one ring contains a heteroatom. A said optionally substituted heteroaryl group is typically unsubstituted or substituted with 1, 2 or 3 substituents which can be the same or different. The substituents are, for example, selected from halogen atoms, for example, fluorine, chlorine or bromine atoms, alkoxycarbonyl groups in which the alkyl moiety has from 1 to 4 carbon atoms, carbamoyl groups, nitro groups, hydroxy groups, $C_{1-4}$ alkyl groups, optionally substituted by one or more halogen atoms and $C_{1-4}$ alkoxy groups, optionally substituted by one or more halogen atoms. When a heteroaryl radical carries 2 or more substituents, the substituents can be the same or different. Unless otherwise specified, the substituents on a heteroaryl radical are typically themselves unsubstituted.

Examples of heteroaryl groups include pyridyl, pyrazinyl, pyrimidinyl, pyridazinyl, furyl, tetrazolyl, benzofuranyl, oxadiazolyl, oxazolyl, isoxazolyl, benzoxazolyl, imidazolyl, benzimidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl, and the various pyrrolopyridyl radicals.

In another embodiment, the heteroaryl is a (5- to 10-membered)-$C_{2-9}$ heteroaryl. In another embodiment, the heteroaryl is optionally substituted with 1, 2, or 3 groups independently selected from the group consisting of halogen, hydroxy, —CN, —ORb, —SRb, —$N(Rb)_2$, —$C_{1-4}$ alkyl optionally substituted with 1, 2, or 3 halogen atoms, optionally substituted $C_{6-10}$ aryl, optionally substituted (5- to 10-membered)-$C_{1-9}$ heteroaryl, and (5- to 10-membered)-$C_{2-9}$ heterocyclyl; said cycloalkyl, alkylcycloalkyl, aryl, alkylaryl, heteroaryl, alkylheteroaryl, heterocyclyl, and alkylheterocyclyl is optionally fused to a further (second) ring.

The mention of optionally substituted heteroaryl radicals or rests within the present disclosure is intended to cover the N-oxides obtainable from these radicals when they comprise N-atoms.

As used herein, the term "alkylheteroaryl" when employed in the definition of a substituent refers to an heteroaryl group as defined above which is linked through an alkylene radical with the core structure which it substitutes. In another embodiment, the alkylheteroaryl is a —$C_{1-4}$ alkyl-(5- to 10-membered)-$C_{1-9}$ heteroaryl.

The term "pharmaceutically acceptable" refers to compositions and molecular entities that are physiologically tolerable and do not typically produce an allergic reaction or a similar unfavorable reaction, such as gastric disorders, dizziness and suchlike, when administered to a human or animal. For example, the term "pharmaceutically acceptable" means it is approved by a regulatory agency of a state or federal government or is included in the U.S. Pharmacopoeia or other generally recognized pharmacopoeia for use in animals, and more particularly in humans.

The term "treatment" or "treating" refers to administering a therapy in an amount, manner or mode effective to improve a condition, symptom, or parameter associated with a condition or to prevent progression of a condition, to either a statistically significant degree or to a degree detectable to one skilled in the art. An effective amount, manner, or mode can vary depending on the subject and can be tailored to the patient.

By an "effective" amount or a "therapeutically effective amount" of a drug or pharmacologically active agent is meant a nontoxic but sufficient amount of the drug or agent to provide the desired effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The term "prevention" or "to prevent" refers to the reduction in the risk of acquiring or developing a given disease or disorder, or the reduction or inhibition of the recurrence or a disease or disorder.

The term "about", as used herein in connection with a measured quantity, refers to the normal variations in that measured quantity, as expected by the skilled artisan making the measurement and exercising a level of care commensurate with the objective of measurement and precision of the measuring equipment. Typically, the term "about" includes the recited number ±10%. Thus, "about 10" means 9 to 11.

As used herein, the term "optionally substituted" refers to a group that can be unsubstituted or substituted.

The term "no more than" prior to a number or series of numbers is understood to include the number adjacent to the term "no more than," and all preceding numbers or integers that could logically be included, as clear from context. When "no more than" is present before a series of numbers or a range, it is understood that "no more than" can modify each of the numbers in the series or range.

The term "patient" as used herein refers to a human. In some embodiments, the patient is an adult. In some embodiments, the patient is a geriatric patient. In some embodiments, the patient is a child. In some embodiments, the patient is an infant. In some embodiments, the patient is a toddler. In some embodiments, the patient is a preadolescent. In some embodiments, the patient is an adolescent.

As used herein, the term "child" is a human being between the stages of birth and puberty.

The term "puberty" is the process of physical changes through which a child's body matures into an adult body capable of sexual reproduction. On average, girls begin puberty around ages 10-11 and end puberty around 15-17; boys begin around ages 11-12 and end around 16-17.

As used herein, the term "infant" is the synonym for "baby," the very young offspring of a human. The term "infant" is typically applied to young children under one year of age.

As used herein, the term "toddler" refers to a child of 12 to 36 months old.

As used herein, the term "preadolescent" refers to a person of 10-13 years old.

As used herein, the term "adolescent" refers to a person between ages 10 and 19.

The term "solvate" means any form of the active compound of the disclosure which has another molecule (for example a polar solvent such as water or ethanol, a cyclodextrin or a dendrimer) attached to it through noncovalent bonds. Methods of solvation are known within the art.

The disclosure also provides salts of the Compounds of the Disclosure. Non-limiting examples are sulphates; hydrohalide salts; phosphates; lower alkane sulphonates; arylsulphonates; salts of $C_{1-20}$ aliphatic mono-, di- or tribasic acids which can contain one or more double bonds, an aryl nucleus or other functional groups such as hydroxy, amino, or keto; salts of aromatic acids in which the aromatic nuclei may or may not be substituted with groups such as hydroxyl, lower alkoxyl, amino, mono- or di-lower alkylamino sulphonamido. Also included within the scope of the disclosure are quaternary salts of the tertiary nitrogen atom with lower alkyl halides or sulphates, and oxygenated derivatives of the tertiary nitrogen atom, such as the N-oxides. In preparing dosage formulations, those skilled in the art will select the pharmaceutically acceptable salts.

Solvates and salts can be prepared by methods known in the state of the art. Note that the non-pharmaceutically acceptable solvates also fall within the scope of the disclosure because they can be useful in preparing pharmaceutically acceptable salts and solvates.

The Compounds of the Disclosure also seek to include compounds that differ only in the presence of one or more isotopically enriched atoms. For example, compounds having the present structures except for the replacement of a hydrogen by a deuterium or tritium, or the replacement of a carbon by a carbon enriched in $^{11}C$, $^{13}C$ or $^{14}C$ or the replacement of a nitrogen by a $^{15}N$ enriched nitrogen are within the scope of this disclosure.

Some of the compounds disclosed herein can contain one or more asymmetric centers and can thus give rise to enantiomers, diastereomers, and other stereoisomeric forms, such as epimers. The present disclosure is meant to encompass the uses of all such possible forms, as well as their racemic and resolved forms and mixtures thereof. The individual enantiomers can be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centers present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Some reactions for preparing Compounds of the Disclosure involve employing amino protecting groups. As used herein, an "amine protecting group" or "amino protecting group" refers to a group that blocks (i.e., protects) the amine functionality while reactions are carried out on other functional groups or parts of the molecule. Those skilled in the art will be familiar with the selection, attachment, and cleavage of amine protecting groups and will appreciate that many different protective groups are know in the art, the suitability of one protective group or another being dependent on the particular synthetic scheme planned. Treatises on the subject are available for consultation, such as Wuts, P. G. M. & Greene, T. W., Greene's *Protective Groups in Organic Synthesis,* 4rd Ed. (J. Wiley & Sons, 2007), herein incorporated by reference in its entirety. Suitable amine protecting groups include methyl carbamate, tert-butyloxycarbonyl (tert-butyl carbamate; BOC), 9-fluorenylmethyl carbamate, benzyl carbamate, 2-(trimethylsilyl)ethyl carbamate, trifluoroacetamide, benzylamine, allylamine, tritylamine, trichloroacetyl, trifluoroacetyl, p-toluenesulfonyl, and allyl carbamate. In another embodiment, the protected amino group can be a phthalimide-protected amino group (NPhth).

As used herein, the term "enzyme replacement therapy" or "ERT" refers to administering an exogenously-produced natural or recombinant enzyme or analog thereof to a patient in need thereof. In the case of a lyosomal storage disease, for example, the patient accumulates harmful levels of a substrate (i.e., material stored) in lysosomes due to a deficiency or defect in an enzyme responsible for metabolizing the substrate, or due to a deficiency in an enzymatic activator required for proper enzymatic function. Enzyme replacement therapy is provided to the patient to reduce the levels of (i.e., debulk) accumulated substrate in affected tissues. Enzyme replacement therapies for treating lysosomal storage diseases are known in the art. In accordance with a combination therapy of the disclosure, a lysosomal enzyme, e.g., β-glucocerebrosidase, can be used for enzyme replacement therapy to reduce the levels of corresponding substrate, e.g., β-glucocerebroside, in a patient having a lysosomal storage disease such as Gaucher's disease.

As used herein, the term "substrate reduction therapy" or "SRT" is a therapeutic approach used to treat certain metabolic disorders, e.g., lysosomal storage disorders, in which substrate, e.g., glycolipid, accumulation is counteracted not by replacing the deficient enzyme but by reducing the substrate level to better balance residual activity of the deficient enzyme. See, e.g., Coutinho et al., *Int. J. Mol. Sci.* 17:1065 (2016). Substrate reduction therapy and enzyme replacement therapy (see above) can have unique, independent, and potentially complementary mechanisms of action in the treatment of lyosomal storage disease and other diseases.

The general principle of SRT is that a substrate reduction agent is administered to a patient to partially inhibit the biosynthesis of the substrate, which accumulates in the absence of a specific lysosomal enzyme. As used herein, the term "substrate reduction agent" is a small molecule that reduces the number of substrate molecules requiring catabolism within the lysosome, thus contributing to balance the rate of synthesis with the impaired rate of catabolism. Substrate reduction agents are known in the art.

As used herein, an "effective amount" of an enzyme, when administered to a subject in a combination therapy of the disclosure, is an amount sufficient to improve the clinical course of a lysosomal storage disease, where clinical improvement is measured by any of the variety of defined parameters well known to the skilled artisan.

As used herein the term "small molecule chaperone" refers to a compound, other than a Compound of the Disclosure, that is capable of binding allosterically or competitively to a mutated enzyme, e.g., β-galactosidase, thereby stabilizing the enzyme against degradation. In some embodiments, the small molecule chaperone facilitates proper folding and transport of an enzyme to its site of action. Small molecule chaperones for the treatment of lysosomal storage diseases are known in the art. See, e.g., US 2016/0207933 A1 and WO 2011/049737 A1.

α-Synucleinopathies are neurodegenerative diseases characterized by the abnormal accumulation of aggregates of α-synuclein protein in neurons, nerve fibres, or glial cells. There is a well-established clinical association between mutations in the glucocerebrosidase gene and the development of more prevalent multifactorial disorders including Parkinson's disease and other synucleinopathies. See, Siebert, M., et al., *Brain* 137:1304-1322 (2014). According to Siebert et al., there is a reciprocal relationship between glucocerebrosidase activity (wild-type and mutant) and α-synuclein in synucleinopathiesm such as Parkinson's disease and dementia with Lewy bodies. This reciprocal relationship suggests that therapies for Gaucher's disease, which are targeted towards augmenting glucocerebrosidase activity or decreasing glucocerebrosides storage could prove to be provising strategies for modulating α-synuclein proteostasis and its subsequent aggregation and oligomerization.

Synthesis of Compounds of the Disclosure

Compounds of the Disclosure can be prepared using methods known to those skilled in the art in view of this disclosure, or by illustrative methods shown in the schemes below. For example, Compounds of the Disclosure having formula (IA) can be prepared as shown in Schemes 1-8 below and Compounds of the Disclosure having formula (IB) can be prepared as shown in Schemes 9-12 below. Additional methods of synthesis are described and illustrated in the working examples set forth below.

Scheme 1

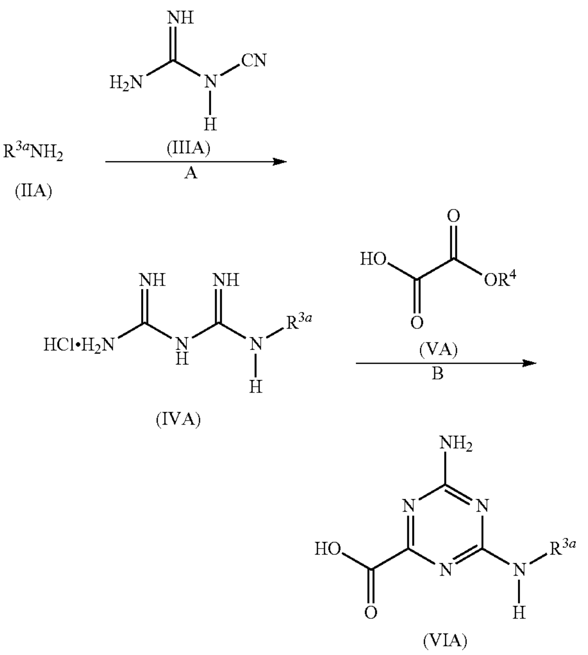

(IIA)
(IIIA)
(IVA)
(VA)
(VIA)

$R^4$ = Me or Et $R^{3a}$ is as defined above for formula (IA).

Method 1

Step 1 (Reaction A)

In a first method, according to the disclosure, a compound of formula (IIA) wherein $R^{3a}$ as defined above is reacted with a dicyandiamide (IIIA) to yield a biguanidine compound of formula (IVA) as illustrated in reaction A of the scheme above (Scheme 1).

Reaction A is used to prepare compounds of formula (IVA) by reaction of compound of formula (HA) with a compound of formula (IIIA). Said reaction can be performed under standard conditions in the presence of a suitable acid or base (e.g., copper sulfate, sodium carbonate, ammonia, methanolic sodium methoxide, hydrogen chloride, hydrogen sulfide or mixtures thereof) and an appropriate solvent (e.g., butanol, water, tetrahydrofuran, xylene, acetone, methanol, ethanol, acetonitrile, 2-propanol, dichloromethane dimethylformamide, dimethylsulfoxide or mixture thereof) and, for example, at around room temperature, reflux temperature or microwave irradiation reaction conditions.

The reaction can also be carried out in the presence of an appropriate catalyst (or salt thereof) such as iron (III) chloride or copper (II) chloride and also optionally in the presence of an additive or protecting groups such as chlorotrimethylsilane or trimethylsilyl trifluoromethanesulfonate.

The reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).

Step 2 (Reaction B)

The biguanidine (hydrochloride salt or not) compound of formula (IVA) is subsequently reacted with a compound of formula (VA), wherein $R^4$ can be methyl or ethyl, to yield a compound of formula (VIA) as illustrated in reaction B of scheme above (Scheme 1).

Reaction B is carried out under standard condensation conditions, for example in the presence of a suitable base (e.g., sodium hydride, sodium methoxide, sodium ethoxide, sodium tert-butoxide, 1,8-diazabicyclo(5.4.0)undec-7-ene or potassium carbonate) and an appropriate solvent (e.g., ethanol, methanol, dimethylformamide or mixture thereof) and for example at around room temperature or reflux temperature.

The reaction can be carried out with protecting groups present and those protecting groups can be removed after the reaction. Suitable protecting groups are known to the person skilled in the art (see T. W. Greene, "Protective Groups in Organic Synthesis," 3rd Edition, New York, 1999).

Scheme 2

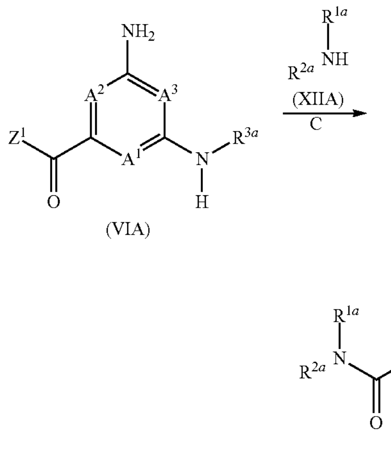

Wherein $Z^1$ is Cl or OH $A^1$, $A^2$, $A^3$, $R^{1a}$, $R^{2a}$, and $R^{3a}$ are as defined above for formula (IA).

Method 2 (Reaction C)

Reaction C can be used to prepare compounds of formula (IA) by reaction of compound of formula (VIA) with a compound of formula (XIIA). The carboxylic acid or acid chloride of the compound of formula (VIA) is subsequently converted to a substituted amide group to yield the compound of formula (IA) according to the disclosure as illustrated in reaction C of Scheme 2. Reaction C is carried out under standard amide coupling conditions, for example in the presence of a suitable coupling agent (e.g. 1,1'-carbonyldiimidazole, N,N'-cyclohexylcarbodiimide, 1-(3-dimethylaminopropyl)-3-ethylcarbodiimide (or hydrochloride thereof), N,N'-disuccinimidyl carbonate, benzotriazol-1-yloxytris(dimethylamino)phosphonium hexafluoro-phosphate, 2-(1H-benzotriazol-1-yl)-1,1,3,3-tetramethyluronium hexafluorophosphate (i.e. O-(1H-benzotriazol-1-yl)-N,N,N',N'-tetramethyluronium hexafluorophosphate), benzotriazol-1-yloxytris-pyrrolidinophosphonium hexafluorophosphate, bromo-tris-pyrrolidinophosphonium hexafluorophosphate, 2-(1H-benzotriazol-1-yl)-1,1,3,3-tetramethyluronium tetrafluorocarbonate, 1-cyclohexylcarbodiimide-3-propyloxymethyl polystyrene, O-(7-azabenzotriazol-1-yl)-N,N,N',N'-tetramethyluronium hexafluorophosphate, O-benzotriazol-1-yl-N,N,N',N'-tetramethyluronium hexfluoroborate), optionally in the presence of a suitable base (e.g. sodium hydride, sodium bicarbonate, potassium carbonate, pyridine, triethylamine, dimethylaminopyridine, diisopropylamine, sodium hydroxide, potassium tert-butoxide and/or lithium diisopropylamide (or variants thereof) and an appropriate solvent (e.g. tetrahydrofurane, pyridine, toluene, dichloromethane, chloroform, acetonitrile, dimethylformamide, trifluoromethylbenzene, dioxane or triethylamine). Such reactions may be performed in the presence of a further additive such as 1-hydroxybenzotriazole hydrate.

The reaction mixture is stirred at low temperature or room temperature or heated until the starting materials have been consumed. The reaction may be carried out with protecting groups present and those protecting groups may be removed after the reaction. Suitable protecting groups are known to the person skilled in the art (see T. W. Greene, "Protective Groups in Organic Synthesis", 3rd Edition, New York, 1999).

Compounds of formula (IA) can be delivered as a free base or can be converted to a salt form (for example HCl salt) by standard salt formation procedures.

Scheme 3

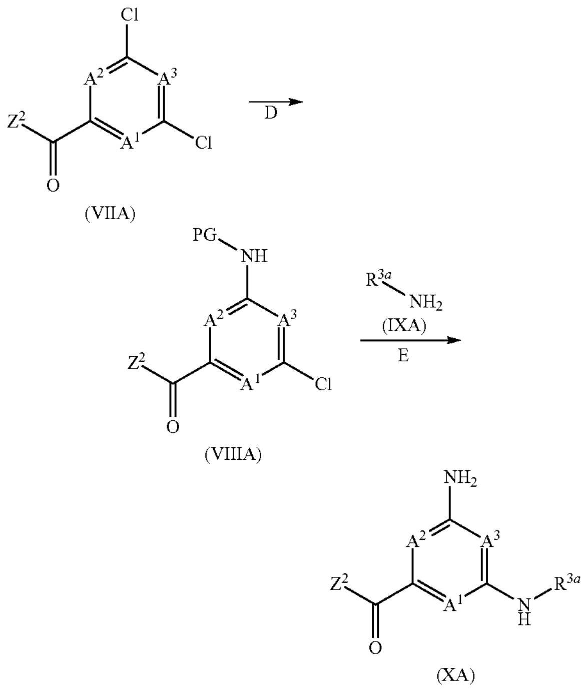

$Z^2$ = —$NR^{1a}R^{2a}$, —OPG $A^1$, $A^2$, $A^3$, $R^{1a}$, $R^{2a}$, and $R^{3a}$ are as defined above for formula (IA), and PG is a protecting group.

Method 3

Step 1 (Reaction D)

In another method, according to the disclosure, a compound of formula (VIIA), wherein $Z^2$ can be —$NR^{1a}R^{2a}$, —OPG, where PG is a protecting group and each of $R^{1a}$ and $R^{2a}$ are as defined above is reacted with an amine source (for instance tert-Octylamine) to yield a compound of formula (VIIIA) as illustrated in reaction D of the scheme above (Scheme 3).

One of the chlorides of the compound of formula (VIIIA) is subsequently substituted by reaction with an amine to form the corresponding amino group to yield the compound of formula (XA) according to the disclosure as illustrated in reaction D of the scheme above (Scheme 3).

Reaction D can be performed under standard conditions in the presence of a suitable palladium catalyst, such as $Pd(dba)_2$, palladium acetate or $Pd_2(dba)_3$, the appropriate base (cesium carbonate or triethylamine, among others) and a suitable ligand such as 1,2,3,4,5-Pentaphenyl-1'-(di-tert-butylphosphino)ferrocene, Xantphos or XPhos in the appropriate solvent (e.g., butanol, toluene, dioxane or mixture thereof) and, for example, at around room temperature or reflux temperature.

Alternatively, the transformation can be carried out in the presence of a suitable base (e.g., N,N-Diisopropylethylamine or triethylamine) and an appropriate solvent, such as dimethyl sulphoxide, tetrahydrofuran, dichloromethane, acetonitrile, dimethylformamide, methanol, ethanol, or mixture thereof.

The reaction can be carried out with protecting groups present and those protecting groups can be removed after reaction. Suitable protecting groups are known to the person skilled in the art (see T. W. Greene, "Protective Groups in Organic Synthesis," $3^{rd}$ Edition, New York, 1999).

Step 2 (Reaction E)

Subsequently, the remaining chloride of a compound of formula (VIIIA), wherein $Z^1$ can be —$NR^{1a}R^{2a}$, —OPG, where PG is a protecting group and each of $R^{1a}$ and $R^{2a}$ are as defined above, is reacted with an amine group (IXA) wherein $R^{3a}$ is defined above to yield a compound of formula (XA) as illustrated in reaction E of the scheme above (Scheme 3).

The compound of formula (XA) can be used as its free base or it can be transformed into iys salt form (e.g., a HCl salt) by standard salt formation procedures. Reaction E is carried out under standard nucleophilic substitution conditions, for example in the presence of a suitable base (e.g., triethylamine, pyridine, potassium carbonate or N,N-diisopropylethylamine) or acid (e.g., sulfuric acid, hydrogen chloride or acetic acid) or absence of base or acid, optionally in the presence of a suitable catalyst, ligand and base (e.g., $Pd(dba)_2$, XantPhos and cesium carbonate, or 1,1'-bis(diphenylphosphino)ferrocene (Dppf), $Pd(OAc)_2$ and $K_3PO_4$) and an appropriate solvent (e.g., ethanol, water, acetonitrile, N,N-dimethylacetamide, propanol, N-methylpyrrolidine, 1-methylpiperizine, dimethylformamide, dioxane, butanol or mixture thereof).

The reaction mixture is stirred at a low temperature, room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," $3^{rd}$ Edition, New York, 1999).

Scheme 4

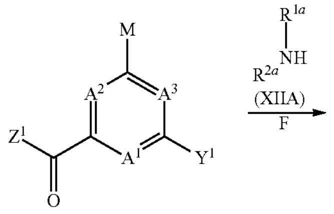

(XIA)

-continued

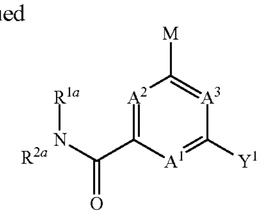

(XIIA)

$Z^1$ = —Cl, —OH $Y^1$ = —Cl, —HN—$R^{3a}$

M = —Cl, —$NH_2$ $R^{1a}$, $R^{2a}$, and $R^{3a}$ are as defined above for formula (IA).

Method 4 (Reaction F)

In a fourth method, according to the disclosure, a compound of formula (XIA) wherein $R^{3a}$ is as defined above, is reacted with a an amine compound (XIIA) where each of $R^{1a}$ and $R^{2a}$ are as defined above to yield an amide compound of formula (XIIA) as illustrated in reaction F of the scheme above (Scheme 4).

Reaction F is carried out under standard amide formation conditions, for example the carboxylic acid or acid chloride of the compound of formula (XIA) is converted to a substituted amide group to yield the compound of formula (XIIA) according to the invention, for example in the presence of a suitable coupling agent (e.g. Propylphosphonic anhydride, (1-[Bis(dimethylamino)methylene]-1H-1,2,3-triazolo[4,5-b]pyridinium 3-oxid hexafluorophosphate), 1,1'-carbonyldiimidazole, N,N'-cyclohexylcarbodiimide, 1-(3-dimethylaminopropyl)-3-ethylcarbodiimide (or hydrochloride thereof), N,N'-disuccinimidyl carbonate, benzotriazol-1-yloxytris(dimethylamino)phosphonium hexafluoro-phosphate, 2-(1H-benzotriazol-1-yl)-1,1,3,3-tetramethyluronium hexafluorophosphate (i.e. O-(1H-benzotriazol-1-yl)-N,N,N',N'-tetramethyluronium hexafluorophosphate), benzotriazol-1-yloxytris-pyrrolidinophosphonium hexafluorophosphate, bromo-tris-pyrrolidinophosphonium hexafluorophosphate, 2-(1H-benzotriazol-1-yl)-1,1,3,3-tetramethyluronium tetrafluorocarbonate, 1-cyclohexylcarbodiimide-3-propyloxymethyl polystyrene, O-(7-azabenzotriazol-1-yl)-N,N,N',N'-tetramethyluronium hexafluorophosphate, O-benzotriazol-1-yl-N,N,N',N'-tetramethyluronium hexfluoroborate), optionally in the presence of a suitable base (e.g. sodium hydride, sodium bicarbonate, potassium carbonate, pyridine, triethylamine, dimethylaminopyridine, diisopropylamine, N,N-Diisopropylethylamine, sodium hydroxide, potassium tert-butoxide and/or lithium diisopropylamide (or variants thereof) and an appropriate solvent (e.g. tetrahydrofurane, pyridine, toluene, dichloromethane, chloroform, acetonitrile, dimethylformamide, trifluoromethylbenzene, dioxane or triethylamine). Such reactions may be performed in the presence of a further additive such as 1-hydroxybenzotriazole hydrate.

The acid chloride of the compound XIA when used can be prepared from the corresponding carboxylic acid under standard acid chloride formation conditions, for example in the presence of thionyl chlorid or oxalyl chloride.

The reaction mixture is stirred at low temperature or room temperature or heated until the starting materials have been consumed. The reaction may be carried out with protecting groups present and those protecting groups may be removed after the reaction. Suitable protecting groups are known to the person skilled in the art (see T. W. Greene, "Protective Groups in Organic Synthesis", 3rd Edition, New York, 1999).

Scheme 5

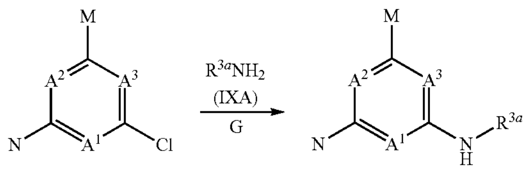

(XIIIA) (XIIIA)

N = —$CONR^{1a}R^{2a}$, —COOPG, —$SO_2Me$
M = —$NH_2$, —Cl $R^{1a}$, $R^{2a}$, and $R^{3a}$ are as defined above for formula (IA).

Method 5 (Reaction G)

In another method, according to the disclosure, an aryl chloride compound of formula (XIIIA), wherein M can be —$NH_2$ or —Cl, and N can be —$CONR^{1a}R^{2a}$, —COOPG, or —$SO_2Me$, where PG is a protecting group and each of $R^{1a}$ and $R^{2a}$ are as defined above is reacted with an amine compound of formula (IXA) wherein $R^{3a}$ is as defined above, to yield a compound of formula (XIVA) as illustrated in reaction G of the scheme above (Scheme 5).

The aryl chloride of the compound of formula (XIIIA) is substituted by reaction with an amine (IXA) to form the corresponding amino group to yield the compound of formula (XIVA) according to the disclosure as illustrated in reaction G of the schemes above (Scheme 5).

Reaction G is carried out under standard nucleophilic substitution conditions, for example in the presence of a suitable base (e.g., Sodium hydride, triethylamine, pyridine, potassium carbonate or N,N-diisopropylethylamine) or acid (e.g., sulfuric acid, hydrogen chloride or acetic acid) or absence of base or acid, optionally in the presence of a suitable catalyst (e.g., $Pd(dba)_2$ or $Pd(OAc)_2$) ligand (e.g., XantPhos, BINAP or 1,1'-Bis(diphenylphosphino)ferrocene (Dppf)), and base (e.g., cesium carbonate, or $K_3PO_4$) and an appropriate solvent (e.g., ethanol, water, acetonitrile, N,N-dimethylacetamide, propanol, N-methylpyrrolidine, 1-methylpiperizine, dioxane, dimethylformamide, butanol or mixture thereof).

The reaction mixture is stirred at a low temperature, room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Scheme 6

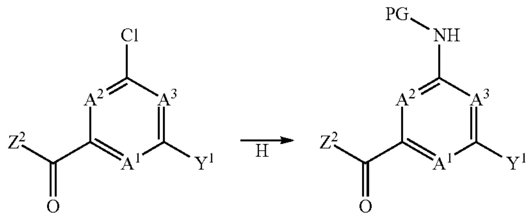

(XVA) (XVIA)

$Z^2$ = —$NR^{1a}R^{2a}$, —OPG
$Y^1$ = —Cl, —HN—$R^{3a}$ $R^{1a}$, $R^{2a}$, and $R^{3a}$ are as defined above for formula (IA).

Method 6 (Reaction H)

In another method, according to the disclosure, a compound of formula (XVA), wherein $Y^1$ can be —Cl, or —$HNR^{3a}$; and $Z^2$ can be —$NR^{1a}R^{2a}$, or -OPG, where PG is a protecting group and each of $R^{1a}$, $R^{2a}$ and $R^{3a}$ are as defined above is reacted with an amine source (for instance tert-Octylamine, tert-butyl carbamate, or diphenylmethanimine) to yield a compound of formula (XVIA) as illustrated in reaction H of the scheme above (Scheme 6).

An aryl chloride of the compound of formula (XVA) is substituted by reaction with an amine to form the corresponding protected amino group to yield the compound of formula (XVIA) according to the disclosure as illustrated in reaction H of the scheme above (Scheme 6).

Reaction H can be performed under standard conditions in the presence of a suitable palladium catalyst, such as $Pd(dba)_2$, palladium acetate or $Pd_2(dba)_3$, the appropriate base (cesium carbonate, Sodium tert-butoxide or triethylamine, among others) and a suitable ligand (e.g., 1,2,3,4,5-Pentaphenyl-1'-(di-tert-butylphosphino)ferrocene, BINAP, Xantphos or XPhos) in the appropriate solvent (e.g., butanol, toluene, dioxane or mixture thereof) and, for example, at around room temperature or reflux temperature.

Alternatively, the transformation can be carried out in the presence of a suitable base (e.g., N,N-diisopropylethylamine or triethylamine) and an appropriate solvent, such as dimethyl sulphoxide, tetrahydrofuran, dichloromethane, acetonitrile, dimethylformamide, methanol, ethanol, or mixture thereof.

The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Scheme 7

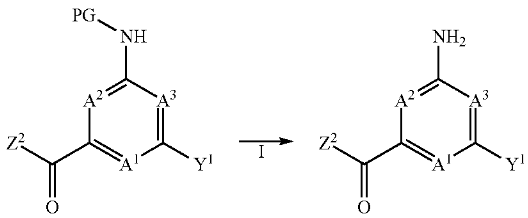

(XVIA) (XVIIA)

$Z^2$ = —$NR^{1a}R^{2a}$, —OPG
$Y^1$ = —Cl, —HN—$R^{3a}$ $R^{1a}$, $R^{2a}$, and $R^{3a}$ are as defined above for formula (IA).

Method 7 (Reaction I)

In another method, a compound of formula (XVIA), wherein $Y^1$ can be —Cl, or —$HNR^{3a}$, $Z^2$ can be —$NR^{1a}R^{2a}$, or -OPG, where PG is a protecting group and each of $R^{1a}$, $R^{2a}$ and $R^{3a}$ are as defined above, is reacted to yield a compound of formula (XVIIA) as illustrated in reaction I of the scheme above (Scheme 7).

The protecting group on the amine moiety of the compound of formula (XVIA) (for instance tert-Octylamine, tert-butyl carbamate, or diphenylmethanimine) is treated to form the corresponding primary amino group of the compound of formula (XVIIA) according to the disclosure as illustrated in reaction I of the schemes above (Scheme 7).

The compound (XVIIA) can be delivered as its free base or transformed into its salt form (for example HCl salt) by standard salt formation procedures.

Reaction I can be carried out under standard deprotection conditions, for example in the presence of HCl, Trifluoroacetic acid or, Boron tribromide. Such reactions may be performed in the presence of an appropriate solvent (e.g., tetrahydrofuran, dioxane, dichloromethane or mixture thereof).

The reaction mixture is stirred at a low temperature, room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Scheme 8

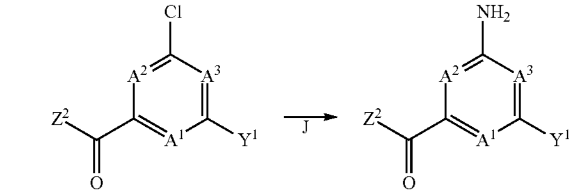

(XVA) (XVIIA)

$Z^2$ = —$NR^{1a}R^{2a}$, —OPG $Y^1$ = —Cl, —HN—$R^{3a}$ $R^{1a}$, $R^{2a}$, and $R^{3a}$ are as defined above for formula (IA).

Method 8 (Reaction J)

In another method, according to the disclosure, a compound of formula (XVA), wherein $Y^1$ can be —Cl, or —$HNR^{3a}$, $Z^2$ can be —$NR^{1a}R^{2a}$, —OPG, where PG is a protecting group and each of $R^{1a}$, $R^{2a}$ and $R^{3a}$re as defined above is reacted with an amine precursor (for instance sodium azide) to yield a compound of formula (XVIIA) as illustrated in reaction J of the scheme above (Scheme 8).

An aryl chloride of the compound of formula (XVA) is substituted by reaction with an azide and, subsequently, reduced with a reduction agent to form the corresponding amino group and yield the compound of formula (XVIIA) according to the disclosure as illustrated in reaction J of the scheme above (Scheme 8).

The compound (XVIIA) can be delivered as its free base or transformed into its salt form (for example HCl salt) by standard salt formation procedures.

Reaction J can be performed under standard conditions in the presence of sodium azide in the appropriate solvent (e.g., dimethylformamide) and, for example, at around room temperature or reflux temperature. Subsequently, the reaction mixture is treated with a reducing agent (e.g, sodium borohydride) in the appropriate solvent (e.g., methanol)

The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Scheme 9

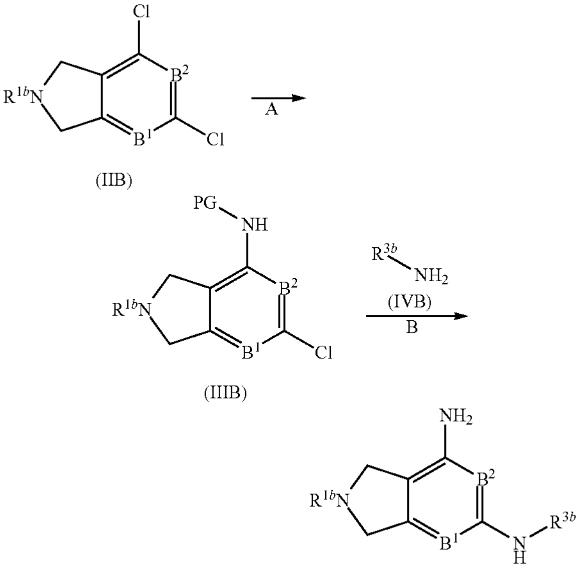

(IIB) (IIIB) (VB)

$B^1$, $B^2$, $R^{1b}$ and $R^{3b}$ are as defined above for formula (IB).

Step 1 (Reaction A)

In another method, according to the disclosure, a compound of formula (IIB), where $R^{1b}$ is as defined above is reacted with an amine source to yield a compound of formula (IIIB) as illustrated in reaction A of the scheme above (Scheme 9).

One of the chlorides of the compound of formula (IIB) is subsequently substituted by reaction with an amine to form the corresponding amino group to yield the compound of formula (IIIB) according to the disclosure as illustrated in reaction A of the scheme above (Scheme 9).

Reaction A can be performed under standard conditions in the presence of a suitable palladium catalyst, such as $Pd(dba)_2$, palladium acetate or $Pd_2(dba)_3$, the appropriate base (cesium carbonate or triethylamine, among others) and a suitable ligand such as 1,2,3,4,5-Pentaphenyl-1'-(di-tert-butylphosphino)ferrocene, Xantphos or XPhos in the appropriate solvent (e.g., butanol, toluene, dioxane or mixture thereof) and, for example, at around room temperature or reflux temperature.

Alternatively, the transformation can be carried out in the presence of a suitable base (e.g., N,N-Diisopropylethylamine or triethylamine) and an appropriate solvent, such as dimethyl sulphoxide, tetrahydrofuran, dichloromethane, acetonitrile, dimethylformamide, methanol, ethanol, or mixture thereof.

The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Step 2 (Reaction B)

Subsequently, a compound of formula (IIIB), where PG is a protecting group and $R^{1b}$ is as defined above, is reacted with an aniline group wherein $R^{3b}$ is defined above to yield a compound of formula (VB) as illustrated in reaction B of the scheme above (Scheme 9).

The remaining chloride of the compound of formula (IIIB) is subsequently substituted by reaction with an amine (IVB) to form the corresponding amino group to yield the compound of formula (VB) according to the disclosure as illustrated in reaction B of the schemes above (Scheme 9).

Reaction B is carried out under standard nucleophilic substitution conditions, for example in the presence of a suitable base (e.g., triethylamine, pyridine, potassium carbonate or N,N-diisopropylethylamine) or acid (e.g., sulfuric acid, hydrogen chloride or acetic acid) or absence of base or acid, optionally in the presence of a suitable catalyst, ligand and base (e.g., $Pd(dba)_2$, XantPhos and cesium carbonate) and an appropriate solvent (e.g., ethanol, water, acetonitrile, N,N-dimethylacetamide, propanol, N-methylpyrrolidine, 1-methylpiperizine, dioxane, butanol or mixture thereof).

The reaction mixture is stirred at a low temperature, room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Scheme 10

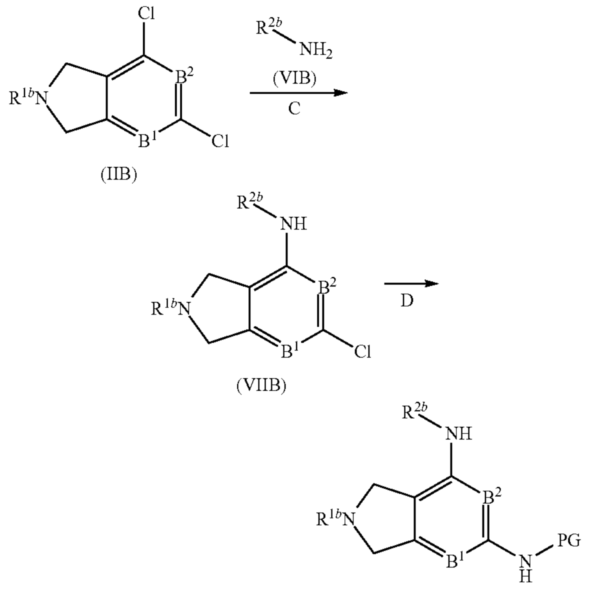

(IIB)

(VIIB)

(VIIIB)

$R^{1b}$, $R^{2b}$, $B^1$, and $B^2$ are as defined above for formula (IB), and PG is a protecting group.

Step 1 (Reaction C)

In another method, according to the disclosure, a compound of formula (IIB), where $R^{1b}$ is as defined above, is reacted with an aniline group wherein $R^{2b}$ is defined above (VIB) to yield a compound of formula (VIIB) as illustrated in reaction C of the scheme above (Scheme 10).

One of the chlorides of the compound of formula (IIB) is subsequently substituted by reaction with an aniline (VIB) to form the corresponding amino group to yield the compound of formula (VIIB) according to the disclosure as illustrated in reaction C of the scheme above (Scheme 10).

Reaction C is carried out under standard nucleophilic substitution conditions, for example in the presence of a suitable base (e.g., triethylamine, pyridine, potassium carbonate or N,N-diisopropylethylamine) or acid (e.g., sulfuric acid, hydrogen chloride or acetic acid) or absence of base or acid, optionally in the presence of a suitable catalyst, ligand and base (e.g., $Pd(dba)_2$, XantPhos and cesium carbonate) and an appropriate solvent (e.g., ethanol, water, acetonitrile, N,N-dimethylacetamide, propanol, N-methylpyrrolidine, 1-methylpiperizine, dioxane, butanol or mixture thereof).

The reaction mixture is stirred at a low temperature, room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Step 2 (Reaction D)

Subsequently, a compound of formula (VIIB), where each of $R^{1b}$ and $R^{2b}$ are as defined above, is reacted with an amine source to yield a compound of formula (VIIIB) as illustrated in reaction D of the scheme above (Scheme 10).

The remaining chloride of the compound of formula (VIIB) is subsequently substituted by reaction with an amine to form the corresponding amino group to yield the compound of formula (VIIIB) according to the disclosure as illustrated in reaction D of the schemes above (Scheme 10).

Reaction D can be performed under standard conditions in the presence of a suitable palladium catalyst, such as $Pd(dba)_2$, palladium acetate or $Pd_2(dba)_3$, the appropriate base (cesium carbonate or triethylamine, among others) and a suitable ligand such as 1,2,3,4,5-Pentaphenyl-1'-(di-tert-butylphosphino)ferrocene, Xantphos or XPhos in the appropriate solvent (e.g., butanol, toluene, dioxane or mixture thereof) and, for example, at around room temperature or reflux temperature.

Alternatively, the transformation can be carried out in the presence of a suitable base (e.g., N,N-Diisopropylethylamine or triethylamine) and an appropriate solvent, such as dimethyl sulphoxide, tetrahydrofuran, dichloromethane, acetonitrile, dimethylformamide, methanol, ethanol, or mixture thereof.

The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Scheme 11

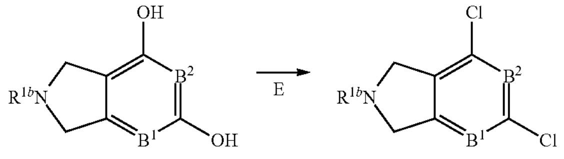

(IXB) (IIB)

$R^{1b}$, $B^1$, and $B^2$ are as defined above.

Step 1 (Reaction E)

Subsequently, the hydroxyl groups of the compound of formula (IXB) are transformed to chlorides to yield a compound of formula (IIB) according to the disclosure as illustrated in reaction E of the Scheme 11 above.

Reaction E is carried out under standard chlorinated conditions, in the presence of appropriate chlorinated agents, such as phosphoryl chloride, phosphorus pentachloride, cobalt chloride or bis(trichloromethyl) carbonate, and a suitable base (e.g., triethylamine, N,N-diethylaniline, N,N-diisopropylethylamine or 4-(dimethylamino)pyridine) and an appropriate solvent, such as dimethylformamide, dichloromethane, tetrahydrofuran or mixture thereof.

The reaction mixture is stirred at a low temperature, room temperature, or heated until the starting materials have been consumed. The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Scheme 12

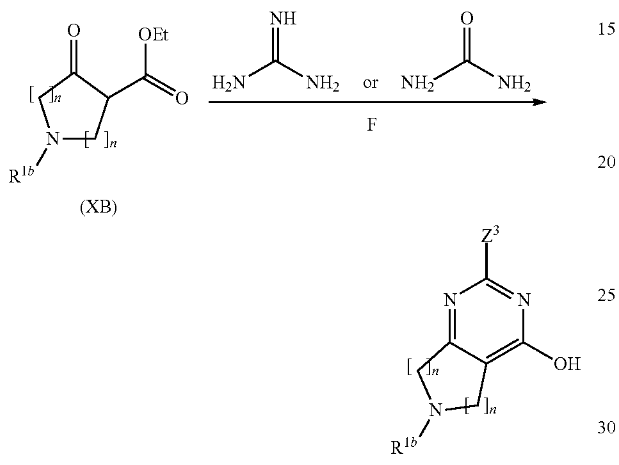

(XB)

(XIB)

$Z^3$: —OH, —$NH_2$ $R^{1b}$ is as defined above and each n is independently 1, 2, 3, or 4.

Step 1 (Reaction F)

In another method, according to the disclosure, a compound of formula (XB), where $R^{1b}$ is as defined above is reacted with urea or guanidine to yield a compound of formula (XIB) as illustrated in reaction F of the scheme above (Scheme 12).

Reaction F is carried out under standard cyclocondensation conditions, for example in the presence of a suitable base (e.g., sodium hydride, sodium methoxide, sodium ethoxide, sodium tert-butoxide, 1,8-diazabicyclo(5.4.0)undec-7-ene or potassium carbonate) and an appropriate solvent (e.g., ethanol, methanol, dimethylformamide or mixture thereof) and for example at around room temperature or reflux temperature.

The reaction can be carried out with protecting groups present and those protecting groups can be removed after reaction. Suitable protecting groups are known to the person skilled in the art (see T. W. Greene, "Protective Groups in Organic Synthesis," 3rd Edition, New York, 1999).

Use of the Compounds of the Disclosure

The utility of Compounds of the Disclosure, including pharmaceutically acceptable salts or solvates, in the present methods can be demonstrated in appropriate in vitro or in vivo assays. Compounds of the Disclosure have the ability to increase β-glucocerebrosidase. Therefore, Compounds of the Disclosure can be used/administered to treat and/or prevent conditions associated with alteration of the activity of β-glucocerebrosidase in a patient, such as for example lysosomal storage diseases and α-synucleinopathies. In one aspect, the lysosomal storage disease is Gaucher's disease. In another aspect, the α-synucleinopathy is Parkinson's disease. In another aspect, a condition associated with alteration of the activity of β-glucocerebrosidase is a disease or disorder selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging. See, e.g., Maegawa G. H. B. et al., *The Journal of Biological Chemistry* 284(35):23502-23516 (2009); Jung O. et al., *Expert Rev. Proteomics.* 13(5):471-479 (2016); Mazzulli J. R. et al., *The Journal of Neuroscience* 36(29):7693-7706 (2016); Khanna R. et al., *FEBS Journal* 277:1618-1638 (2010); Parenti G. et al., *Molecular Therapy* 23(7):1138-1148 (2015); and Sun Y. et al., *The Journal of Biological Chemistry* 287(6):4275-4287 (2012).

In another aspect, the present disclosure is directed to a method of treating or preventing a condition associated with the alteration of the activity of β-glucocerebrosidase in a patient in need thereof, comprising administering to the patient in need thereof an effective amount of a Compound of the Disclosure. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to a method of treating or preventing a lysosomal storage disease, such as Gaucher's disease, in a patient in need thereof, comprising administering an effective amount of a Compound of the Disclosure. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to a method of treating or preventing an α-synucleinopathy, such as Parkinson's disease, in a patient in need thereof, comprising administering an effective amount of a Compound of the Disclosure. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to method of treating or preventing a disease or disorder in a patient selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging, comprising administering an effective amount of a Compound of the Disclosure to a patient in need thereof. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, any method described herein can further comprise administering to the patient at least one other therapeutic agent. In another aspect, the therapeutic agent is an effective amount of an enzyme for enzyme replacement therapy. In another aspect, the enzyme is β-glucocerebrosidase or an analog thereof. In another aspect, the enzyme is imiglucerase. In another aspect, the therapeutic agent is an effective amount of a small molecule chaperone. In another aspect, the small molecule chaperone binds competitively to an enzyme. In another aspect, the small molecule chaperone is selected from the group consisting of iminoalditols, iminosugars, aminosugars, thiophenylglycosides, glycosidase, sulfatase, glycosyl transferase, phosphatase, and peptidase inhibitors. In another aspect, the small molecule chaperone is selected from the group consisting of isofagomine, N-nonyl-1-deoxynojirimycin (NN-DNJ), ambroxol, and miglustat. In another aspect, the small molecule chaperone is selected from the group consisting of isofagomine, N-nonyl-1-deoxynojirimycin (NN-DNJ), and ambroxol. In another aspect, the small molecule chaperone is miglustat.

In another aspect, the therapeutic agent is an effective amount of substrate reduction agent for substrate reduction therapy. In another aspect, the substrate reduction agent is miglustat.

In another aspect, the present disclosure is directed to a Compound of the Disclosure, as described herein, for use in the prevention or treatment of a condition associated with the alteration of the activity of β-glucocerebrosidase in a patient in need thereof. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to a Compound of the Disclosure, as described herein, for use in the prevention or treatment of a lysosomal storage disease, such as Gaucher's disease. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to a Compound of the Disclosure, as described herein, for use in the prevention or treatment of an α-synucleinopathy, such as Parkinson's disease. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to a Compound of the Disclosure, as described herein, for use in the prevention or treatment of a disease or disorder selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is also directed to the use of a Compound of the Disclosure, as described herein, for the treatment or prevention of a condition associated with the alteration of the activity of β-glucocerebrosidase in a patient in need thereof, such as those described herein. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to a Compound of the Disclosure, as described herein, for use as a medicament. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to use of a Compound of the Disclosure, as described herein, in the preparation of a medicament for the prevention or treatment of a condition associated with the alteration of the activity of β-glucocerebrosidase in a patient in need thereof, such as lysosomal storage diseases and α-synucleinopathies described herein. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

In another aspect, the present disclosure is directed to a pharmaceutical composition comprising a Compound of the Disclosure, as described herein, and at least one pharmaceutically acceptable excipient, for use in the treatment or prevention of a condition associated with the alteration of the activity of β-glucocerebrosidase in a patient in need thereof, such as lysosomal storage diseases and α-synucleinopathies described herein. In another aspect, the Compound of the Disclosure is a compound of formula (IA), or a pharmaceutically acceptable salt or solvate thereof, as described herein. In another aspect, the Compound of the Disclosure is a compound of formula (IB), or a pharmaceutically acceptable salt or solvate thereof, as described herein.

Pharmaceutical Compositions

The present disclosure is also directed to pharmaceutical compositions, comprising an effective amount of a Compound of the Disclosure and at least one pharmaceutically acceptable excipient. In another aspect, the composition comprises an effective amount of a compound of formula (IA), or a pharmaceutically acceptable salt or solvate thereof, as described herein, and at least one pharmaceutically acceptable excipient. In another aspect, the composition comprises an effective amount of a compound of formula (IB), or a pharmaceutically acceptable salt or solvate thereof, as described herein, and at least one pharmaceutically acceptable excipient.

Due to their activity, Compounds of the Disclosure can be used in human medicine. As described above, Compounds of the Disclosure are useful, e.g., for treating or preventing lysosomal storage diseases, such as Gaucher's disease, and α-synucleinopathies, such as Parkinson's disease. Compounds of the Disclosure can be administered to any patient suffering any of said conditions. The term "patient" as used herein refers to any human that can experience the beneficial effects of a Compound of the Disclosure.

When administered to a patient, a Compound of the Disclosure can be administered as a component of a composition that comprises a pharmaceutically acceptable excipient or carrier.

Compounds of the Disclosure can be administered in combination with at least one other therapeutic agent. Administration of Compounds of the Disclosure with at least one other therapeutic agent can be sequential or concurrent. In another aspect, the Compound of the Invention and the at least one other therapeutic agent are administered in separate dosage forms. In another aspect, the Compound of the Invention and the at least one other therapeutic agent are administered concurrently in the same dosage form.

The term "excipient" refers to a vehicle, diluent, or adjuvant that is administered with the active ingredient. Such pharmaceutical excipients can be sterile liquids, such as water and oils, including those of petroleum, animal, vegetable, or synthetic origin, such as peanut oil, soybean oil, mineral oil, sesame oil, and similar. Water or saline aqueous solutions and aqueous dextrose and glycerol solutions, for example, for injectable solutions, can be used as vehicles. Suitable pharmaceutical vehicles are described in "Remington's Pharmaceutical Sciences" by E. W. Martin, 21st Edition, 2005; or "Handbook of Pharmaceutical Excipients," Rowe C. R.; Paul J. S.; Marian E. Q., sixth Edition, incorporated herein by reference.

Examples of pharmaceutical compositions include any solid composition (tablets, pills, capsules, granules, etc.) or liquid compositions (solutions, suspensions, or emulsions) for oral, topical, or parenteral administration.

In another embodiment, the pharmaceutical compositions are in an oral delivery form. Pharmaceutical forms suitable for oral administration can be tablets and capsules, and can contain conventional excipients known in the art, such as binders, for example syrup, gum Arabic, gelatin, sorbitol, tragacanth, or polyvinylpyrrolidone; fillers, for example lactose, sugar, cornstarch, calcium phosphate, sorbitol, or glycine; lubricants for the preparation of tablets, for example magnesium stearate; disintegrants, for example starch, polyvinylpyrrolidone, sodium starch glycolate, or microcrystalline cellulose; or pharmaceutically acceptable wetting agents, such as sodium lauryl sulphate.

Solid oral compositions can be prepared by conventional methods of blending, filling, or preparation of tablets. Repeated blending operations can be used to distribute the active ingredient in all the compositions that use large amounts of fillers. Such operations are conventional in the art. The tablets can be prepared, for example, by dry or wet granulation and optionally can be coated by well known methods in normal pharmaceutical practice, in particular using enteric coating.

Pharmaceutical compositions can also be adapted for parenteral administration, such as sterile solutions, suspensions, or lyophilized products in the appropriate unit dosage form. Suitable excipients, such as fillers, buffering agents, or surfactants can be used.

The mentioned formulations can be prepared using standard methods, such as those described or referred to in the Spanish and U.S. Pharmacopoeias and similar reference texts.

In general, the effective amount of a Compound of the Disclosure to be administered depends on the relative efficacy of the compound chosen, the severity of the condition or disorder being treated, and the patient's weight. The active compound can be administered one or more times a day, for example 1, 2, 3, or 4 times daily, with typical total daily doses in the range from about 0.01 mg/kg of body weight/day to about 1000 mg/kg of body weight/day. In another embodiment, the effective dosage amount of a Compound of the Disclosure is about 500 mg/kg of body weight/day or less. In another embodiment, the effective dosage amount of a Compound of the Disclosure is about 100 mg/kg of body weight/day or less. In another embodiment, the effective dosage amount ranges from about 0.01 mg/kg of body weight/day to about 100 mg/kg of body weight/day of a Compound of the Disclosure; in another embodiment, from about 0.02 mg/kg of body weight/day to about 50 mg/kg of body weight/day of a Compound of the Disclosure; and in another embodiment, from about 0.025 mg/kg of body weight/day to about 20 mg/kg of body weight/day of a Compound of the Disclosure.

A composition of the disclosure can be prepared by a method comprising admixing a Compound of the Disclosure with a pharmaceutically acceptable excipient or carrier. Admixing can be accomplished using methods known for admixing a compound and a pharmaceutically acceptable excipient or carrier. In another embodiment, the Compound of the Disclosure is present in the composition in an effective amount.

The following examples are illustrative, but not limiting, of the compounds, compositions and methods of the present disclosure. Suitable modifications and adaptations of the variety of conditions and parameters normally encountered in clinical therapy and which are obvious to those skilled in the art in view of this disclosure are within the spirit and scope of the disclosure.

EXAMPLES

General Experimental Conditions

Hereinafter, the term "h" means hours, "eq" means equivalents, "min" means minutes, "HPLC" means high-performance liquid chromatography, "TLC" means thin layer chromatography, "LC-MS" or "HPLC-MS" means Liquid chromatography-mass spectrometry, "$CDCl_3$" means deuterated chloroform, "DMSO-$d_6$" means deuterated dimethyl sulfoxide, "DCM" means Dichloromethane, "MeOH" meand methanol, "ACN" meand acetonitrile, "THF" means tetrahydrofurane, "DMF" means dimethylformamide, "EtOAc" means ethyl acetate, "$NaHCO_3$" means sodium bicarbonate, "DIPE" means Diisopropylether, "DIPEA" means N,N-Diisopropylethylamine, "HATU" means 1-[Bis(dimethylamino)methylene]-1H-1,2,3-triazolo[4,5-b]pyridinium 3-oxid hexafluorophosphate, "Pd2(dba)3" means tris(dibenzylideneacetone)-dipalladium(0), "Pd(PPh3)4" means palladium-tetrakis(triphenylphosphine), "DavePhos" means 2-dicyclohexylphosphino-2'-(N,N-dimethylamino)biphenyl, "XPhos" means 2-Dicyclohexylphosphino-2',4',6'-triisopropylbiphenyl, "$Zn(CN)_2$" means zinc(II) cyanide, "Pd2$(dba)_3$" means tris(dibenzylideneacetone)-dipalladium (0), "XantPhos" means 4,5-Bis(diphenylphosphino)-9,9-dimethylxanthene, "SnCl2" means tin(II) chloride, and "TBTU" O-(Benzotriazol-1-yl)-N,N,N',N'-tetramethyluronium tetrafluoroborate".

The compound IUPAC names given herein were generated with ChemBioDraw Ultra 12.0. or 12.0.2. $^1H$ NMR spectra were recorded on a Bruker (400 MHz).

HPLC spectra were recorded on Waters 2695, Agilent 1260 Infinity-2 & Waters UPLC-H class.

LC-MS analysis of the compounds was conducted as per one of the following methods:

Method-A1: SunFire C18 (50 mm×2.1 mm, 5 μm); wavelength: PDA MaxPlot 210.0-400 nm; flow: 0.30 mL/min; column temperature: 35° C.; run time: 9 min; mobile phase A: ACN/MeOH (50:50), B: 100 mM ammonium acetate solution, C: water; gradient: A:B:C 0.5 min in 10:5:85+from 10:5:85 to 95:5:0 in 4 min+4.5 min in 95:5:0; chromatographic system: Waters Alliance HT 2795 and PDA 2996; mass spectrometer: Micromass ZQ2000 single quadrupole (ESI).

Method-B1: SunFire C18 (100 mm×2.1 mm, 3.5 μm); wavelength: PDA MaxPlot 210.0-400 nm; flow: 0.30 mL/min; column temperature: 35° C.; run time: 30 min; mobile phase A: ACN/MeOH (50:50), B: 100 mM ammonium acetate solution, C: water; gradient: A:B:C 5 min in 10:5:85+from 10:5:85 to 95:5:0 in 15 min+10 min in 95:5:0; chromatographic system: Waters Alliance HT 2795 and PDA 2996; mass spectrometer: Micromass ZQ2000 single quadrupole (ESI).

Method-C1: Acquity UPLC BEH C18 (50 mm×2.1 mm, 1.7 μm); wavelength: 215 nm; flow: 0.6 mL/min; run time: 3.0 min; Mobile phase A: 0.1% of formic acid in water and B: 0.1% formic acid in acetonitrile; Time and mobile phase-gradient (time in min/% B): 0/95, 0.3/95, 2.0/5, 3.5/5, 3.6/95 MASS: Agilent 1290 infinity, Mass: 6150 SQD (ESI/APCI).

Method-D1: XSelect C18 (50 mm×4.6 mm, 3.5 μm); wavelength: PDA MaxPlot 210.0-400 nm; flow: 1.6 ml/min; column temperature: 50° C.; run time: 5 min; mobile phase A: $H_2O$ 0.1% Formic Acid, B: Acetonitrile 0.1% Formic acid; gradient of B 5-95% B in 3.5 min; chromatographic system: Waters Alliance HT 2795 and PDA 2996; mass spectrometer: 3100 Detector single quadrupole (ESI).

Method-E1: Sunfire C18 (150 mm×19 mm, 10 μm); wavelength: the wavelength is selected taking into consideration the UV maximum absorption of the target; flow: 9-14 mL/min; column temperature: 30-35° C.; run time: 30 min; mobile phase, A: ACN (in occasions was used MeOH:ACN (1:1) to enhance the separation between the target and the impurities); B: ammonium bicarbonate solution (pH 7); gradient: adjusted to each sample to increase the separation between the target and the impurities; chromatographic system: Dionex 3000 (PLCP001) equipped with a foxy R1 fraction collector.

Method-F1: BEH C18 (50 mm×2.1 mm, 1.7 μm); wavelength: PDA MaxPlot 210.0-400 nm; flow: 0.50 mL/min; column temperature: 35° C.; run time: 20 min; mobile phase A: 50 mM ammonium formiate solution adjusted at pH 4 with formic acid, B: water, C: ACN; gradient: A:B:C 0.5 min in 5:80:15+from 5:80:15 to 10:85:5 in 4.5 min+4 min in 10:85:5; chromatographic system: Acquity H Class UPLC; mass spectrometer: Acquity QDa.

Method-A2: Acquity UPLC BEH C18 (50 mm×2.1 mm, 1.7 μm); wavelength: 215 nm; flow: 0.6 mL/min; run time: 4.0 min; Mobile phase A: 0.1% of formic acid in water and B: 0.1% of formic acid in acetonitrile; Time and mobile phase-gradient (time in min/% A): 0.0/95, 0.3/95, 2.0/5, 3.5/5, 3.6/95, 4.2/95; MASS: Waters Acquity UPLC with SQD(ESI/APCI).

Method-B2: SunFire C18 (50 mm×2.1 mm, 5 μm); wavelength: PDA MaxPlot 210.0-400 nm; flow: 0.30 mL/min; column temperature: 35° C.; run time: 9 min; mobile phase A: ACN/MeOH (50:50), B: 100 mM ammonium acetate solution, C: water; gradient: A:B:C 0.5 min in 10:5:85+from 10:5:85 to 95:5:0 in 4 min+4.5 min in 95:5:0; chromatographic system: Waters Alliance HT 2795 and PDA 2996; mass spectrometer: Micromass ZQ2000 single quadrupole (ESI).

Method-C2: SunFire C18 (100 mm×2.1 mm, 3.5 μm); wavelength: PDA MaxPlot 210.0-400 nm; flow: 0.30 mL/min; column temperature: 35° C.; run time: 30 min; mobile phase A: ACN/MeOH (50:50), B: 100 mM ammonium acetate solution, C: water; gradient: A:B:C 5 min in 10:5:85+from 10:5:85 to 95:5:0 in 15 min+10 min in 95:5:0; chromatographic system: Waters Alliance HT 2795 and PDA 2996; mass spectrometer: Micromass ZQ2000 single quadrupole (ESI).

General Procedure A

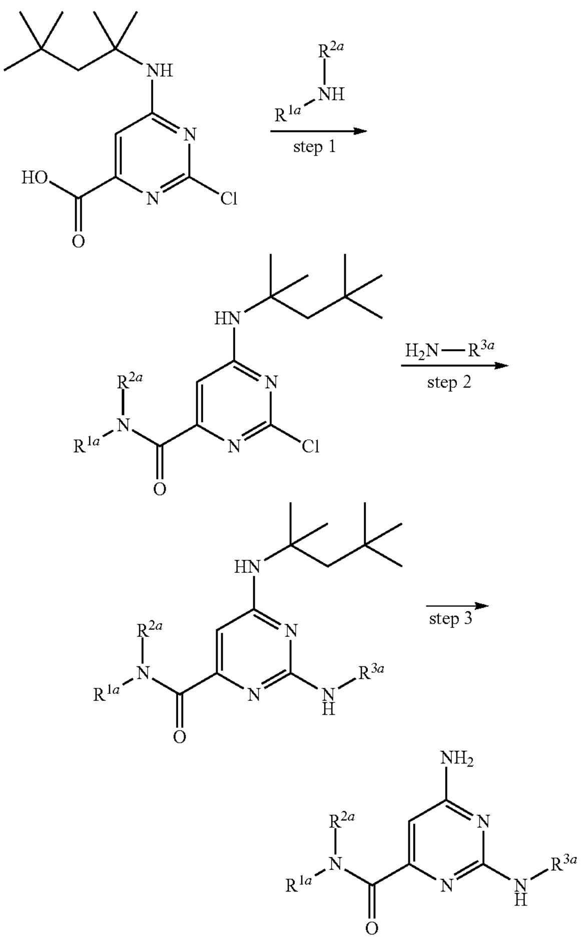

Step 1

To a stirred solution of 2-chloro-6-((2,4,4-trimethylpentan-2-yl)amino)pyrimidine-4-carboxylic acid (1.0 eq), the appropriate amine (1.5 eq) (ex: 1-phenylpiperazine) and HATU (0.7 eq) in DMF (15 mL/mmol) was added DIPEA (1.3 eq). The resulting mixture was stirred at room temperature for 14-16 h. The reaction mixture was quenched with saturated sodium bicarbonate. The aqueous layer was extracted with ethyl acetate (×3), dried over anhydrous sodium sulphate, filtered, and concentrated to dryness. The obtained crude was purified by flash column chromatography (EtOAc/Hexane 15%-30%) to obtain the desired amide product (ex: ((2-chloro-6-((2,4,4-trimethylpentan-2-yl)amino)pyrimidin-4-yl)(4-phenylpiperazin-1-yl)methanone).

Step 2

To a stirred solution of the appropriate aryl chloride (ex: (2-chloro-6-((2,4,4-trimethylpentan-2-yl)amino)pyrimidin-4-yl)(4-phenylpiperazin-1-yl)methanone) (1.0 eq) in n-butanol (7.0 mL/mmol), were added the appropriate aniline (ex: 2-aminophenol) (1.1 eq) and sulphuric acid (catalytic, 1 drop) at room temperature. The reaction mixture was stirred at 100-115° C. for 18 h. The reaction mixture was then allowed to cool to room temperature and quenched with saturated sodium bicarbonate. The aqueous layer was extracted with ethyl acetate (3×), dried over anhydrous sodium sulphate, filtered, and concentrated to dryness. The obtained crude was purified by flash column chromatography (EtOAc/Hexane 15%-30%) to obtain the desired amine product. (ex: (2-((2-hydroxyphenyl)amino)-6-((2,4,4-trimethylpentan-2-yl)amino)pyrimidin-4-yl)(4-phenylpiperazin-1-yl)methanone).

Step 3

A stirred solution of the appropriate protected amine (ex: (2-((2-hydroxyphenyl)amino)-6-((2,4,4-trimethylpentan-2-yl)amino)pyrimidin-4-yl)(4-phenylpiperazin-1-yl)methanone) (1.0 eq) in TFA (15.0 mL/mmol) was stirred at 60° C. or at room temperature for 2-16 h. The reaction mixture was then evaporated completely to get a residue which was neutralized with saturated $NaHCO_3$. The aqueous mixture was extracted with ethyl acetate (3×), dried over anhydrous sodium sulphate, filtered, and concentrated to dryness. The obtained crude was purified by flash column chromatography (MeOH/DCM 0%-10%) and/or by HPLC-semipreparative (Method-D) to obtain the desired amine product (ex: (6-amino-2-((2-hydroxyphenyl)amino)pyrimidin-4-yl)(4-phenylpiperazin-1-yl)methanone).

General Procedure A[1] for the Synthesis of Example 1

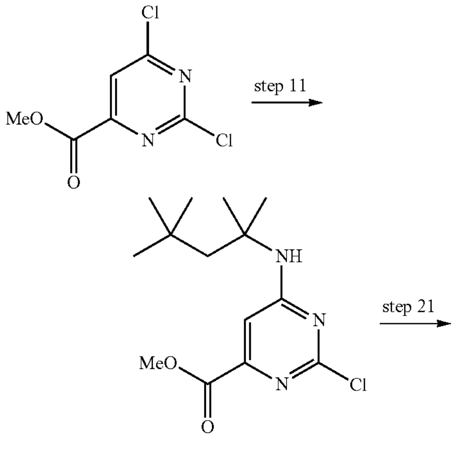

-continued

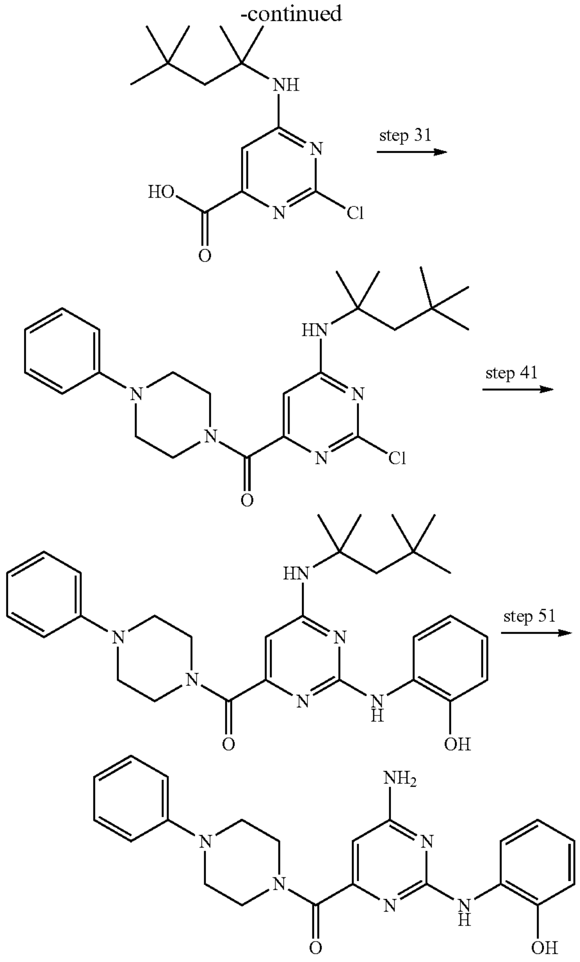

Step 11: Preparation of Intermediate 1

Methyl 2-chloro-6-((2,4,4-trimethylpentan-2-yl)amino)pyrimidine-4-carboxylate

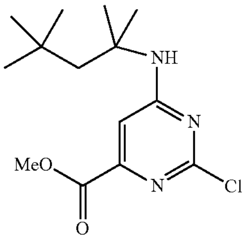 [SMILES: COC(=O)c1cc(NC(C)(C)CC(C)(C)C)nc(Cl)n1]

To a stirred mixture of methyl 2,6-dichloropyrimidine-4-carboxylate (10 g, 48.3 mmol, 1.0 eq), tert-octylamine (11.6 mL, 72.46 mmol, 1.5 eq) in THF (10 mL) was added DIPEA (12.6 mL, 72.46 mmol, 1.5 eq). The resulting mixture was stirred at room temperature for 16 h. TLC analysis (EtOAc/Hex 10%) showed complete conversion. The mixture was diluted with water and extracted with ethyl acetate (3×), dried over anhydrous sodium sulphate, filtered and concentrated to dryness. The resultant crude was purified by flash column chromatography (EtOAc/Heptane 50-100) to obtain methyl 2,6-dichloropyrimidine-4-carboxylate as a white solid.

Yield: (10.4 g, 72%).

ES-MS $[M+H]^+$: 300.0, Rt=6.76 min (Method-A1).

Step 21: Preparation of Intermediate 2

2-Chloro-6-((2,4,4-trimethylpentan-2-yl)amino)pyrimidine-4-carboxylic acid

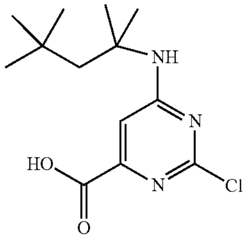 [SMILES: CC(C)(C)CC(C)(C)Nc1cc(C(=O)O)nc(Cl)n1]

To a stirred mixture of methyl 2,6-dichloropyrimidine-4-carboxylate (2.0 g, 6.6 mmol, 1.0 eq.) in THF:$H_2O$ (1:1, 50 mL) was added lithium hydroxide (0.86 g, 35.9 mmol, 5.5 eq). The resulting mixture was stirred at room temperature for 2 h. TLC analysis (EtOAc/Hex 10%) showed complete conversion. The mixture was acidified with the addition of conc. HCl and extracted with ethyl acetate (3×), dried over anhydrous sodium sulphate, filtered and concentrated to dryness to obtain 2-chloro-6-((2,4,4-trimethylpentan-2-yl)amino)pyrimidine-4-carboxylic acid as a white solid, which was used without further purification.

Yield: (1.02 g, 54% yield).

ES-MS $[M+H]^+$: 286.0, Rt=5.59 min (Method-A1).

Step 31: Preparation of Intermediate 3

(2-Chloro-6-((2,4,4-trimethylpentan-2-yl)amino)pyrimidin-4-yl)(4-phenylpiperazin-1-yl)methanone

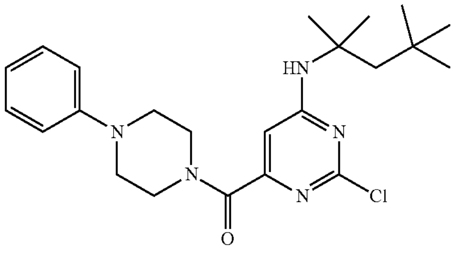 [SMILES: CC(C)(C)CC(C)(C)Nc1cc(C(=O)N2CCN(c3ccccc3)CC2)nc(Cl)n1]

To a stirred solution of 2-chloro-6-((2,4,4-trimethylpentan-2-yl)amino)pyrimidine-4-carboxylic acid (0.40 g, 1.40 mmol, 1.0 eq), 1-phenylpiperazine (0.32 mL, 2.09 mmol, 1.5 eq) and HATU (0.40 g, 1.00 mmol, 0.7 eq) in DMF (20 mL) was added DIPEA (0.32 mL, 1.84 mmol, 1.3 eq). The resulting mixture was stirred at room temperature for 14 h. TLC analysis (EtOAc/Hex 50%) showed complete conversion. The reaction mixture was quenched with saturated sodium bicarbonate. The aqueous layer was extracted with ethyl acetate (3×), dried over anhydrous sodium sulphate, filtered and concentrated to dryness. The resultant crude was purified by flash column chromatography (EtOAc/Heptane 50-100) to obtain (2-chloro-6-((2,4,4-trimethylpentan-2-yl)amino)pyrimidin-4-yl)(4-phenylpiperazin-1-yl)methanone as a brown solid.

Yield: (0.206 g, 35% yield).

ES-MS $[M+H]^+$:430.0, Rt=7.146 min (Method-A1).

Step 41: Intermediate 4

(2-((2-Hydroxyphenyl)amino)-6-((2,4,4-trimethylpentan-2-yl)amino)pyrimidin-4-yl)(4-phenylpiperazin-1-yl)

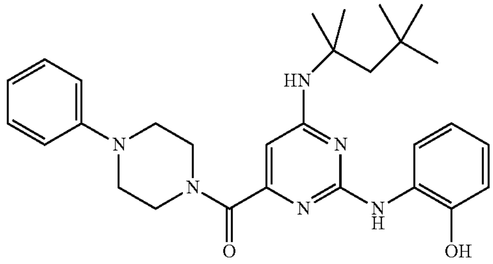 [SMILES: CC(C)(C)CC(C)(C)Nc1cc(C(=O)N2CCN(c3ccccc3)CC2)nc(Nc2ccccc2O)n1]

To a stirred solution of (2-chloro-6-((2,4,4-trimethylpentan-2-yl)amino)pyrimidin-4-yl)(4-phenylpiperazin-1-yl)methanone (0.206 g, 0.48 mmol, 1.0 eq) in 1-butanol (3 mL) were added 2-aminophenol (0.060 g, 0.55 mmol, 1.1 eq) and sulphuric acid (catalytic, 1 drop) at room temperature. The reaction mixture was stirred at 100° C. for 18 h. The reaction mixture was allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography (EtOAc/Heptane 50-100) to obtain (2-((2-hydroxyphenyl)amino)-6-((2,4,4-trimethylpentan-2-yl)amino)pyrimidin-4-yl)(4-phenylpiperazin-1-yl)methanone, as a white solid.

Yield: (0.155 g, 65%).

ES-MS $[M+H]^+$:503.1, Rt=7.052 min (Method-A1).

Example 1

(6-Amino-2-((2-hydroxyphenyl)amino)pyrimidin-4-yl)(4-phenylpiperazin-1-yl)methanone

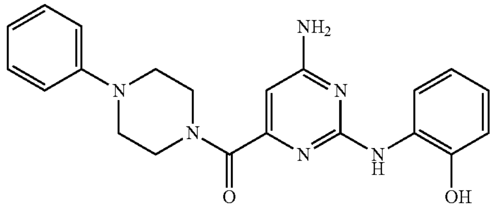 [SMILES: Nc1cc(C(=O)N2CCN(c3ccccc3)CC2)nc(Nc2ccccc2O)n1]

A stirred solution of (2-((2-hydroxyphenyl)amino)-6-((2,4,4-trimethylpentan-2-yl)amino)pyrimidin-4-yl)(4-phenylpiperazin-1-yl)methanone (0.155 g, 0.30 mmol, 1.0 eq) in TFA (2.0 mL) was stirred at 60° C. for 2 h. The reaction mixture was then evaporated completely to get the residue which was basified with saturated $NaHCO_3$. The aqueous mixture was extracted with ethyl acetate (3×), dried over anhydrous sodium sulphate, filtered and concentrated to dryness. The resultant crude was purified by flash column chromatography (MeOH/$CH_2Cl_2$ 10%) to obtain the title compound (6-amino-2-((2-hydroxyphenyl)amino)pyrimidin-4-yl)(4-phenylpiperazin-1-yl)methanone as a white solid.

Yield: (0.069 g, 58%).

ES-MS $[M-H]^-$: 389.1, Rt=16.93 min (Method-B1).

$^1H$ NMR (400 MHz, DMSO-$d_6$) δ 10.14 (brs, 1H), 8.09-7.78 (m, 2H), 7.47-7.11 (m, 2H), 7.08-6.92 (m, 4H), 6.82 (td, J=3.8, 1.2 Hz, 3H), 6.76-6.62 (m, 1H), 6.00 (s, 1H), 3.72 (t, J=5.3 Hz, 2H), 3.59 (t, J=5.1 Hz, 2H), 3.19 (t, J=5.3 Hz, 2H), 3.11 (t, J=5.2 Hz, 2H).

Intermediate 5

(2-((3-Methoxyphenyl)amino)-6-((2,4,4-trimethylpentan-2-yl)amino)pyrimidin-4-yl)(4-phenylpiperazin-1-yl)methanone

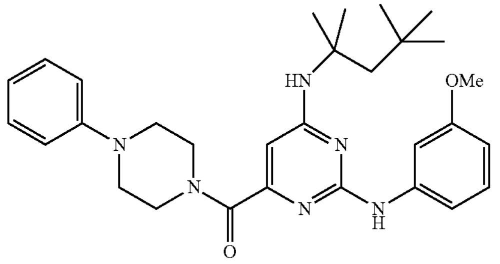 [SMILES: COc1cccc(Nc2nc(NC(C)(C)CC(C)(C)C)cc(C(=O)N3CCN(c4ccccc4)CC3)n2)c1]

Intermediate 5 was synthesized following the procedure described for preparing Intermediate 4 using m-anisidine, and isolated as a light brown powder.

Yield: (0.115 g, 96%).

ES-MS $[M+H]^+$: 517.1, Rt=7.257 min (Method-A1).

Example 2

(6-Amino-2-((3-methoxyphenyl)amino)pyrimidin-4-yl)(4-phenylpiperazin-1-yl)methanone

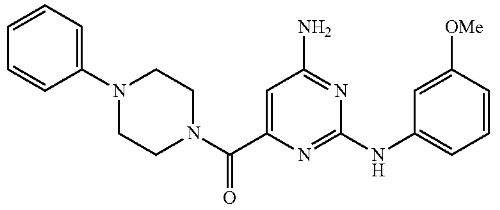 [SMILES: COc1cccc(Nc2nc(N)cc(C(=O)N3CCN(c4ccccc4)CC3)n2)c1]

The title compound was synthesized following the procedure described for preparing Example 1 using (2-((3-methoxyphenyl)amino)-6-((2,4,4-trimethylpentan-2-yl) amino) pyrimidin-4-yl)(4-phenylpiperazin-1-yl)methanone, and isolated as a white powder.

Yield: (0.039 g, 43%).

ES-MS $[M+H]^+$: 405.0, Rt=17.96 min (Method-B1).

$^1H$ NMR (400 MHz, DMSO-$d_6$) δ 9.11 (s, 1H), 7.53 (t, J=2.3 Hz, 1H), 7.27 (ddd, J=8.2, 2.0, 0.9 Hz, 1H), 7.23 (dd, J=8.8, 7.2 Hz, 2H), 7.10 (t, J=8.1 Hz, 1H), 6.99-6.93 (m, 2H), 6.87-6.78 (m, 3H), 6.46 (ddd, J=8.2, 2.5, 0.9 Hz, 1H), 5.99 (s, 1H), 3.72 (q, J=3.8 Hz, 2H), 3.69 (s, 3H), 3.59 (t, J=5.1 Hz, 2H), 3.19 (t, J=5.3 Hz, 2H), 3.14 (d, J=5.1 Hz, 2H).

Intermediate 6

(4-Phenylpiperazin-1-yl)(2-(p-tolylamino)-6-((2,4,4-trimethylpentan-2-yl)amino)pyrimidin-4-yl)methanone

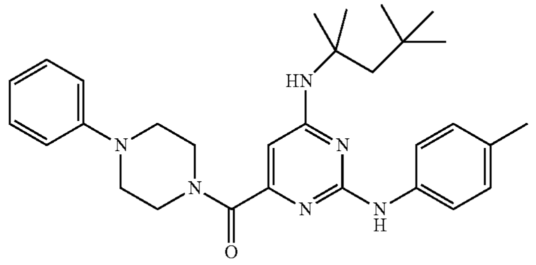 [SMILES: Cc1ccc(Nc2nc(NC(C)(C)CC(C)(C)C)cc(C(=O)N3CCN(c4ccccc4)CC3)n2)cc1]

The title compound was synthesized following the procedure described for preparing Intermediate 4 using p-toluidine, and isolated as a light brown powder.

Yield: (0.094 g, 67%).

ES-MS $[M+H]^+$: 501.2, Rt=7.458 min (Method-A1).

Example 3

(6-Amino-2-(p-tolylamino)pyrimidin-4-yl)(4-phenylpiperazin-1-yl)methanone

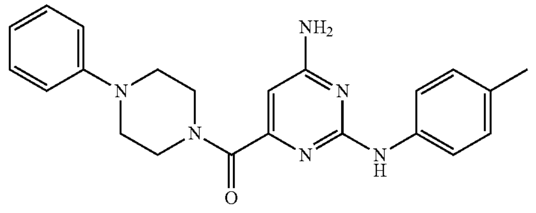 [SMILES: Cc1ccc(Nc2nc(N)cc(C(=O)N3CCN(c4ccccc4)CC3)n2)cc1]

The title compound was synthesized following the procedure described for preparing Example 1 using (4-phenylpiperazin-1-yl)(2-(p-tolylamino)-6-((2,4,4-trimethylpentan-2-yl) amino)pyrimidin-4-yl)methanone, and isolated as a white powder.

Yield: (0.034 g, 48%).

ES-MS $[M+H]^+$: 389.0, Rt=18.640 min (Method-B1).

$^1H$ NMR (400 MHz, DMSO-$d_6$) δ 9.00 (s, 1H), 7.70-7.58 (m, 2H), 7.23 (dd, J=8.6, 7.2 Hz, 2H), 7.02 (d, J=8.8 Hz, 2H), 7.01-6.91 (m, 2H), 6.88-6.78 (m, 3H), 5.96 (s, 1H), 3.75-3.68 (m, 2H), 3.59 (t, J=5.1 Hz, 2H), 3.20 (d, J=5.4 Hz, 2H), 3.16-3.08 (m, 2H), 2.22 (s, 3H).

Intermediate 7

N-benzyl-2-chloro-N-methyl-6-((2,4,4-trimethylpentan-2-yl)amino)pyrimidine-4-carboxamide

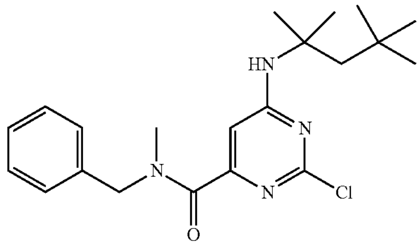 [SMILES: CN(Cc1ccccc1)C(=O)c1cc(NC(C)(C)CC(C)(C)C)nc(Cl)n1]

The title compound was synthesized following the procedure described for preparing Intermediate 3 using N-methyl-1-phenylmethanamine, and isolated as a light brown powder.

Yield: (0.310 g, 46%).

ES-MS $[M+H]^+$: 389.0, Rt=7.09 min (Method-A1).

Intermediate 8

N-benzyl-2-((2-hydroxyphenyl)amino)-N-methyl-6-((2,4,4-trimethylpentan-2-yl)amino)pyrimidine-4-carboxamide

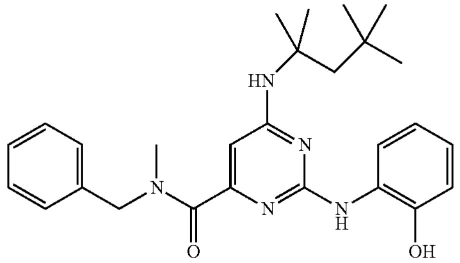 [SMILES: CN(Cc1ccccc1)C(=O)c1cc(NC(C)(C)CC(C)(C)C)nc(Nc2ccccc2O)n1]

The title compound was synthesized following the procedure described for preparing Intermediate 4 using 2-aminophenol, and isolated as a light brown powder.

Yield: (0.220 g, 60%).

ES-MS $[M+H]^+$: 462.1, Rt=6.95 min (Method-A1).

Example 4

6-Amino-N-benzyl-2-((2-hydroxyphenyl)amino)-N-methylpyrimidine-4-carboxamide

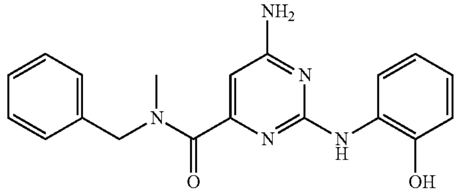 [SMILES: CN(Cc1ccccc1)C(=O)c1cc(N)nc(Nc2ccccc2O)n1]

The title compound was synthesized following the procedure described for preparing Example 1 using N-benzyl-2-((2-hydroxyphenyl)amino)-N-methyl-6-((2,4,4-trimethylpentan-2-yl)amino)pyrimidine-4-carboxamide, and isolated as a white powder.

Yield: (0.135 g, 81%).

ES-MS $[M-H]^-$: 350.1, Rt=16.50 min (Method-B1).

$^1H$ NMR (400 MHz, DMSO-$d_6$) δ 10.12 (d, J=39.7 Hz, 1H), 8.43-7.70 (m, 2H), 7.48-7.35 (m, 1H), 7.35-7.23 (m, 4H), 6.98 (d, J=8.2 Hz, 2H), 6.87-6.80 (m, 2H), 6.79-6.68 (m, 1H), 5.99 (d, J=6.9 Hz, 1H), 4.60 (d, J=29.1 Hz, 2H), 2.84 (d, J=28.8 Hz, 3H).

Intermediate 9

2-Chloro-N-methyl-N-phenyl-6-((2,4,4-trimethylpentan-2-yl)amino)pyrimidine-4-carboxamide

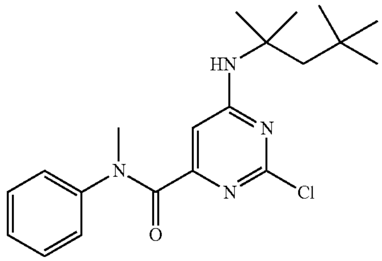 [SMILES: CN(C(=O)c1cc(NC(C)(C)CC(C)(C)C)nc(Cl)n1)c1ccccc1]

The title compound was synthesized following the procedure described for preparing Intermediate 3 using N-methylaniline, and isolated as a light brown powder.

Yield: (0.196 g, 60%).

ES-MS $[M+H]^+$: 375.0, Rt=6.823 min (Method-A1).

Intermediate 10

2-((2-Hydroxyphenyl)amino)-N-methyl-N-phenyl-6-((2,4,4-trimethylpentan-2-yl)amino)pyrimidine-4-carboxamide

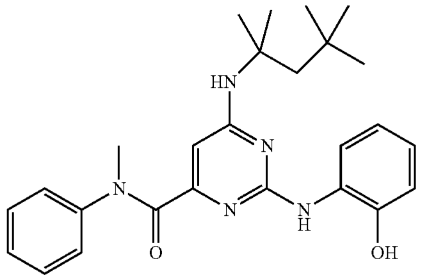

The title compound was synthesized following the procedure described for preparing Intermediate 4 using 2-chloro-N-methyl-N-phenyl-6-((2,4,4-trimethylpentan-2-yl)amino)-pyrimidine-4-carboxamide and 2-aminophenol, and isolated as a light brown powder.

Yield: (0.085 g, 36%).

ES-MS $[M+H]^+$: 448.1, Rt=6.824 min (Method-A1).

Example 5

6-Amino-2-((2-hydroxyphenyl)amino)-N-methyl-N-phenylpyrimidine-4-carboxamide

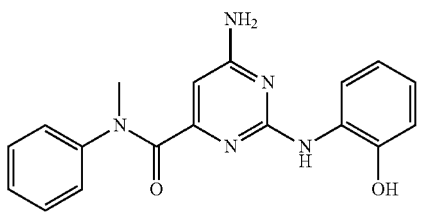 [SMILES: CN(C(=O)c1cc(N)nc(Nc2ccccc2O)n1)c1ccccc1]

The title compound was synthesized following the procedure described for preparing Example 1 using 2-((2-hydroxyphenyl)amino)-N-methyl-N-phenyl-6-((2,4,4-trimethyl-pentan-2-yl)amino)pyrimidine-4-carboxamide, and isolated as a white powder.

Yield: (0.046 g, 73%).

ES-MS $[M-H]^-$: 336.0, Rt=15.46 min (Method-B1).

$^1H$ NMR (400 MHz, DMSO-$d_6$) δ 10.10 (s, 1H), 7.63 (brs, 2H), 7.44-7.00 (m, 5H), 6.85-6.76 (m, 4H), 6.76-6.66 (m, 1H), 5.91 (s, 1H), 3.33 (d, J=6.4 Hz, 3H).

Intermediate 11

N-methyl-N-phenyl-2-(p-tolylamino)-6-((2,4,4-trimethylpentan-2-yl)amino)pyrimidine-4-carboxamide

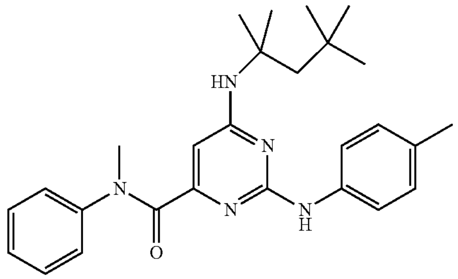 [SMILES: Cc1ccc(Nc2nc(NC(C)(C)CC(C)(C)C)cc(C(=O)N(C)c3ccccc3)n2)cc1]

The title compound was synthesized following the procedure described for preparing Intermediate 4 using 2-chloro-N-methyl-N-phenyl-6-((2,4,4-trimethylpentan-2-yl)amino)-pyrimidine-4-carboxamide and p-toluidine, and isolated as a light brown powder.

Yield: (0.106 g, 71% yield).

ES-MS $[M+H]^+$: 446.1, Rt=7.189 min (Method-A1).

Example 6

6-Amino-N-methyl-N-phenyl-2-(p-tolylamino)pyrimidine-4-carboxamide

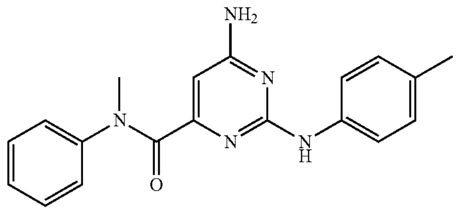 [SMILES: Cc1ccc(Nc2nc(N)cc(C(=O)N(C)c3ccccc3)n2)cc1]

The title compound was synthesized following the procedure described for preparing Example 1 using N-methyl-N-phenyl-2-(p-tolylamino)-6-((2,4,4-trimethylpentan-2-yl)-amino)pyrimidine-4-carboxamide, and isolated as a white powder.

Yield: (0.033 g, 50%).

ES-MS $[M+H]^+$: 334.1, Rt=17.108 min (Method-B1).

$^1H$ NMR (400 MHz, DMSO-$d_6$) δ 8.73 (bs, 1H), 7.42-7.05 (m, 7H), 6.96 (d, J=8.2 Hz, 2H), 6.68-6.49 (m, 2H), 5.90 (s, 1H), 3.34 (d, J=0.4 Hz, 3H), 2.21 (s, 3H).

Intermediate 12

2-((3-Methoxyphenyl)amino)-N-methyl-N-phenyl-6-((2,4,4-trimethylpentan-2-yl)amino)pyrimidine-4-carboxamide

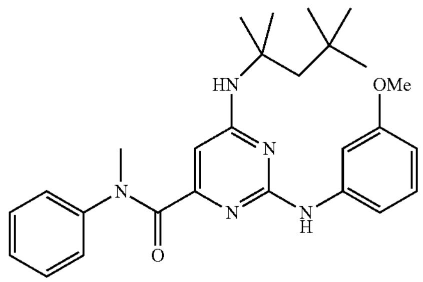 [SMILES: COc1cccc(Nc2nc(NC(C)(C)CC(C)(C)C)cc(C(=O)N(C)c3ccccc3)n2)c1]

This compound was synthesized following the procedure described for preparing Intermediate 4 using 2-chloro-N-methyl-N-phenyl-6-((2,4,4-trimethylpentan-2-yl)amino)-pyrimidine-4-carboxamide and m-anisidine, and isolated as a light brown powder.

Yield: (0.120 g, 68%).

ES-MS $[M+H]^+$: 462.1, Rt=6.975 min (Method-A1).

Example 7

6-Amino-2-((3-methoxyphenyl)amino)-N-methyl-N-phenylpyrimidine-4-carboxamide

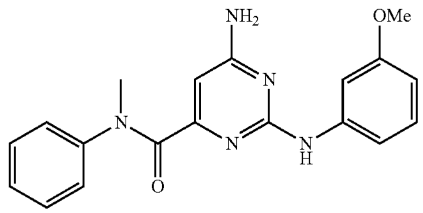 [SMILES: COc1cccc(Nc2nc(N)cc(C(=O)N(C)c3ccccc3)n2)c1]

The title compound was synthesized following the procedure described for preparing Example 1 using 2-((3-methoxyphenyl)amino)-N-methyl-N-phenyl-6-((2,4,4-trimethyl-pentan-2-yl)amino)pyrimidine-4-carboxamide, and isolated as a white powder.

Yield: (0.053 g, 59%).

ES-MS $[M+H]^+$: 350.0, Rt=16.374 min (Method-B1).

$^1H$ NMR (400 MHz, DMSO-$d_6$) δ 8.87 (s, 1H), 7.41-7.14 (m, 6H), 7.13-6.99 (m, 2H), 6.66 (brs, 2H), 6.47-6.40 (m, 1H), 5.87 (s, 1H), 3.71 (s, 3H), 3.34 (s, 3H).

Intermediate 13

(2-Chloro-6-((2,4,4-trimethylpentan-2-yl)amino) pyrimidin-4-yl)(isoindolin-2-yl)methanone

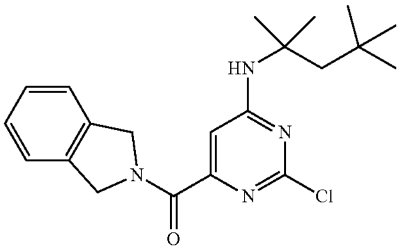 [SMILES: CC(C)(C)CC(C)(C)Nc1cc(C(=O)N2Cc3ccccc3C2)nc(Cl)n1]

The title compound was synthesized following the procedure described for preparing Intermediate 3 using isoindoline hydrochloride, and isolated as a white powder.

Yield: (0.029 g, 71% yield).

ES-MS $[M+H]^+$: 387.0, Rt=7.657 min (Method-A1).

Intermediate 14

(2-((2-Hydroxyphenyl)amino)-6-((2,4,4-trimethylpentan-2-yl)amino)pyrimidin-4-yl)(isoindolin-2-yl) methanone

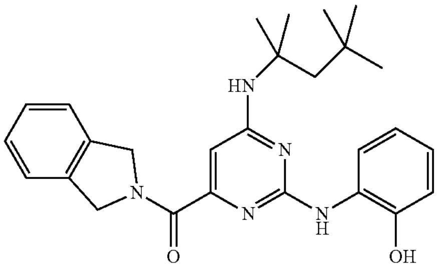 [SMILES: CC(C)(C)CC(C)(C)Nc1cc(C(=O)N2Cc3ccccc3C2)nc(Nc2ccccc2O)n1]

The title compound was synthesized following the procedure described for preparing Intermediate 4 using (2-chloro-6-((2,4,4-trimethylpentan-2-yl)amino)pyrimidin-4-yl)-(isoindolin-2-yl)methanone, and isolated as a white powder.

Yield: (0.240 g, 70%).

ES-MS $[M+H]^+$: 460.1, Rt=7.398 min (Method-A1).

Example 8

(6-Amino-2-((2-hydroxyphenyl)amino)pyrimidin-4-yl)(isoindolin-2-yl)methanone

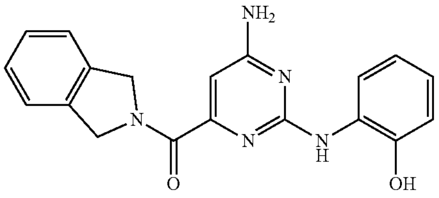

The title compound was synthesized following the procedure described for preparing Example 1 using (2-((2-hydroxyphenyl)amino)-6-((2,4,4-trimethylpentan-2-yl) amino)-pyrimidin-4-yl)(isoindolin-2-yl)methanone, and isolated as a pink powder.

Yield: (0.029 g, 16%).

ES-MS $[M+H]^+$: 348.0, Rt=16.891 min (Method-B1).

$^1$H NMR (400 MHz, DMSO-$d_6$) δ 10.06 (s, 1H), 8.06-7.76 (m, 2H), 7.49-7.36 (m, 1H), 7.36-7.21 (m, 3H), 6.99 (brs, 2H), 6.94-6.82 (m, 2H), 6.81-6.67 (m, 1H), 6.21 (s, 1H), 4.98 (s, 2H), 4.82 (s, 2H).

Intermediate 15

2-Chloro-N-methyl-N-(1,2,3,4-tetrahydronaphthalen-2-yl)-6-((2,4,4-trimethylpentan-2-yl)amino)pyrimidine-4-carboxamide

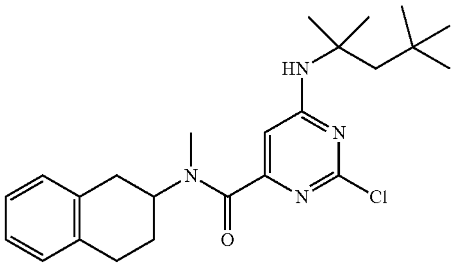

The title compound was synthesized following the procedure described for preparing Intermediate 3 using N-methyl-1,2,3,4-tetrahydronaphthalen-2-amine, and isolated as a yellow powder.

Yield: (0.326 g, 55%).

ES-MS $[M-H]^-$: 429.0, Rt=7.592 min (Method-A1).

Intermediate 16

2-((2-Hydroxyphenyl)amino)-N-methyl-N-(1,2,3,4-tetrahydronaphthalen-2-yl)-6-((2,4,4-trimethylpentan-2-yl)amino)pyrimidine-4-carboxamide

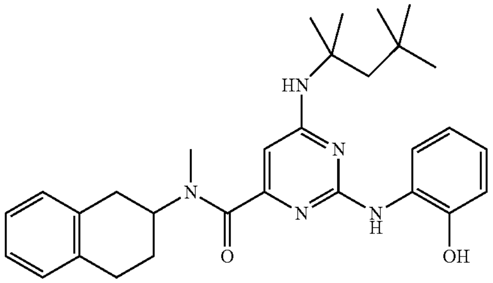 [SMILES: CN(C(=O)c1cc(NC(C)(C)CC(C)(C)C)nc(Nc2ccccc2O)n1)C1CCc2ccccc2C1]

The title compound was synthesized following the procedure described for preparing Intermediate 4 using 2-chloro-N-methyl-N-(1,2,3,4-tetrahydronaphthalen-2-yl)-6-((2,4,4-trimethylpentan-2-yl)amino)pyrimidine-4-carboxamide, and isolated as a yellow powder.

Yield: (0.334 g, 87%).

ES-MS $[M-H]^-$: 500.1, Rt=7.452 min (Method-A1).

Example 9

6-Amino-2-((2-hydroxyphenyl)amino)-N-methyl-N-(1,2,3,4-tetrahydronaphthalen-2-yl)pyrimidine-4-carboxamide

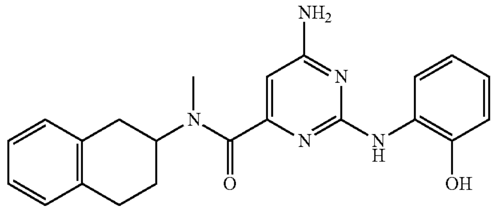 [SMILES: CN(C(=O)c1cc(N)nc(Nc2ccccc2O)n1)C1CCc2ccccc2C1]

The title compound was synthesized following the procedure described for preparing Example 1 using 2-((2-hydroxyphenyl)amino)-N-methyl-N-(1,2,3,4-tetrahydronaphthalen-2-yl)-6-((2,4,4-trimethylpentan-2-yl)amino)pyrimidine-4-carboxamide, and isolated as a yellow powder.

Yield: (0.048 g, 19%).

ES-MS $[M+H]^+$: 388.0, Rt=18.006 min (Method-B1).

$^1$H NMR (400 MHz, DMSO-$d_6$) δ 10.17 (brs, 1H), 8.05-7.83 (m, 3H), 7.12 (s, 1H), 7.08-6.97 (m, 2H), 6.96-6.90 (m, 2H), 6.89-6.80 (m, 2H), 6.80-6.67 (m, 1H), 5.96-5.91 (m, 1H), 4.71-4.55 (m, 0.3H), 3.97-3.88 (m, 0.7H), 3.21-2.96 (m, 1H), 2.96-2.85 (m, 3H), 2.85-2.71 (m, 2H), 2.71-2.57 (m, 1H), 2.02-1.85 (m, 2H).

Intermediate 17

2-Chloro-N-(2,3-dihydro-1H-inden-2-yl)-N-methyl-6-((2,4,4-trimethylpentan-2-yl)amino)pyrimidine-4-carboxamide

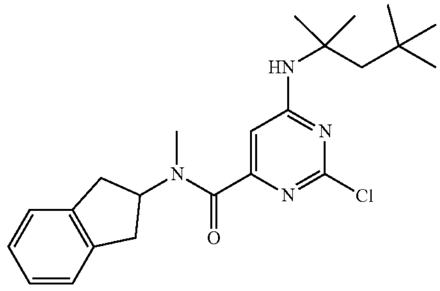 [SMILES: CN(C(=O)c1cc(NC(C)(C)CC(C)(C)C)nc(Cl)n1)C1Cc2ccccc2C1]

The title compound was synthesized following the procedure described for preparing Intermediate 3 using N-methyl-2,3-dihydro-1H-inden-2-amine, and isolated as a yellow powder.

Yield: (0.531 g, 98%).

ES-MS $[M+H]^+$: 415.0, Rt=7.590 min (Method-A1).

Intermediate 18

N-(2,3-dihydro-1H-inden-2-yl)-2-((2-hydroxyphenyl)amino)-N-methyl-6-((2,4,4-trimethylpentan-2-yl)amino)pyrimidine-4-carboxamide

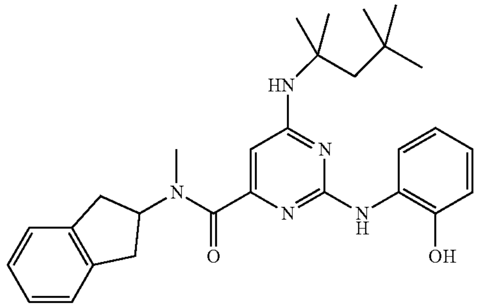 [SMILES: CN(C(=O)c1cc(NC(C)(C)CC(C)(C)C)nc(Nc2ccccc2O)n1)C1Cc2ccccc2C1]

The title compound was synthesized following the procedure described for preparing Intermediate 4 using 2-chloro-N-(2,3-dihydro-1H-inden-2-yl)-N-methyl-6-((2,4,4-trimethyl-pentan-2-yl)amino)pyrimidine-4-carboxamide, and isolated as a yellow powder.

Yield: (0.475 g, 76%).

ES-MS $[M+H]^+$: 488.1, Rt=7.464 min (Method-A1).

Example 10

6-Amino-N-(2,3-dihydro-1H-inden-2-yl)-2-((2-hydroxyphenyl)amino)-N-methylpyrimidine-4-carboxamide

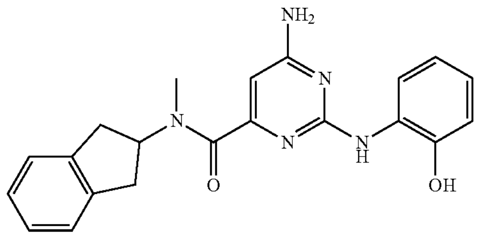 [SMILES: CN(C(=O)c1cc(N)nc(Nc2ccccc2O)n1)C1Cc2ccccc2C1]

The title compound was synthesized following the procedure described for preparing Example 1 using N-(2,3-dihydro-1H-inden-2-yl)-2-((2-hydroxyphenyl)amino)-N-methyl-6-((2,4,4-trimethylpentan-2-yl)amino)pyrimidine-4-carboxamide, and isolated as a yellow powder.

Yield: (0.239 g, 64%).

ES-MS $[M+H]^+$: 376.0, Rt=17.717 min (Method-B1).

$^1$H NMR (400 MHz, DMSO-$d_6$) δ 10.18 (brs, 1H), 7.97-7.80 (m, 2H), 7.26 (dd, J=5.4, 3.4 Hz, 1H), 7.21-7.07 (m, 3H), 7.02-6.93 (m, 2H), 6.87-6.80 (m, 2H), 6.77 (ddd, J=8.7, 6.3, 2.4 Hz, 1H), 5.94 (d, J=14.9 Hz, 1H), 5.41-5.28 (m, 1H), 4.70 (p, J=7.7 Hz, 1H), 3.17 (dd, J=16.3, 8.4 Hz, 1H), 3.05 (h, J=7.5 Hz, 3H), 2.77 (d, J=16.1 Hz, 3H).

Intermediate 19

2-Chloro-N-phenyl-6-((2,4,4-trimethylpentan-2-yl)amino)pyrimidine-4-carboxamide

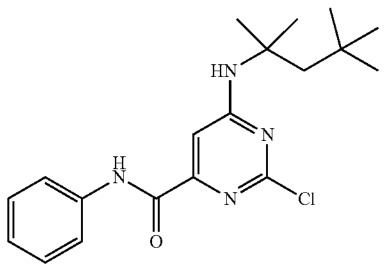 [SMILES: CC(C)(C)CC(C)(C)Nc1cc(C(=O)Nc2ccccc2)nc(Cl)n1]

The title compound was synthesized following the procedure described for preparing Intermediate 3 using aniline, and isolated as a yellow powder.

Yield: (0.307 g, 81%).

ES-MS $[M+H]^+$: 361.0, Rt=7.526 min (Method-A1).

Intermediate 20

2-((2-Hydroxyphenyl)amino)-N-phenyl-6-((2,4,4-trimethylpentan-2-yl)amino)pyrimidine-4-carboxamide

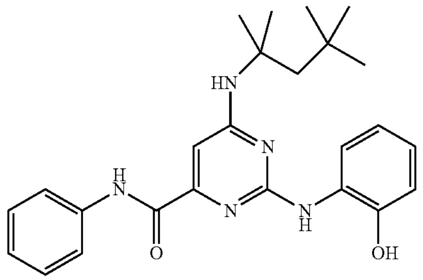 [SMILES: CC(C)(C)CC(C)(C)Nc1cc(C(=O)Nc2ccccc2)nc(Nc2ccccc2O)n1]

The title compound was synthesized following the procedure described for preparing Intermediate 4 using 2-chloro-N-phenyl-6-((2,4,4-trimethylpentan-2-yl)amino)pyrimidine-4-carboxamide, and isolated as a yellow powder.

Yield: (0.220 g, 60%).

ES-MS $[M+H]^+$: 434.1, Rt=7.571 min (Method-A1).

Example 11

6-Amino-2-((2-hydroxyphenyl)amino)-N-phenylpyrimidine-4-carboxamide

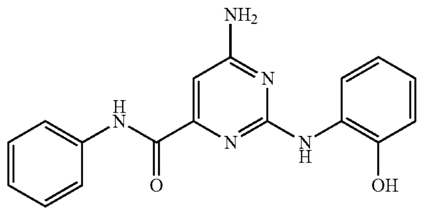 [SMILES: Nc1cc(C(=O)Nc2ccccc2)nc(Nc2ccccc2O)n1]

The title compound was synthesized following the procedure described for preparing Example 1 using 2-((2-hydroxyphenyl)amino)-N-phenyl-6-((2,4,4-trimethylpentan-2-yl)amino)-pyrimidine-4-carboxamide, and isolated as a yellow powder.

Yield: (0.028 g, 17%).

ES-MS $[M+H]^+$: 322.0, Rt=17.818 min (Method-B1).

$^1$H NMR (400 MHz, DMSO-$d_6$) δ 10.26 (s, 1H), 9.98 (s, 1H), 8.24 (dd, J=7.5, 2.0 Hz, 1H), 7.92 (s, 1H), 7.81 (dd, J=8.7, 1.2 Hz, 2H), 7.38 (dd, J=8.5, 7.4 Hz, 2H), 7.24-7.05 (m, 3H), 6.97-6.74 (m, 3H), 6.61 (s, 1H).

Intermediate 21

2-Chloro-N-(1,2,3,4-tetrahydronaphthalen-2-yl)-6-((2,4,4-trimethylpentan-2-yl)amino)pyrimidine-4-carboxamide

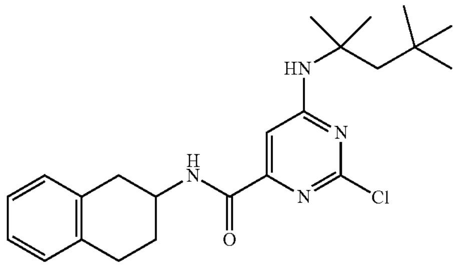 [SMILES: CC(C)(C)CC(C)(C)Nc1cc(C(=O)NC2CCc3ccccc3C2)nc(Cl)n1]

The title compound was synthesized following the procedure described for preparing Intermediate 3 using 1,2,3,4-tetrahydronaphthalen-2-amine, and isolated as a yellow powder.

Yield: (0.111 g, 15%).

ES-MS $[M+H]^+$: 415.0, Rt=8.074 min (Method-A1).

Intermediate 22

2-((2-Hydroxyphenyl)amino)-N-(1,2,3,4-tetrahydronaphthalen-2-yl)-6-((2,4,4-trimethylpentan-2-yl)amino)pyrimidine-4-carboxamide

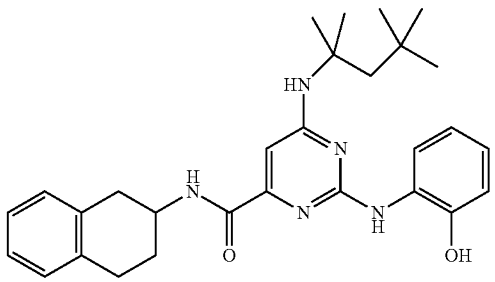 [SMILES: CC(C)(C)CC(C)(C)Nc1cc(C(=O)NC2CCc3ccccc3C2)nc(Nc2ccccc2O)n1]

The title compound was synthesized following the procedure described for preparing Intermediate 4 using 2-chloro-N-(1,2,3,4-tetrahydronaphthalen-2-yl)-6-((2,4,4-trimethyl-pentan-2-yl)amino)pyrimidine-4-carboxamide, and isolated as a yellow powder.

Yield: (0.038 g, 29%).

ES-MS $[M+H]^+$: 488.1, Rt=7.614 min (Method-A1).

Example 12

6-Amino-2-((2-hydroxyphenyl)amino)-N-(1,2,3,4-tetrahydronaphthalen-2-yl)pyrimidine-4-carboxamide

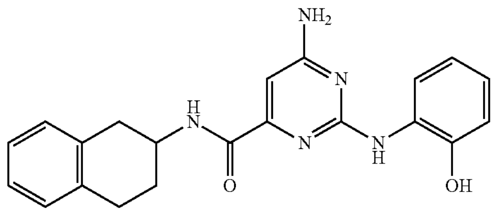 [SMILES: Nc1cc(C(=O)NC2CCc3ccccc3C2)nc(Nc2ccccc2O)n1]

The title compound was synthesized following the procedure described for preparing Example 1 using 2-((2-hydroxyphenyl)amino)-N-(1,2,3,4-tetrahydronaphthalen-2-yl)-6-((2,4,4-trimethylpentan-2-yl)amino)pyrimidine-4-carboxamide, and isolated as a brown powder.

Yield: (0.012 g, 44%).

ES-MS $[M-H]^-$: 374.0, Rt=18.723 min (Method-B1).

$^1$H NMR (400 MHz, DMSO-$d_6$) δ 9.95 (s, 1H), 8.30 (d, J=8.2 Hz, 1H), 8.09 (dd, J=8.0, 1.5 Hz, 1H), 7.78 (s, 1H), 7.25-6.98 (m, 6H), 6.93-6.77 (m, 2H), 6.71 (ddd, J=8.8, 6.9, 2.0 Hz, 1H), 6.55 (s, 1H), 4.40-3.92 (m, 1H), 3.01 (dd, J=16.2, 5.2 Hz, 1H), 2.90-2.82 (m, 3H), 2.17-1.95 (m, 1H), 1.93-1.72 (m, 1H).

Intermediate 23

2-Chloro-N-(2,3-dihydro-1H-inden-2-yl)-6-((2,4,4-trimethylpentan-2-yl)amino)pyrimidine-4-carboxamide

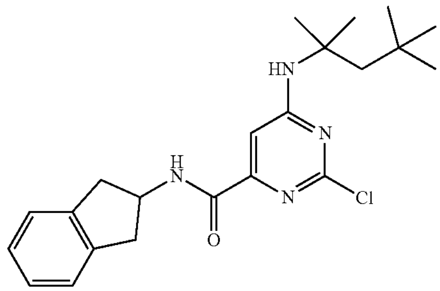 [SMILES: CC(C)(C)CC(C)(C)Nc1cc(C(=O)NC2Cc3ccccc3C2)nc(Cl)n1]

The title compound was synthesized following the procedure described for preparing Intermediate 3 using 2,3-dihydro-1H-inden-2-amine, and isolated as a brown solid.

Yield: (0.169 g, 40%).

ES-MS $[M+H]^+$: 401.0, Rt=7.634 min (Method-A1).

Intermediate 24

N-(2,3-dihydro-1H-inden-2-yl)-2-((2-hydroxyphenyl)amino)-6-((2,4,4-trimethylpentan-2-yl)amino)pyrimidine-4-carboxamide

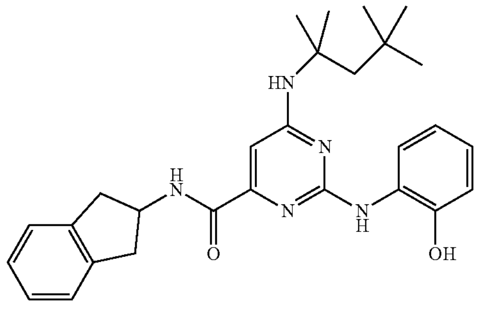 [SMILES: CC(C)(C)CC(C)(C)Nc1cc(C(=O)NC2Cc3ccccc3C2)nc(Nc2ccccc2O)n1]

The title compound was synthesized following the procedure described for preparing Intermediate 4 using 2-chloro-N-(2,3-dihydro-1H-inden-2-yl)-6-((2,4,4-trimethylpentan-2-yl)amino)pyrimidine-4-carboxamide, and isolated as a yellow solid.

Yield: (0.100 g, 50%).

ES-MS $[M+H]^+$: 474.1, Rt=7.296 min (Method-A1).

Example 13

6-Amino-N-(2,3-dihydro-1H-inden-2-yl)-2-((2-hydroxyphenyl)amino)pyrimidine-4-carboxamide

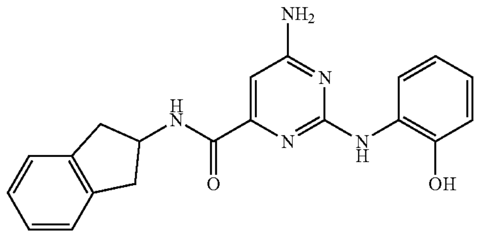 [SMILES: Nc1cc(C(=O)NC2Cc3ccccc3C2)nc(Nc2ccccc2O)n1]

The title compound was synthesized following the procedure described for preparing Example 1 N-(2,3-dihydro-1H-inden-2-yl)-2-((2-hydroxyphenyl)amino)-6-((2,4,4-trimethyl-pentan-2-yl)amino)pyrimidine-4-carboxamide, and isolated as an orange powder.

Yield: (0.021 g, 33%).

ES-MS $[M+H]^+$: 362.0, Rt=18.309 min (Method-B1).

$^1$H NMR (400 MHz, DMSO-$d_6$) δ 9.95 (s, 1H), 8.49 (d, J=7.9 Hz, 1H), 8.08 (dd, J=8.0, 1.5 Hz, 1H), 7.79 (s, 1H), 7.25 (dd, J=5.4, 3.3 Hz, 2H), 7.19-7.13 (m, 2H), 7.09 (brs, 2H), 6.90-6.76 (m, 2H), 6.70 (ddd, J=8.0, 6.9, 2.1 Hz, 1H), 6.53 (s, 1H), 4.67 (qt, J=7.7, 6.5 Hz, 1H), 3.22 (dd, J=15.8, 7.5 Hz, 2H), 2.96 (dd, J=15.8, 6.4 Hz, 2H).

Intermediate 25

(2-(((1S,2S)-2-Hydroxycyclohexyl)amino)-6-((2,4,4-trimethylpentan-2-yl)amino)pyrimidin-4-yl)(4-phenylpiperazin-1-yl)methanone

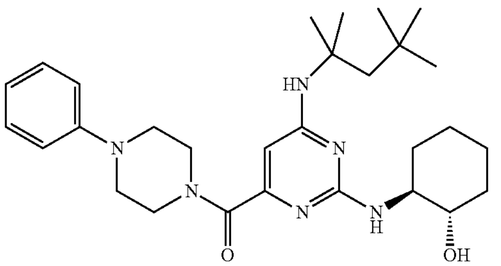 [SMILES: CC(C)(C)CC(C)(C)Nc1cc(C(=O)N2CCN(c3ccccc3)CC2)nc(N[C@H]2CCCC[C@@H]2O)n1]

To a stirred solution of (2-chloro-6-((2,4,4-trimethylpentan-2-yl)amino)pyrimidin-4-yl)(4-phenylpiperazin-1-yl) methanone (0.148 g, 0.345 mmol, 1.0 eq) in DMF (1 mL) were added (1S,2S)-2-aminocyclohexan-1-ol (0.119 g, 1.03 mmol, 3.0 eq) and $K_2CO_3$ (96 mg, 0.69 mmol, 2.0 eq). The reaction mixture was stirred at 120° C. for 18 h. The reaction mixture was allowed to cool to room temperature and diluted with water. The aqueous layer was extracted with ethyl acetate (3×), dried over anhydrous sodium sulphate, filtered and concentrated to dryness to obtain 2-(((1S,2S)-2-hydroxycyclohexyl)amino)-6-((2,4,4-trimethylpentan-2-yl)amino)pyrimidin-4-yl)(4-phenylpiperazin-1-yl)methanone as a brown oil, which was used without further purification.

Yield: (0.180 g, crude).

ES-MS $[M+H]^+$: 509.2, Rt=7.112 min (Method-A1).

Example 14

(6-Amino-2-(((1S,2S)-2-hydroxycyclohexyl)amino) pyrimidin-4-yl)(4-phenylpiperazin-1-yl)methanone

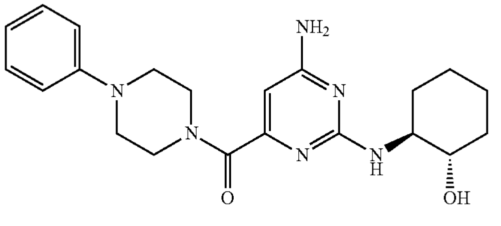 [SMILES: Nc1cc(C(=O)N2CCN(c3ccccc3)CC2)nc(N[C@H]2CCCC[C@@H]2O)n1]

The title compound was synthesized following the procedure described for preparing Example 1 using 2-(((1S, 2S)-2-hydroxycyclohexyl)amino)-6-((2,4,4-trimethylpentan-2-yl)amino)-pyrimidin-4-yl)(4-phenylpiperazin-1-yl) methanone, and isolated as a light brown powder.

Yield: (0.007 g, 6%).

ES-MS $[M+H]^+$: 397.0, Rt=16.59 min (Method-B1).

1H NMR (400 MHz, DMSO-$d_6$) δ 7.23 (dd, J=8.7, 7.2 Hz, 2H), 6.98-6.92 (m, 2H), 6.81 (t, J=7.3 Hz, 2H), 6.52 (brs, 2H), 6.26 (brs, 1H), 5.77 (s, 1H), 4.65 (s, 1H), 4.08-3.45 (m, 6H), 3.22-2.90 (m, 4H), 2.06-1.78 (m, 2H), 1.65-1.54 (s, 2H), 1.27-1.09 (m, 4H).

Intermediate 26

N-benzyl-2-(((1S,2S)-2-hydroxycyclohexyl)amino)-N-methyl-6-((2,4,4-trimethylpentan-2-yl)amino) pyrimidine-4-carboxamide

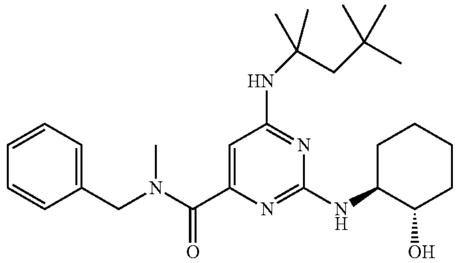 [SMILES: CN(Cc1ccccc1)C(=O)c1cc(NC(C)(C)CC(C)(C)C)nc(N[C@H]2CCCC[C@@H]2O)n1]

The title compound was synthesized following the procedure described for preparing Intermediate 24 using N-benzyl-2-chloro-N-methyl-6-((2,4,4-trimethylpentan-2-yl) amino)-pyrimidine-4-carboxamide, and isolated as a white powder.

Yield: (0.10 g, 31%).

ES-MS $[M+H]^+$: 468.1, Rt=7.046 min (Method-A1).

Example 15

6-Amino-N-benzyl-2-(((1S,2S)-2-hydroxycyclohexyl)amino)-N-methylpyrimidine-4-carboxamide

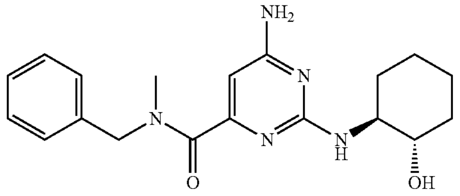 [SMILES: CN(Cc1ccccc1)C(=O)c1cc(N)nc(N[C@H]2CCCC[C@@H]2O)n1]

The title compound was synthesized following the procedure described for preparing Example 1 using N-benzyl-2-(((1S,2S)-2-hydroxycyclohexyl)amino)-N-methyl-6-((2,4,4-trimethyl-pentan-2-yl)amino)pyrimidine-4-carboxamide, and isolated as a white powder.

Yield: (0.013 g, 5%).

ES-MS $[M+H]^+$: 356.1, Rt=16.109 min (Method-B1).

$^1$H NMR (400 MHz, DMSO-$d_6$) δ 7.69-7.11 (m, 5H), 6.67-6.44 (m, 2H), 6.39-6.07 (m, 1H), 5.92-5.65 (m, 1H), 4.59 (s, 2H), 3.61-3.42 (m, 1H), 2.81 (d, J=41.4 Hz, 3H), 2.18-1.72 (m, 2H), 1.68-1.36 (m, 2H), 1.34-0.92 (m, 6H).

General Procedure B

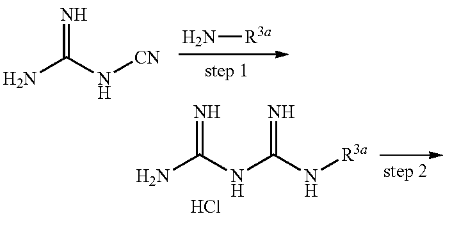

-continued

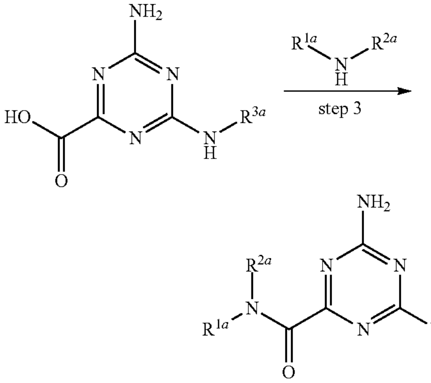

Step 1

To a mixture of the appropriate amine (ex: 3-bromoaniline) (1.0 eq) and dicyandiamide (1.0 eq) was added 3M HCl (0.33 mL/mmol) at room temperature. The reaction mixture was heated to 90° C. for 18 h. After completion of the reaction, the reaction mixture was allowed to cool to room temperature and evaporated under reduced pressure and co-distilled twice with toluene. The crude was washed with diethyl ether or triturated with EtOAc and dried to get the desired biguanide product (ex: 3-bromophenylbiguanide hydrochloride).

Step 2

To a stirred solution of the appropriate biguanide compound (ex: 3-bromophenylbiguanide hydrochloride) (1.0 eq) and diethyl oxalate (3.0 eq) in methanol (5.12 mL/mmol) was added sodium methoxide 25% in methanol (1.0-5 eq). The resulting mixture was stirred under reflux for 16 h. The reaction mixture was then cooled to room temperature and concentrated to dryness. The resulting solid was poured into water and filtered off to obtain a white solid, which was treated with LiOH (5 eq) in THF:$H_2O$ (1:1, 12 mL/mmol) and stirred at room temperature for 3 h. The mixture was then acidified with concentrated HCl and the resulting suspension filtered to obtain the desired carboxylic acid derivative (ex: 4-amino-6-((3-bromophenyl)amino)-1,3,5-triazine-2-carboxylic acid).

Step 3

Following General Procedure A, step 1.

General Procedure B1-1 for the Synthesis of Example 16

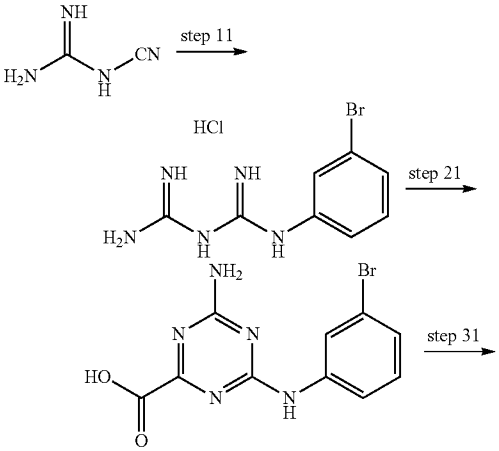

-continued

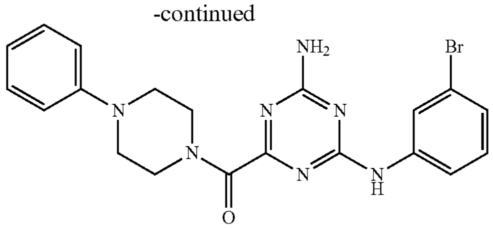

Step 11: Preparation of Intermediate 27

3-Bromophenylbiguanide hydrochloride

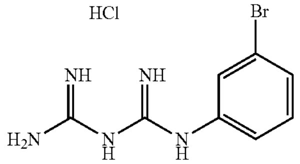 [SMILES: N=C(N)NC(=N)Nc1cccc(Br)c1 ; Cl]

To a mixture of 3-bromoaniline (2.0 g, 11.63 mmol, 1.0 eq) and dicyandiamide (0.978 g, 11.63 mmol, 1.0 eq) was added 3M HCl (3.84 mL) at room temperature. The reaction mixture was heated to 90° C. for 18 h. After completion of the reaction, the reaction mixture was allowed to cool to room temperature and evaporated under reduced pressure completely and co-distilled twice with toluene. The crude product was washed with diethyl ether and dried to get the desired product as white solid.

Yield: (1.79 g, 53%).

ES-MS $[M+H]^+$: 255.9, Rt=7.149 min (Method-A1).

Step 21: Preparation of Intermediate 28

4-Amino-6-((3-bromophenyl)amino)-1,3,5-triazine-2-carboxylic acid

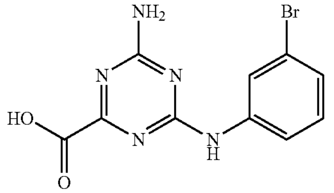 [SMILES: Nc1nc(Nc2cccc(Br)c2)nc(C(=O)O)n1]

To a stirred solution of 3-bromophenylbiguanide hydrochloride (0.30 g, 1.17 mmol, 1.0 eq) and diethyl oxalate (0.48 mL, 3.51 mmol, 3.0 eq) in MeOH (6 mL) was added NaOMe 25% in MeOH (0.32 mL, 1.17 mmol, 1.0 eq). The resulting mixture was stirred under reflux for 16 h. The reaction mixture was then cooled to room temperature and concentrated to dryness. The resulting solid was poured into water and filtered off to obtain a white solid, which was treated with LiOH (0.127 g, 5.3 mmol, 5 eq) in THF:$H_2O$ (1:1, 14 mL) and stirred at room temperature for 3 h. The mixture was then acidified with conc. HCl and the resulting suspension filtered to obtain 4-amino-6-((3-bromophenyl)amino)-1,3,5-triazine-2-carboxylic acid as a white solid.

Yield: (0.298 g, 82% over 2 steps).

ES-MS $[M+H]^+$: 311.9, Rt=0.648 min (Method-A1).

Step 31: Preparation of Example 16

(4-Amino-6-((3-bromophenyl)amino)-1,3,5-triazin-2-yl)(4-phenylpiperazin-1-yl)methanone

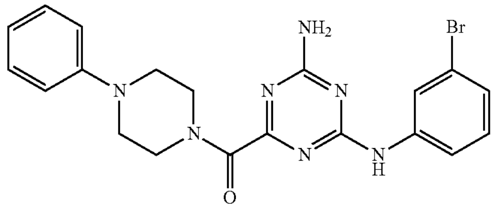 [SMILES: Nc1nc(Nc2cccc(Br)c2)nc(C(=O)N2CCN(c3ccccc3)CC2)n1]

The title compound was synthesized following the procedure described for Intermediate 3 using 4-amino-6-((3-bromophenyl)amino)-1,3,5-triazine-2-carboxylic acid, and isolated as a white powder.

Yield: (0.040 g, 18%).

ES-MS $[M+H]^+$: 455.9, Rt=18.585 min (Method-B1).

$^1$H NMR (400 MHz, DMSO-$d_6$) δ 9.96 (brs, 1H), 8.02 (t, J=2.0 Hz, 1H), 7.80-7.72 (m, 1H), 7.53-7.45 (m, 2H), 7.31-7.20 (m, 3H), 7.20-7.12 (m, 1H), 6.96 (d, J=7.8 Hz, 2H), 6.82 (t, J=7.2 Hz, 1H), 3.80-3.65 (m, 2H), 3.47 (t, J=5.0 Hz, 2H), 3.18 (t, J=5.3 Hz, 2H), 3.13 (t, J=5.1 Hz, 2H).

Example 17

4-Amino-N-benzyl-6-((3-bromophenyl)amino)-N-methyl-1,3,5-triazine-2-carboxamide

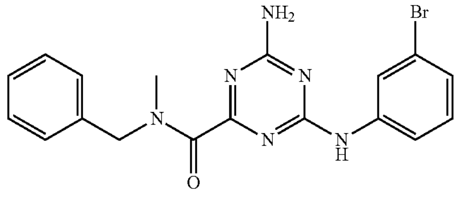 [SMILES: CN(Cc1ccccc1)C(=O)c1nc(N)nc(Nc2cccc(Br)c2)n1]

This compound was synthesized following the procedure described for Intermediate 3 using 4-amino-6-((3-bromophenyl)amino)-1,3,5-triazine-2-carboxylic acid and N-methyl-1-phenylmethanamine, and isolated as a white powder.

Yield: (0.068 g, 34% yield).

ES-MS $[M+H]^+$: 414.9, Rt=18.216 min (Method-B1).

$^1$H NMR (400 MHz, DMSO-$d_6$) δ 9.99-9.85 (m, 1H), 8.00 (dt, J=9.3, 2.0 Hz, 1H), 7.82-7.70 (m, 1H), 7.55-7.40 (m, 2H), 7.42-7.34 (m, 3H), 7.31 (dq, J=7.6, 1.5 Hz, 2H), 7.24 (td, J=8.0, 0.9 Hz, 1H), 7.17 (ddt, J=7.9, 2.0, 1.0 Hz, 1H), 4.52 (d, J=68.5 Hz, 2H), 2.80 (d, J=24.2 Hz, 3H).

Example 18

4-Amino-6-((3-bromophenyl)amino)-N-methyl-N-phenyl-1,3,5-triazine-2-carboxamide

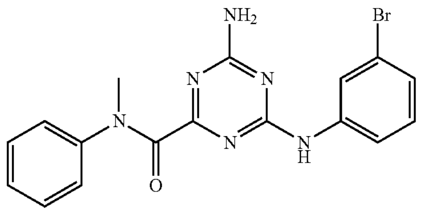 [SMILES: CN(C(=O)c1nc(N)nc(Nc2cccc(Br)c2)n1)c1ccccc1]

The title compound was synthesized following the procedure described for Intermediate 3 using 4-amino-6-((3-bromophenyl)amino)-1,3,5-triazine-2-carboxylic acid and N-methylaniline, and isolated as a white powder.

Yield: (0.029 g, 29%).

ES-MS $[M+H]^+$: 398.9, Rt=17.847 min (Method-B1).

$^1$H NMR (400 MHz, DMSO-$d_6$) δ 7.41-6.89 (m, 12H), 3.32 (s, 3H).

Example 19

4-Amino-6-((3-bromophenyl)amino)-N-(1,2,3,4-tetrahydronaphthalen-2-yl)-1,3,5-triazine-2-carboxamide

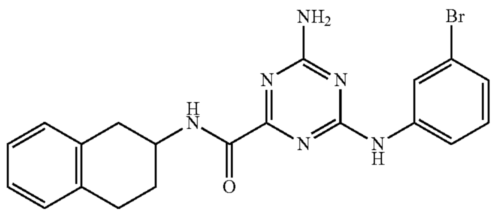 [SMILES: Nc1nc(Nc2cccc(Br)c2)nc(C(=O)NC2CCc3ccccc3C2)n1]

The title compound was synthesized following the procedure described for Intermediate 3 using 4-amino-6-((3-bromophenyl)amino)-1,3,5-triazine-2-carboxylic acid and 1,2,3,4-tetrahydronaphthalen-2-amine, and isolated as a white powder.

Yield: (0.008 g, 3%).

ES-MS $[M+H]^+$: 438.9, Rt=19.904 min (Method-B1).

$^1$H NMR (400 MHz, DMSO-$d_6$) δ 10.04 (brs, 1H), 8.31 (d, J=7.9 Hz, 1H), 8.06 (t, J=2.0 Hz, 1H), 7.80 (d, J=8.3 Hz, 1H), 7.54-7.43 (m, 2H), 7.41-7.13 (m, 2H), 7.12-7.05 (m, 4H), 4.30-3.99 (m, 1H), 3.03 (dd, J=16.5, 4.6 Hz, 1H), 2.92-2.71 (m, 3H), 2.08-1.93 (m, 1H), 1.78 (ddt, J=12.4, 10.3, 8.0 Hz, 1H).

General Procedure B1-2 for the Synthesis of Example 20

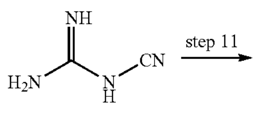

-continued

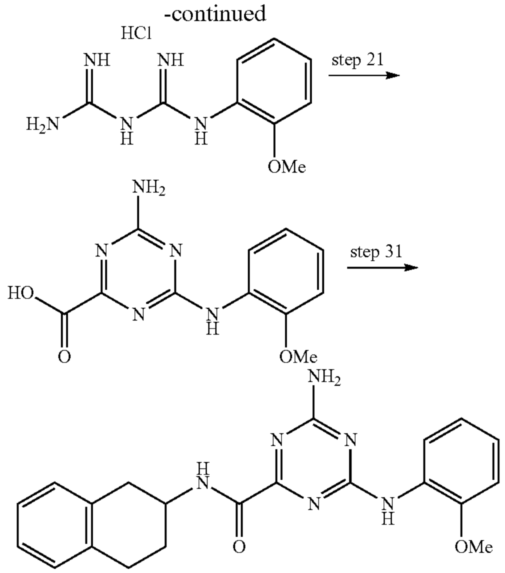

Step 11: Preparation of Intermediate 29

2-Methoxyphenylbiguanide hydrochloride

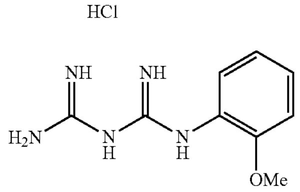 [SMILES: Cl ; COc1ccccc1NC(=N)NC(=N)N]

To a mixture of o-anisidine (1.0 g, 8.13 mmol, 1.0 eq) and dicyandiamide (0.700 g, 8.29 mmol, 0.7 eq) was added 3M HCl (2.84 mL) at room temperature. The reaction mixture was heated to 90° C. for 16 h. After completion of the reaction, the reaction mixture was allowed to cool to room temperature and evaporated under reduced pressure completely and co-distilled twice with toluene. The crude was washed with diethyl ether and dried to get the desired product as pink solid.

Yield: (1.96 g, 99%).

ES-MS $[M+H]^+$: 208.1, Rt=7.037 min (Method-A1).

Step 21: Preparation of Intermediate 30

4-Amino-6-((2-methoxyphenyl)amino)-1,3,5-triazine-2-carboxylic acid

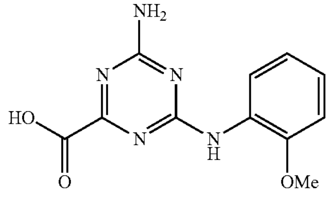 [SMILES: COc1ccccc1Nc1nc(N)nc(C(=O)O)n1]

To a stirred solution of 2-methoxyphenylbiguanide hydrochloride (0.83 g, 3.4 mmol, 1.0 eq) and diethyl oxalate (1.46 mL, 10.8 mmol, 3.0 eq) in MeOH (18 mL) was added NaOMe 25% in MeOH (0.96 mL, 16.8 mmol, 5.0 eq). The resulting mixture was stirred under reflux for 16 h. The reaction mixture was then cooled to room temperature and concentrated to dryness. The resulting solid was poured into water and filtered off to obtain a white solid, which was treated with LiOH (0.290 g, 12.1 mmol, 5.0 eq) in THF:$H_2O$ (1:1, 30 mL) and stirred at room temperature for 3 h. The mixture was then acidified with conc.HCl and the resulting suspension filtered to obtain 4-amino-6-((2-methoxyphenyl)amino)-1,3,5-triazine-2-carboxylic acid as a yellow solid.

Yield: (0.517 g, 58% over 2 steps).

ES-MS $[M+H]^+$: 261.0, Rt=0.567 min (Method-A1).

Step 31: Preparation of Example 20

4-Amino-6-((2-methoxyphenyl)amino)-N-(1,2,3,4-tetrahydronaphthalen-2-yl)-1,3,5-triazine-2-carboxamide

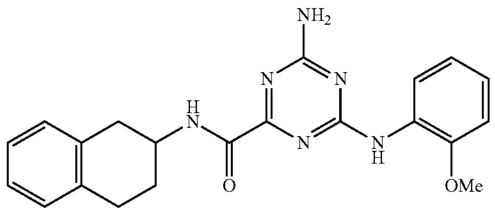 [SMILES: COc1ccccc1Nc1nc(N)nc(C(=O)NC2CCc3ccccc3C2)n1]

The title compound was synthesized following the procedure described for Intermediate 3 using 4-amino-6-((2-methoxyphenyl)amino)-1,3,5-triazine-2-carboxylic acid and 1,2,3,4-tetrahydronaphthalen-2-amine, and isolated as a white powder.

Yield: (0.028 g, 14%).

ES-MS $[M+H]^+$: 391.0, Rt=19.011 min (Method-B1).

$^1H$ NMR (400 MHz, DMSO-$d_6$) δ 8.52-8.35 (m, 1H), 8.33 (s, 1H), 8.01 (d, J=7.9 Hz, 1H), 7.346-7.29 (m, 2H), 7.23-6.99 (m, 6H), 6.92 (td, J=7.5, 1.7 Hz, 1H), 4.22-4.02 (m, 1H), 3.83 (s, 3H), 3.00 (dd, J=16.2, 5.3 Hz, 1H), 2.92-2.68 (m, 3H), 1.99 (td, J=8.5, 4.6 Hz, 1H), 1.87-1.64 (m, 1H).

General Procedure C

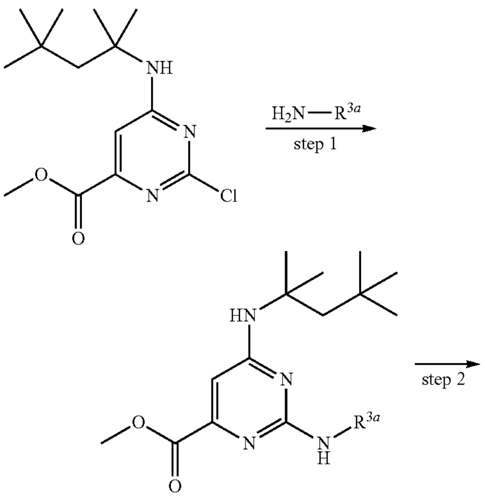

-continued

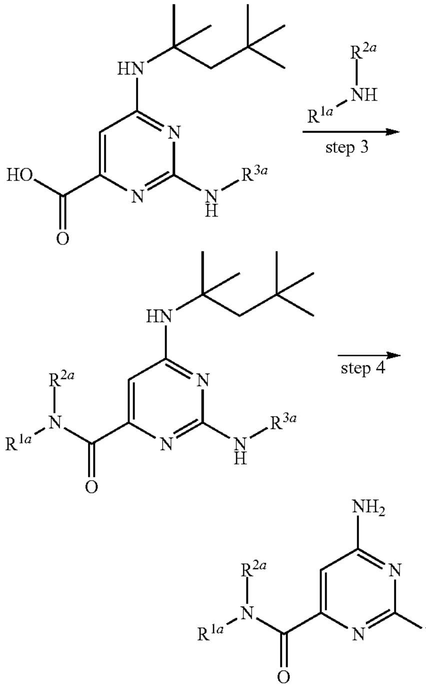

Step 1

To a stirred solution of the appropriate aryl chloride (intermediate 1) (ex: methyl 2-chloro-6-((2,4,4-trimethylpentan-2-yl)amino)pyrimidine-4-carboxylate) (1.0 eq) in 1-butanol (6 mL/mmol) at room temperature were added the appropriate amine (ex: p-toluidine) (1.2 eq), catalytic sulphuric acid (2 drops) and heated to 100° C. for 16 h. After completion of the reaction, the reaction mixture was cooled to room temperature and slowly basified with saturated $NaHCO_3$ and the organic product was extracted into EtOAc. The organic layer was dried over anhydrous sodium sulphate and solvent was evaporated under reduced pressure to get crude product. The crude product was purified by column chromatography (silica gel 230-400 mesh) using 1% to 3% methanol in DCM as eluent to get the desired amine compound (ex: methyl 2-(p-tolylamino)-6-((2,4,4-trimethylpentan-2-yl)amino)pyrimidine-4-carboxylate).

Step 2

Sodium hydroxide (2 eq) was added to a stirred solution of the appropriate carboxylic esther (ex: methyl 2-(p-tolylamino)-6-((2,4,4-trimethylpentan-2-yl)amino)pyrimidine-4-carboxylate) (1 eq) in MeOH:water (10:1 mL) at 0° C. The reaction mixture was stirred at room temperature for 16 h. The reaction mixture was concentrated under reduced pressure. The residue was diluted with water and acidify by 2N HCl at 0° C. The product was precipitated out which was filtered and dried under vacuum to get the crude carboxylic acid product (ex: 2-(p-tolylamino)-6-((2,4,4-trimethylpentan-2-yl)amino)pyrimidine-4-carboxylic acid). The crude product was used in the next step without purification.

Step 3

50% Propylphosphonic anhydride (T3P) (2 eq) solution in EtOAc was added to a suspension of the appropriate carboxylic acid (ex: 2-(p-tolylamino)-6-((2,4,4-trimethylpentan-2-yl)amino)pyrimidine-4-carboxylic acid) (0.25 g, 0.70 mmol, 1 eq), the appropriate amine (ex: N-methyl-1-phenylmethanamine (2 eq) and N,N-diisopropylethylamine) (5 eq) in DCM (3 mL/mmol) at 0° C. The reaction mixture was warmed to room temperature and stirred for 16 h. The reaction mixture was quenched with minimum amount of aqueous $NaHCO_3$ solution, the organic product was extracted with DCM (3×25 mL). The combined organic extracts were dried over anhydrous sodium sulphate. Solvent was distilled under reduced pressure to give the crude compound. The crude product was purified by column chromatography (silica gel 230-400 mesh; 2-4% MeOH in DCM as eluent) to afford the desired amide compound (ex: N-benzyl-N-methyl-2-(p-tolylamino)-6-(2,4,4-trimethylpentan-2-ylamino)pyrimidine-4-carboxamide).

Step 4

Following General Procedure A, Step 3.

General Procedure C1 for the Synthesis of Example 21

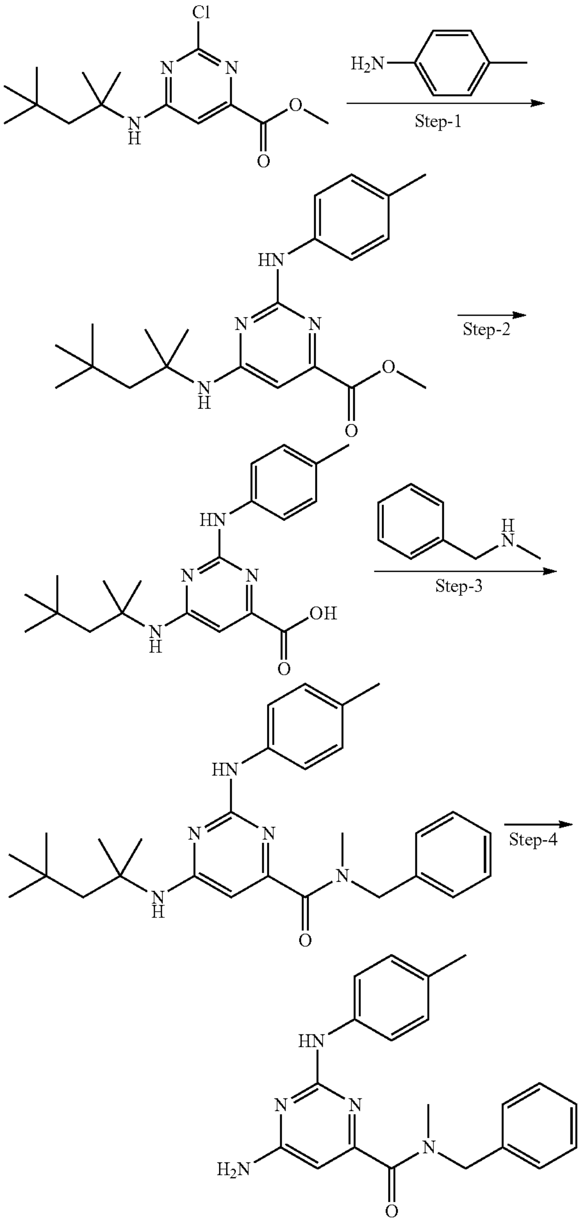

Step-1: Preparation of Intermediate 31

Methyl 2-(p-tolylamino)-6-(2,4,4-trimethylpentan-2-ylamino)pyrimidine-4-carboxylate

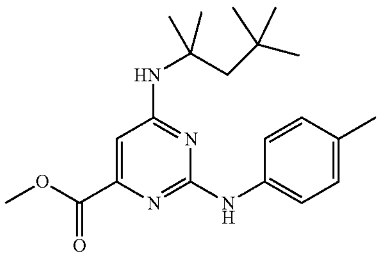

To a stirred solution of methyl 2-chloro-6-((2,4,4-trimethylpentan-2-yl)amino)pyrimidine-4-carboxylate (0.5 g, 1.66 mmol, 1.0 eq) in 1-butanol (10 mL) at RT were added p-toluidine (0.21 g, 2.0 mmol, 1.2 eq), catalytic $H_2SO_4$ (2 drops) and heated to 100° C. for 16 h. After completion of the reaction, the reaction mixture was cooled to RT and slowly basified with saturated $NaHCO_3$ and the organic product was extracted into EtOAc. The organic layer was dried over anhydrous $Na_2SO_4$ and solvent was evaporated under reduced pressure to get crude product. The crude product was purified by column chromatography (silica gel 230-400 mesh) using 1% to 3% MeOH in DCM as eluent to get methyl 2-(p-tolylamino)-6-((2,4,4-trimethylpentan-2-yl)amino)pyrimidine-4-carboxylate as pale yellow solid (the mass showed in LCMS was trans esterification with BuOH).

Yield: (0.35 g, 56%).

ES-MS $[M+H]^+$: 413.32; Rt=2.40 min (Method-C1).

Step-2: Preparation of Intermediate 32

2-(p-Tolylamino)-6-(2,4,4-trimethylpentan-2-ylamino)pyrimidine-4-carboxylic acid

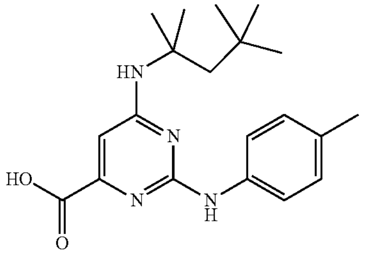 [SMILES: Cc1ccc(Nc2nc(NC(C)(C)CC(C)(C)C)cc(C(=O)O)n2)cc1]

Sodium hydroxide (0.076 g, 1.89 mmol, 2 eq) was added to a stirred solution of methyl 2-(p-tolylamino)-6-((2,4,4-trimethylpentan-2-yl)amino)pyrimidine-4-carboxylate (0.35 g, 0.94 mmol, 1 eq) in MeOH:water (10:1 mL) at 0° C. The reaction mixture was stirred at room temperature for 16 h. The reaction mixture was concentrated under reduced pressure. The residue was diluted with water (8 mL) and acidify by 2N HCl at 0° C. The product was precipitated out which was filtered and dried under vacuum to get crude 2-(p-tolylamino)-6-((2,4,4-trimethylpentan-2-yl)amino)pyrimidine-4-carboxylic acid. The crude product was used in the next step without purification.

Yield: (0.25 g, crude).

ES-MS $[M+H]^+$: 357.18; Rt=2.07 min (Method-C1).

Step-3: Preparation of Intermediate 33

N-benzyl-N-methyl-2-(p-tolylamino)-6-(2,4,4-trimethylpentan-2-ylamino)pyrimidine-4-carboxamide

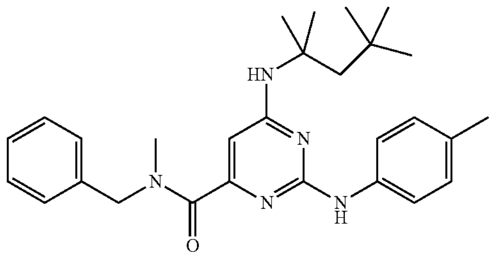 [SMILES: Cc1ccc(Nc2nc(NC(C)(C)CC(C)(C)C)cc(C(=O)N(C)Cc3ccccc3)n2)cc1]

50% propylphosphonic anhydride (T3P) (0.89 mL, 1.40 mmol, 2 eq) solution in EtOAc was added to a suspension of 2-(p-tolylamino)-6-((2,4,4-trimethylpentan-2-yl)amino)pyrimidine-4-carboxylic acid (0.25 g, 0.70 mmol, 1 eq), N-methyl-1-phenylmethanamine (0.17 g, 1.40 mmol, 2 eq) and N,N-diisopropylethylamine (0.45 g, 3.51 mmol, 5 eq) in DCM (10 mL) at 0° C. The reaction mixture was warmed to RT and stirred for 16 h. The reaction mixture was quenched with minimum amount of aqueous $NaHCO_3$ solution, the organic product was extracted with DCM (3×25 mL). The combined organic extracts were dried over anhydrous $Na_2SO_4$. Solvent was distilled under reduced pressure to give the crude compound. The crude product was purified by column chromatography (silica gel 230-400 mesh; 2-4% MeOH in DCM as eluent) to afford 0.21 g of N-benzyl-N-methyl-2-(p-tolylamino)-6-(2,4,4-trimethylpentan-2-ylamino)pyrimidine-4-carboxamide as off-white solid.

Yield: (0.21 g, 48% over 2 step).

ES-MS $[M+H]^+$: 460.82; Rt=2.32 min (Method-C1).

$^1H$ NMR (400 MHz, DMSO-$d_6$): δ 8.91-8.87 (d, J=14.8 Hz, 1H), 7.58-7.52 (m, 2H), 7.36-7.26 (m, 5H), 7.02-7.00 (m, 2H), 6.88 (s, 1H), 6.02-6.00 (d, J=8.4 Hz, 1H), 4.61-4.58 (m, 2H), 2.87 (s, 2H), 2.79 (s, 1H), 2.22 (s, 3H), 1.90-1.99 (m, 2H), 1.43-1.41 (m, 6H), 0.93-0.90 (m, 9H).

Step-4: Preparation of Example 21

6-Amino-N-benzyl-N-methyl-2-(p-tolylamino)pyrimidine-4-carboxamide

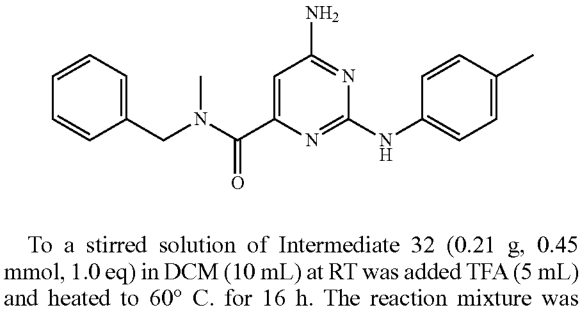

To a stirred solution of Intermediate 32 (0.21 g, 0.45 mmol, 1.0 eq) in DCM (10 mL) at RT was added TFA (5 mL) and heated to 60° C. for 16 h. The reaction mixture was evaporated completely to get the residue which was basified with saturated $NaHCO_3$ and the organic product was extracted into DCM. The organic layer was dried over anhydrous $Na_2SO_4$ and solvent was evaporated under reduced pressure. The crude product was purified by column chromatography (silica gel 230-400 mesh) using 2% to 5%

MeOH in DCM as eluent to get 6-amino-N-benzyl-N-methyl-2-(p-tolylamino)pyrimidine-4-carboxamide as pale brown gummy liquid.

Yield: (78 mg, 49%).

ES-MS $[M+H]^+$: 348.22; Rt=1.87 min (Method-C1).

$^1H$ NMR (400 MHz, DMSO-$d_6$): δ 9.01-8.96 (d, J=16.4 Hz, 1H), 7.65-7.56 (m, 2H), 7.38-7.25 (m, 5H), 7.02-6.98 (m, 2H), 6.77 (s, br, 2H), 5.96-5.94 (d, J=8 Hz, 1H), 4.62-4.57 (m, 2H), 2.88-2.80 (m, 3H), 2.22 (s, 3H).

Intermediate 34

N-(1,2,3,4-tetrahydronaphthalen-2-yl)-2-(p-tolylamino)-6-((2,4,4-trimethylpentan-2-yl)amino)pyrimidine-4-carboxamide

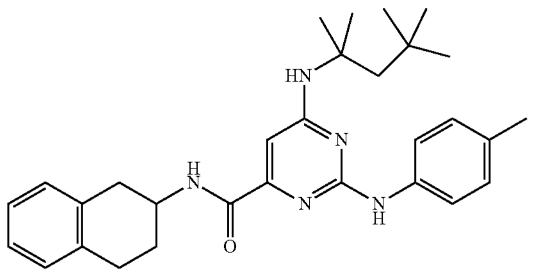 [SMILES: Cc1ccc(Nc2nc(NC(C)(C)CC(C)(C)C)cc(C(=O)NC3CCc4ccccc4C3)n2)cc1]

The title compound was synthesized following the procedure described for preparing Intermediate 33.

Yield: (full conversion, continue without purification).

ES-MS $[M+H]^+$: 486 (raw material).

Example 22

6-Amino-N-(1,2,3,4-tetrahydronaphthalen-2-yl)-2-(p-tolylamino)pyrimidine-4-carboxamide

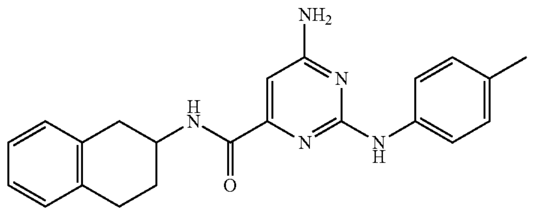 [SMILES: Cc1ccc(Nc2nc(N)cc(C(=O)NC3CCc4ccccc4C3)n2)cc1]

The title compound was synthesized following the procedure described for preparing Example 21.

Yield: (14 mg, 21%).

ES-MS $[M+H]^+$: 374; Rt=3.10 min (Method-C1).

General Procedure $A^2$ for the Synthesis of Example 23

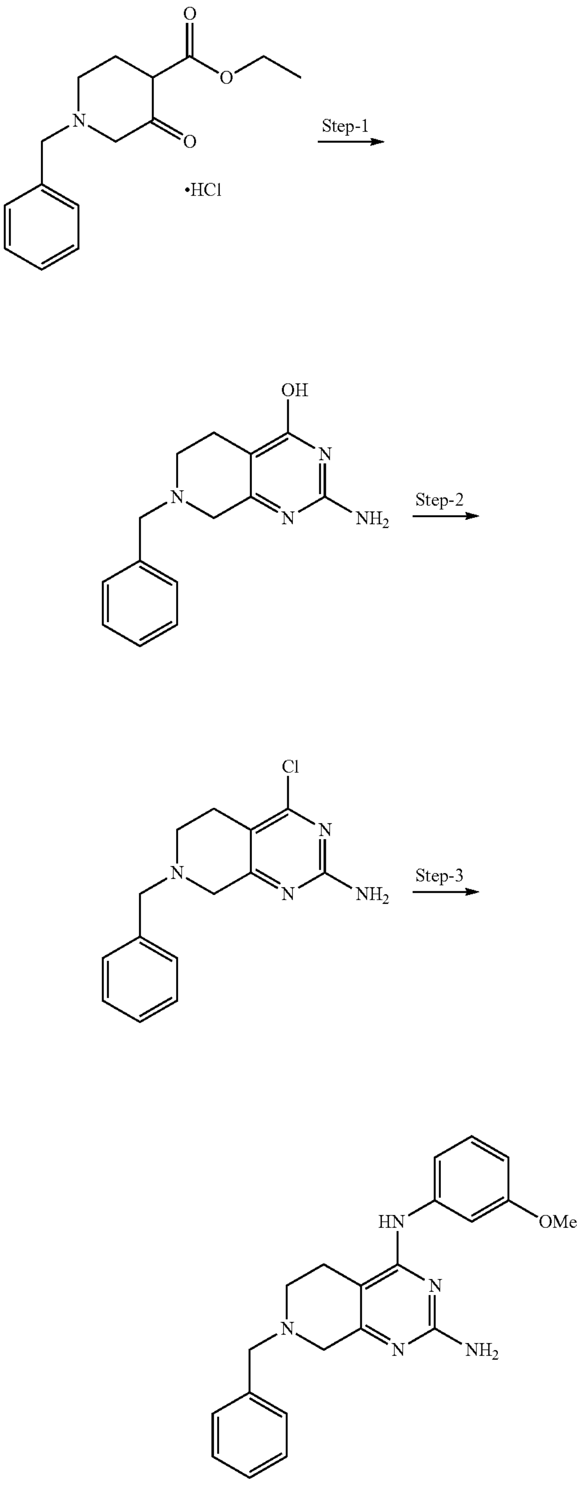

Step-1: Preparation of Intermediate 35

2-Amino-7-benzyl-5,6,7,8-tetrahydropyrido[3,4-d] pyrimidin-4-ol

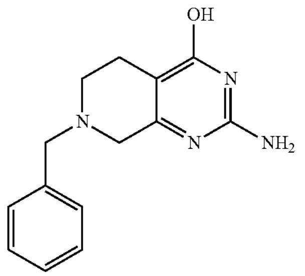 [SMILES: Nc1nc(O)c2c(n1)CN(Cc1ccccc1)CC2]

In a sealed tube, NaOMe (30/a in MeOH; 6.06 mL, 33.6 mmol, 5.0 eq) was added to a stirred solution of ethyl 1-benzyl-3-oxopiperidine-4-carboxylate (HCl salt) (2.0 g, 6.73 mmol, 1.0 eq) in EtOH (30 mL) and stirred for 10 min at RT. To the reaction mixture was added guanidine hydrochloride (0.96 g, 10.1 mmol, 1.5 eq) at RT. The reaction mixture was heated to 100° C. under stirring condition for 16 h. The solvent was evaporated under reduced pressure, diluted with water and pH-6 was adjusted with dilute HCl to get intermediate 1 as a pure solid which was filtered and dried under reduced pressure.

Yield: (1.2 g, 61%).

ES-MS $[M+H]^+$: 257.09, Rt=0.59 min (Method-A2).

$^1H$ NMR (400 MHz, DMSO-$d_6$): δ 11.11 (br s, 1H), 7.35-7.23 (m, 5H), 6.36 (s, 2H), 3.58 (s, 2H), 3.06 (s, 2H), 2.56-2.53 (t, J=12 Hz, 2H), 2.25 (m, 2H).

Step-2: Preparation of Intermediate 36

7-Benzyl-4-chloro-5,6,7,8-tetrahydropyrido[3,4-d] pyrimidin-2-amine

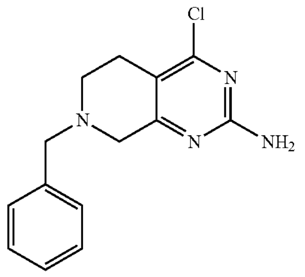 [SMILES: Nc1nc(Cl)c2c(n1)CN(Cc1ccccc1)CC2]

N,N-dimethylaniline (0.01 mL, catalytic) was added to the solution of compound intermediate 1 (0.3 g, 1.1 mmol, 1.0 eq) in $POCl_3$ (3 mL) at RT and heated at 100° C. for 2 h. After completion of reaction, solvent was evaporated under reduced pressure and co-distilled twice by toluene to obtain crude. The crude was used for next step as such without any purification.

Yield: (0.3 g, Crude).

Step-3: Preparation of Example 23

7-Benzyl-N4-(3-methoxyphenyl)-5,6,7,8-tetrahydropyrido[3,4-d]pyrimidine-2,4-diamine

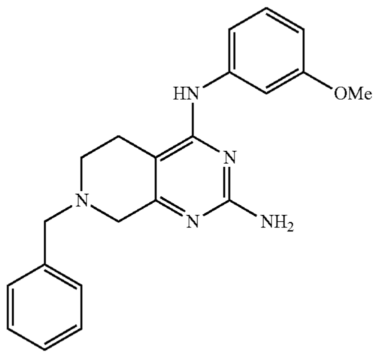 [SMILES: COc1cccc(Nc2nc(N)nc3c2CCN(Cc2ccccc2)C3)c1]

m-Anisidine (0.27 g, 2.2 mmol, 2.0 eq) was added to a solution of intermediate 35 (0.3 g, 1.0 mmol, 1.0 eq) in 1,4-dioxane (5 mL) at RT and heated at 100° C. for 16 h. The reaction mixture was quenched with minimum amount of aqueous $NaHCO_3$ solution, the organic product was extracted with EtOAc (2×10 mL). The combined organic extracts were dried over anhydrous $Na_2SO_4$. Solvent was distilled under reduced pressure to give the crude compound. The crude compound was purified by reverse phase Prep HPLC to afford pure compound 7-benzyl-N4-(3-methoxyphenyl)-5,6,7,8-tetrahydropyrido[3,4-d]pyrimidine-2,4-diamine.

Yield: (0.03 g, 7.6%).

ES-MS $[M+H]^+$: 362.26, Rt=1.49 min (Method-A2).

$^1H$ NMR (300 MHz, DMSO-$d_6$): δ 7.87 (s, 1H), 7.45 (s, 1H), 7.37-7.27 (m, 6H), 7.16-7.12 (t, J=16 Hz, 1H), 6.54-6.52 (d, J=8 Hz, 1H), 5.88 (s, 2H), 3.73 (s, 3H), 3.63 (s, 2H), 3.20 (s, 2H), 2.71-2.68 (t, J=12 Hz, 2H), 2.50 (m, 2H).

Example 24

7-Benzyl-N4-(2-methoxyphenyl)-5,6,7,8-tetrahydropyrido[3,4-d]pyrimidine-2,4-diamine

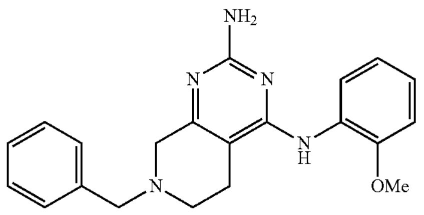 [SMILES: COc1ccccc1Nc1nc(N)nc2c1CCN(Cc1ccccc1)C2]

To a stirred solution of 7-benzyl-4-chloro-5,6,7,8-tetrahydropyrido[3,4-d]pyrimidin-2-amine (intermediate 35, 0.200 g, 0.728 mmol, 1.0 eq) in 1-butanol (3 mL) were added o-anisidine (0.179 g, 1.456 mmol, 2.0 eq) and sulphuric acid (catalytic, 2 drops) at room temperature. The reaction mixture was stirred at 100° C. for 18 h. The reaction mixture was allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography ($MeOH/CH_2Cl_2$ 10%) to obtain 6-benzyl- N2-(3-methoxyphenyl)-5,6,7,8-tetrahydropyrido[4,3-d]pyrimidine-2,4-diamine, as a white solid.

Yield: (0.131 g, 50%).

ES-MS [M+H]$^+$: 362.15, Rt=17.26 min (Method-C2).

$^1$H NMR (400 MHz, DMSO-$d_6$) δ 8.15 (dt, J=7.9, 1.0 Hz, 1H), 7.42-7.28 (m, 4H), 7.32-7.24 (m, 1H), 7.11 (brs, 1H), 7.08-6.88 (m, 2H), 6.95-6.63 (m, 1H), 5.98 (s, 2H), 3.79 (s, 3H), 3.71 (s, 2H), 3.31 (s, 2H), 2.68 (t, J=5.8 Hz, 2H), 2.53 (t, J=5.4 Hz, 2H).

Example 25

2-((2-Amino-7-benzyl-5,6,7,8-tetrahydropyrido[3,4-d]pyrimidin-4-yl)amino)phenol

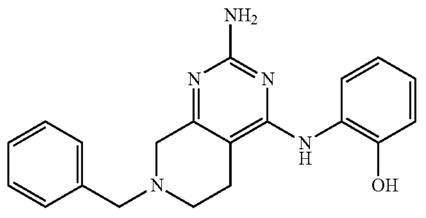 [SMILES: Nc1nc2c(c(Nc3ccccc3O)n1)CCN(Cc1ccccc1)C2]

The title compound was synthesized following the procedure described for preparing Example 24 but using 2-aminophenol instead of o-anisidine in step-3, and isolated as a pale yellow solid.

Yield: (0.102 g, 41% yield).

ES-MS [M+H]$^+$: 348.1, Rt=15.236 min (Method-C2).

$^1$H NMR (400 MHz, DMSO-$d_6$) δ 9.96 (s, 1H), 7.81 (dd, J=8.0, 1.6 Hz, 1H), 7.44-7.31 (m, 5H), 7.31-7.23 (m, 1H), 6.92 (ddd, J=8.0, 7.2, 1.6 Hz, 1H), 6.85 (dd, J=8.0, 1.6 Hz, 1H), 6.78 (ddd, J=8.0, 7.2, 1.7 Hz, 1H), 6.09 (s, 2H), 3.72 (s, 2H), 3.39 (s, 2H), 2.67 (t, J=5.8 Hz, 2H), 2.53 (t, J=5.1 Hz, 2H).

Example 26

7-Benzyl-N4-(4-methoxyphenyl)-5,6,7,8-tetrahydropyrido[3,4-d]pyrimidine-2,4-diamine

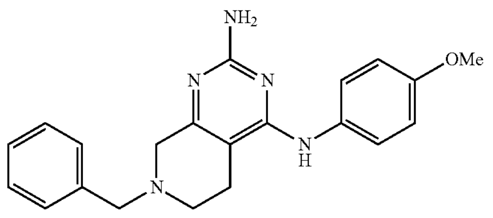 [SMILES: COc1ccc(Nc2nc(N)nc3c2CCN(Cc2ccccc2)C3)cc1]

The title compound was synthesized following the procedure described for preparing Example 24 but using 4-methoxyaniline instead of o-anisidine in step-3, and isolated as a pale yellow solid.

Yield: (0.056 g, 22% yield).

ES-MS [M+H]$^+$: 362.1, Rt=15.734 min (Method-C2).

1H NMR (400 MHz, DMSO-$d_6$) δ 8.11 (brs, 1H), 7.48 (d, J=9.0 Hz, 2H), 7.42-7.31 (m, 4H), 7.32-7.13 (m, 1H), 6.86 (d, J=9.0 Hz, 2H), 6.12 (s, 2H), 3.76-3.79 (m, 5H), 3.41 (s, 2H), 2.66 (t, J=5.4 Hz, 2H), 2.53 (t, J=5.5 Hz, 2H).

General Procedure B2 for the Synthesis of Example 27

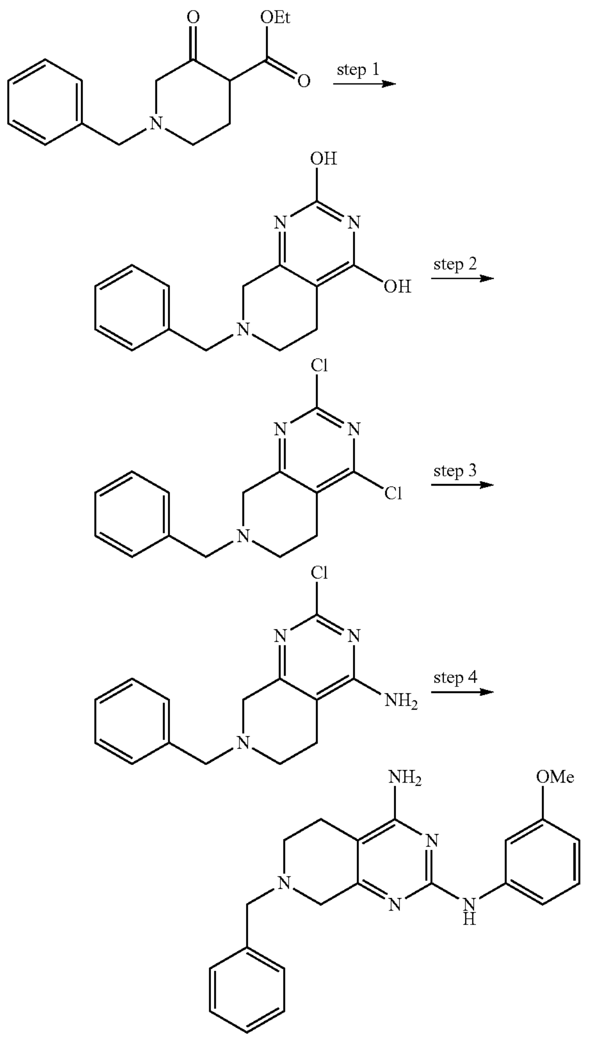

Step 1: Preparation of Intermediate 37

7-Benzyl-5,6,7,8-tetrahydropyrido[3,4-d]pyrimidine-2,4-diol

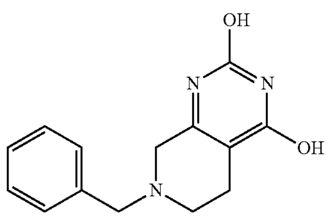 [SMILES: Oc1nc(O)c2c(n1)CN(Cc1ccccc1)CC2]

NaOMe 25% in MeOH (1.92 mL, 8.4 mmol, 5.0 eq) was added to a solution of ethyl 1-benzyl-3-oxopiperidine-4-carboxylate hydrochloride (500 mg, 1.68 mmol, 1.0 eq) and urea (0.50 g, 8.4 mmol, 5.0 eq) in EtOH (10 mL). The reaction mixture was stirred at reflux for 4 h. TLC analysis (EtOAc/Hex 50%) showed the reaction was completed. The reaction mixture was concentrated to dryness and was purified by flash column chromatography (MeOH/DCM 10-20%), to afford 7-benzyl-5,6,7,8-tetrahydropyrido[3,4-d] pyrimidine-2,4-diol, as a white solid.

Yield: (0.604 g, >theorical yield).

ES-MS $[M+H]^+$: 258.1, Rt=8.32 min (Method-B2).

$^1H$ NMR (400 MHz, $CDCl_3$): 10.96 (s, 1H), 10.64 (s, 1H), 7.41-7.21 (m, 5H), 3.20-3.09 (m, 4H), 2.60 (t, J=5.8 Hz, 2H), 2.21 (t, J=5.7 Hz, 2H).

Step 2: Preparation of Intermediate 38

7-Benzyl-2,4-dichloro-5,6,7,8-tetrahydropyrido[3,4-d]pyrimidine

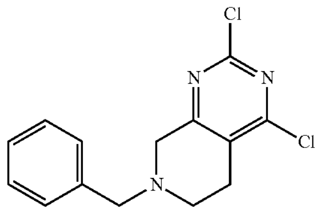 [SMILES: Clc1nc(Cl)c2c(n1)CN(Cc1ccccc1)CC2]

7-Benzyl-5,6,7,8-tetrahydropyrido[3,4-d]pyrimidine-2,4-diol (4.3 g, 16.79 mmol, 1.0 eq) was added in portions over phosphoryl chloride (15 mL, 1 mL/mmol). The reaction mixture was heated at 100° C. under stirring condition for 21 h. The reaction mixture was cooled to room temperature and evaporated under reduced pressure and co-distilled twice with toluene. The crude was redissolved in 10% MeOH/DCM and was taken up in saturated $NaHCO_3$, extracted with DCM (5×) and 2-methyl-THF (3×) and DCM/MeOH 5% (2×). The organic layers were dried over $Na_2SO_4$, filtered and concentrated. The crude product was purified by flash column chromatography (EtOAc/Hex 10-30-40-50%) to obtain, as a pale yellow solid, 7-benzyl-2,4-dichloro-5,6,7,8-tetrahydropyrido[3,4-d]pyrimidine.

Yield: (2.6 g, 53% yield).

ES-MS $[M+H]^+$: 296.1, 294.1, Rt=11.14 min (Method-B2).

Step 3: Preparation of Intermediate 39

7-Benzyl-2-chloro-5,6,7,8-tetrahydropyrido[3,4-d] pyrimidin-4-amine

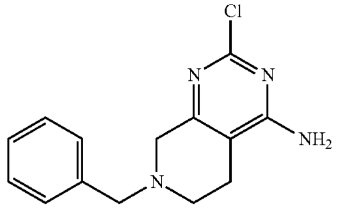 [SMILES: Nc1nc(Cl)nc2c1CCN(Cc1ccccc1)C2]

$NH_3$ (7 N in MeOH, 0.540 mL, 3.785 mmol, 5.0 eq) was added to a suspension of 7-benzyl-2,4-dichloro-5,6,7,8-tetrahydropyrido[3,4-d]pyrimidine (0.222 g, 0.757 mmol, 1.0 eq) in THF (8 mL). The resulting yellow suspension was warmed up to 60° C. and stirred at this temperature for 3 h. TLC analysis (EtOAc/Hex 10%) showed no reaction. More $NH_3$ (7 N in MeOH, 20 eq) was added to the reaction mixture and this was stirred at 60° C. for another hour. TLC analysis (EtOAc/Hex 10%) showed no reaction. More $NH_3$ (7 N in MeOH, 100 eq) was added to the reaction mixture and this was stirred at reflux for 5 h TLC analysis (EtOAc/Hex 10%) showed formation of two new spots. Reaction mixture was concentrated to dryness and purified by flash column chromatography (MeOH/DCM 2-5%) to obtain 7-benzyl-2-chloro-5,6,7,8-tetrahydropyrido[3,4-d]pyrimidin-4-amine, as a beige solid.

Yield: (0.074 g, 27% yield).

ES-MS $[M+H]^+$: 275.0, 277.1, Rt=9.27 min (Method-B2).

$^1H$ NMR (400 MHz, DMSO-$d_6$): 7.40-7.24 (m, 5H), 3.62 (s, 2H), 3.27 (s, 2H), 2.66 (d, J=6.6 Hz, 2H), 2.33 (s, 2H).

Step 4: Preparation of Example 27

7-Benzyl-$N^2$-(3-methoxyphenyl)-5,6,7,8-tetrahydropyrido[3,4-d]pyrimidine-2,4-diamine

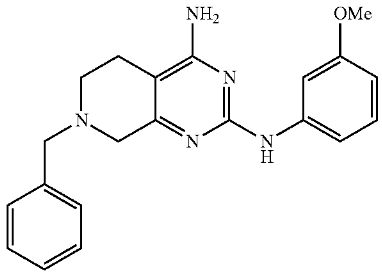 [SMILES: COc1cccc(Nc2nc(N)c3c(n2)CN(Cc2ccccc2)CC3)c1]

To a stirred solution of 7-benzyl-2-chloro-5,6,7,8-tetrahydropyrido[3,4-d]pyrimidin-4-amine (0.070 g, 0.255 mmol, 1.0 eq) in 1-butanol (3 mL) were added m-anisidine (0.063 g, 0.510 mmol, 2.0 eq) and sulphuric acid (catalytic, 2 drops) at room temperature. The reaction mixture was stirred at 100° C. for 21 h. The reaction mixture was allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography (MeOH/DCM 3-5%). The product obtained was slurred with mixture EtOAc/Hex 1:1 to obtain 7-benzyl-$N^2$-(3-methoxyphenyl)-5,6,7,8-tetrahydropyrido[3,4-d]pyrimidine-2,4-diamine, as a white solid.

Yield: (0.026 g, 30% yield).

ES-MS $[M+H]^+$: 362.1, Rt=19.24 min (Method-C2).

$^1H$ NMR (400 MHz, DMSO-$d_6$): 8.70 (s, 1H), 7.51 (s, 1H), 7.41-7.32 (m, 4H), 7.26 (d, J=9.6 Hz, 2H), 7.06 (t, J=8.2 Hz, 1H), 6.39 (s, 3H), 3.69 (s, 3H), 3.64 (s, 2H), 3.27 (s, 2H), 2.68 (s, 2H), 2.36 (s, 2H).

Example 28

7-Benzyl-N2-(2-methoxyphenyl)-5,6,7,8-tetrahydro-pyrido[3,4-d]pyrimidine-2,4-diamine

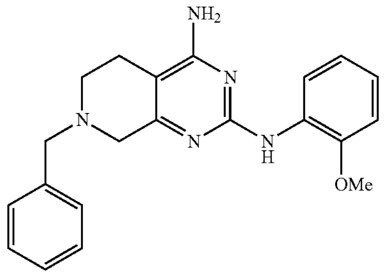 [SMILES: COc1ccccc1Nc1nc(N)c2c(n1)CN(Cc1ccccc1)CC2]

The title compound was synthesized from Intermediate 36 following the procedure described for preparing Example 27 using o-anisidine and isolated as a pale brown solid.

Yield: (0.072 g, 47% yield).

ES-MS $[M+H]^+$: 362.1, Rt=19.32 min (Method-C2).

$^1H$ NMR (300 MHz, DMSO-$d_6$) δ 7.79-7.34 (m, 1H), 6.82-6.40 (m, 6H), 6.23-5.91 (m, 3H), 5.69 (brs, 2H), 3.00 (s, 3H), 2.80 (s, 2H), 2.41 (s, 2H), 1.84 (t, J=5.7 Hz, 2H), 1.56-1.48 (m, 2H).

Example 29

2-((4-Amino-7-benzyl-5,6,7,8-tetrahydropyrido[3,4-d]pyrimidin-2-yl)amino)phenol

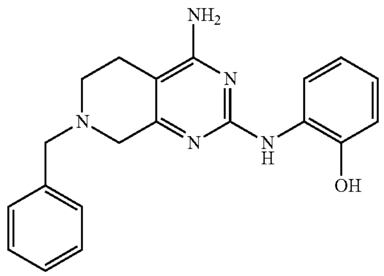 [SMILES: Nc1nc(Nc2ccccc2O)nc2c1CCN(Cc1ccccc1)C2]

The title compound was synthesized from Intermediate 36 following the procedure described for preparing Example 27 using 2-aminophenol and isolated as a white solid.

Yield: (0.029 g, 31% yield).

ES-MS $[M+H]^+$: 348.0, Rt=18.068 min (Method-C2).

$^1H$ NMR (400 MHz, DMSO-$d_6$) δ 10.74 (brs, 1H), 7.88 (s, 1H), 7.81-7.60 (m, 1H), 7.38-7.31 (m, 4H), 7.31-7.23 (m, 1H), 6.89-6.67 (m, 3H), 6.63 (brs, 2H), 3.64 (s, 2H), 3.23 (s, 2H), 2.68 (t, J=5.8 Hz, 2H), 2.38-2.30 (m, 2H).

Example 30

7-Benzyl-N2-(4-methoxyphenyl)-5,6,7,8-tetrahydro-pyrido[3,4-d]pyrimidine-2,4-diamine

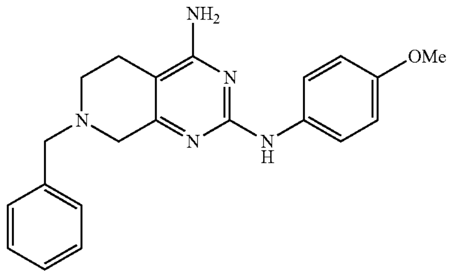 [SMILES: COc1ccc(Nc2nc(N)c3c(n2)CN(Cc2ccccc2)CC3)cc1]

The title compound was synthesized following the procedure described for preparing Example 27 but using 4-methoxyaniline instead of m-anisidine in step 4, and isolated as a white solid.

Yield: (0.032 g, 12% yield).

ES-MS $[M+H]^+$: 362.11, Rt=16.790 min (Method-C2).

$^1H$ NMR (400 MHz, DMSO-$d_6$) δ 8.47 (s, 1H), 7.61 (d, J=9.1 Hz, 2H), 7.44-7.23 (m, 4H), 7.30-7.10 (m, 1H), 6.77 (d, J=9.1 Hz, 2H), 6.29 (brs, 2H), 3.68 (s, 3H), 3.63 (s, 2H), 3.22 (s, 2H), 2.67 (t, J=5.8 Hz, 2H), 2.34 (t, J=6.1 Hz, 2H).

General Procedure C2 for the Synthesis of Example 31

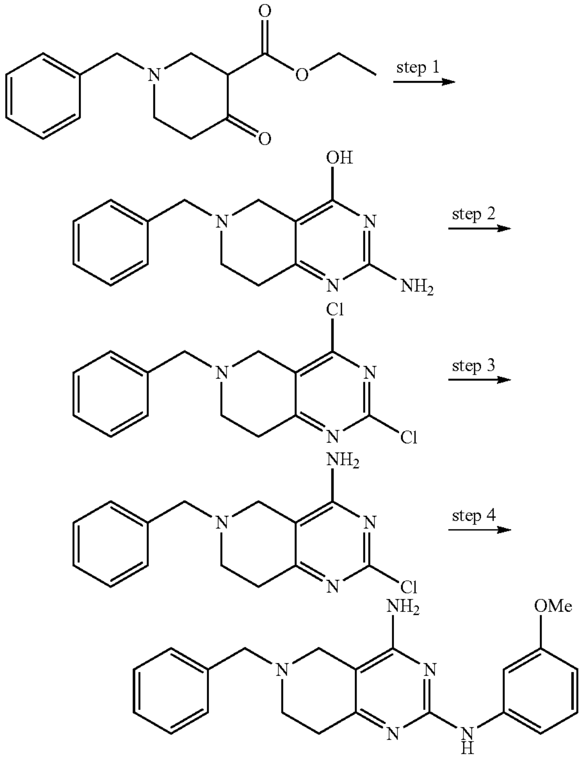

Step 1: Preparation of Intermediate 40

6-Benzyl-5,6,7,8-tetrahydropyrido[4,3-d]pyrimidine-2,4-diol

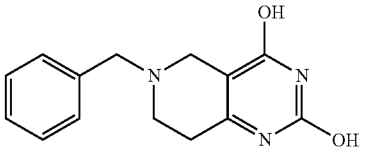 [SMILES: Oc1nc(O)c2c(n1)CCN(Cc1ccccc1)C2]

NaOMe 25% in MeOH (0.440 mL, 1.91 mmol, 5.0 eq) was added to a solution of ethyl 1-benzyl-4-oxopiperidine-3-carboxylate (0.10 g, 0.382 mmol, 1.0 eq) and urea (0.115 g, 1.91 mmol, 5.0 eq) in EtOH (3 mL). The reaction mixture was stirred at reflux for 18 h. TLC analysis (EtOAc/Hex 50%) showed the reaction was completed. The reaction mixture was concentrated to dryness, water was added and the resulting solid was filtrated and dried to afford 6-benzyl-5,6,7,8-tetrahydropyrido[4,3-d]pyrimidine-2,4-diol, as light brown solid, which was used without further purification.

Yield: (0.172 g, crude).

ES-MS $[M+H]^+$: 258.19, Rt=0.42 min (Method-B2).

Step 2: Preparation of Intermediate 41

6-Benzyl-2,4-dichloro-5,6,7,8-tetrahydropyrido[4,3-d]pyrimidine

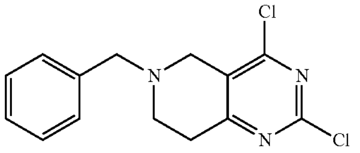 [SMILES: Clc1nc(Cl)c2c(n1)CCN(Cc1ccccc1)C2]

6-benzyl-5,6,7,8-tetrahydropyrido[4,3-d]pyrimidine-2,4-diol (0.172 g, 0.67 mmol, 1 eq) was added in portions over phosphoryl chloride (1 mL/mmol). The reaction mixture was heated at 100° C. under stirring condition for 18 h. The reaction mixture was cooled to room temperature and evaporated under reduced pressure and co-distilled twice with toluene to obtain 6-benzyl-2,4-dichloro-5,6,7,8-tetrahydropyrido[4,3-d]pyrimidine as a brown solid, which was used without further purification.

Yield: (0.097 g, crude).

ES-MS $[M+H]^+$: 296.08, 294.05, Rt=1.88 min (Method-B2).

Step 3: Preparation of Intermediate 42

6-Benzyl-2-chloro-5,6,7,8-tetrahydropyrido[4,3-d]pyrimidin-4-amine

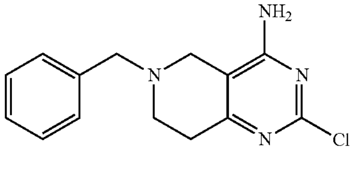 [SMILES: Nc1nc(Cl)nc2c1CN(Cc1ccccc1)CC2]

$NH_3$ (7 N in MeOH, 0.145 mL, 0.996 mmol, 5.0 eq) was added to a suspension of 6-benzyl-2,4-dichloro-5,6,7,8-tetrahydropyrido[4,3-d]pyrimidine (0.097 g, 0.332 mmol, 1.0 eq) in THF (0.7 mL). The resulting yellow suspension was stirred at 60° C. in a sealed tube for 16 h. TLC analysis (EtOAc/Hex 10%) showed partial conversion. Additional $NH_3$ (7 N in MeOH, 20 eq) was added to the reaction mixture and this was stirred at 60° C. for 3 days. LC-MS analysis (Method-B) showed formation of desired product. Reaction mixture was concentrated to dryness to obtain 6-benzyl-2-chloro-5,6,7,8-tetrahydropyrido[4,3-d]pyrimidin-4-amine, as a beige solid, which was used without further purification.

Yield: (0.092 g, crude).

ES-MS $[M+H]^+$: 277.14, 275.09, Rt=0.92 min (Method-B2).

Step 4: Preparation of Example 31

6-Benzyl-N2-(3-methoxyphenyl)-5,6,7,8-tetrahydropyrido[4,3-d]pyrimidine-2,4-diamine hydrochloride

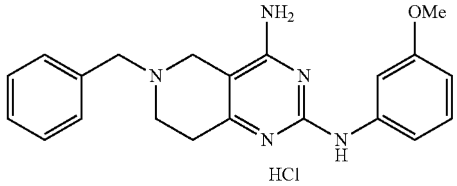 [SMILES: COc1cccc(Nc2nc(N)c3c(n2)CCN(Cc2ccccc2)C3)c1 ; Cl]

To a stirred solution of 6-benzyl-2-chloro-5,6,7,8-tetrahydropyrido[4,3-d]pyrimidin-4-amine (0.092 g, 0.332 mmol, 1.0 eq) in 1-butanol (3 mL) were added m-anisidine (0.082 g, 0.664 mmol, 2.0 eq) and sulphuric acid (catalytic, 2 drops) at room temperature. The reaction mixture was stirred at 100° C. for 18 h. The reaction mixture was allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography (EtOAc/Heptane 50-100) to obtain 6-benzyl-N2-(3-methoxyphenyl)-5,6,7,8-tetrahydropyrido[4,3-d]pyrimidine-2,4-diamine, as a white solid, which was treated with HCl (6N in iPrOH) and stirred at rt for 1 h. The resulting solid was filtered and triturated with DIPE to obtain 6-benzyl-N2-(3-methoxyphenyl)-5,6,7,8-tetrahydropyrido[4,3-d]pyrimidine-2,4-diamine hydrochloride as a light brown powder.

Yield: (0.032 g, 27%).

ES-MS $[M+H]^+$: 362.17, Rt=17.08 min (Method-C2).

$^1H$ NMR (400 MHz, DMSO-$d_6$) δ 12.05 (brs, 1H), 10.15 (s, 1H), 8.35 (brs, 1H), 7.76-7.61 (m, 2H), 7.48 (p, J=3.9 Hz, 3H), 7.37-7.17 (m, 2H), 7.10 (dd, J=7.8, 2.0 Hz, 1H), 6.72 (dd, J=8.2, 2.5 Hz, 1H), 4.45 (s, 2H), 4.05-3.81 (m, 1H), 3.77 (s, 3H), 3.69-3.38 (m, 4H), 3.28-3.23-2.88 (m, 1H).

General Procedure D2 for the Synthesis of Example 32

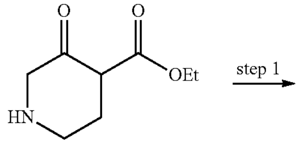

-continued

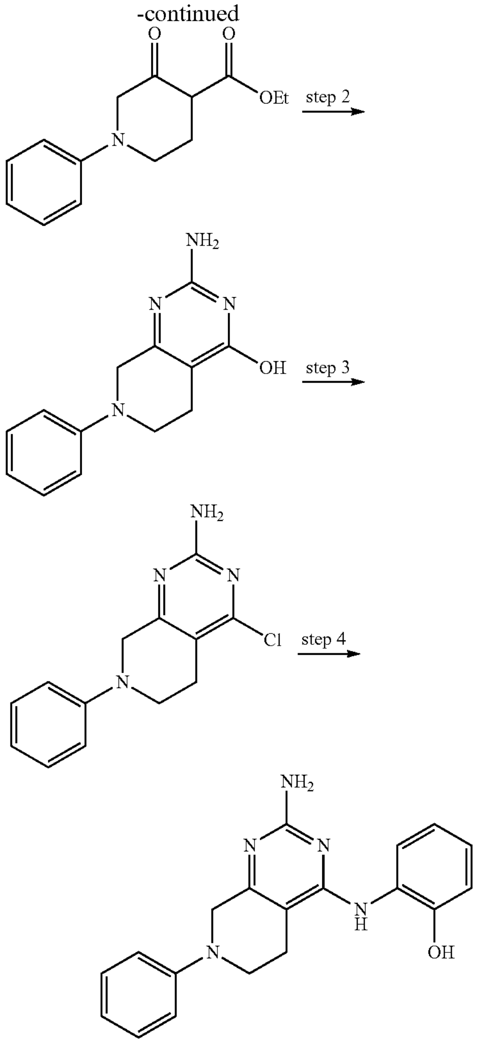

Step 1: Preparation of Intermediate 43

Ethyl 3-oxo-1-phenylpiperidine-4-carboxylate

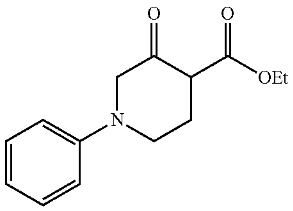 [SMILES: CCOC(=O)C1CCN(c2ccccc2)CC1=O]

BINAP (0.239 g, 0.38 mmol, 4 mol %) and Pd2(dba)$_3$ (0.176 g, 0.19 mmol, 2 mol %) were added over a degassed solution of ethyl 3-oxopiperidine-4-carboxylate (1.64 g, 9.58 mmol, 1.0 eq), bromobenzene (1.1 mL, 10.54 mmol, 1.1 eq) and NaOtBu (2.76 g, 28.74 mmol, 3.0 eq) in toluene (20 mL). The resulting mixture was stirred under reflux for 90 min. TLC analysis (MeOH/$CH_2Cl_2$ 5%) showed complete conversion. The reaction mixture was allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography (EtOAc/Hex 10-20%) to obtain ethyl 3-oxo-1-phenylpiperidine-4-carboxylate as a yellow oil.

Yield: (1.6 g, 63%).

ES-MS [M+H]$^+$: 247.7, Rt=11.39 min (Method-B2).

$^1$H NMR (400 MHz, Chloroform-d) δ 12.44 (s, 1H), 7.68 (t, J=7.0 Hz, 2H), 7.35-7.22 (m, 3H), 4.65 (qd, J=7.1, 1.9 Hz, 2H), 4.23 (s, 2H), 3.77 (d, J=5.8 Hz, 2H), 2.85 (ddd, J=7.7, 3.9, 1.9 Hz, 2H), 1.72 (td, J=7.1, 1.9 Hz, 3H).

Step 2: Preparation of Intermediate 44

2-Amino-7-phenyl-5,6,7,8-tetrahydropyrido[3,4-d]pyrimidin-4-ol

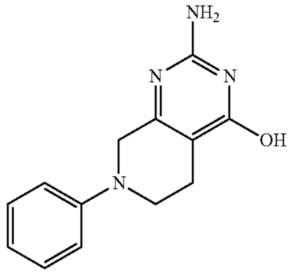 [SMILES: Nc1nc(O)c2c(n1)CN(c1ccccc1)CC2]

NaOMe (25% in MeOH, 3.7 mL, 16.2 mmol, 5.0 eq) was added to a solution of ethyl 3-oxo-1-phenylpiperidine-4-carboxylate (0.8 g, 3.24 mmol, 1.0 eq) and guanidine hydrochloride (0.464 g, 4.86 mmol, 1.5 eq) in EtOH (20 mL). The reaction mixture was stirred under nitrogen at reflux for 2 h. The reaction mixture was cooled to rt adsorbed in silica gel. The resultant crude was purified by flash column chromatography (MeOH/$CH_2Cl_2$ 10%) to afford 2-amino-7-phenyl-5,6,7,8-tetrahydropyrido[3,4-d]pyrimidin-4-ol as white solid.

Yield: (0.678 g, 83%).

ES-MS [M+H]$^+$: 243.0 (Method-B2).

$^1$H NMR (400 MHz, DMSO-d$_6$) δ 9.96 (brs, 1H), 6.36 (q, J=7.9 Hz, 2H), 6.16-6.06 (m, 2H), 5.95-5.85 (m, 1H), 5.56-5.43 (m, 2H), 3.06-2.97 (m, 2H), 2.60-2.52 (m, 2H), 1.70-1.61 (m, 2H), 1.58-1.48 (m, 2H).

Step 3: Preparation of Intermediate 45

4-Chloro-7-phenyl-5,6,7,8-tetrahydropyrido[3,4-d]pyrimidin-2-amine

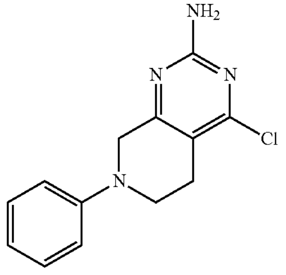 [SMILES: Nc1nc(Cl)c2c(n1)CN(c1ccccc1)CC2]

2-Amino-7-phenyl-5,6,7,8-tetrahydropyrido[3,4-d]pyrimidin-4-ol (0.68 g, 2.81 mmol, 1.0 eq) was added in portions over phosphoryl chloride (1 mL/mmol). The reaction mixture was heated at 100° C. under stirring condition for 2 h. The reaction mixture was cooled to room temperature and evaporated under reduced pressure and co-distilled twice with toluene. The resultant crude was purified by flash column chromatography (MeOH/$CH_2Cl_2$ 10%) to afford 4-chloro-7-phenyl-5,6,7,8-tetrahydropyrido[3,4-d]pyrimidin-2-amine as a brown oil.

Yield: (0.72 g, impure).

ES-MS $[M+H]^+$: mass not detected (Method-B2).

Step 4: Preparation of Example 32

2-((2-Amino-7-phenyl-5,6,7,8-tetrahydropyrido[3,4-d]pyrimidin-4-yl)amino)phenol

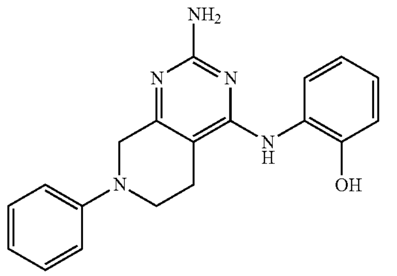 [SMILES: Nc1nc2c(c(Nc3ccccc3O)n1)CCN(c1ccccc1)C2]

To a stirred solution of 4-chloro-7-phenyl-5,6,7,8-tetrahydropyrido[3,4-d]pyrimidin-2-amine (0.720 g, 2.77 mmol, 1.0 eq) in 1-butanol (20 mL) were added 2-aminophenol (0.302 g, 2.77 mmol, 1.0 eq) and sulphuric acid (catalytic, 2 drops) at room temperature. The reaction mixture was stirred at 100° C. for 16 h. The reaction mixture was allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography (EtOAc/Hexane 10-50%) to obtain 2-((2-amino-7-phenyl-5,6,7,8-tetrahydropyrido[3,4-d]pyrimidin-4-yl)amino)phenol, as a beige solid.

Yield: (0.023 g, 2.5%).

ES-MS $[M+H]^+$: 334.2, Rt=17.309 min (Method-C2).

$^1$H NMR (400 MHz, DMSO-$d_6$) δ 10.07 (brs, 1H), 8.01 (d, J=7.9 Hz, 1H), 7.56 (s, 1H), 7.24 (t, J=7.7 Hz, 2H), 7.01 (d, J=8.1 Hz, 2H), 6.96-6.85 (m, 2H), 6.78 (q, J=6.8 Hz, 2H), 6.14 (s, 2H), 4.02 (s, 2H), 3.73-3.55 (m, 2H), 2.62-2.53 (s, 2H).

Preparation of Compounds of Formula (IA) of Examples 33-141

Intermediate 46

2-(((1S,2S)-2-hydroxycyclohexyl)amino)-N-methyl-N-phenyl-6-((2,4,4-trimethylpentan-2-yl)amino)pyrimidine-4-carboxamide

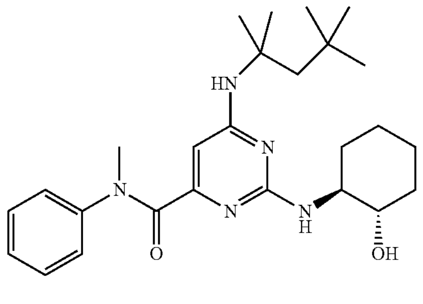 [SMILES: CN(C(=O)c1cc(NC(C)(C)CC(C)(C)C)nc(N[C@H]2CCCC[C@@H]2O)n1)c1ccccc1]

To a stirred solution of 2-chloro-N-methyl-N-phenyl-6-((2,4,4-trimethylpentan-2-yl)amino)pyrimidine-4-carboxamide (Intermediate 10) (0.160 g, 0.43 mmol, 1.0 eq) in DMF (1.5 mL) were added (1S,2S)-2-aminocyclohexan-1-ol (0.150 g, 1.30 mmol, 3.0 eq) and sulphuric acid (catalytic, 1 drop) at room temperature. The reaction mixture was stirred at 130° C. for 18 h. The reaction mixture was then allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography (EtOAc/Heptane 50-100) to obtain 2-(((1S,2S)-2-hydroxycyclohexyl)amino)-N-methyl-N-phenyl-6-((2,4,4-trimethylpentan-2-yl)amino)pyrimidine-4-carboxamide as a white solid.

Yield: (0.020 g, 10%).

ES-MS $[M+H]^+$:454.2, Rt=7.305 min (Method-A1)

Example 33

6-Amino-2-(((1S,2S)-2-hydroxycyclohexyl)amino)-N-methyl-N-phenylpyrimidine-4-carboxamide

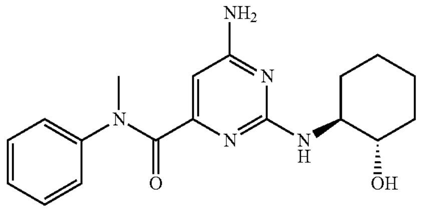 [SMILES: CN(C(=O)c1cc(N)nc(N[C@H]2CCCC[C@@H]2O)n1)c1ccccc1]

Synthesized following General Procedure A, Step 3. Isolated as a white solid.

Yield: (0.023 g, 38%).

ES-MS $[M+H]^+$: 342.1, Rt=15.226 min (Method-B1).

$^1$H NMR (400 MHz, DMSO-$d_6$) δ 7.29 (m, 2H), 7.25-7.10 (m, 3H), 6.46 (brs, 2H), 6.03 (s, 1H), 5.72 (s, 1H), 4.60 (s, 1H), 3.31 (d, J=6.1 Hz, 3H), 3.19 (s, 2H), 1.82 (m, 2H), 1.56 (m, 2H), 1.14 (m, 4H).

Intermediate 47

Methyl 2-chloro-6-((2-methoxyphenyl)amino)pyrimidine-4-carboxylate

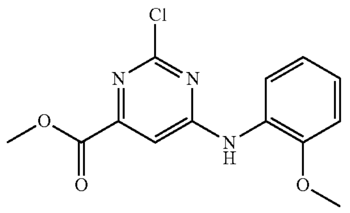

To a stirred mixture of methyl 2,6-dichloropyrimidine-4-carboxylate (5.0 g, 24.14 mmol, 1.0 eq), 2-methoxyaniline (2.73 mL, 24.14 mmol, 1.0 eq) in methanol (50 mL) was added natrium carbonate (2.81 g, 26.55 mmol, 1.1 eq). The resulting mixture was stirred at room temperature for 16 h. The mixture was evaporated to dryness and the resulting residue was partitioned between water and EtOAc. Aqueous layer was extracted with EtOAc (×2), dried over anhydrous sodium sulphate, filtered and concentrated to dryness. The resultant crude was purified by flash column chromatography (EtOAc/Heptane 50-100) to obtain methyl 2-chloro-6-((2-methoxyphenyl)amino)pyrimidine-4-carboxylate as a white solid.

Yield: (5.26 g, 74%).

ES-MS $[M+H]^+$: 294.1, Rt=6.09 min (Method-A1)

Intermediate 48

Methyl 6-((2-methoxyphenyl)amino)-2-((2,4,4-trimethylpentan-2-yl)amino)pyrimidine-4-carboxylate

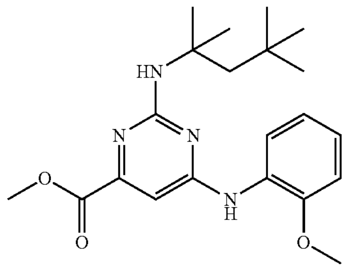

To a stirred mixture of methyl 2-chloro-6-((2-methoxyphenyl)amino)pyrimidine-4-carboxylate (0.40 g, 1.34 mmol, 1.0 eq), tert-octylamine (1.1 mL, 6.72 mmol, 5.0 eq) in DMF (4 mL) was added DIPEA (1.2 mL, 6.72 mmol, 5.0 eq). The resulting mixture was stirred at 120° C. for 16 h. The mixture was diluted with water and extracted with ethyl acetate (×3), dried over anhydrous sodium sulphate, filtered and concentrated to dryness. The resultant crude was purified by flash column chromatography (EtOAc/Heptane 50-100) to obtain methyl 6-((2-methoxyphenyl)amino)-2-((2,4,4-trimethylpentan-2-yl)amino)pyrimidine-4-carboxylate as a colorless wax.

Yield: (0.094 g, 20% yield).

ES-MS $[M+H]^+$: 387.2, Rt=7.57 min (Method-A1)

Intermediate 49

6-((2-Methoxyphenyl)amino)-2-((2,4,4-trimethylpentan-2-yl)amino)pyrimidine-4-carboxylic acid

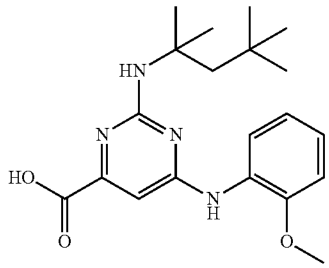 [SMILES: COc1ccccc1Nc1cc(C(=O)O)nc(NC(C)(C)CC(C)(C)C)n1]

To a stirred mixture of methyl 6-((2-methoxyphenyl)amino)-2-((2,4,4-trimethylpentan-2-yl)amino)pyrimidine-4-carboxylate (0.094 g, 0.243 mmol, 1.0 eq.) in THF:$H_2O$ (1:1, 3 mL) was added lithium hydroxide (0.051 g, 1.216 mmol, 5.0 eq). The resulting mixture was stirred at room temperature for 2 h. The mixture was evaporated to dryness, acidified with the addition of conc. HCl, and extracted with EtOAc/MeOH (×3), dried over anhydrous sodium sulphate, filtered and concentrated to dryness to obtain 6-((2-methoxyphenyl)amino)-2-((2,4,4-trimethylpentan-2-yl)amino)pyrimidine-4-carboxylic acid as a pale yellow solid, which was used without further purification.

Yield: (0.084 g, 93% yield).

ES-MS $[M+H]^+$: 373.1, Rt=6.790 min (Method-A1).

Intermediate 50

(6-((2-Methoxyphenyl)amino)-2-((2,4,4-trimethylpentan-2-yl)amino)pyrimidin-4-yl)(4-phenylpiperazin-1-yl)methanone

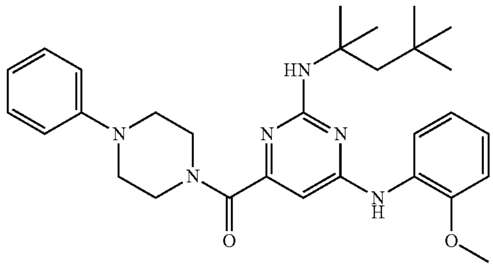 [SMILES: COc1ccccc1Nc1cc(C(=O)N2CCN(c3ccccc3)CC2)nc(NC(C)(C)CC(C)(C)C)n1]

To a stirred solution of 6-((2-methoxyphenyl)amino)-2-((2,4,4-trimethylpentan-2-yl)amino)pyrimidine-4-carboxylic acid (0.084 g, 0.225 mmol, 1.0 eq), 1-phenylpiperazine (0.045 mL, 0.293 mmol, 1.3 eq) and HATU (0.102 g, 0.270 mmol, 1.2 eq) in DMF (1 mL) was added DIPEA (0.059 mL, 0.337 mmol, 1.5 eq). The resulting mixture was stirred at room temperature for 14 h. The reaction mixture was quenched with saturated sodium bicarbonate. The aqueous layer was extracted with ethyl acetate (×3), dried over anhydrous sodium sulphate, filtered and concentrated to dryness. The resultant crude was purified by flash column chromatography (EtOAc/Heptane 50-100) to obtain (6-((2-methoxyphenyl)amino)-2-((2,4,4-trimethylpentan-2-yl)amino)pyrimidin-4-yl)(4-phenylpiperazin-1-yl)methanone as a yellow wax.

Yield: (0.059 g, 51% yield).

ES-MS $[M+H]^+$:517.2 Rt=7.707 min (Method-A1).

Example 34

(2-Amino-6-((2-methoxyphenyl)amino)pyrimidin-4-yl)(4-phenylpiperazin-1-yl)methanone

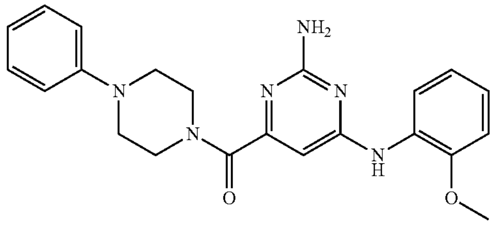 [SMILES: COc1ccccc1Nc1cc(C(=O)N2CCN(c3ccccc3)CC2)nc(N)n1]

Synthesized following General Procedure A, Step 3. Isolated as a white solid. No further purification.

Yield: (0.033 g, 72% yield).

ES-MS $[M-H]^-$: 403.3, Rt=17.701 min (Method-B1).

$^1H$ NMR (400 MHz, MeOD) δ 8.02 (d, J=7.9 Hz, 1H), 7.33-7.17 (m, 2H), 7.17-7.05 (m, 1H), 7.05-6.91 (m, 4H), 6.87 (td, J=7.3, 1.0 Hz, 1H), 6.19 (d, J=0.5 Hz, 1H), 3.88 (s, 3H), 3.87-3.80 (m, 2H), 3.71-3.61 (m, 2H), 3.28-3.21 (m, 2H), 3.18 (dd, J=6.2, 4.2 Hz, 2H).

Intermediate 51

(2-Chloro-6-((2,4,4-trimethylpentan-2-yl)amino) pyrimidin-4-yl)(3,4-dihydroisoquinolin-2(1H)-yl) methanone

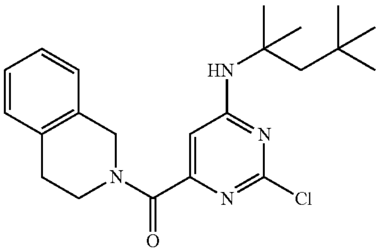 [SMILES: CC(C)(C)CC(C)(C)Nc1cc(C(=O)N2CCc3ccccc3C2)nc(Cl)n1]

Synthesized following General Procedure A, Step 1.
Yield: (0.163 g, 39%).
ES-MS [M+H]$^+$: 401.9, Rt=7.443 min (Method-A1).

Intermediate 52

(3,4-Dihydroisoquinolin-2(1H)-yl)(2-((2-hydroxy-phenyl)amino)-6-((2,4,4-trimethylpentan-2-yl) amino)pyrimidin-4-yl))methanone

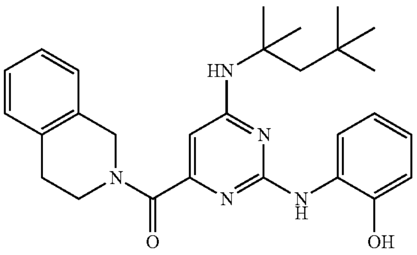 [SMILES: CC(C)(C)CC(C)(C)Nc1cc(C(=O)N2CCc3ccccc3C2)nc(Nc2ccccc2O)n1]

Synthesized following General Procedure A, Step 2.
Yield: (0.090 g, 47%).
ES-MS [M+H]$^+$: 474.9, Rt=7.34 min (Method-A1).

Example 35

(6-Amino-2-((2-hydroxyphenyl)amino)pyrimidin-4-yl)(3,4-dihydroisoquinolin-2(1H)-yl)methanone

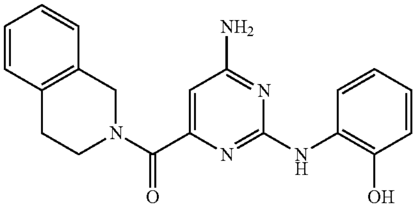 [SMILES: Nc1cc(C(=O)N2CCc3ccccc3C2)nc(Nc2ccccc2O)n1]

Synthesized following General Procedure A, Step 3.
Yield: (0.013 g, 29%).
ES-MS [M+H]+: 362.1, Rt=17.016 min (Method-B1).

$^1$H NMR (400 MHz, DMSO-$d_6$) δ 10.13 (d, J=4.3 Hz, 1H), 8.28-7.56 (m, 2H), 7.19 (dddt, J=13.9, 10.8, 7.0, 3.1 Hz, 4H), 6.99 (s, 2H), 6.92-6.78 (m, 2H), 6.78-6.62 (m, 1H), 5.98 (dd, J=21.5, 4.3 Hz, 1H), 4.69 (dd, J=29.8, 3.9 Hz, 2H), 3.72 (dt, J=60.2, 4.9 Hz, 2H), 2.85 (dt, J=16.3, 5.4 Hz, 2H).

Intermediate 53

(2-Chloro-6-((2,4,4-trimethylpentan-2-yl)amino) pyrimidin-4-yl)(3,4-dihydroquinolin-1(2H)-yl) methanone

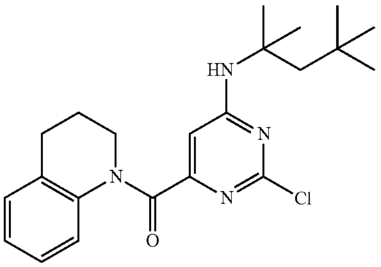 [SMILES: CC(C)(C)CC(C)(C)Nc1cc(C(=O)N2CCCc3ccccc32)nc(Cl)n1]

Synthesized following General Procedure A, Step 1.
Yield: (0.168 g, 40%).
ES-MS [M+H]$^+$: 401.9, Rt=7.372 min (Method-A1).

Intermediate 54

(3,4-Dihydroquinolin-1(2H)-yl)(2-((2-hydroxyphenyl)amino)-6-((2,4,4-trimethylpentan-2-yl)amino) pyrimidin-4-yl)methanone

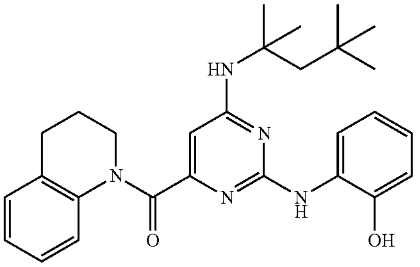 [SMILES: CC(C)(C)CC(C)(C)Nc1cc(C(=O)N2CCCc3ccccc32)nc(Nc2ccccc2O)n1]

Synthesized following General Procedure A, Step 2.
Yield: (0.052 g, 26%).
ES-MS [M+H]$^+$: 474.9, Rt=7.40 min (Method-A1).

Example 36

(6-Amino-2-((2-hydroxyphenyl)amino)pyrimidin-4-yl)(3,4-dihydroquinolin-1(2H)-yl)methanone

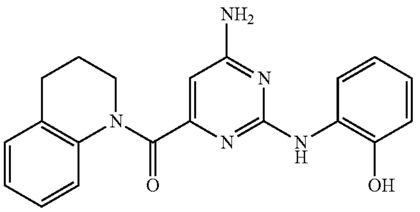 [SMILES: Nc1cc(C(=O)N2CCCc3ccccc32)nc(Nc2ccccc2O)n1]

Synthesized following General Procedure A, Step 3.
Yield: (0.010 g, 28%).
ES-MS [M+H]$^+$: 362.0, Rt=16.970 min (Method-B1).

$^1H$ NMR (400 MHz, DMSO-$d_6$) δ 10.24-9.84 (m, 1H), 7.64 (d, J=58.7 Hz, 2H), 7.23-7.12 (m, 1H), 7.07-6.86 (m, 4H), 6.82-6.69 (m, 2H), 6.70-6.58 (m, 1H), 5.99 (d, J=1.4 Hz, 1H), 3.71 (t, J=6.3 Hz, 2H), 2.79 (t, J=6.6 Hz, 2H), 2.02-1.83 (m, 2H).

Intermediate 55

(2-Chloro-6-((2,4,4-trimethylpentan-2-yl)amino) pyrimidin-4-yl)(indolin-1-yl)methanone

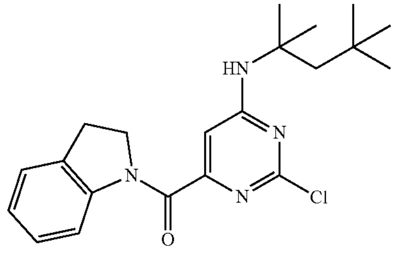 [SMILES: CC(C)(C)CC(C)(C)Nc1cc(C(=O)N2CCc3ccccc32)nc(Cl)n1]

Synthesized following General Procedure A, Step 1.

Yield: (0.188 g, 46%).

ES-MS [M+H]$^+$: 387.9, Rt=7.57 min (Method-A1).

Intermediate 56

(2-((2-Hydroxyphenyl)amino)-6-((2,4,4-trimethylpentan-2-yl)amino)pyrimidin-4-yl)(indolin-1-yl) methanone

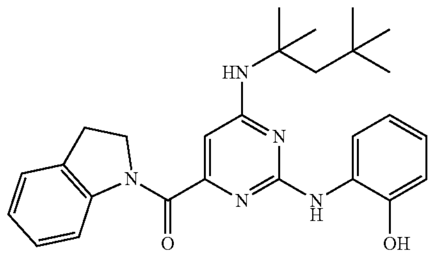 [SMILES: CC(C)(C)CC(C)(C)Nc1cc(C(=O)N2CCc3ccccc32)nc(Nc2ccccc2O)n1]

BINAP (0.030 g, 0.05 mmol, 10 mol %) and Pd2(dba)$_3$ (0.025 g, 0.03 mmol, 6 mol %) were added over a degassed solution of (2-chloro-6-((2,4,4-trimethylpentan-2-yl)amino) pyrimidin-4-yl)(indolin-1-yl)methanone (0.142 g, 0.40 mmol, 1.0 eq), 2-aminophenol (0.060 g, 0.55 mmol, 1.5 eq) and cessium carbonate (0.50 g, 1.4 mmol, 3.5 eq) in dioxane (2.8 mL). The resulting mixture was stirred at 100° C. for 18 h. The reaction mixture was allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography (EtOAc/Hexane 10-20%) to obtain (2-((2-hydroxyphenyl)amino)-6-((2,4,4-trimethylpentan-2-yl)amino)pyrimidin-4-yl)(indolin-1-yl)methanone as a white solid.

Yield: (0.105 g, 62%).

ES-MS [M+H]$^+$: 460.9, Rt=7.214 min (Method-A1).

Example 37

(6-Amino-2-((2-hydroxyphenyl)amino)pyrimidin-4-yl)(indolin-1-yl)methanone

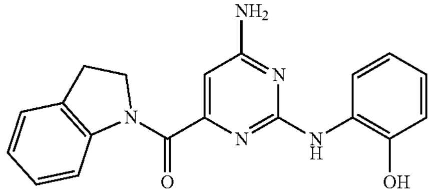 [SMILES: Nc1cc(C(=O)N2CCc3ccccc32)nc(Nc2ccccc2O)n1]

Synthesized following General Procedure A, Step 3. This product was purified by HPLC-semipreparative (Method-E1)

Yield: (0.012 g, 16%).

ES-MS [M+H]$^+$: 348.1, Rt=16.999 min (Method-B1).

$^1H$ NMR (400 MHz, DMSO-$d_6$) δ 10.10 (s, 1H), 8.09 (d, J=8.0 Hz, 1H), 7.97 (d, J=7.8 Hz, 1H), 7.89 (s, 1H), 7.29 (d, J=7.4 Hz, 1H), 7.22 (t, J=7.9 Hz, 1H), 7.06 (d, J=13.6 Hz, 3H), 6.85-6.80 (m, 2H), 6.79-6.65 (m, 1H), 6.14 (s, 1H), 4.15 (t, J=8.3 Hz, 2H), 3.10 (t, J=8.3 Hz, 2H).

Intermediate 57

(2-Chloro-6-((2,4,4-trimethylpentan-2-yl)amino) pyrimidin-4-yl)(isoindolin-2-yl)methanone

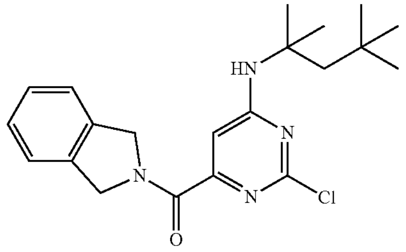 [SMILES: CC(C)(C)CC(C)(C)Nc1cc(C(=O)N2Cc3ccccc3C2)nc(Cl)n1]

Synthesized following General Procedure A, Step 1.

Yield: (0.535 g, 55%).

ES-MS [M+H]$^+$: 387.9, Rt=7.614 min (Method-A1).

Intermediate 58

Isoindolin-2-yl(2-((3-methoxyphenyl)amino)-6-((2,4,4-trimethylpentan-2-yl)amino)-pyrimidin-4-yl) methanone

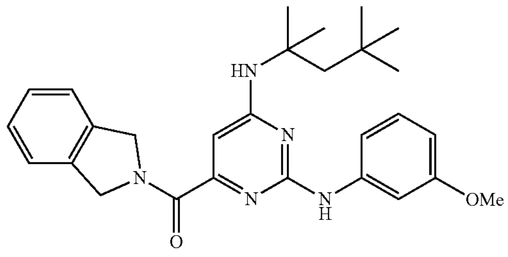 [SMILES: COc1cccc(Nc2nc(NC(C)(C)CC(C)(C)C)cc(C(=O)N3Cc4ccccc4C3)n2)c1]

Synthesized following General Procedure A, Step 2.

Yield: (0.078 g, 32%).

ES-MS [M+H]$^+$: 474.3, Rt=5.571 min (Method-A1).

Example 38

(6-Amino-2-((3-methoxyphenyl)amino)pyrimidin-4-yl)(isoindolin-2-yl)methanone

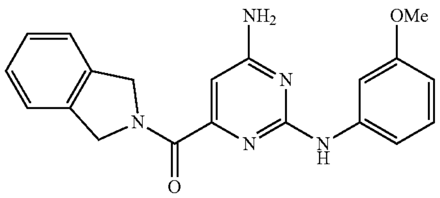 [SMILES: COc1cccc(Nc2nc(N)cc(C(=O)N3Cc4ccccc4C3)n2)c1]

Synthesized following General Procedure A, Step 3.

Yield: (0.034 g, 49%).

ES-MS [M+H]+: 362.0, Rt=17.882 min (Method-B1).

$^1$H NMR (400 MHz, DMSO-$d_6$) δ 9.09 (s, 1H), 7.51 (t, J=2.3 Hz, 1H), 7.45-7.37 (m, 1H), 7.34-7.22 (m, 4H), 7.12 (t, J=8.1 Hz, 1H), 6.95-6.79 (m, 2H), 6.47 (ddt, J=8.2, 2.5, 0.7 Hz, 1H), 6.20 (d, J=0.5 Hz, 1H), 5.04 (s, 2H), 4.83 (s, 2H), 3.70 (d, J=0.5 Hz, 3H).

Intermediate 59

(2-((3-Hydroxyphenyl)amino)-6-((2,4,4-trimethylpentan-2-yl)amino)pyrimidin-4-yl)(isoindolin-2-yl) methanone

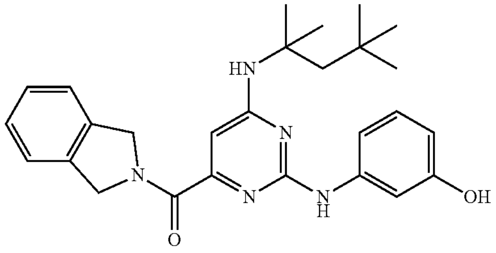 [SMILES: CC(C)(C)CC(C)(C)Nc1cc(C(=O)N2Cc3ccccc3C2)nc(Nc2cccc(O)c2)n1]

Synthesized following General Procedure A, Step 2.

Yield: (0.094 g, 40%).

ES-MS [M+H]$^+$: 460.2, Rt=7.138 min (Method-A1).

Example 39

(6-Amino-2-((3-hydroxyphenyl)amino)pyrimidin-4-yl)(isoindolin-2-yl)methanone

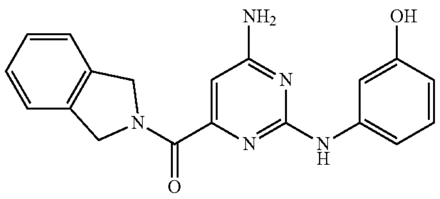

Synthesized following General Procedure A, Step 3. This compound was purified by HPLC-semipreparative (Method-E1).

Yield: (0.022 g, 31%).

ES-MS [M+H]$^+$: 348.2, Rt=15.841 min (Method-B1).

$^1$H NMR (400 MHz, DMSO-$d_6$) δ 9.15 (s, 1H), 8.95 (s, 1H), 7.45-7.36 (m, 1H), 7.36-7.27 (m, 3H), 7.24-7.12 (m, 2H), 6.99 (t, J=8.0 Hz, 1H), 6.79 (s, 2H), 6.32 (dd, J=7.9, 2.3 Hz, 1H), 6.20 (s, 1H), 5.04 (s, 2H), 4.83 (s, 2H).

Intermediate 60

Isoindolin-2-yl(2-(m-tolylamino)-6-((2,4,4-trimethylpentan-2-yl)amino)pyrimidin-4-yl)methanone

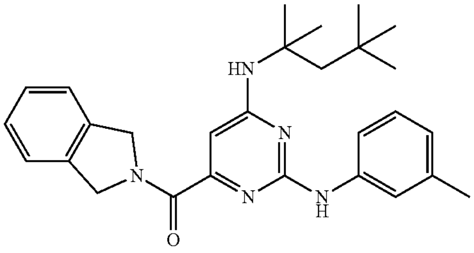 [SMILES: Cc1cccc(Nc2nc(NC(C)(C)CC(C)(C)C)cc(C(=O)N3Cc4ccccc4C3)n2)c1]

Synthesized following General Procedure A, Step 2.

Yield: (0.107 g, 36%).

ES-MS [M+H]$^+$: 457.9, Rt=3.20 min (Method-D1).

Example 40

(6-Amino-2-(m-tolylamino)pyrimidin-4-yl)(isoindolin-2-yl)methanone

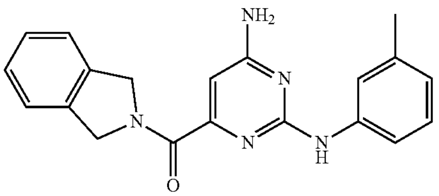 [SMILES: Cc1cccc(Nc2nc(N)cc(C(=O)N3Cc4ccccc4C3)n2)c1]

Synthesized following General Procedure A, Step 3.

Yield: (0.038 g, 47%).

ES-MS [M+H]$^+$: 346.1, Rt=18.670 min (Method-B1).

$^1$H NMR (400 MHz, DMSO-$d_6$) δ 9.00 (s, 1H), 7.66-7.56 (m, 1H), 7.53 (d, J=2.3 Hz, 1H), 7.49-7.36 (m, 1H), 7.34-7.26 (m, 3H), 7.11 (t, J=7.8 Hz, 1H), 6.96-6.81 (m, 2H), 6.72 (dq, J=7.4, 0.9 Hz, 1H), 6.20 (s, 1H), 5.05 (s, 2H), 4.82 (s, 2H), 2.25 (s, 3H).

Intermediate 61

(2-((3-Chlorophenyl)amino)-6-((2,4,4-trimethylpentan-2-yl)amino)pyrimidin-4-yl)(isoindolin-2-yl) methanone

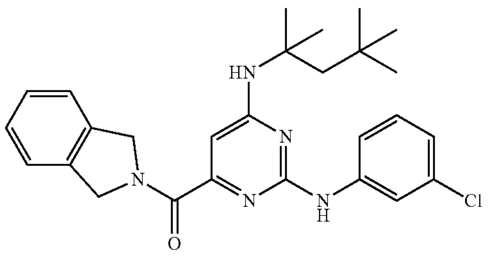 [SMILES: CC(C)(C)CC(C)(C)Nc1cc(C(=O)N2Cc3ccccc3C2)nc(Nc2cccc(Cl)c2)n1]

Synthesized following General Procedure A, Step 2.

Yield: (0.070 g, 31%).

ES-MS $[M+H]^+$: 478.1, Rt=7.918 min (Method-A1).

Example 41

(2-((3-Chlorophenyl)amino)-6-((2,4,4-trimethylpentan-2-yl)amino)pyrimidin-4-yl)(isoindolin-2-yl) methanone

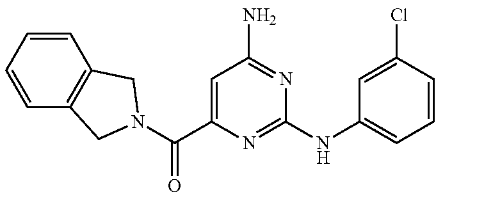 [SMILES: Nc1cc(C(=O)N2Cc3ccccc3C2)nc(Nc2cccc(Cl)c2)n1]

Synthesized following General Procedure A, Step 3.

Yield: (0.020 g, 37%).

ES-MS $[M+H]^+$: 366.1, Rt=19.152 min (Method-B1).

$^1$H NMR (400 MHz, DMSO-$d_6$) δ 9.34 (s, 1H), 7.94 (t, J=2.1 Hz, 1H), 7.69 (ddd, J=8.3, 2.0, 0.9 Hz, 1H), 7.50-7.36 (m, 1H), 7.36-7.18 (m, 4H), 6.96 (s, 1H), 6.95-6.81 (m, 1H), 6.25 (d, J=0.7 Hz, 1H), 5.04 (s, 2H), 4.83 (s, 2H).

General Procedure D-1

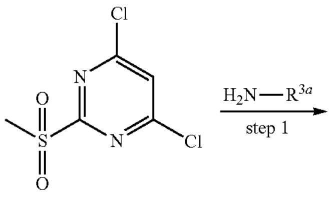

-continued

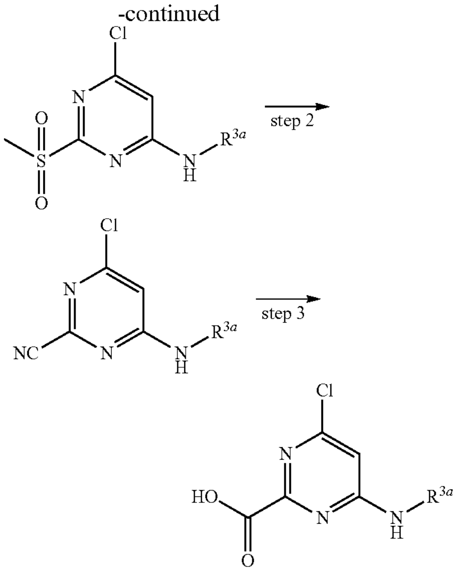

Step 1

To a stirred solution of the appropriate aryl chloride derivative (ex: 4,6-dichloro-2-(methylsulfonyl)pyrimidine) (1.0 eq) in dioxane (2 mL/mmol) were added the appropriate amine (ex: 2-methoxyaniline) (1.0 eq) and DIPEA (3.71 mL, 21.3 mmol, 1.2 eq). The resulting mixture was stirred at room temperature for 16 h. The mixture diluted with water and extracted with EtOAc (×3). Combined organic layers were washed with brine, dried over magnesium sulphate, filtered and concentrated to obtain the desired amine compound (ex: 6-chloro-N-(2-methoxyphenyl)-2-(methylsulfonyl)pyrimidin-4-amine).

Step 2

To a stirred solution of the appropriate sulphonyl derivative (ex: 6-chloro-N-(2-methoxyphenyl)-2-(methylsulfonyl) pyrimidin-4-amine) (1.0 eq) in DMSO (4 mL/mmol) was added potassium cyanide (1.0 eq). The resulting mixture was stirred at room temperature for 30 min. Then water was added, and the solution was extracted with EtOAc (×3). Combined organic layers were washed with brine, dried over magnesium sulphate, filtered and concentrated. The resultant crude was purified by flash column chromatography (EtOAc/Hexane 50%) to obtain the desired carbonitrile derivative (ex: 4-chloro-6-((2-methoxyphenyl)amino)pyrimidine-2-carbonitrile).

Step 3

To a stirred solution of the appropriate carbonitrile (ex: 4-chloro-6-((2-methoxyphenyl)amino)pyrimidine-2-carbonitrile) (1.0 eq) in water (7 mL/mmol) and ethanol (7 mL/mmol) was added KOH (10.0 eq) at room temperature. The resulting mixture was stirred under reflux for 1 h. The mixture was then cooled to room temperature and acidified to pH 3~4 by the addition of 3N HCl. Then, EtOAc was added and the layers were separated. The aqueous layer was extracted with EtOAc (×3). Combined organic layers were washed with brine, dried over magnesium sulphate, filtered and concentrated. The resultant crude was purified by flash column chromatography (EtOAc/Hexane 30 to 100%) to obtain the desired carboxylic acid compound (ex: 4-chloro-6-((2-methoxyphenyl)amino)pyrimidine-2-carboxylic acid)

Intermediate 62

6-Chloro-N-(2-methoxyphenyl)-2-(methylsulfonyl) pyrimidin-4-amine

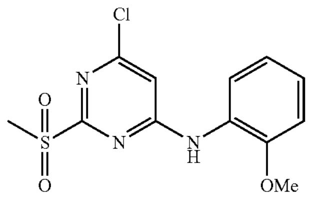 [SMILES: COc1ccccc1Nc1cc(Cl)nc(S(C)(=O)=O)n1]

Synthesized following General Procedure D-1, Step 1. Isolated as a white solid.

Yield: (7.0 g, 95%).

ES-MS $[M+H]^+$: 314.0, Rt=5.78 min (Method-A1).

Intermediate 63

4-Chloro-6-((2-methoxyphenyl)amino)pyrimidine-2-carbonitrile

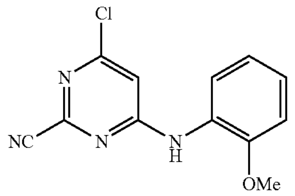 [SMILES: COc1ccccc1Nc1cc(Cl)nc(C#N)n1]

Synthesized following General Procedure D-1, Step 2. Isolated as a white solid

Yield: (1.69 g, 50%).

ES-MS $[M+H]^+$: 261.0, Rt=2.77 min (Method-D1).

Intermediate 64

4-Chloro-6-((2-methoxyphenyl)amino)pyrimidine-2-carboxylic acid

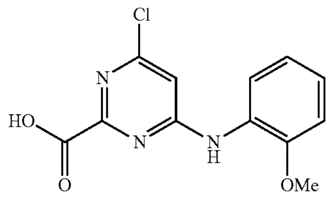 [SMILES: COc1ccccc1Nc1cc(Cl)nc(C(=O)O)n1]

Synthesized following General Procedure D-1, Step 3. Isolated as a yellow solid.

Yield: (1.31 g, 65%).

ES-MS $[M+H]^+$: 280.0, Rt=2.42 min (Method-D1).

Intermediate 65

2-Chloro-6-((2-methoxyphenyl)amino)pyrimidine-4-carboxylic acid

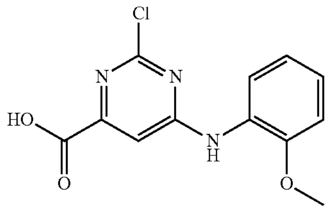 [SMILES: COc1ccccc1Nc1cc(C(=O)O)nc(Cl)n1]

To a stirred mixture of methyl 2-chloro-6-((2-methoxyphenyl)amino)pyrimidine-4-carboxylate (6.17 g, 21.00 mmol, 1.0 eq.) in THF:$H_2O$ (1:1, 240 mL) was added lithium hydroxide (4.41 g, 105.03 mmol, 5.0 eq). The resulting mixture was stirred at room temperature for 1 h. The mixture was evaporated to dryness, acidified with the addition of conc. HCl, and extracted with EtOAc/MeOH (×3), dried over anhydrous sodium sulphate, filtered and concentrated to dryness to obtain 2-chloro-6-((2-methoxyphenyl)amino)pyrimidine-4-carboxylic acid as a yellow solid, which was used without further purification.

Yield: (5.97 g, quant. yield).

ES-MS $[M+H]^+$:280.0 Rt=4.53 min (Method-A1).

General Procedure D-2

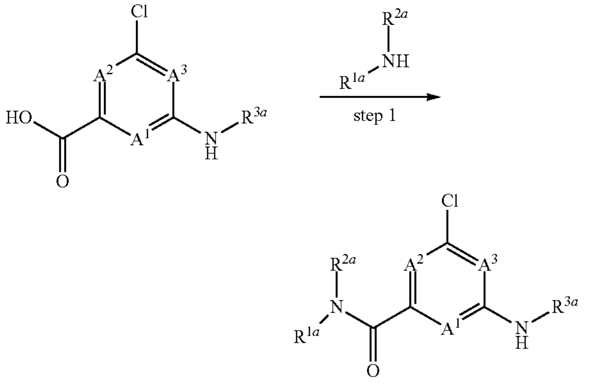

Step 1

The appropriate carboxylic acid compound (ex: 4-chloro-6-((2-methoxyphenyl)-amino)pyrimidine-2-carboxylic acid) (1.0 eq) was dissolved in $SOCl_2$ (5 mL/mmol) under $N_2$ atmosphere and stirred at 90° C. for 3 h. The mixture was then cooled to room temperature and the excess of $SOCl_2$ was removed under vacuum. The resulting crude residue was dissolved in THF (5 mL/mmol) and then the appropriate amine (ex: 1-phenylpiperazine) (1.0 eq) and $Et_3N$ (1 eq) were added. The mixture was stirred at room temperature for 16 h. The mixture was then diluted with water and extracted with EtOAc (×3). Combined organic layers were washed with brine, dried over $MgSO_4$, filtered and concentrated. The resultant crude was purified by flash column chromatography (EtOAc/Hexane 50 to 100%) to obtain the desired amide (ex: (4-chloro-6-((2-methoxyphenyl)amino)pyrimidin-2-yl)(4-phenylpiperazin-1-yl)methanone).

Step 1 Alternative Procedure (Step 1B)

T3P (2.0 eq of a 50% solution in ethyl acetate) was added to a suspension of the appropriate carboxylic acid (ex: 4-chloro-6-((2-methoxyphenyl)amino)pyrimidine-2-carboxylic acid) (1.0 eq), the corresponding amine (ex: (2-methoxyphenyl)amino) (1.5 eq) and DIPEA (5.0 eq.) in DCM (5 mL/mmol). The resulting mixture was stirred at room temperature for 16 h. The reaction mixture was quenched with sat. aq. $NaHCO_3$ solution. The mixture was extracted with ethyl acetate (×3), dried over anhydrous sodium sulphate, filtered and concentrated to dryness. The resultant crude was purified by flash column chromatography (EtOAc/Hexane 50 to 100%) to obtain the desired product (ex: 4-chloro-N-(2,3-dihydro-1H-inden-2-yl)-6-((2-methoxyphenyl)amino)pyrimidine-2-carboxamide).

Intermediate 66

(4-Chloro-6-((2-methoxyphenyl)amino)pyrimidin-2-yl)(4-phenylpiperazin-1-yl)methanone

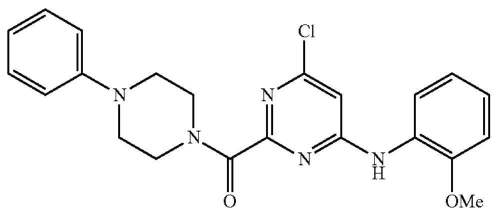 [SMILES: COc1ccccc1Nc1cc(Cl)nc(C(=O)N2CCN(c3ccccc3)CC2)n1]

Synthesized following General Procedure D-2, Step 1. Isolated as a brown solid.

Yield: (0.485 g, 53%).

ES-MS $[M+H]^+$: 424.0, Rt=6.605 min (Method-A1).

Intermediate 67

4-Chloro-N-(2,3-dihydro-1H-inden-2-yl)-6-((2-methoxyphenyl)amino)pyrimidine-2-carboxamide

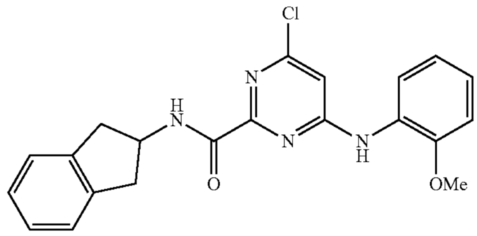 [SMILES: COc1ccccc1Nc1cc(Cl)nc(C(=O)NC2Cc3ccccc3C2)n1]

Synthesized following General Procedure D-2, Step 1B.

Yield: (0.61 g, 66%).

ES-MS $[M-H]^-$: 395.9, Rt=6.820 min (Method-A1).

Intermediate 68

4-Chloro-6-((2-methoxyphenyl)amino)-N-phenylpyrimidine-2-carboxamide

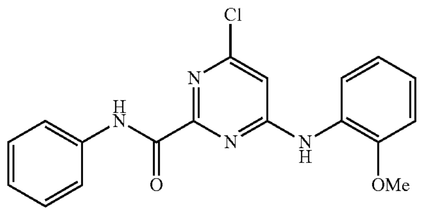 [SMILES: COc1ccccc1Nc1cc(Cl)nc(C(=O)Nc2ccccc2)n1]

Synthesized following General Procedure D-2, Step 1B.

Yield: (0.65 g, 76%).

ES-MS $[M-H]^-$: 355.9, Rt=2.89 min (Method-D1).

Intermediate 69

2-Chloro-N-(2,3-dihydro-1H-inden-2-yl)-6-((2-methoxyphenyl)amino)pyrimidine-4-carboxamide

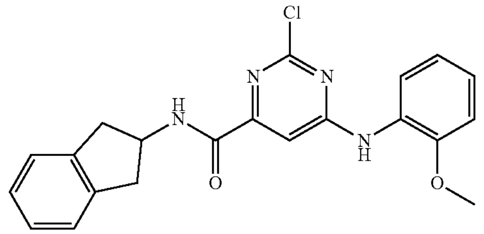 [SMILES: COc1ccccc1Nc1cc(C(=O)NC2Cc3ccccc3C2)nc(Cl)n1]

Synthesized following Procedure D-2, Step 1B.

Yield: (0.229 g, 27% yield).

ES-MS $[M+H]^+$:395.1 Rt=7.078 min (Method-A1).

Intermediate 70

2-Chloro-N-(2,3-dihydro-1H-inden-2-yl)-6-((2-methoxyphenyl)amino)-N-methylpyrimidine-4-carboxamide

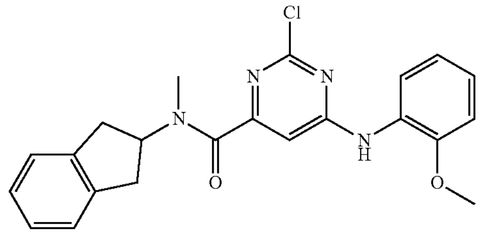 [SMILES: COc1ccccc1Nc1cc(C(=O)N(C)C2Cc3ccccc3C2)nc(Cl)n1]

Synthesized following General Procedure D-2, Step 1B.

Yield: (0.693 g, 79% yield).

ES-MS $[M+H]^+$:409.0 Rt=6.801 min (Method-A1).

Intermediate 71

2-Chloro-6-((2-methoxyphenyl)amino)-N-methyl-N-(1,2,3,4-tetrahydronaphthalen-2-yl)pyrimidine-4-carboxamide

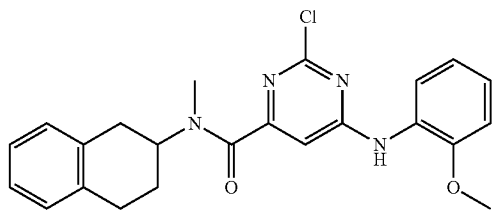 [SMILES: COc1ccccc1Nc1cc(C(=O)N(C)C2CCc3ccccc3C2)nc(Cl)n1]

Synthesized following Procedure D-2, Step 1B.

Yield: (0.326 g, 47% yield).

ES-MS $[M+H]^+$:423.0 Rt=6.890 min (Method-A1).

Intermediate 72

2-Chloro-6-((2-methoxyphenyl)amino)-N-(1,2,3,4-tetrahydronaphthalen-2-yl)pyrimidine-4-carboxamide

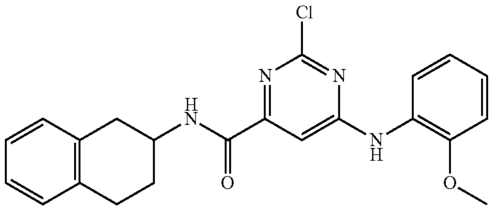

Synthesized following Procedure D-2, Step 1B.
Yield: (0.479 g, 76% yield).
ES-MS $[M+H]^+$:409.0 Rt=7.212 min (Method-A1).

Intermediate 73

(2-Chloro-6-((2-methoxyphenyl)amino)pyrimidin-4-yl)(3,4-dihydroisoquinolin-2(1H)-yl)methanone

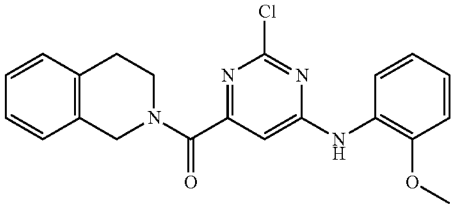 [SMILES: COc1ccccc1Nc1cc(C(=O)N2CCc3ccccc3C2)nc(Cl)n1]

Synthesized following General Procedure D-2, Step 1B.
Yield: (0.816 g, 96% yield).
ES-MS $[M+H]^+$:395.0 Rt=6.662 min (Method-A1).

Intermediate 74

(2-Chloro-6-((2-methoxyphenyl)amino)pyrimidin-4-yl)(isoindolin-2-yl)methanone

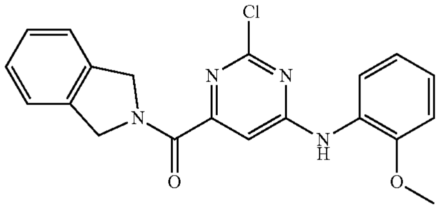 [SMILES: COc1ccccc1Nc1cc(C(=O)N2Cc3ccccc3C2)nc(Cl)n1]

Synthesized following General Procedure D-2, Step 1B.
Yield: (0.603 g, 74% yield).
ES-MS $[M+H]^+$:381.0 Rt=6.823 min (Method-A1).

General Procedure D-3

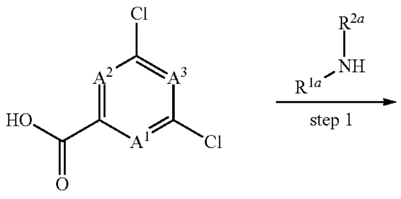

-continued

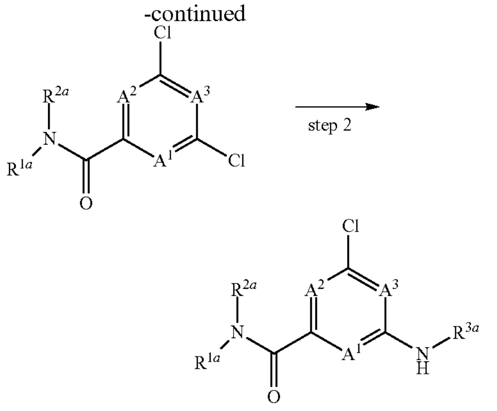

Step 1

Method 1: To a stirred solution of 4,6-dichloropicolinic acid (1.0 eq) in DCM (3 m/mmol) and DMF (10 drops) was added oxalyl chloride (1.5 eq) at 0° C. The resulting mixture was stirred at room temperature for 1 h. The mixture was then concentrated to dryness and dissolved in DCM (3 m/mmol) and DIPEA (2.0-3.0 eq). The appropriate amine (ex: N-methylaniline) (1.2 eq) was then added and the resulting mixture was stirred at room temperature for 4 h. After completion, the mixture was concentrated to drynes and the crude was subjected to column chromatography on silica gel (Hexane:EtOAc, from 90:10 to 75:25) to obtain the desired amide product (ex: 4,6-dichloro-N-methyl-N-phenylpicolinamide).

Method 2: T3P (2.0 eq of a 50% solution in EtOAc) was added to a suspension of 4,6-dichloropicolinic acid (1.0 eq), the appropriate amine (ex: 1-phenylpiperazine) (1.1 eq.) and DIPEA (5.0 eq.) in DCM (4 m/mmol). The resulting mixture was stirred at room temperature for 16 h. The reaction mixture was quenched with sat. aq. $NaHCO_3$ solution. The mixture was extracted with ethyl acetate (×3), dried over anhydrous sodium sulphate, filtered and concentrated to dryness. The resultant crude was purified by flash column chromatography (EtOAc/Heptane 50-100) to obtain the desired product (ex: (4,6-dichloropyridin-2-yl)(4-phenylpiperazin-1-yl)methanone).

Step 2

Method 1: To a stirred solution of the appropriate amine (ex: 2-methoxyaniline) (0.80 g, 6.5 mmol, 2.0 eq) in DMF (7 mL) was added NaH (0.785 g of a 60% suspension in mineral oil, 19.62 mmol, 6.0 eq) at 0° C. The resulting mixture was stirred at rt for 30 min. Then, the appropriate aryl dichloride (ex: 4,6-dichloro-N-methyl-N-phenylpicolinamide) was added and the mixture was stirred at 100° C. for 30 min. The mixture was poured into brine and extracted with EtOAc. Combined organic layers were washed with more brine and with HCl 10%, dried with $Na_2SO_4$, filtered and concentrated. The crude was subjected to column chromatography on silica gel (Hexane:EtOAc, from 95:05 to 80:20) to obtain the desired product (ex: 6-chloro-4-((2-methoxyphenyl)amino)-N-methyl-N-phenylpicolinamide).

Method 2: Dppf (6 mol %) and $Pd(OAc)_2$ (3 mol %) were added over a degassed solution of the appropriate dichloride (ex: 4,6-dichloro-N-(2,3-dihydro-1H-inden-2-yl)picolinamide) (1.0 eq), the appropriate arylamine (ex: ex: 2-methylaniline) (1.0 eq) and $K_3PO_4$ (2.0 eq) in dioxane (5 mL/mmol). The resulting mixture was stirred at 90° C. under nitrogen atmosphere for 2 h. The mixture was then diluted with EtOAc and water. Layers were separated. Aqueous layer was extracted with EtOAc (×2). Combined organic layers were washed with water and brine, dried over anhydrous $MgSO_4$, filtered and concentrated. The resultant crude was purified by flash column chromatography (Hexane: EtOAc 60:40) to obtain the desired product. (ex: 4-chloro-N-(2,3-dihydro-1H-inden-2-yl)-6-(o-tolylamino)picolinamide).

Intermediate 75

4,6-Dichloro-N-methyl-N-phenylpicolinamide

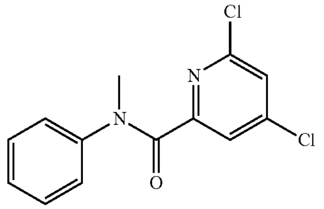 [SMILES: CN(C(=O)c1cc(Cl)cc(Cl)n1)c1ccccc1]

Synthesized following General Procedure D-3, Step 1, Method 1.

Yield: (0.940 g, 63%).

ES-MS $[M+H]^+$: 282.2, Rt=7.64 min (Method-A1).

Intermediate 76

(4,6-Dichloropyridin-2-yl)(4-phenylpiperazin-1-yl) methanone

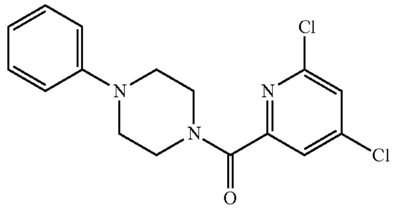 [SMILES: O=C(c1cc(Cl)cc(Cl)n1)N1CCN(c2ccccc2)CC1]

Synthesized following General Procedure D-3, Step 1, Method 2. Isolated as a white solid.

Yield: (2.224 g, 85% yield).

ES-MS $[M+H]^+$:336.0 Rt=6.618 min (Method-A1).

Intermediate 77

(4,6-Dichloropyridin-2-yl)(isoindolin-2-yl)methanone

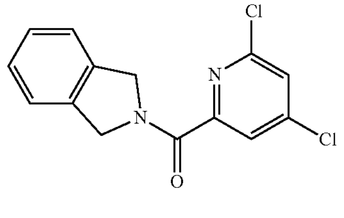 [SMILES: O=C(c1cc(Cl)cc(Cl)n1)N1Cc2ccccc2C1]

Synthesized following General Procedure D-3, Step 1, Method 2. Isolated as a pale brown solid.

Yield: (1.271 g, 84%).

ES-MS $[M+H]^+$: 294.1, Rt=2.90 min (Method-D1).

Intermediate 78

(4,6-Dichloropyridin-2-yl)(4-phenylpiperazin-1-yl) methanone

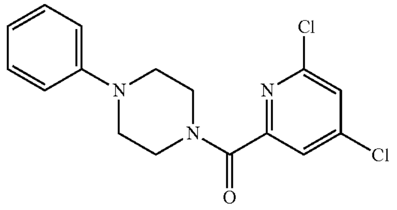 [SMILES: O=C(c1cc(Cl)cc(Cl)n1)N1CCN(c2ccccc2)CC1]

Synthesized following General Procedure D-3, Step 1, Method 2.

Yield: (2.224 g, 85% yield).

ES-MS $[M+H]^+$:336.0 Rt=6.618 min (Method-A1).

Intermediate 79

4,6-Dichloro-N-(2,3-dihydro-1H-inden-2-yl)picolinamide

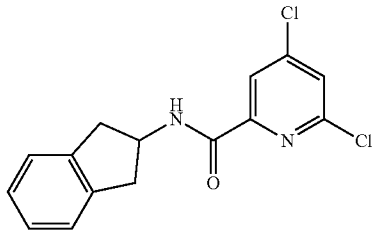 [SMILES: O=C(NC1Cc2ccccc2C1)c1cc(Cl)cc(Cl)n1]

Synthesized following General Procedure D-3, Step 1, Method 1. Isolated as a grey solid.

Yield: (0.825 g, 51%).

ES-MS $[M+H]^+$: 308.0, Rt=7.439 min (Method-A1).

Intermediate 80

4,6-Dichloro-N-(2,3-dihydro-1H-inden-2-yl)picolinamide

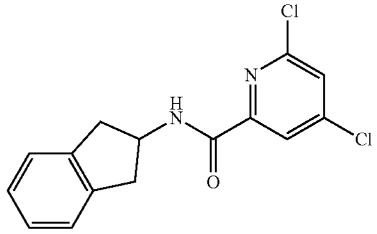 [SMILES: O=C(NC1Cc2ccccc2C1)c1cc(Cl)cc(Cl)n1]

Synthesized following General Procedure D-3, Step 1, Method 2.

Yield: (3.15 g, quant.).

ES-MS $[M+H]^+$: 308.0, Rt=7.089 min (Method-A1).

Intermediate 81

(4,6-Dichloropyridin-2-yl)(4-phenylpiperazin-1-yl) methanone

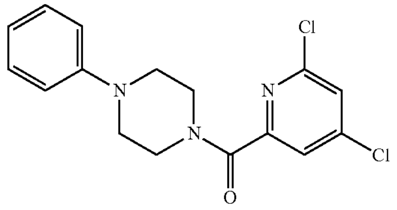 [SMILES: O=C(c1cc(Cl)cc(Cl)n1)N1CCN(c2ccccc2)CC1]

Synthesized following General Procedure D-3, Step 1, Method 2.

Yield: (3.40 g, 97% yield).

ES-MS $[M+H]^+$:337.9 Rt=6.771 min (Method-A1).

Intermediate 82

4,6-Dichloro-N-phenylpicolinamide

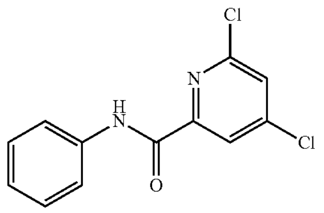 [SMILES: O=C(Nc1ccccc1)c1cc(Cl)cc(Cl)n1]

Synthesized following General Procedure D-3, Step 1, Method 2.

Yield: (3.64 g, 87%).

ES-MS $[M+H]^+$: 267.0, Rt=6.93 min (Method-A1).

Intermediate 83

(4,6-Dichloropyridin-2-yl)(isoindolin-2-yl)methanone

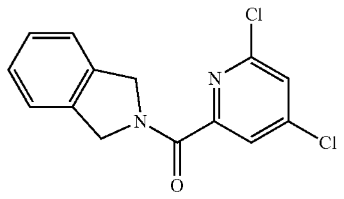 [SMILES: O=C(c1cc(Cl)cc(Cl)n1)N1Cc2ccccc2C1]

Synthesized following General Procedure D-3, Step 1, Method 2.

Yield: (1.271 g, 84%).

ES-MS $[M+H]^+$: 294.1, Rt=6.943 min (Method-A1).

Intermediate 84

(4,6-Dichloropyridin-2-yl)(indolin-1-yl)methanone

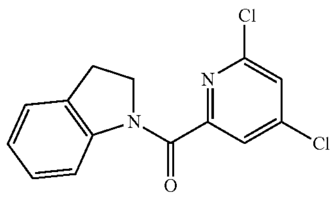 [SMILES: O=C(c1cc(Cl)cc(Cl)n1)N1CCc2ccccc21]

Synthesized following General Procedure D-3, Step 1, Method 2. The compound was used without further purification.

Yield: (1.5 g, 98%).

ES-MS $[M+H]^+$: 294.1, Rt=3.09 min (Method-D1).

Intermediate 85

4,6-Dichloro-N-phenylpicolinamide

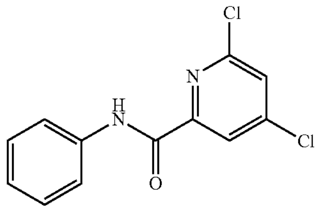 [SMILES: O=C(Nc1ccccc1)c1cc(Cl)cc(Cl)n1]

Synthesized following General Procedure D-3, Step 1, Method 1.

Yield: (0.122 g, 83%).

ES-MS $[M+H]^+$: 267.0, Rt=6.82 min (Method-A1).

Intermediate 86

4,6-Dichloro-N-(1,2,3,4-tetrahydronaphthalen-2-yl) picolinamide

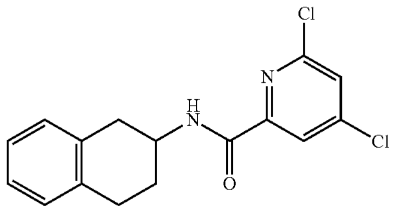 [SMILES: O=C(NC1CCc2ccccc2C1)c1cc(Cl)cc(Cl)n1]

Synthesized following General Procedure D-3, Step 1, Method 1.

Yield: (0.720 g, 67%).

ES-MS $[M+H]^+$: 322.1, Rt=6.443 min (Method-A1).

Intermediate 87

4,6-Dichloro-N-phenylpicolinamide

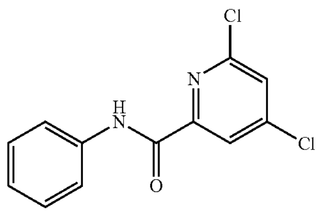 [SMILES: O=C(Nc1ccccc1)c1cc(Cl)cc(Cl)n1]

Synthesized following General Procedure D-3, Step 1, Method 2. The crude product was used without further purification.

Yield: (1.25 g, 89%).

ES-MS $[M+H]^+$: 267.0, Rt=6.82 min (Method-A1).

Intermediate 88

4,6-Dichloro-N-(2,3-dihydro-1H-inden-2-yl)picolinamide

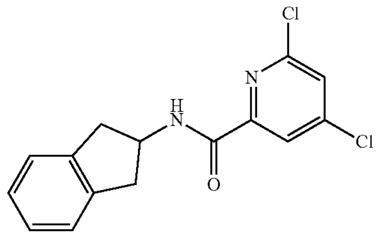 [SMILES: O=C(NC1Cc2ccccc2C1)c1cc(Cl)cc(Cl)n1]

Synthesized following General Procedure D-3, Step 1, Method 2.

Yield: (1.08 g, 68%).

ES-MS $[M+H]^+$: 308.0, Rt=7.04 min (Method-A1).

Intermediate 89

4,6-Dichloro-N-(2,3-dihydro-1H-inden-2-yl)-N-methylpicolinamide

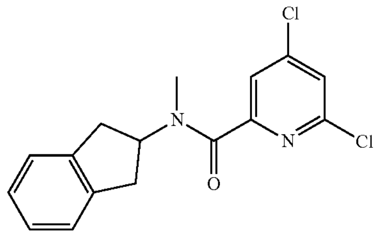 [SMILES: CN(C(=O)c1cc(Cl)cc(Cl)n1)C1Cc2ccccc2C1]

Synthesized following General Procedure D-3, Step 1, Method 2.

Yield: (0.624 g, 25%).

ES-MS $[M+H]^+$: 321.1, Rt=6.842 min (Method-A1).

Intermediate 90

4,6-Dichloro-N-methyl-N-phenylpicolinamide

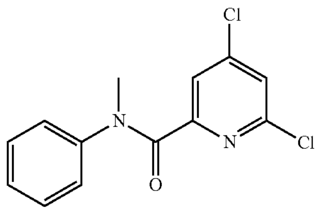 [SMILES: CN(C(=O)c1cc(Cl)cc(Cl)n1)c1ccccc1]

Synthesized following General Procedure D-3, Step 1, Method 2.

Yield: (2.22 g, 76%).

ES-MS $[M+H]^+$: 281.0, Rt=6.327 min (Method-A1).

Intermediate 91

4,6-Dichloro-N-(2,3-dihydrobenzo[b][1,4]dioxin-6-yl)picolinamide

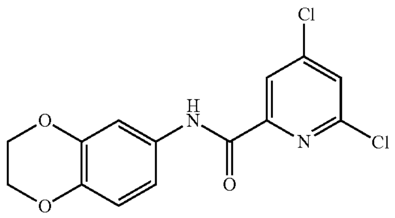 [SMILES: O=C(Nc1ccc2c(c1)OCCO2)c1cc(Cl)cc(Cl)n1]

Synthesized following General Procedure D-3, Step 1, Method 2.

Yield: (3.18 g, 94%).

ES-MS $[M+H]^+$: 325.0, Rt=6.800 min (Method-A1).

Intermediate 92

4,6-Dichloro-N-(m-tolyl)picolinamide

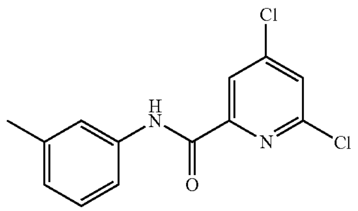 [SMILES: Cc1cccc(NC(=O)c2cc(Cl)cc(Cl)n2)c1]

Synthesized following General Procedure D-3, Step 1, Method 2.

Yield: (0.639 g, 87%).

ES-MS $[M-H]^-$: 279.2, Rt=7.133 min (Method-A1).

Intermediate 93

4,6-Dichloro-N-(3,4-dimethylphenyl)picolinamide

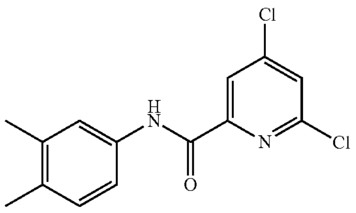 [SMILES: Cc1ccc(NC(=O)c2cc(Cl)cc(Cl)n2)cc1C]

Synthesized following General Procedure D-3, Step 1, Method 2.

Yield: (0.470 g, 61%).

ES-MS [M−H]$^-$: 279.2, Rt=7.133 min (Method-A1).

Intermediate 94

(4,6-Dichloropyridin-2-yl)(3,4-dihydroisoquinolin-2(1H)-yl)methanone

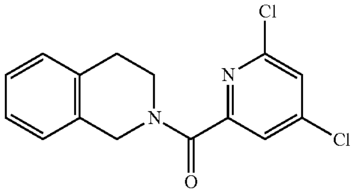 [SMILES: O=C(c1cc(Cl)cc(Cl)n1)N1CCc2ccccc2C1]

Synthesized following General Procedure D-3, Step 1, Method 2.

Yield: (0.50 g, quant.).

ES-MS [M+H]$^+$: 307.0, Rt=6.76 min (Method-A1).

Intermediate 95

6-Chloro-4-((2-methoxyphenyl)amino)-N-methyl-N-phenylpicolinamide

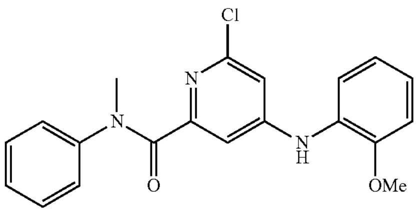 [SMILES: COc1ccccc1Nc1cc(Cl)nc(C(=O)N(C)c2ccccc2)c1]

Synthesized following General Procedure D-3, Step 2, Method 1. The product is isolated as a baige solid.

Yield: (0.140 g, 7%).

ES-MS [M+H]$^+$: 368.2, Rt=6.98 min (Method-A1).

Intermediate 96

(6-Chloro-4-((2-methoxyphenyl)amino)pyridin-2-yl)(4-phenylpiperazin-1-yl)methanone

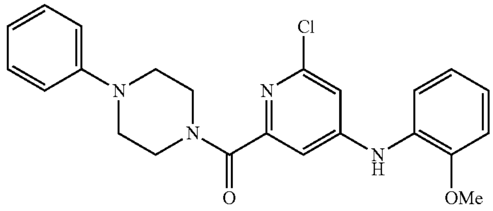 [SMILES: COc1ccccc1Nc1cc(Cl)nc(C(=O)N2CCN(c3ccccc3)CC2)c1]

Synthesized following General Procedure D-3, Step 2, Method 1.

Yield: (0.548 g, 20%).

ES-MS [M+H]$^+$: 423.1, Rt=6.742 min (Method-A1).

Intermediate 97

(6-Chloro-4-((2-fluorophenyl)amino)pyridin-2-yl)(4-phenylpiperazin-1-yl)methanone

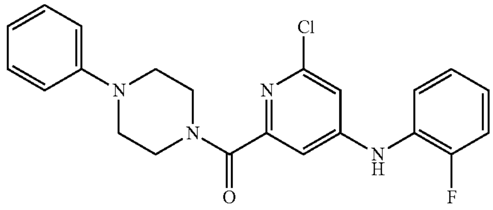 [SMILES: O=C(c1cc(Nc2ccccc2F)cc(Cl)n1)N1CCN(c2ccccc2)CC1]

Synthesized following General Procedure D-3, Step 2, Method 1.

Yield: (0.180 g, 34%).

ES-MS [M+H]$^+$: 411.1, Rt=6.737 min (Method-A1).

Intermediate 98

(6-Chloro-4-((2-chlorophenyl)amino)pyridin-2-yl)(4-phenylpiperazin-1-yl)methanone

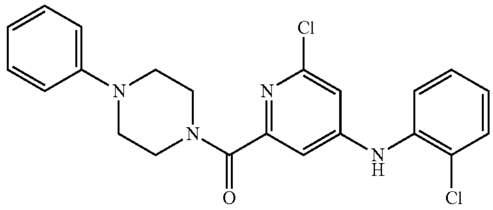 [SMILES: O=C(c1cc(Nc2ccccc2Cl)cc(Cl)n1)N1CCN(c2ccccc2)CC1]

Synthesized following General Procedure D-3, Step 2, Method 1.

Yield: (0.415 g, used crude).

ES-MS [M+H]$^+$: 427.0, Rt=6.956 min (Method-A1).

Intermediate 99

(6-Chloro-4-((2-methoxyphenyl)amino)pyridin-2-yl)(isoindolin-2-yl)methanone

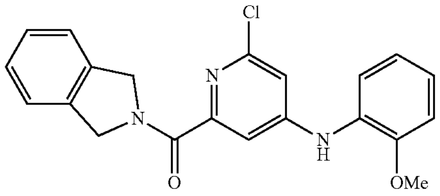

Synthesized following General Procedure D-3, Step 2, Method 1. The product was isolated as a green solid.

Yield: (0.228 g, 14%).

ES-MS $[M+H]^+$: 380.1, Rt=6.998 min (Method-A1).

Intermediate 100

(6-Chloro-4-((2-methoxyphenyl)amino)pyridin-2-yl)(indolin-1-yl)methanone

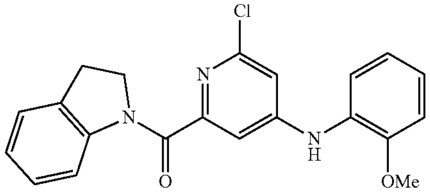 [SMILES: COc1ccccc1Nc1cc(Cl)nc(C(=O)N2CCc3ccccc32)c1]

Synthesized following General Procedure D-3, Step 2, Method 1. The product was isolated as a brown solid.

Yield: (used crude).

ES-MS $[M+H]^+$: 380.1, Rt=3.64 min (Method-C)

Intermediate 101

6-Chloro-4-((2-methoxyphenyl)amino)-N-phenylpicolinamide

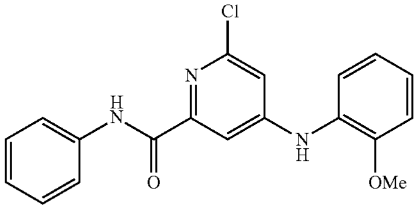 [SMILES: COc1ccccc1Nc1cc(Cl)nc(C(=O)Nc2ccccc2)c1]

Synthesized following General Procedure D-3, Step 2, Method 1.

Yield: (0.100 g, 34%).

ES-MS $[M+H]^+$: 354.2, Rt=6.54 min (Method-A1).

Intermediate 102

6-Chloro-4-((2-methoxyphenyl)amino)-N-(1,2,3,4-tetrahydronaphthalen-2-yl)picolinamide

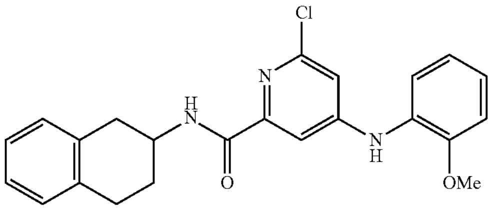 [SMILES: COc1ccccc1Nc1cc(Cl)nc(C(=O)NC2CCc3ccccc3C2)c1]

Synthesized following General Procedure D-3, Step 2, Method 1.

Yield: (0.239 g, 80%).

ES-MS $[M+H]^+$: 409.2, Rt=7.57 min (Method-A1).

Intermediate 103

6-Chloro-4-((2-methoxyphenyl)amino)-N-phenylpicolinamide and 4-chloro-6-((2-methoxyphenyl)amino)-N-phenylpicolinamide

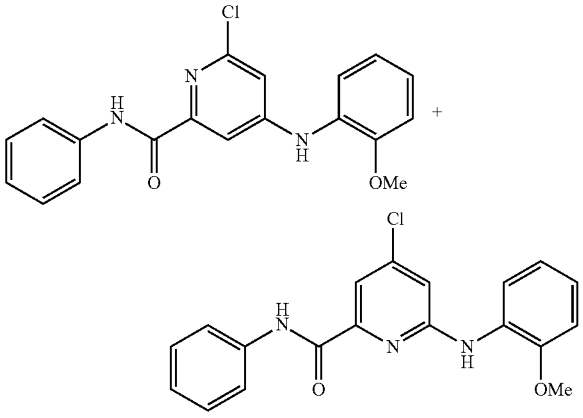

Synthesized following General Procedure D-3, Step 2, Method 1. Isolated as a mixture of the above compounds.

Yield: (0.81 g, 85%).

ES-MS $[M+H]^+$: 354.0, Rt=7.084 and 7.257 min (Method-A1).

Intermediate 104

6-Chloro-N-(2,3-dihydro-1H-inden-2-yl)-4-((2-methoxyphenyl)amino)picolinamide

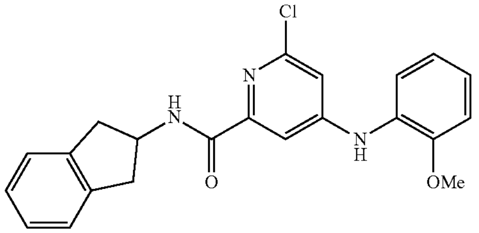 [SMILES: COc1ccccc1Nc1cc(Cl)nc(C(=O)NC2Cc3ccccc3C2)c1]

Synthesized following General Procedure D-3, Step 2, Method 1.

Yield: (0.327 g, 23%).

ES-MS $[M+H]^+$: 394.9, Rt=7.216 min (Method-A1).

Intermediate 105

6-Chloro-N-(2,3-dihydro-1H-inden-2-yl)-4-((2-methoxyphenyl)(methyl)amino)-picolinamide

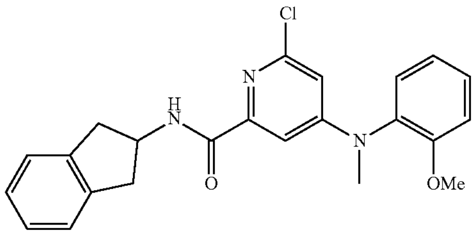 [SMILES: COc1ccccc1N(C)c1cc(Cl)nc(C(=O)NC2Cc3ccccc3C2)c1]

Synthesized following General Procedure D-3, Step 2, Method 1.

Yield: (0.200 g, 12%)

ES-MS $[M+H]^+$: 408.0, Rt=7.27 min (Method-A1).

Intermediate 106

6-Chloro-N-(2,3-dihydro-1H-inden-2-yl)-4-((2-fluorophenyl)amino)picolinamide and 4-chloro-N-(2,3-dihydro-1H-inden-2-yl)-6-((2-fluorophenyl)amino) picolinamide

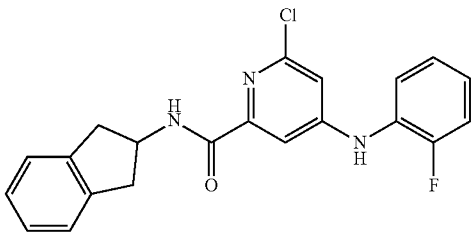

+

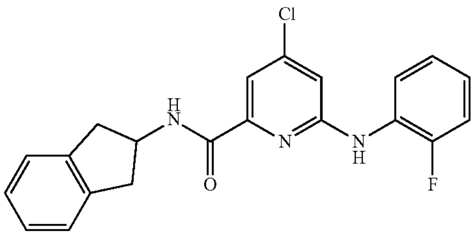

Synthesized following General Procedure D-3, Step 2, Method 1. Isolated as a mixture of the title compounds.

Yield: (0.130 g, 80%).

ES-MS $[M+H]^+$: 382.0, Rt=7.120 and 7.410 min (Method-A1).

Intermediate 107

6-Chloro-4-((2-chlorophenyl)amino)-N-(2,3-dihydro-1H-inden-2-yl)picolinamide

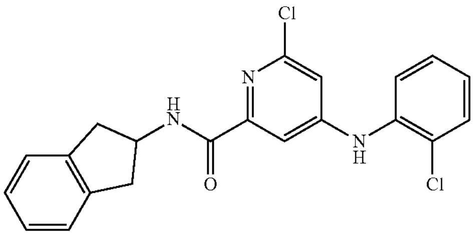 [SMILES: O=C(NC1Cc2ccccc2C1)c1cc(Nc2ccccc2Cl)cc(Cl)n1]

Synthesized following General Procedure D-3, Step 2, Method 1.

Yield: (0.270 g, 42%).

ES-MS $[M+H]^+$: 398.1, Rt=7.268 min (Method-A1).

Intermediate 108

6-Chloro-N-(2,3-dihydro-1H-inden-2-yl)-4-((2-methoxy-4-methylphenyl)amino)-picolinamide

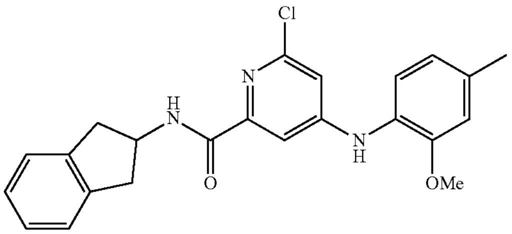 [SMILES: COc1cc(C)ccc1Nc1cc(Cl)nc(C(=O)NC2Cc3ccccc3C2)c1]

Synthesized following General Procedure D-3, Step 2, Method 1.

Yield: (0.150 g, 30%).

ES-MS $[M+H]^+$: 408.1, Rt=3.50 min (Method-A1).

Intermediate 109

6-Chloro-N-(2,3-dihydro-1H-inden-2-yl)-4-((4-fluoro-2-methoxyphenyl)amino)picolinamide

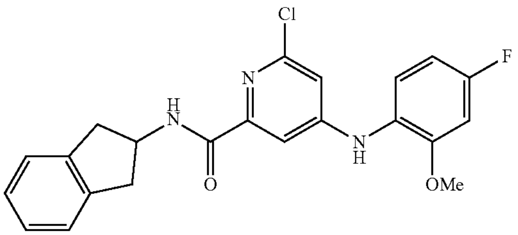 [SMILES: COc1cc(F)ccc1Nc1cc(Cl)nc(C(=O)NC2Cc3ccccc3C2)c1]

Synthesized following General Procedure D-3, Step 2, Method 1.

Yield: (0.170 g, 15%).

ES-MS $[M-H]^-$: 410.2, Rt=7.28 min (Method-A1).

Intermediate 110

4-(Benzo[d][1,3]dioxol-4-ylamino)-6-chloro-N-phenylpicolinamide

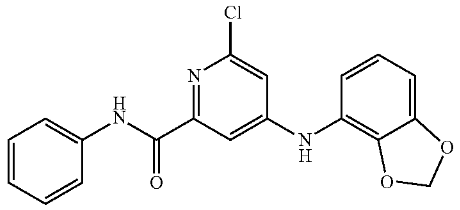

Synthesized following General Procedure D-3, Step 2, Method 1.

Yield: (0.365 g, 26%).

ES-MS $[M+H]^+$: 368.0, Rt=3.12 min (Method-A1).

Intermediate 111

6-Chloro-4-((2-fluorophenyl)amino)-N-phenylpicolinamide

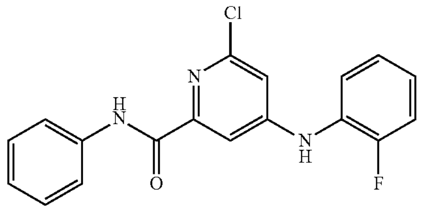 [SMILES: O=C(Nc1ccccc1)c1cc(Nc2ccccc2F)cc(Cl)n1]

Synthesized following General Procedure D-3, Step 2, Method 1.

Yield: (0.189 g, 14%).

ES-MS $[M-H]^-$: 340.2, Rt=7.153 min (Method-A1).

Intermediate 112

4-Chloro-6-((2-fluorophenyl)amino)-N-phenylpicolinamide

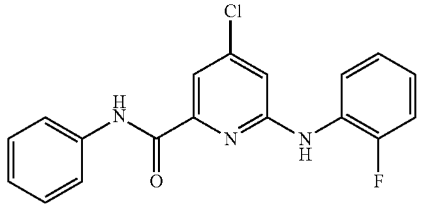 [SMILES: O=C(Nc1ccccc1)c1cc(Cl)cc(Nc2ccccc2F)n1]

Synthesized following General Procedure D-3, Step 2, Method 1.

Yield: (0.146 g, 10%).

ES-MS $[M-H]^-$: 340.2, Rt=7.270 min (Method-A1).

Intermediate 113

4-Chloro-N-(2,3-dihydro-1H-inden-2-yl)-6-(o-tolylamino)picolinamide

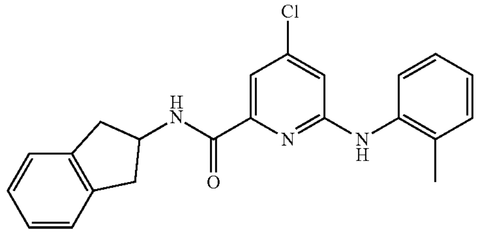 [SMILES: Cc1ccccc1Nc1cc(Cl)cc(C(=O)NC2Cc3ccccc3C2)n1]

Synthesized following General Procedure D-3, Step 2, Method 2.

Yield: (0.063 g, 24%).

ES-MS $[M+H]^+$: 378.9, Rt=7.875 min (Method-A1).

Intermediate 114

(4-Chloro-6-((2-hydroxyphenyl)amino)pyridin-2-yl)(4-phenylpiperazin-1-yl)methanone

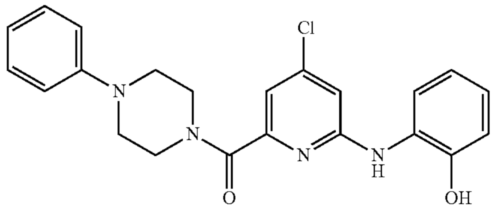 [SMILES: O=C(c1cc(Cl)cc(Nc2ccccc2O)n1)N1CCN(c2ccccc2)CC1]

Synthesized following General Procedure D-3, Step 2, Method 2. This compound was used after work up without further purification.

Yield: (0.243 g, used crude).

ES-MS $[M+H]^+$: 409.1, Rt=2.72 min (Method-A1).

Intermediate 115

6-(Benzo[d][1,3]dioxol-4-ylamino)-4-chloro-N-(2,3-dihydro-1H-inden-2-yl)picolinamide

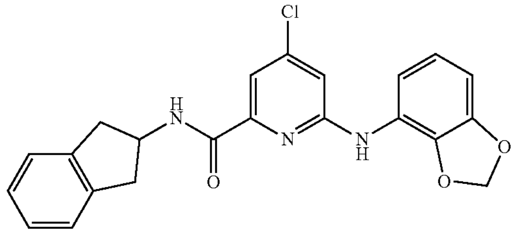 [SMILES: O=C(NC1Cc2ccccc2C1)c1cc(Cl)cc(Nc2cccc3c2OCO3)n1]

Synthesized following General Procedure D-3, Step 2, Method 2. This compound was used after work up without further purification.

Yield: (0.283 g, used crude).

ES-MS $[M+H]^+$: 408.1, Rt=7.155 min (Method-A1).

Intermediate 116

4-Chloro-N-(2,3-dihydro-1H-inden-2-yl)-6-((2-fluoro-3-methylphenyl)amino)picolinamide

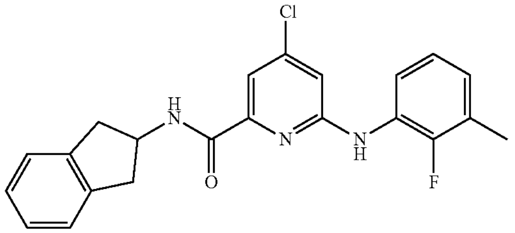 [SMILES: Cc1cccc(Nc2cc(Cl)cc(C(=O)NC3Cc4ccccc4C3)n2)c1F]

Synthesized following General Procedure D-3, Step 2, Method 2. This compound was used after work up without further purification.

Yield: (0.275 g, used crude).

ES-MS $[M+H]^+$: 396.9, Rt=7.463 min (Method-A1).

Intermediate 117

4-Chloro-N-(2,3-dihydro-1H-inden-2-yl)-6-((2-hydroxy-3-methylphenyl)amino)picolinamide

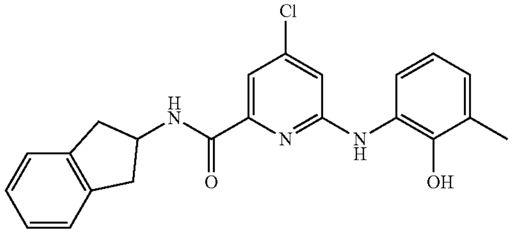 [SMILES: Cc1cccc(Nc2cc(Cl)cc(C(=O)NC3Cc4ccccc4C3)n2)c1O]

Synthesized following General Procedure D-3, Step 2, Method 2. This compound was used after work up without further purification.

Yield: (0.274 g, used crude).

ES-MS $[M+H]^+$: 394.9, Rt=7.171 min (Method-A1).

Intermediate 118

4-Chloro-N-(2,3-dihydro-1H-inden-2-yl)-6-((3-fluorophenyl)amino)picolinamide

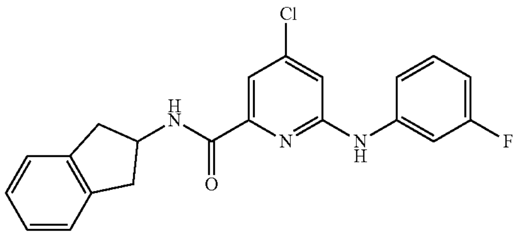 [SMILES: O=C(NC1Cc2ccccc2C1)c1cc(Cl)cc(Nc2cccc(F)c2)n1]

Synthesized following General Procedure D-3, Step 2, Method 2. This compound was used after work up without further purification.

Yield: (0.265 g, used crude).

ES-MS $[M+H]^+$: 382.9, Rt=7.331 min (Method-A1).

Intermediate 119

4-Chloro-6-((2-methoxyphenyl)amino)-N-phenylpicolinamide

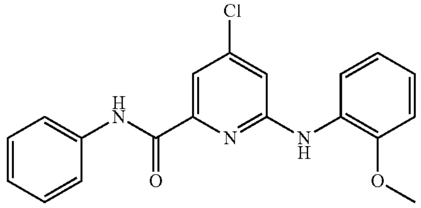 [SMILES: COc1ccccc1Nc1cc(Cl)cc(C(=O)Nc2ccccc2)n1]

Synthesized following General Procedure D-3, Step 2, Method 2.

Yield: (0.157 g, 10%).

ES-MS $[M+H]^+$: 354.9, Rt=7.247 min (Method-A1).

Intermediate 120

6-(Benzo[d][1,3]dioxol-4-ylamino)-4-chloro-N-phenylpicolinamide

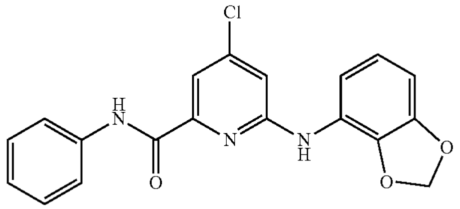 [SMILES: O=C(Nc1ccccc1)c1cc(Cl)cc(Nc2cccc3c2OCO3)n1]

Synthesized following General Procedure D-3, Step 2, Method 2.

Yield: (0.365 g, 26%).

ES-MS $[M+H]^+$: 368.0, Rt=3.22 min (Method-D1).

Intermediate 121

(6-(Benzo[d][1,3]dioxol-4-ylamino)-4-chloropyridin-2-yl)(isoindolin-2-yl)methanone

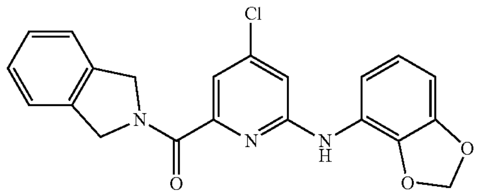 [SMILES: O=C(c1cc(Cl)cc(Nc2cccc3c2OCO3)n1)N1Cc2ccccc2C1]

Synthesized following General Procedure D-3, Step 2, Method 2.

Yield: (0.230 g, used crude).

ES-MS $[M+H]^+$: 394.9, Rt=6.985 min (Method-A1).

Intermediate 122

(4-Chloro-6-((2-methoxyphenyl)amino)pyridin-2-yl)(isoindolin-2-yl)methanone

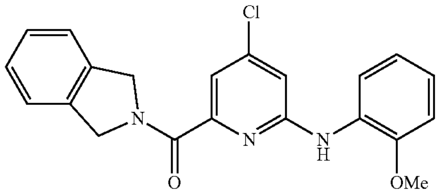 [SMILES: COc1ccccc1Nc1cc(Cl)cc(C(=O)N2Cc3ccccc3C2)n1]

Synthesized following General Procedure D-3, Step 2, Method 2.

Yield: (0.240 g, used crude).

ES-MS $[M+H]^+$: 380.1, Rt=7.149 min (Method-A1).

Intermediate 123

4-Chloro-N-(2,3-dihydro-1H-inden-2-yl)-6-(m-tolylamino)picolinamide

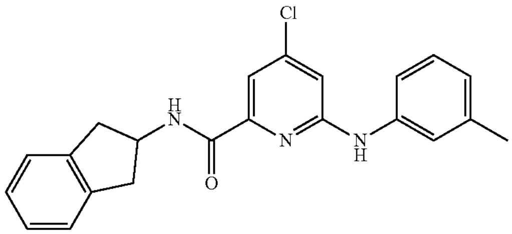 [SMILES: Cc1cccc(Nc2cc(Cl)cc(C(=O)NC3Cc4ccccc4C3)n2)c1]

Synthesized following General Procedure D-3, Step 2, Method 2.

Yield: (0.696 g, used crude).

ES-MS $[M+H]^+$: 378.1, Rt=7.394 min (Method-A1).

Intermediate 124

4-Chloro-N-(2,3-dihydro-1H-inden-2-yl)-6-((4-fluorophenyl)amino)picolinamide

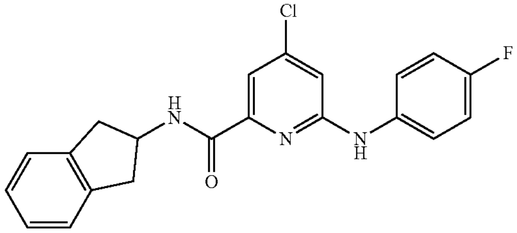 [SMILES: O=C(NC1Cc2ccccc2C1)c1cc(Cl)cc(Nc2ccc(F)cc2)n1]

Synthesized following General Procedure D-3, Step 2, Method 2.

Yield: (0.265 g, used crude).

ES-MS $[M+H]^+$: 382.0, Rt=7.212 min (Method-A1).

Intermediate 125

4-Chloro-6-((2-cyanophenyl)amino)-N-(2,3-dihydro-1H-inden-2-yl)picolinamide

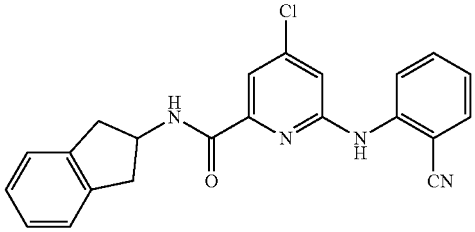 [SMILES: N#Cc1ccccc1Nc1cc(Cl)cc(C(=O)NC2Cc3ccccc3C2)n1]

Synthesized following General Procedure D-3, Step 2, Method 2.

Yield: (0.405 g, used crude).

ES-MS $[M+H]^+$: 389.1, Rt=6.895 min (Method-A1).

Intermediate 126

4-Chloro-N-(2,3-dihydro-1H-inden-2-yl)-6-((3-methoxyphenyl)amino)picolinamide

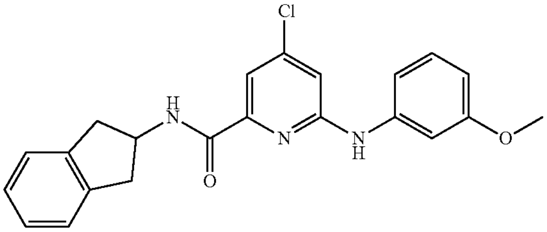 [SMILES: COc1cccc(Nc2cc(Cl)cc(C(=O)NC3Cc4ccccc4C3)n2)c1]

Synthesized following General Procedure D-3, Step 2, Method 2.

Yield: (0.274 g, used crude).

ES-MS $[M+H]^+$: 394.0, Rt=7.222 min (Method-A1).

Intermediate 127

4-Chloro-N-(2,3-dihydro-1H-inden-2-yl)-6-((2-methoxyphenyl)amino)picolinamide

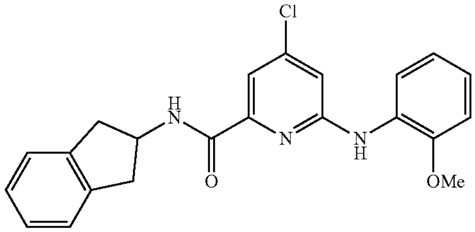

Synthesized following General Procedure D-3, Step 2, Method 1. Isolated as a beige solid.

Yield: (0.285 g, 74%).

ES-MS $[M+H]^+$: 395.0, Rt=7.538 min (Method-A1).

Intermediate 128

(4-Chloro-6-((2-methoxyphenyl)amino)pyridin-2-yl)(isoindolin-2-yl)methanone

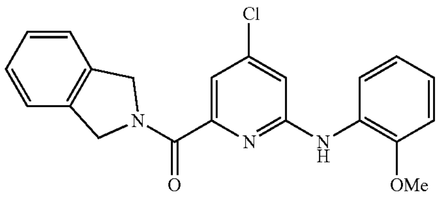

Synthesized following General Procedure D-3, Step 1, Method 2.

Yield: (0.240 g, used crude).

ES-MS $[M+H]^+$: 380.1, Rt=7.149 min (Method-A1).

Intermediate 129

4-Chloro-N-(2,3-dihydro-1H-inden-2-yl)-6-(m-tolylamino)picolinamide

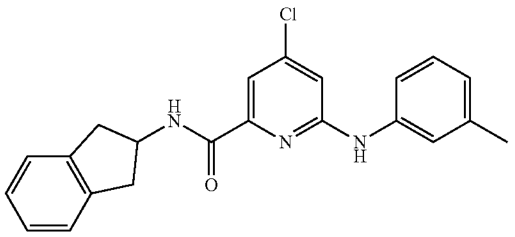 [SMILES: Cc1cccc(Nc2cc(Cl)cc(C(=O)NC3Cc4ccccc4C3)n2)c1]

Synthesized following General Procedure D-3, Step 1, Method 2.

Yield: (0.696 g, used crude).

ES-MS $[M+H]^+$: 378.1, Rt=7.394 min (Method-A1).

Intermediate 130

4-Chloro-N-(2,3-dihydro-1H-inden-2-yl)-6-((4-fluorophenyl)amino)picolinamide

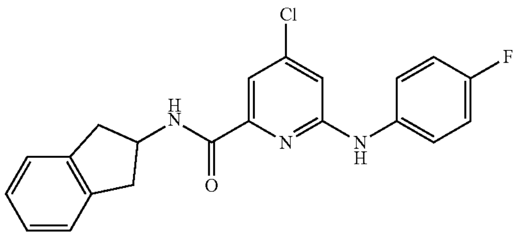 [SMILES: O=C(NC1Cc2ccccc2C1)c1cc(Cl)cc(Nc2ccc(F)cc2)n1]

Synthesized following General Procedure D-3, Step 1, Method 2.

Yield: (0.265 g, used crude).

ES-MS $[M+H]^+$: 382.0, Rt=7.212 min (Method-A1).

Intermediate 131

4-Chloro-6-((2-cyanophenyl)amino)-N-(2,3-dihydro-1H-inden-2-yl)picolinamide

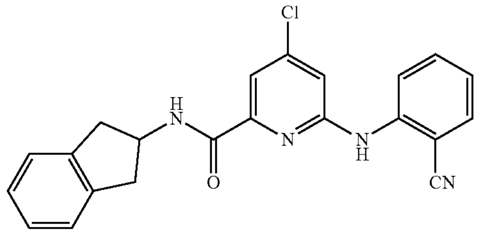 [SMILES: N#Cc1ccccc1Nc1cc(Cl)cc(C(=O)NC2Cc3ccccc3C2)n1]

Synthesized following General Procedure D-3, Step 1, Method 2.

Yield: (0.405 g, used crude).

ES-MS $[M+H]^+$: 389.1, Rt=6.895 min (Method-A1).

Intermediate 132

4-Chloro-N-(2,3-dihydro-1H-inden-2-yl)-6-((3-methoxyphenyl)amino)picolinamide

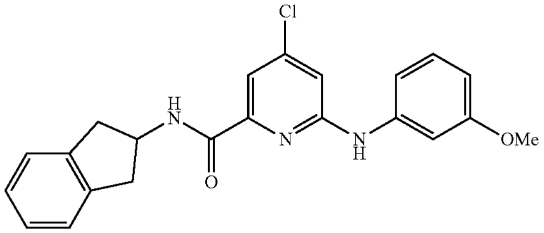 [SMILES: COc1cccc(Nc2cc(Cl)cc(C(=O)NC3Cc4ccccc4C3)n2)c1]

Synthesized following General Procedure D-3, Step 1, Method 2.

Yield: (0.274 g, used crude).

ES-MS $[M+H]^+$: 394.0, Rt=7.222 min (Method-A1).

Intermediate 133

(4-Chloro-6-((3-fluorophenyl)amino)pyridin-2-yl)(4-phenylpiperazin-1-yl)methanone

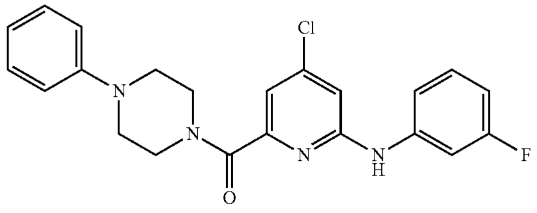 [SMILES: O=C(c1cc(Cl)cc(Nc2cccc(F)c2)n1)N1CCN(c2ccccc2)CC1]

Synthesized following General Procedure D-3, Step 1, Method 2.

Yield: (0.244 g, used crude).

ES-MS $[M+H]^+$: 411.0, Rt=7.008 min (Method-A1).

Intermediate 134

4-Chloro-N-(2,3-dihydro-1H-inden-2-yl)-6-((2-methoxyphenyl)amino)-N-methyl-picolinamide

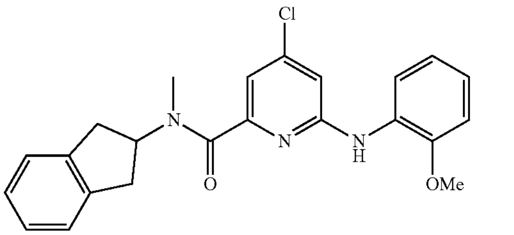 [SMILES: COc1ccccc1Nc1cc(Cl)cc(C(=O)N(C)C2Cc3ccccc3C2)n1]

Synthesized following General Procedure D-3, Step 1, Method 2.

Yield: (0.254 g, used crude).

ES-MS $[M+H]^+$: 408.1, Rt=7.192 min (Method-A1).

Intermediate 135

4-Chloro-N-(2,3-dihydro-1H-inden-2-yl)-6-((3-fluorophenyl)amino)-N-methylpicolinamide

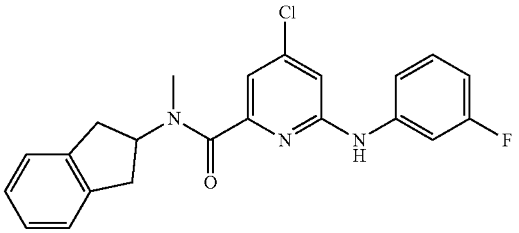 [SMILES: CN(C(=O)c1cc(Cl)cc(Nc2cccc(F)c2)n1)C1Cc2ccccc2C1]

Synthesized following General Procedure D-3, Step 1, Method 2.

Yield: (0.246 g, used crude).

ES-MS $[M+H]^+$: 394.1, Rt=7.157 min (Method-A1).

Intermediate 136

4-Chloro-N-(2,3-dihydro-1H-inden-2-yl)-6-((3-fluoro-2-methylphenyl)amino)picolinamide

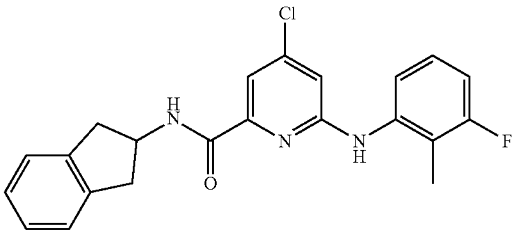 [SMILES: Cc1c(F)cccc1Nc1cc(Cl)cc(C(=O)NC2Cc3ccccc3C2)n1]

Synthesized following General Procedure D-3, Step 1, Method 2.

Yield: (0.257 g, used crude).

ES-MS $[M+H]^+$: 394.1, Rt=7.371 min (Method-A1).

Intermediate 137

4-Chloro-N-(2,3-dihydro-1H-inden-2-yl)-6-((3-methoxyphenyl)amino)picolinamide

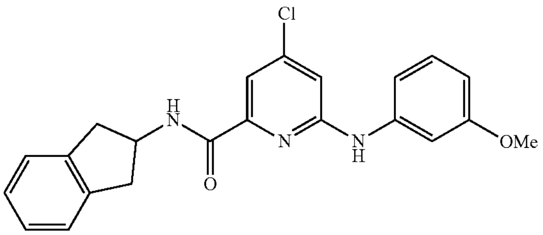 [SMILES: COc1cccc(Nc2cc(Cl)cc(C(=O)NC3Cc4ccccc4C3)n2)c1]

Synthesized following General Procedure D-3, Step 1, Method 2.

Yield: (0.274 g, used crude).

ES-MS $[M-H]^-$: 394.1, Rt=7.222 min (Method-A1).

Intermediate 138

4-Chloro-6-((2-cyanophenyl)amino)-N-(2,3-dihydro-1H-inden-2-yl)picolinamide

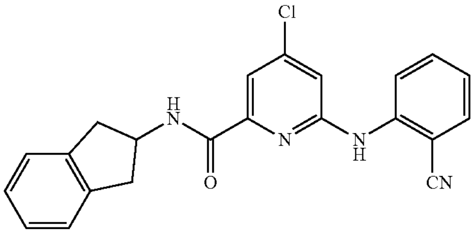 [SMILES: N#Cc1ccccc1Nc1cc(Cl)cc(C(=O)NC2Cc3ccccc3C2)n1]

Synthesized following General Procedure D-3, Step 1, Method 2.

Yield: (0.405 g, used crude).

ES-MS $[M-H]^-$: 387.3, Rt=6.895 min (Method-A1).

Intermediate 139

4-Chloro-6-((3,5-difluorophenyl)amino)-N-(2,3-dihydro-1H-inden-2-yl)picolinamide

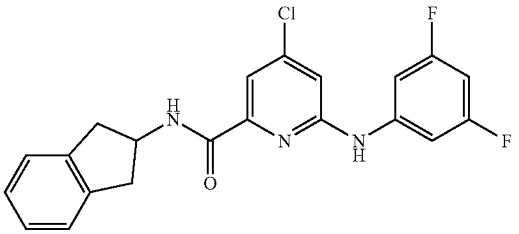 [SMILES: O=C(NC1Cc2ccccc2C1)c1cc(Cl)cc(Nc2cc(F)cc(F)c2)n1]

Synthesized following General Procedure D-3, Step 1, Method 2.

Yield: (0.260 g, used crude).

ES-MS $[M-H]^-$: 400.1, Rt=7.411 min (Method-A1).

Intermediate 140

4-Chloro-N-(2,3-dihydro-1H-inden-2-yl)-6-((4-fluorophenyl)amino)picolinamide

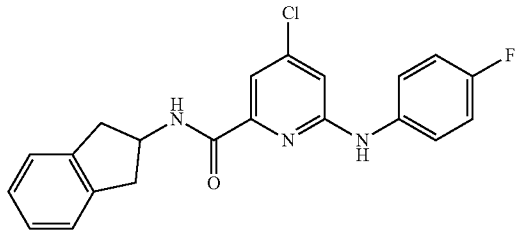 [SMILES: O=C(NC1Cc2ccccc2C1)c1cc(Cl)cc(Nc2ccc(F)cc2)n1]

Synthesized following General Procedure D-3, Step 1, Method 2.

Yield: (0.265 g, used crude).

ES-MS $[M-H]^-$: 380.3, Rt=7.212 min (Method-A1).

Intermediate 141

4-Chloro-N-(2,3-dihydro-1H-inden-2-yl)-6-(m-tolylamino)picolinamide

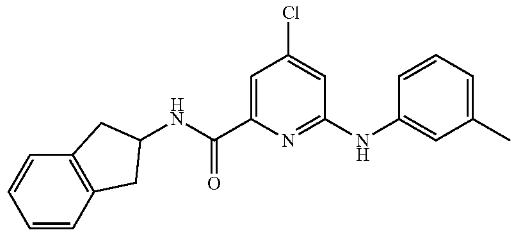 [SMILES: Cc1cccc(Nc2cc(Cl)cc(C(=O)NC3Cc4ccccc4C3)n2)c1]

Synthesized following General Procedure D-3, Step 1, Method 2.

Yield: (0.263 g, used crude).

ES-MS $[M-H]^-$: 376.3, Rt=7.394 min (Method-A1).

Intermediate 142

4-Chloro-6-((2-hydroxyphenyl)amino)-N-methyl-N-phenylpicolinamide

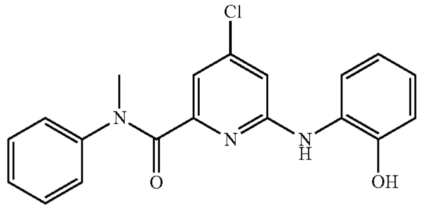 [SMILES: CN(C(=O)c1cc(Cl)cc(Nc2ccccc2O)n1)c1ccccc1]

Synthesized following General Procedure D-3, Step 1, Method 2.

Yield: (0.251 g, used crude).

ES-MS $[M-H]^-$: 376.3, Rt=6.383 min (Method-A1).

Intermediate 143

4-Chloro-N-(2,3-dihydrobenzo[b][1,4]dioxin-6-yl)-6-((2-fluorophenyl)amino)picolinamide

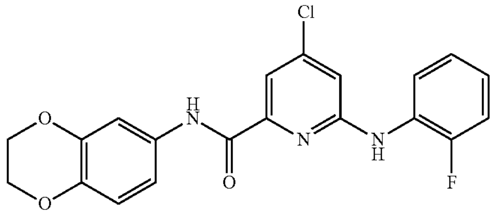 [SMILES: O=C(Nc1ccc2c(c1)OCCO2)c1cc(Cl)cc(Nc2ccccc2F)n1]

Synthesized following General Procedure D-3, Step 1, Method 2.

Yield: (0.245 g, used crude).

ES-MS $[M+H]^+$: 400.1, Rt=7.110 min (Method-A1).

Intermediate 144

4-Chloro-N-(2,3-dihydro-1H-inden-2-yl)-6-((3-hydroxyphenyl)amino)picolinamide

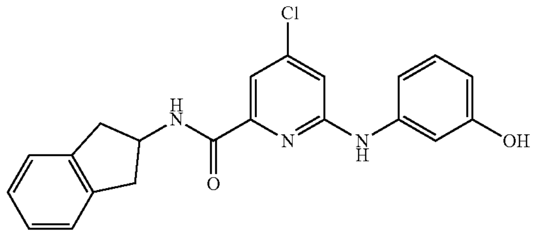 [SMILES: O=C(NC1Cc2ccccc2C1)c1cc(Cl)cc(Nc2cccc(O)c2)n1]

Synthesized following General Procedure D-3, Step 1, Method 2.

Yield: (0.118 g, used crude).

ES-MS $[M-H]^-$: 378.4, Rt=6.718 min (Method-A1).

Intermediate 145

4-Chloro-6-((2-methoxyphenyl)amino)-N-methyl-N-phenylpicolinamide

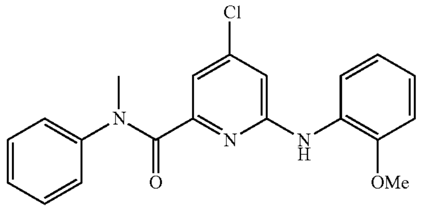 [SMILES: COc1ccccc1Nc1cc(Cl)cc(C(=O)N(C)c2ccccc2)n1]

Synthesized following General Procedure D-3, Step 1, Method 2.

Yield: (0.262 g, used crude).

ES-MS $[M-H]^-$: 368.0, Rt=6.776 min (Method-A1).

Intermediate 146

4-Chloro-6-((2-fluorophenyl)amino)-N-methyl-N-phenylpicolinamide

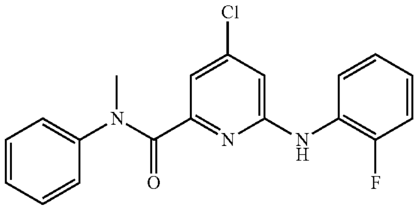

Synthesized following General Procedure D-3, Step 1, Method 2.

Yield: (0.253 g, used crude).

ES-MS [M−H]$^-$: 354.3, Rt=6.700 min (Method-A1).

Intermediate 147

4-Chloro-6-((3-fluorophenyl)amino)-N-methyl-N-phenylpicolinamide

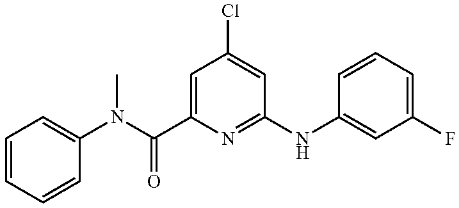 [SMILES: CN(C(=O)c1cc(Cl)cc(Nc2cccc(F)c2)n1)c1ccccc1]

Synthesized following General Procedure D-3, Step 1, Method 2.

Yield: (0.255 g, used crude).

ES-MS [M−H]$^-$: 356.1, Rt=6.733 min (Method-A1).

Intermediate 148

(4-Chloro-6-((3-fluorophenyl)amino)pyridin-2-yl)(isoindolin-2-yl)methanone

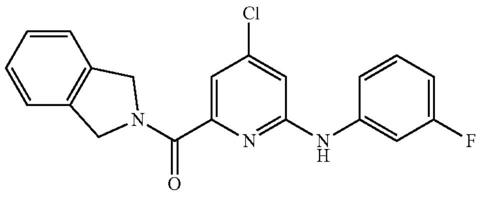 [SMILES: O=C(c1cc(Cl)cc(Nc2cccc(F)c2)n1)N1Cc2ccccc2C1]

Synthesized following General Procedure D-3, Step 1, Method 2.

Yield: (0.500 g, used crude).

ES-MS [M−H]$^-$: 368.0, Rt=6.866 min (Method-A1).

Intermediate 149

4-Chloro-N-(2,3-dihydro-1H-inden-2-yl)-6-((2-hydroxyphenyl)amino)-N-methyl-picolinamide

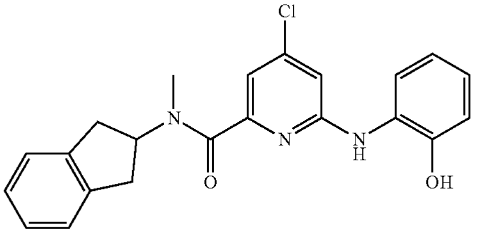

Synthesized following General Procedure D-3, Step 1, Method 2.

Yield: (0.211 g, used crude).

ES-MS [M−H]$^-$: 394.1, Rt=6.845 min (Method-A1).

Intermediate 150

4-Chloro-N-(2,3-dihydro-1H-inden-2-yl)-6-((2-fluorophenyl)amino)-N-methylpicolinamide

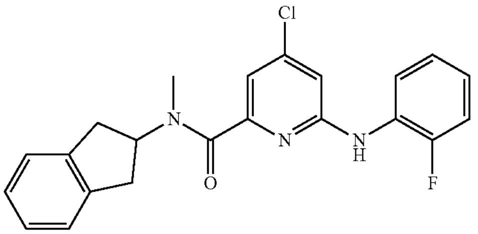

Synthesized following General Procedure D-3, Step 1, Method 2.

Yield: (0.246 g, used crude).

ES-MS [M−H]$^-$: 396.2, Rt=7.122 min (Method-A1).

Intermediate 151

4-Chloro-N-(2,3-dihydro-1H-inden-2-yl)-6-((2-methoxyphenyl)amino)picolinamide

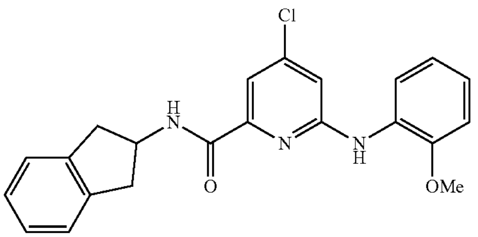

Synthesized following General Procedure D-3, Step 1, Method 2.

Yield: (was not isolated, used crude).

ES-MS [M−H]$^-$: 394.2, Rt=3.34 min (Method-D1).

Intermediate 152

4-Chloro-6-((3-fluorophenyl)amino)-N-phenylpicolinamide

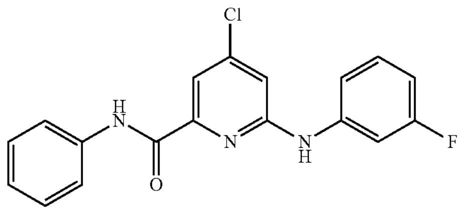 [SMILES: O=C(Nc1ccccc1)c1cc(Cl)cc(Nc2cccc(F)c2)n1]

Synthesized following General Procedure D-3, Step 1, Method 2.

Yield: (0.255 g, used crude).

ES-MS $[M-H]^-$: 342.1, Rt=7.318 min (Method-A1).

Intermediate 153

4-Chloro-6-((3-methoxyphenyl)amino)-N-phenylpicolinamide

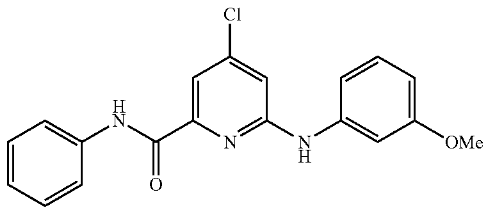 [SMILES: COc1cccc(Nc2cc(Cl)cc(C(=O)Nc3ccccc3)n2)c1]

Synthesized following General Procedure D-3, Step 1, Method 2.

Yield: (0.264 g, used crude).

ES-MS $[M-H]^-$: 354.1, Rt=7.271 min (Method-A1).

Intermediate 154

4-Chloro-6-((3-fluorophenyl)amino)-N-(m-tolyl)picolinamide

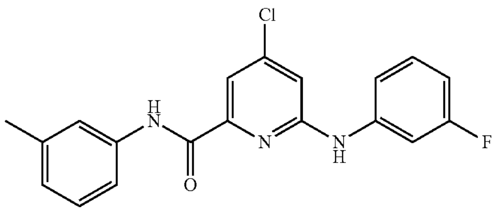 [SMILES: Cc1cccc(NC(=O)c2cc(Cl)cc(Nc3cccc(F)c3)n2)c1]

Synthesized following General Procedure D-3, Step 1, Method 2.

Yield: (0.252 g, used crude).

ES-MS $[M-H]^-$: 356.0, Rt=7.498 min (Method-A1).

Intermediate 155

4-Chloro-N-(3,4-dimethylphenyl)-6-((3-fluorophenyl)amino)picolinamide

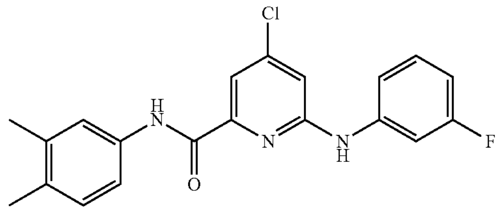 [SMILES: Cc1ccc(NC(=O)c2cc(Cl)cc(Nc3cccc(F)c3)n2)cc1C]

Synthesized following General Procedure D-3, Step 1, Method 2.

Yield: (0.590 g, used crude).

ES-MS $[M-H]^-$: 370.0, Rt=7.573 min (Method-A1).

Intermediate 156

4-Chloro-N-(2,3-dihydro-1H-inden-2-yl)-6-((2-fluorophenyl)amino)picolinamide

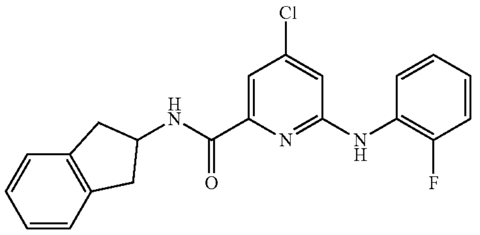 [SMILES: O=C(NC1Cc2ccccc2C1)c1cc(Cl)cc(Nc2ccccc2F)n1]

Synthesized following General Procedure D-3, Step 1, Method 2.

Yield: (3.73 g, used crude).

ES-MS $[M-H]^-$: 382.1, Rt=7.197 min (Method-A1).

General Procedure E

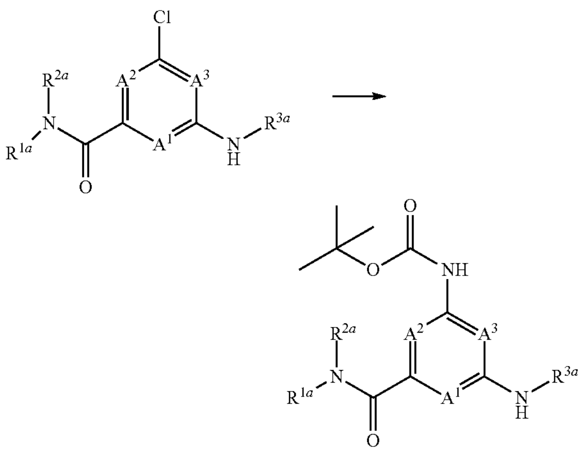

XPhos (5-10 mol %) and Pd2(dba)$_3$ (3-6 mol %) were added over a degassed solution of the appropriate carboxamide (ex: 4-chloro-6-((2-methoxyphenyl)amino)pyrimidine-2-carboxamide) (1.0 eq), tert-butyl carbamate (3.0 eq) and $Cs_2CO_3$ (3.0 eq) in dioxane (4.0 mL/mmol). The resulting mixture was stirred at 100° C. under nitrogen atmosphere for 18 h. The mixture was then diluted with EtOAc and water. Layers were separated. Aqueous layer was extracted with EtOAc (×2). Combined organic layers were washed with water and brine, dried over $MgSO_4$, filtered and concentrated. The resultant crude was purified by flash column chromatography (EtOAc/Hexane 50 to 100%) to obtain the desired product (ex: tert-butyl (6-((2-methoxyphenyl)amino)-2-(4-phenylpiperazine-1-carbonyl)pyrimidin-4-yl)carbamate).

Intermediate 157

Tert-butyl (6-((2-methoxyphenyl)amino)-2-(4-phenylpiperazine-1-carbonyl)pyrimidin-4-yl)carbamate

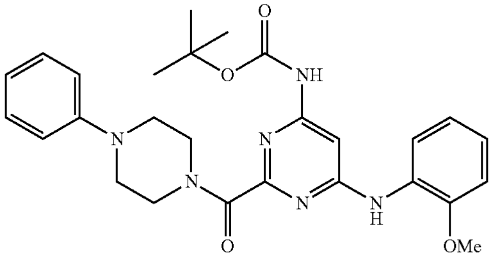 [SMILES: COc1ccccc1Nc1cc(NC(=O)OC(C)(C)C)nc(C(=O)N2CCN(c3ccccc3)CC2)n1]

Synthesized following General Procedure E.

Yield: (0.186 g, 56%).

ES-MS $[M+H]^+$: 505.0, Rt=7.109 min (Method-A1).

Intermediate 158

Tert-butyl (2-((2,3-dihydro-1H-inden-2-yl)carbamoyl)-6-((2-methoxyphenyl)amino)-pyrimidin-4-yl) carbamate

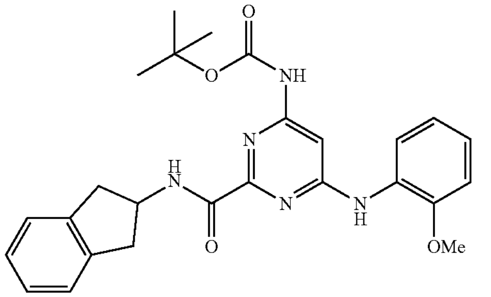 [SMILES: COc1ccccc1Nc1cc(NC(=O)OC(C)(C)C)nc(C(=O)NC2Cc3ccccc3C2)n1]

Synthesized following General Procedure E. Isolated as a yellow solid.

Yield: (0.388 g, 67%).

ES-MS $[M-H]^-$: 476.9, Rt=6.365 min (Method-A1).

Intermediate 159

Tert-butyl (6-((2-methoxyphenyl)amino)-2-(phenylcarbamoyl)pyrimidin-4-yl)carbamate

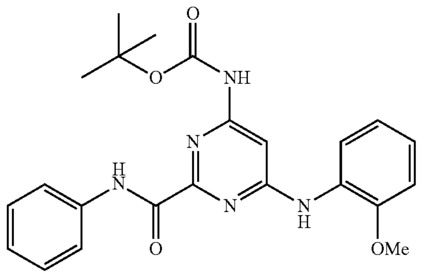 [SMILES: COc1ccccc1Nc1cc(NC(=O)OC(C)(C)C)nc(C(=O)Nc2ccccc2)n1]

Synthesized following General Procedure E.

Yield: (0.070 g, 9%).

ES-MS $[M-H]^-$: 436.9, Rt=2.054 min (Method-D1).

Intermediate 160

Tert-butyl (4-((2-methoxyphenyl)amino)-6-(4-phenylpiperazine-1-carbonyl)pyridin-2-yl)carbamate

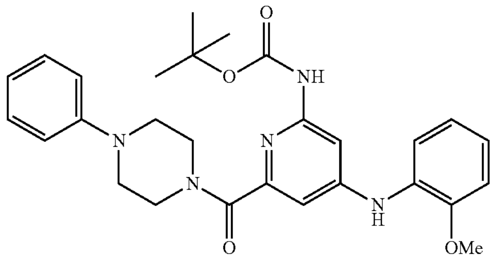 [SMILES: COc1ccccc1Nc1cc(NC(=O)OC(C)(C)C)nc(C(=O)N2CCN(c3ccccc3)CC2)c1]

Synthesized following General Procedure E.

Yield: (0.297 g, 46%).

ES-MS $[M+H]^+$: 504.0, Rt=7.040 min (Method-A1).

Intermediate 161

Tert-butyl (4-((2-fluorophenyl)amino)-6-(4-phenylpiperazine-1-carbonyl)pyridin-2-yl)carbamate

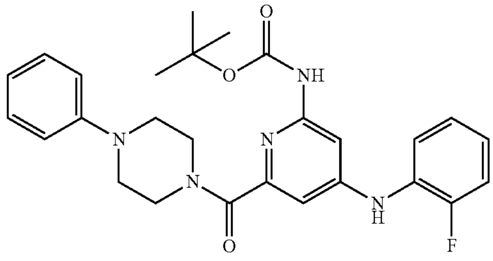 [SMILES: CC(C)(C)OC(=O)Nc1cc(Nc2ccccc2F)cc(C(=O)N2CCN(c3ccccc3)CC2)n1]

Synthesized following General Procedure E.

Yield: (0.050 g, 21%).

ES-MS $[M+H]^+$: 491.1, Rt=7.060 min (Method-A1).

Intermediate 162

Tert-butyl (6-(isoindoline-2-carbonyl)-4-((2-methoxyphenyl)amino)pyridin-2-yl)carbamate

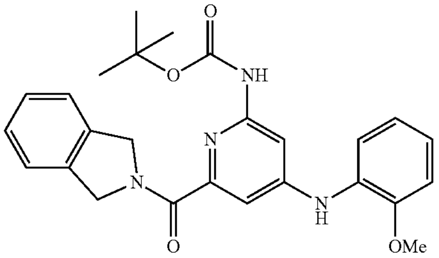 [SMILES: COc1ccccc1Nc1cc(NC(=O)OC(C)(C)C)nc(C(=O)N2Cc3ccccc3C2)c1]

Synthesized following General Procedure E. Isolated as a yellow wax.

Yield: (0.118 g, 43%).

ES-MS $[M+H]^+$: 461.1, Rt=2.804 min (Method-D1).

Intermediate 163

Tert-butyl (6-(indoline-1-carbonyl)-4-((2-methoxyphenyl)amino)pyridin-2-yl)carbamate

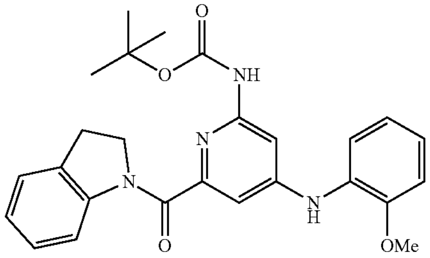 [SMILES: COc1ccccc1Nc1cc(NC(=O)OC(C)(C)C)nc(C(=O)N2CCc3ccccc32)c1]

Synthesized following General Procedure E. Isolated as a as a brown solid.

Yield: (0.690 g, 71%).

ES-MS $[M+H]^+$: 461.1, Rt=7.715 min (Method-A1).

Intermediate 164

Tert-butyl (4-((2-methoxyphenyl)amino)-6-(phenylcarbamoyl)pyridin-2-yl)carbamate and tert-butyl (2-((2-methoxyphenyl)amino)-6-(phenylcarbamoyl)pyridin-4-yl)carbamate

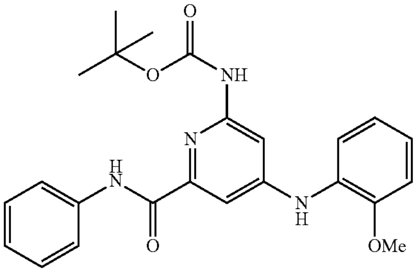

+

-continued

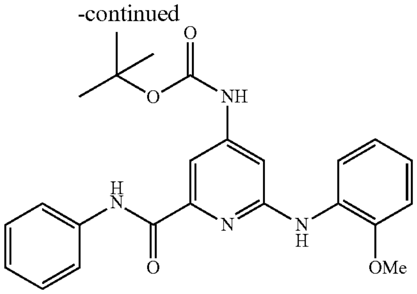

Synthesized following General Procedure E. Isolated as a mixture of the title compounds.

Yield: (0.236 g, 16%).

ES-MS $[M+H]^+$: 435.0, Rt=6.996 and 7.416 min (Method-A1).

Intermediate 165

Tert-butyl (6-((2,3-dihydro-1H-inden-2-yl)carbamoyl)-4-((2-methoxyphenyl)amino)pyridin-2-yl)carbamate

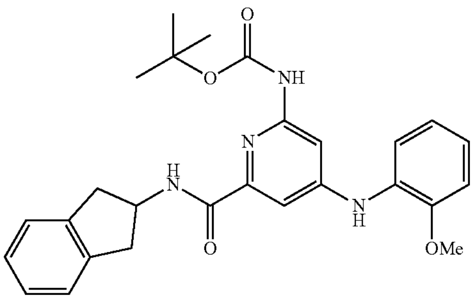 [SMILES: COc1ccccc1Nc1cc(NC(=O)OC(C)(C)C)nc(C(=O)NC2Cc3ccccc3C2)c1]

Synthesized following General Procedure E.

Yield: (0.205 g, 84%).

ES-MS [M+H]+: 475.2, Rt=7.240 min (Method-A1).

Intermediate 166

Tert-butyl (6-((2,3-dihydro-1H-inden-2-yl)carbamoyl)-4-((2-fluorophenyl)amino)pyridin-2-yl)carbamate and tert-butyl (2-((2,3-dihydro-1H-inden-2-yl)carbamoyl)-6-((2-fluorophenyl)amino)pyridin-4-yl)carbamate

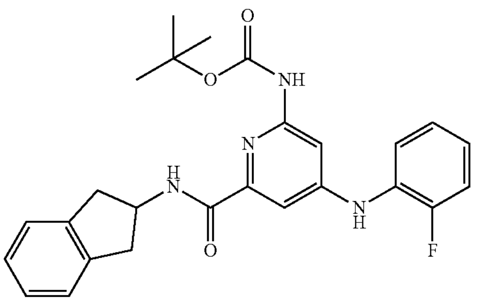

+

-continued

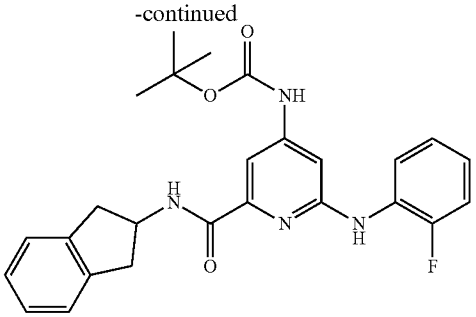

Synthesized following General Procedure E. Isolated as a mixture of the title compounds.

Yield: (0.280 g, 96%).

ES-MS $[M+H]^+$: 463.1, Rt=7.145 and 7.211 min (Method-A1).

Intermediate 167

Tert-butyl (4-((2-chlorophenyl)amino)-6-((2,3-dihydro-1H-inden-2-yl)carbamoyl)pyridin-2-yl)carbamate

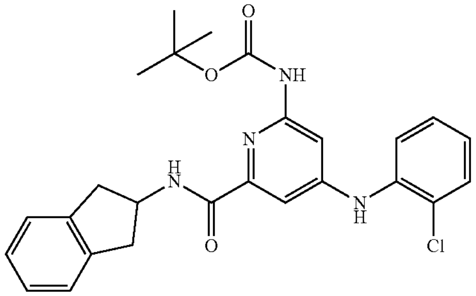 [SMILES: CC(C)(C)OC(=O)Nc1cc(Nc2ccccc2Cl)cc(C(=O)NC2Cc3ccccc3C2)n1]

Synthesized following General Procedure E.

Yield: (0.050 g, 50%).

ES-MS $[M+H]^+$: 479.1, Rt=7.424 min (Method-A1).

Intermediate 168

Tert-butyl (6-((2,3-dihydro-1H-inden-2-yl)carbamoyl)-4-((2-methoxy-4-methylphenyl)-amino)pyridin-2-yl)carbamate

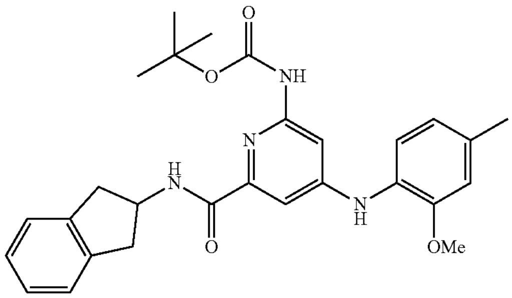 [SMILES: COc1cc(C)ccc1Nc1cc(NC(=O)OC(C)(C)C)nc(C(=O)NC2Cc3ccccc3C2)c1]

Synthesized following General Procedure E.

Yield: (0.098 g, 55%).

ES-MS $[M+H]^+$: 489.2, Rt=3.12 min (Method-D1).

Intermediate 169

Tert-butyl (6-((2,3-dihydro-1H-inden-2-yl)carbamoyl)-4-((4-fluoro-2-methoxyphenyl)-amino)pyridin-2-yl)carbamate

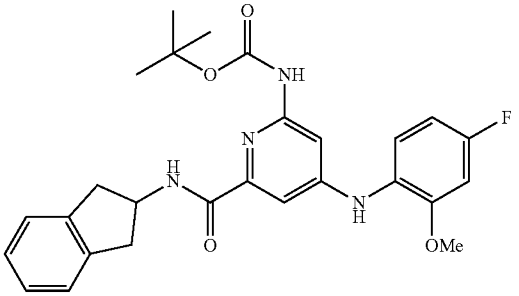 [SMILES: COc1cc(F)ccc1Nc1cc(NC(=O)OC(C)(C)C)nc(C(=O)NC2Cc3ccccc3C2)c1]

Synthesized following General Procedure E.

Yield: (0.250 g, 21%).

ES-MS $[M-H]^-$: 491.1, Rt=7.34 min (Method-A1).

Intermediate 170

Tert-butyl (4-(benzo[d][1,3]dioxol-4-ylamino)-6-(phenylcarbamoyl)pyridin-2-yl)carbamate

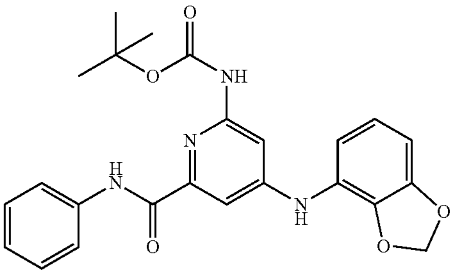

Synthesized following General Procedure E.

Yield: (0.372 g, 43%).

ES-MS $[M+H]^+$: 449.1, Rt=6.948 min (Method-A1).

Intermediate 171

Tert-butyl (4-((2-fluorophenyl)amino)-6-(phenylcarbamoyl)pyridin-2-yl)carbamate

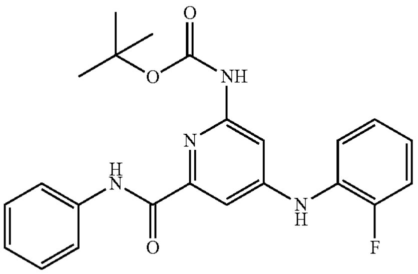 [SMILES: CC(C)(C)OC(=O)Nc1cc(Nc2ccccc2F)cc(C(=O)Nc2ccccc2)n1]

Synthesized following General Procedure E.

Yield: (0.147 g, 63%).

ES-MS $[M+H]^+$: 423.2, Rt=7.247 min (Method-A1).

Intermediate 172

Tert-butyl (2-((2-fluorophenyl)amino)-6-(phenylcarbamoyl)pyridin-4-yl)carbamate

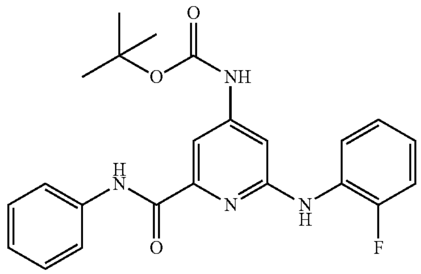 [SMILES: CC(C)(C)OC(=O)Nc1cc(Nc2ccccc2F)nc(C(=O)Nc2ccccc2)c1]

Synthesized following General Procedure E.
Yield: (0.055 g, 31%).
ES-MS $[M+H]^+$: 423.2, Rt=7.361 min (Method-A1).

Intermediate 173

Tert-butyl (4-((2,3-dihydro-1H-inden-2-yl)carbamoyl)-6-((2-methoxyphenyl)amino)-pyrimidin-2-yl) carbamate

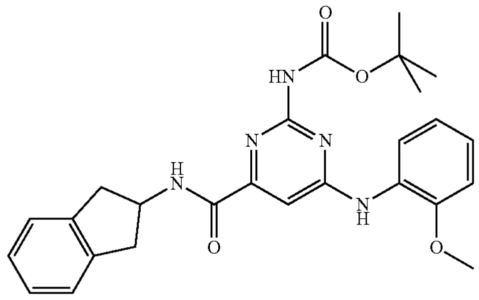 [SMILES: COc1ccccc1Nc1cc(C(=O)NC2Cc3ccccc3C2)nc(NC(=O)OC(C)(C)C)n1]

Synthesized following General Procedure E.
Yield: (0.147 g, 89% yield).
ES-MS $[M+H]^+$:476.1 Rt=7.198 min (Method-A1).

Intermediate 174

Tert-butyl (4-((2,3-dihydro-1H-inden-2-yl)(methyl) carbamoyl)-6-((2-methoxyphenyl)-amino)pyrimidin-2-yl)carbamate

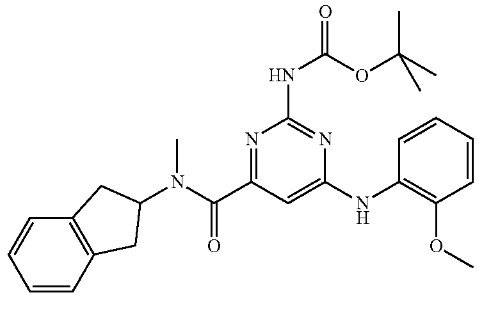 [SMILES: COc1ccccc1Nc1cc(C(=O)N(C)C2Cc3ccccc3C2)nc(NC(=O)OC(C)(C)C)n1]

Synthesized following General Procedure E.
Yield: (0.330 g, 40% yield).
ES-MS $[M+H]^+$:490.1 Rt=6.267 min (Method-A1).

Intermediate 175

Tert-butyl (4-((2-methoxyphenyl)amino)-6-(methyl (1,2,3,4-tetrahydronaphthalen-2-yl)carbamoyl)pyrimidin-2-yl)carbamate

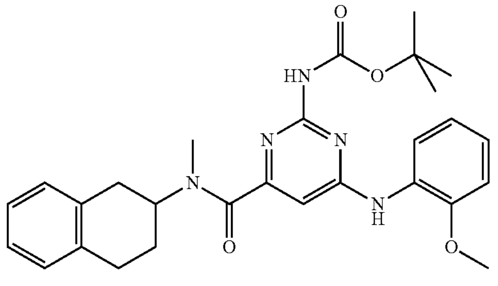 [SMILES: COc1ccccc1Nc1cc(C(=O)N(C)C2CCc3ccccc3C2)nc(NC(=O)OC(C)(C)C)n1]

Synthesized following General Procedure E.
Yield: (0.062 g, 20% yield).
ES-MS $[M+H]^+$:504.1 Rt=6.377 min (Method-A1).

Intermediate 176

Tert-butyl (4-((2-methoxyphenyl)amino)-6-((1,2,3,4-tetrahydronaphthalen-2-yl)carbamoyl)-pyrimidin-2-yl)carbamate

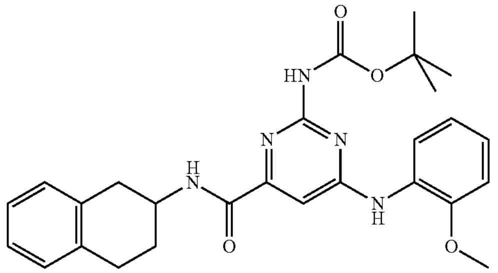 [SMILES: COc1ccccc1Nc1cc(C(=O)NC2CCc3ccccc3C2)nc(NC(=O)OC(C)(C)C)n1]

Synthesized following General Procedure E.
Yield: (0.301 g, 53% yield).
ES-MS $[M+H]^+$:490.2 Rt=7.289 min (Method-A1).

Intermediate 177

Tert-butyl (4-((2-methoxyphenyl)amino)-6-(1,2,3,4-tetrahydroisoquinoline-2-carbonyl)-pyrimidin-2-yl) carbamate

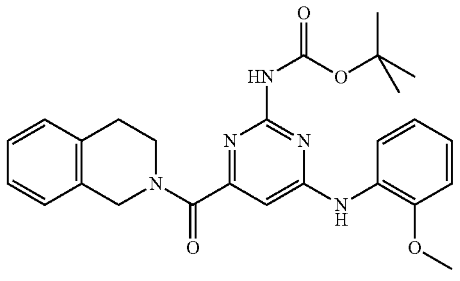 [SMILES: COc1ccccc1Nc1cc(C(=O)N2CCc3ccccc3C2)nc(NC(=O)OC(C)(C)C)n1]

Synthesized following General Procedure E, Yield: (0.343 g, 45% yield). ES-MS $[M+H]^+$:476.2 Rt=6.987 min (Method-A1).

Intermediate 178

Tert-butyl (4-(isoindoline-2-carbonyl)-6-((2-methoxyphenyl)amino)pyrimidin-2-yl)carbamate

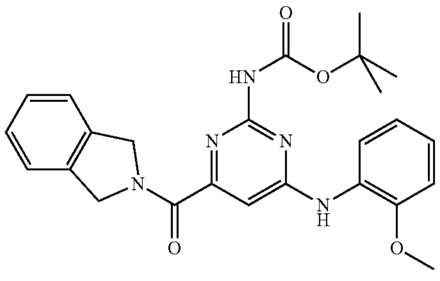 [SMILES: COc1ccccc1Nc1cc(C(=O)N2Cc3ccccc3C2)nc(NC(=O)OC(C)(C)C)n1]

Synthesized following General Procedure E. Yield: (0.078 g, 21% yield). ES-MS $[M+H]^+$:462.1 Rt=7.018 min (Method-A1).

Intermediate 179

Tert-butyl (2-((2,3-dihydro-1H-inden-2-yl)carbamoyl)-6-(o-tolylamino)pyridin-4-yl)carbamate

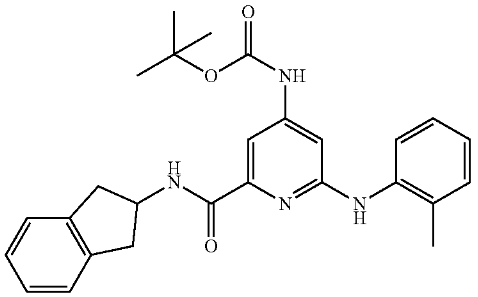 [SMILES: Cc1ccccc1Nc1cc(NC(=O)OC(C)(C)C)cc(C(=O)NC2Cc3ccccc3C2)n1]

Synthesized following General Procedure E. Yield: (0.057 g, 75%). ES-MS $[M+H]^+$: 459.3, Rt=7.472 min (Method-A1).

Intermediate 180

Tert-butyl (2-((2-hydroxyphenyl)amino)-6-(4-phenylpiperazine-1-carbonyl)pyridin-4-yl)carbamate

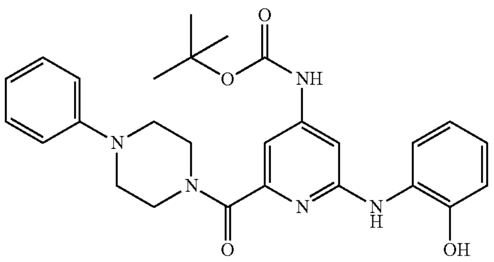 [SMILES: CC(C)(C)OC(=O)Nc1cc(Nc2ccccc2O)nc(C(=O)N2CCN(c3ccccc3)CC2)c1]

Synthesized following General Procedure E. Yield: (0.109 g, 85%). ES-MS $[M+H]^+$: 490.3, Rt=6.973 min (Method-A1).

Intermediate 181

Tert-butyl (2-(benzo[d][1,3]dioxol-4-ylamino)-6-((2,3-dihydro-1H-inden-2-yl)carbamoyl)-pyridin-4-yl) carbamate

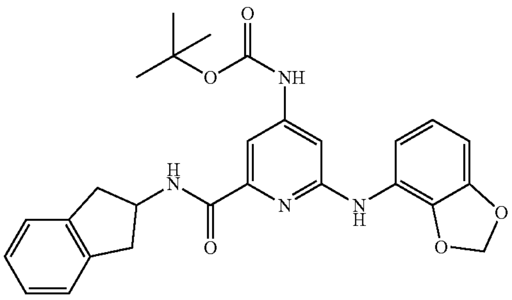 [SMILES: CC(C)(C)OC(=O)Nc1cc(Nc2cccc3c2OCO3)nc(C(=O)NC2Cc3ccccc3C2)c1]

Synthesized following General Procedure E. Yield: (0.195 g, 58%). ES-MS $[M+H]^+$: 489.2, Rt=7.294 min (Method-A1).

Intermediate 182

Tert-butyl (2-((2,3-dihydro-1H-inden-2-yl)carbamoyl)-6-((2-fluoro-3-methylphenyl)-amino)pyridin-4-yl)carbamate

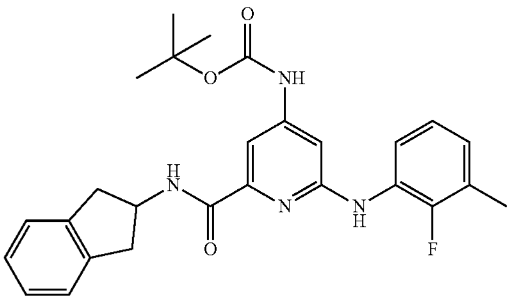 [SMILES: Cc1cccc(Nc2cc(NC(=O)OC(C)(C)C)cc(C(=O)NC3Cc4ccccc4C3)n2)c1F]

Synthesized following General Procedure E. Yield: (0.283 g, 86%). ES-MS $[M+H]^+$: 477.3, Rt=7.601 min (Method-A1).

Intermediate 183

Tert-butyl (2-((2,3-dihydro-1H-inden-2-yl)carbamoyl)-6-((2-hydroxy-3-methylphenyl)-amino)pyridin-4-yl)carbamate

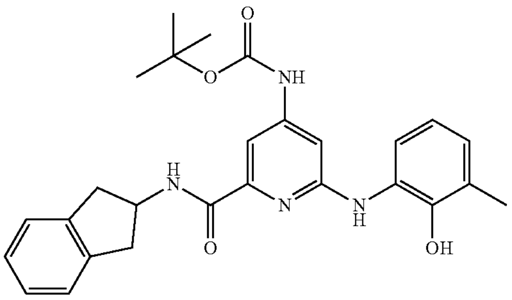 [SMILES: Cc1cccc(Nc2cc(NC(=O)OC(C)(C)C)cc(C(=O)NC3Cc4ccccc4C3)n2)c1O]

Synthesized following General Procedure E.

Yield: (0.251 g, 76%).

ES-MS $[M+H]^+$: 475.3, Rt=7.329 min (Method-A1).

Intermediate 184

Tert-butyl (2-((2,3-dihydro-1H-inden-2-yl)carbamoyl)-6-((3-fluorophenyl)amino)pyridin-4-yl)carbamate

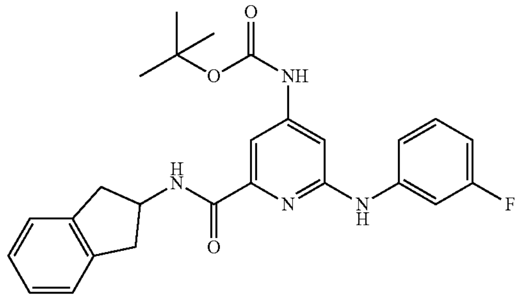 [SMILES: CC(C)(C)OC(=O)Nc1cc(Nc2cccc(F)c2)nc(C(=O)NC2Cc3ccccc3C2)c1]

Synthesized following General Procedure E.

Yield: (0.305 g, 95%).

ES-MS $[M+H]^+$: 463.2, Rt=7.490 min (Method-A1).

Intermediate 185

Tert-butyl (2-((2-methoxyphenyl)amino)-6-(phenylcarbamoyl)pyridin-4-yl)carbamate

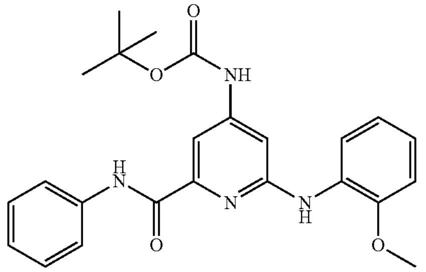

Synthesized following General Procedure E.

Yield: (0.123 g, 85%).

ES-MS $[M+H]^+$: 435.2, Rt=3.40 min (Method-D1).

Intermediate 186

Tert-butyl (2-(benzo[d][1,3]dioxol-4-ylamino)-6-(phenylcarbamoyl)pyridin-4-yl)carbamate

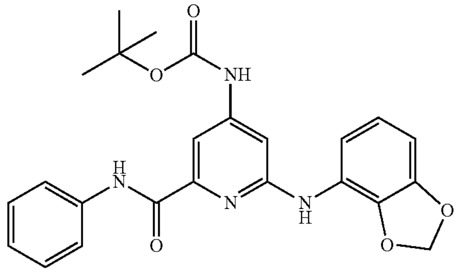 [SMILES: CC(C)(C)OC(=O)Nc1cc(Nc2cccc3c2OCO3)nc(C(=O)Nc2ccccc2)c1]

Synthesized following General Procedure E.

Yield: (0.341 g, 77%).

ES-MS $[M-H]^-$: 447.2, Rt=7.093 min (Method-A1).

Intermediate 187

Tert-butyl (2-(benzo[d][1,3]dioxol-4-ylamino)-6-(isoindoline-2-carbonyl)pyridin-4-yl)carbamate

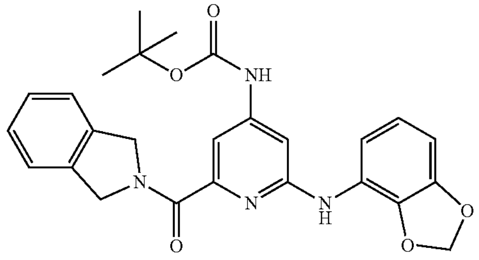 [SMILES: CC(C)(C)OC(=O)Nc1cc(Nc2cccc3c2OCO3)nc(C(=O)N2Cc3ccccc3C2)c1]

Synthesized following General Procedure E.

Yield: (0.253 g, 91%).

ES-MS $[M-H]^-$: 475.2, Rt=7.119 min (Method-A1).

Intermediate 198

Tert-butyl (2-(isoindoline-2-carbonyl)-6-((2-methoxyphenyl)amino)pyridin-4-yl)carbamate

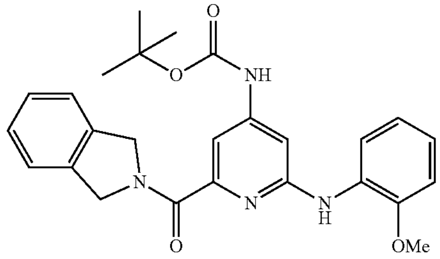 [SMILES: COc1ccccc1Nc1cc(NC(=O)OC(C)(C)C)cc(C(=O)N2Cc3ccccc3C2)n1]

Synthesized following General Procedure E.

Yield: (0.239 g, 82%).

ES-MS $[M+H]^+$: 461.2, Rt=7.309 min (Method-A1).

Intermediate 189

Tert-butyl (2-((2,3-dihydro-1H-inden-2-yl)carbamoyl)-6-(m-tolylamino)pyridin-4-yl)carbamate

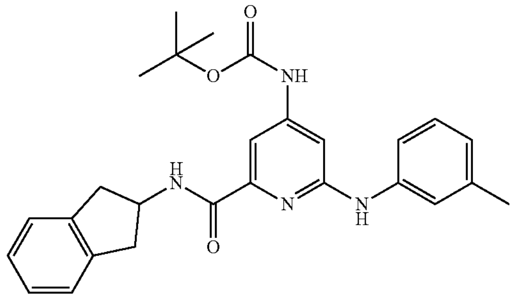 [SMILES: Cc1cccc(Nc2cc(NC(=O)OC(C)(C)C)cc(C(=O)NC3Cc4ccccc4C3)n2)c1]

Synthesized following General Procedure E.

Yield: (0.304 g, 95%).

ES-MS $[M+H]^+$: 459.2, Rt=7.511 min (Method-A1).

Intermediate 190

Tert-butyl (2-((2,3-dihydro-1H-inden-2-yl)carbamoyl)-6-((4-fluorophenyl)amino)pyridin-4-yl)carbamate

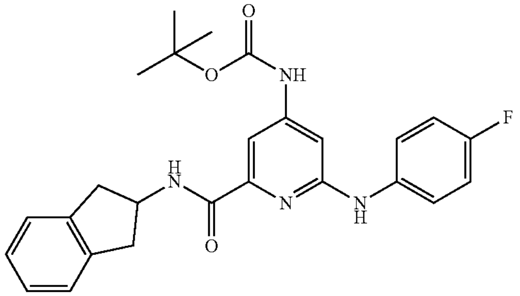 [SMILES: CC(C)(C)OC(=O)Nc1cc(Nc2ccc(F)cc2)nc(C(=O)NC2Cc3ccccc3C2)c1]

Synthesized following General Procedure E.

Yield: (0.314 g, 97% over two steps).

ES-MS $[M+H]^+$: 463.2, Rt=7.360 min (Method-A1).

Intermediate 191

Tert-butyl (2-((2-cyanophenyl)amino)-6-((2,3-dihydro-1H-inden-2-yl)carbamoyl)pyridin-4-yl)carbamate

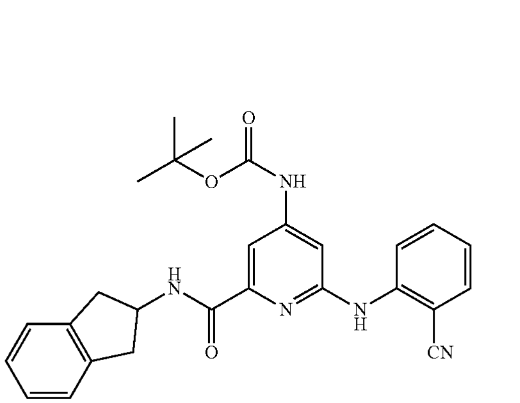 [SMILES: CC(C)(C)OC(=O)Nc1cc(Nc2ccccc2C#N)nc(C(=O)NC2Cc3ccccc3C2)c1]

Synthesized following General Procedure E.

Yield: (0.059 g, 12% over two steps).

ES-MS $[M+H]^+$: 470.2, Rt=7.103 min (Method-A1).

Intermediate 192

Tert-butyl (2-((2,3-dihydro-1H-inden-2-yl)carbamoyl)-6-((3-methoxyphenyl)amino)pyridin-4-yl)carbamate

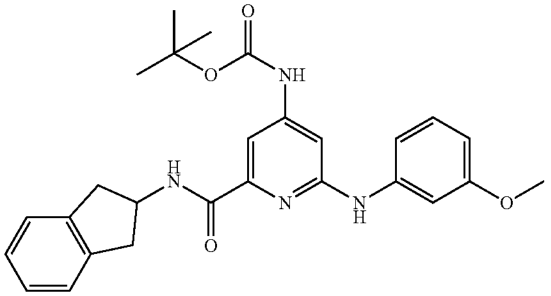 [SMILES: COc1cccc(Nc2cc(NC(=O)OC(C)(C)C)cc(C(=O)NC3Cc4ccccc4C3)n2)c1]

Synthesized following General Procedure E.

Yield: (0.183 g, 55% over two steps).

ES-MS $[M+H]^+$: 475.3, Rt=7.333 min (Method-A1).

General procedure F

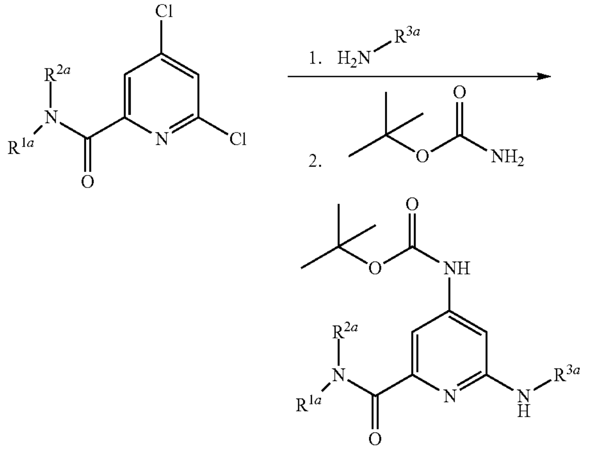

Dppf (6 mol %) and $Pd(OAc)_2$ (3 mol %) were added over a degassed solution of the appropriate aryl dichloride compound (ex: 4,6-dichloropicolinamide) (1.0 eq), the appropriate arylamine (ex: 2-chloroaniline) (1.0 eq) and $K_3PO_4$ (2.0 eq) in dioxane (5 mL/mmol). The resulting mixture was stirred at 90° C. under nitrogen atmosphere for 2 h. Then, tert-butyl carbamate was added (3 eq) together with additional amounts of dppf (6 mol %) and $Pd(OAc)_2$ (2 mol %). The mixture was stirred at 90° C. for 18 h. The mixture was then diluted with EtOAc and water. Layers were separated. Aqueous layer was extracted with EtOAc (x2). Combined organic layers were washed with water and brine, dried over $MgSO_4$, filtered and concentrated. The resultant crude was purified by flash column chromatography (Hexane:EtOAc 60:40) to obtain the desired product (ex: tert-butyl (2-((2-chlorophenyl)amino)-6-((2,3-dihydro-1H-inden-2-yl)carbamoyl)pyridin-4-yl)carbamate).

Intermediate 193

Tert-butyl (2-((2-chlorophenyl)amino)-6-((2,3-dihydro-1H-inden-2-yl)carbamoyl)pyridin-4-yl)carbamate

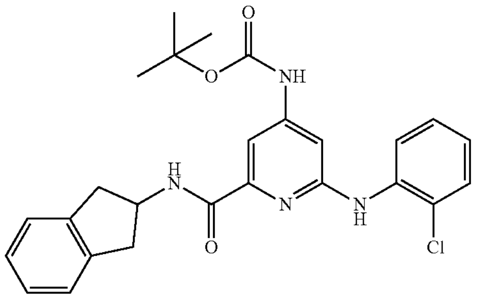 [SMILES: CC(C)(C)OC(=O)Nc1cc(Nc2ccccc2Cl)nc(C(=O)NC2Cc3ccccc3C2)c1]

Synthesized following General Procedure F.

Yield: (0.326 g, 85%).

ES-MS $[M+H]^+$: 479.9, Rt=3.49 min (Method-D1).

Intermediate 194

Tert-butyl (2-((2,3-dihydro-1H-inden-2-yl)carbamoyl)-6-(pyridin-3-ylamino)pyridin-4-yl)carbamate

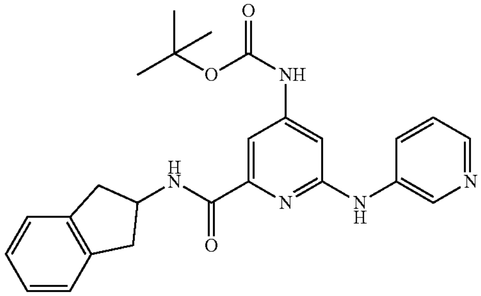 [SMILES: CC(C)(C)OC(=O)Nc1cc(Nc2cccnc2)nc(C(=O)NC2Cc3ccccc3C2)c1]

Synthesized following General Procedure F.

Yield: (0.098 g, 32%).

ES-MS $[M+H]^+$: 446.2, Rt=2.14 min (Method-D1).

Intermediate 195

Tert-butyl (4-((2-hydroxy-4-methylphenyl)amino)-6-(phenylcarbamoyl)pyridin-2-yl)carbamate

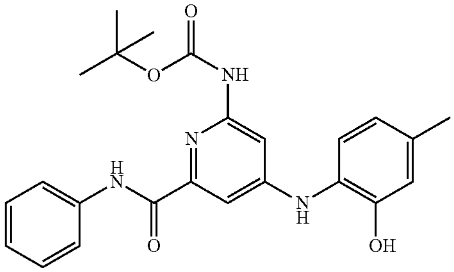 [SMILES: Cc1ccc(Nc2cc(NC(=O)OC(C)(C)C)nc(C(=O)Nc3ccccc3)c2)c(O)c1]

Synthesized following General Procedure F.

Yield: (0.269 g, 83%).

ES-MS $[M+H]^+$: 435.2, Rt=3.00 min (Method-D1).

Intermediate 196

Tert-butyl (4-((4-fluoro-2-hydroxyphenyl)amino)-6-(phenylcarbamoyl)pyridin-2-yl)carbamate

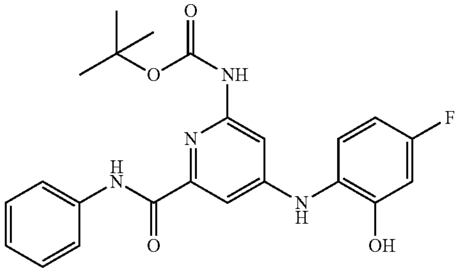 [SMILES: CC(C)(C)OC(=O)Nc1cc(Nc2ccc(F)cc2O)cc(C(=O)Nc2ccccc2)n1]

Synthesized following General Procedure F.

Yield: (0.216 g, 64%).

ES-MS $[M+H]^+$: 439.2, Rt=2.97 min (Method-D1).

Intermediate 197

Tert-butyl (6-(phenylcarbamoyl)-4-(pyridin-2-ylamino)pyridin-2-yl)carbamate

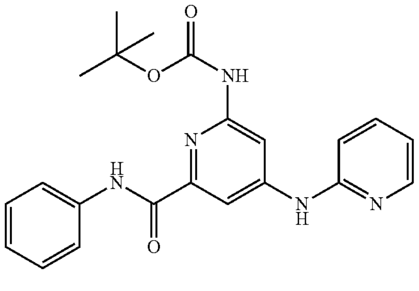 [SMILES: CC(C)(C)OC(=O)Nc1cc(Nc2ccccn2)cc(C(=O)Nc2ccccc2)n1]

Synthesized following General Procedure F.

Yield: (0.230 g, 36%).

ES-MS $[M+H]^+$: 406.3, Rt=7.108 min (Method-A1).

Intermediate 198

Tert-butyl (6-(phenylcarbamoyl)-4-(pyridin-3-ylamino)pyridin-2-yl)carbamate

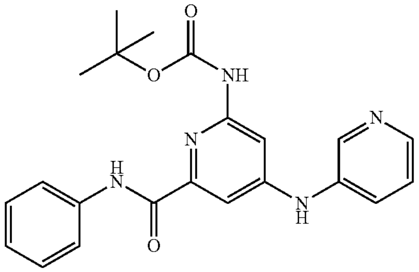 [SMILES: CC(C)(C)OC(=O)Nc1cc(Nc2cccnc2)cc(C(=O)Nc2ccccc2)n1]

Synthesized following General Procedure F.

Yield: (0.220 g, 36%).

ES-MS $[M+H]^+$: 406.3, Rt=6.93 min (Method-A1).

Intermediate 199

Tert-butyl (2-((2,3-dihydro-1H-inden-2-yl)carbamoyl)-6-(m-tolylamino)pyridin-4-yl)carbamate

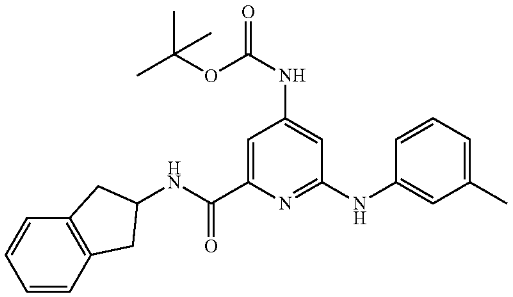 [SMILES: Cc1cccc(Nc2cc(NC(=O)OC(C)(C)C)cc(C(=O)NC3Cc4ccccc4C3)n2)c1]

Synthesized following General Procedure F.
Yield: (0.304 g, 95%).
ES-MS $[M+H]^+$: 459.2, Rt=7.511 min (Method-A1).

Intermediate 200

Tert-butyl (2-((2,3-dihydro-1H-inden-2-yl)carbamoyl)-6-((4-fluorophenyl)amino)pyridin-4-ylcarbamate

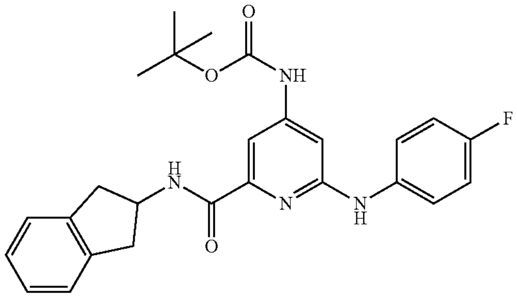 [SMILES: CC(C)(C)OC(=O)Nc1cc(Nc2ccc(F)cc2)nc(C(=O)NC2Cc3ccccc3C2)c1]

Synthesized following General Procedure F.
Yield: (0.314 g, 97% over two steps).
ES-MS $[M+H]^+$: 463.2, Rt=7.360 min (Method-A1).

Intermediate 201

Tert-butyl (2-((2-cyanophenyl)amino)-6-((2,3-dihydro-1H-inden-2-yl)carbamoyl)pyridin-4-yl)carbamate

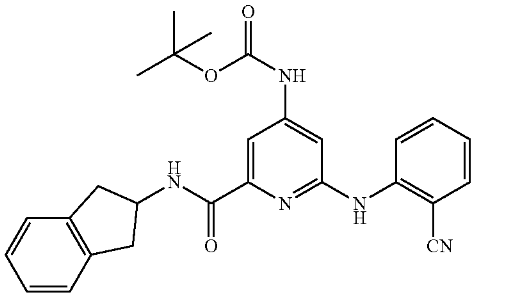 [SMILES: CC(C)(C)OC(=O)Nc1cc(Nc2ccccc2C#N)nc(C(=O)NC2Cc3ccccc3C2)c1]

Synthesized following General Procedure F.
Yield: (0.059 g, 12% over two steps).
ES-MS $[M+H]^+$: 470.2, Rt=7.103 min (Method-A1).

Intermediate 202

Tert-butyl (2-((2,3-dihydro-1H-inden-2-yl)carbamoyl)-6-((3-methoxyphenyl)amino)pyridin-4-yl)carbamate

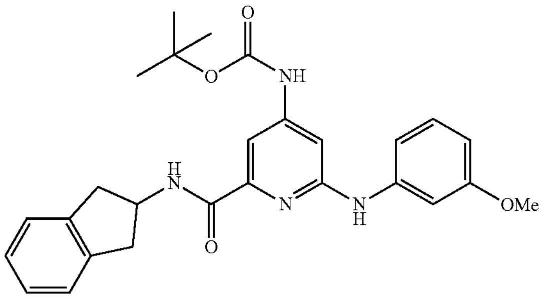 [SMILES: COc1cccc(Nc2cc(NC(=O)OC(C)(C)C)cc(C(=O)NC3Cc4ccccc4C3)n2)c1]

Synthesized following General Procedure F.
Yield: (0.183 g, 55% over two steps).
ES-MS $[M+H]^+$: 475.3, Rt=7.333 min (Method-A1).

Intermediate 203

Tert-butyl (2-(isoindoline-2-carbonyl)-6-((2-methoxyphenyl)amino)pyridin-4-yl)carbamate

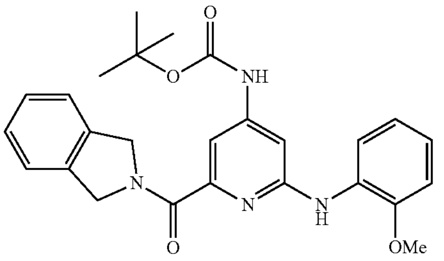 [SMILES: COc1ccccc1Nc1cc(NC(=O)OC(C)(C)C)cc(C(=O)N2Cc3ccccc3C2)n1]

Synthesized following General Procedure F.
Yield: (0.239 g, 82% over two steps).
ES-MS $[M+H]^+$: 461.2, Rt=7.309 min (Method-A1).

Intermediate 204

Tert-butyl (2-((3-fluorophenyl)amino)-6-(4-phenylpiperazine-1-carbonyl)pyridin-4-yl)carbamate

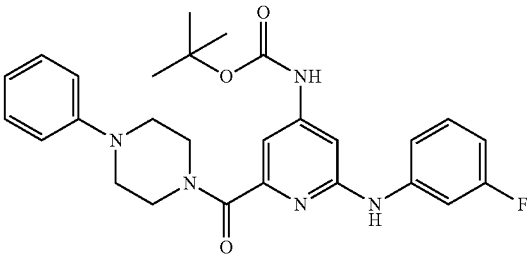 [SMILES: CC(C)(C)OC(=O)Nc1cc(Nc2cccc(F)c2)nc(C(=O)N2CCN(c3ccccc3)CC2)c1]

Synthesized following General Procedure F.
Yield: (0.269 g, 92% over two steps).
ES-MS $[M+H]^+$: 492.2, Rt=7.194 min (Method-A1).

Intermediate 205

Tert-butyl (2-((2,3-dihydro-1H-inden-2-yl)(methyl) carbamoyl)-6-((2-methoxyphenyl)amino)pyridin-4-yl)carbamate

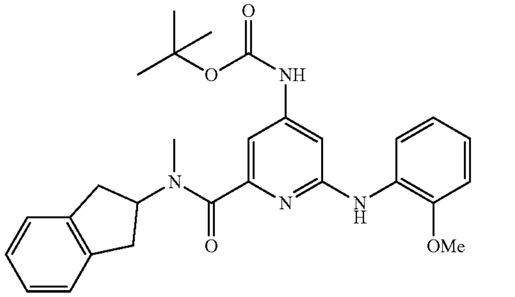

Synthesized following General Procedure F.

Yield: (0.291 g, 96% over two steps).

ES-MS $[M+H]^+$: 489.3, Rt=7.328 min (Method-A1).

Intermediate 206

Tert-butyl (2-((2,3-dihydro-1H-inden-2-yl)(methyl) carbamoyl)-6-((3-fluorophenyl)amino)pyridin-4-yl) carbamate

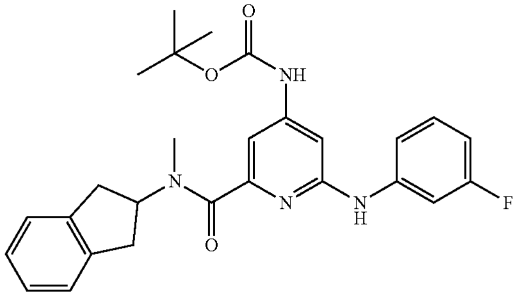 [SMILES: CN(C(=O)c1cc(NC(=O)OC(C)(C)C)cc(Nc2cccc(F)c2)n1)C1Cc2ccccc2C1]

Synthesized following General Procedure F.

Yield: (0.265 g, 89% over two steps).

ES-MS $[M+H]^+$: 477.3, Rt=7.325 min (Method-A1).

Intermediate 207

Tert-butyl (2-((2,3-dihydro-1H-inden-2-yl)carbamoyl)-6-((3-fluoro-2-methylphenyl)amino)pyridin-4-yl)carbamate

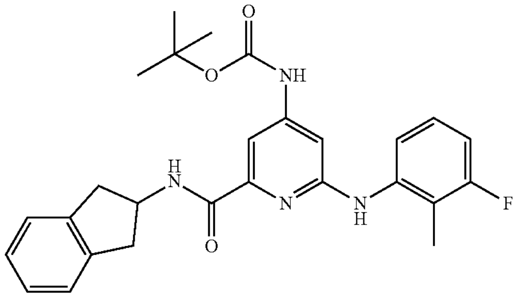 [SMILES: Cc1c(F)cccc1Nc1cc(NC(=O)OC(C)(C)C)cc(C(=O)NC2Cc3ccccc3C2)n1]

Synthesized following General Procedure F.

Yield: (0.173 g, 56% over two steps).

ES-MS $[M+H]^+$: 477.3, Rt=7.485 min (Method-A1).

Intermediate 208

Tert-butyl (2-((2,3-dihydro-1H-inden-2-yl)carbamoyl)-6-((3-methoxyphenyl)amino)pyridin-4-yl)carbamate

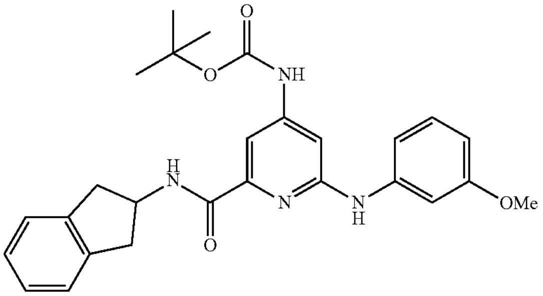 [SMILES: COc1cccc(Nc2cc(NC(=O)OC(C)(C)C)cc(C(=O)NC3Cc4ccccc4C3)n2)c1]

Synthesized following General Procedure F.

Yield: (0.183 g, 55% over two steps).

ES-MS $[M+H]^+$: 475.3, Rt=7.333 min (Method-A1).

Intermediate 209

Tert-butyl (2-((2-cyanophenyl)amino)-6-((2,3-dihydro-1H-inden-2-yl)carbamoyl)pyridin-4-yl)carbamate

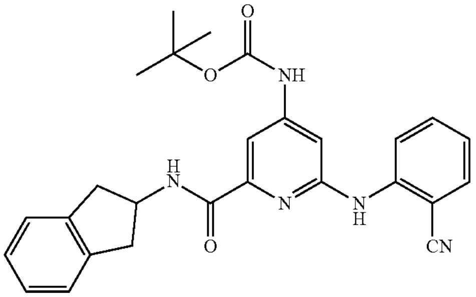

Synthesized following General Procedure F.

Yield: (0.59 g, 12% over two steps).

ES-MS $[M+H]^+$: 470.2, Rt=7.103 min (Method-A1).

Intermediate 210

Tert-butyl (2-((3,5-difluorophenyl)amino)-6-((2,3-dihydro-1H-inden-2-yl)carbamoyl)pyridin-4-yl)carbamate

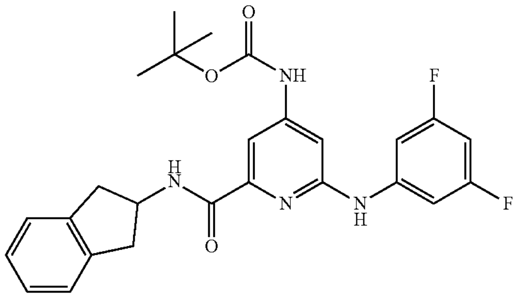 [SMILES: CC(C)(C)OC(=O)Nc1cc(Nc2cc(F)cc(F)c2)nc(C(=O)NC2Cc3ccccc3C2)c1]

Synthesized following General Procedure F.

Yield: (0.382 g, quant. over two steps).

ES-MS $[M+H]^+$: 470.2, Rt=7.103 min (Method-A1).

Intermediate 211

Tert-butyl (2-((2,3-dihydro-1H-inden-2-yl)carbamoyl)-6-((4-fluorophenyl)amino)pyridin-4-yl)carbamate

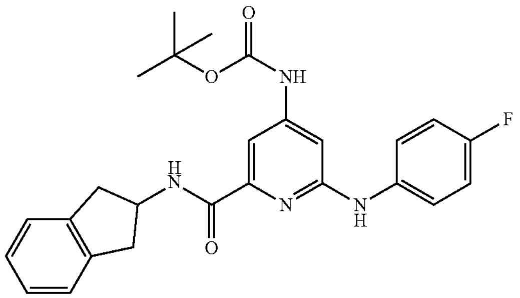 [SMILES: CC(C)(C)OC(=O)Nc1cc(Nc2ccc(F)cc2)nc(C(=O)NC2Cc3ccccc3C2)c1]

Synthesized following General Procedure F.

Yield: (0.314 g, 97% over two steps).

ES-MS $[M+H]^+$: 463.2, Rt=7.360 min (Method-A1).

Intermediate 212

Tert-butyl (2-((2,3-dihydro-1H-inden-2-yl)carbamoyl)-6-(m-tolylamino)pyridin-4-yl)carbamate

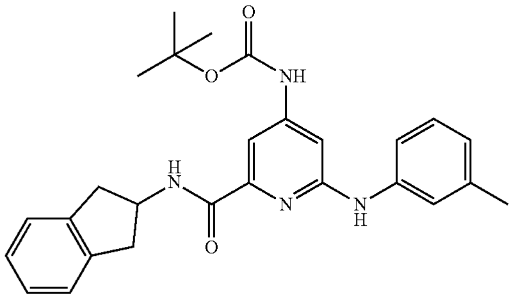 [SMILES: Cc1cccc(Nc2cc(NC(=O)OC(C)(C)C)cc(C(=O)NC3Cc4ccccc4C3)n2)c1]

Synthesized following General Procedure F.

Yield: (0.304 g, 95% over two steps).

ES-MS $[M+H]^+$: 459.2, Rt=7.511 min (Method-A1).

Intermediate 213

Tert-butyl (2-((2-hydroxyphenyl)amino)-6-(methyl(phenyl)carbamoyl)pyridin-4-yl)carbamate

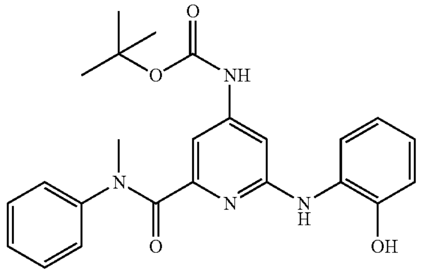 [SMILES: CN(C(=O)c1cc(NC(=O)OC(C)(C)C)cc(Nc2ccccc2O)n1)c1ccccc1]

Synthesized following General Procedure F.

Yield: (0.189 g, 61% over two steps).

ES-MS $[M+H]^+$: 435.2, Rt=6.638 min (Method-A1).

Intermediate 214

Tert-butyl (2-((2,3-dihydrobenzo[b][1,4]dioxin-6-yl)carbamoyl)-6-((2-fluorophenyl)amino)-pyridin-4-yl)carbamate

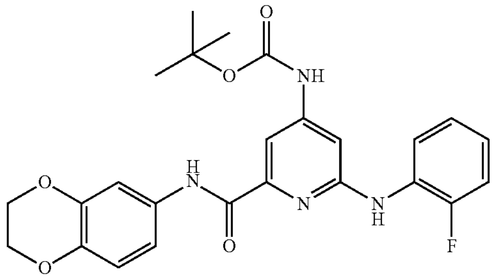 [SMILES: CC(C)(C)OC(=O)Nc1cc(Nc2ccccc2F)nc(C(=O)Nc2ccc3c(c2)OCCO3)c1]

Synthesized following General Procedure F.

Yield: (0.176 g, 60% over two steps).

ES-MS $[M+H]^+$: 481.2, Rt=7.217 min (Method-A1).

Intermediate 215

Tert-butyl (2-((2,3-dihydro-1H-inden-2-yl)carbamoyl)-6-((3-hydroxyphenyl)amino)pyridin-4-yl)carbamate

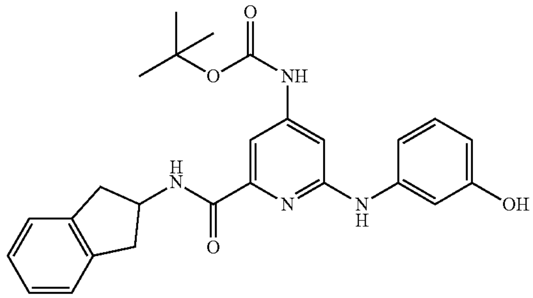 [SMILES: CC(C)(C)OC(=O)Nc1cc(Nc2cccc(O)c2)nc(C(=O)NC2Cc3ccccc3C2)c1]

Synthesized following General Procedure F.

Yield: (0.133 g, 94% over two steps).

ES-MS $[M+H]^{+}$: 461.2, Rt=6.869 min (Method-A1).

Intermediate 216

Tert-butyl (2-((2-methoxyphenyl)amino)-6-(methyl (phenyl)carbamoyl)pyridin-4-yl)carbamate

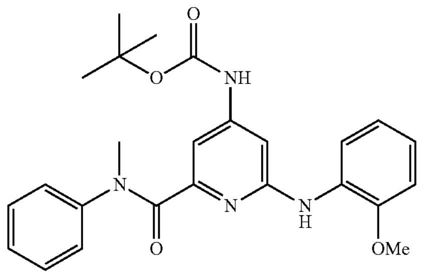 [SMILES: COc1ccccc1Nc1cc(NC(=O)OC(C)(C)C)cc(C(=O)N(C)c2ccccc2)n1]

Synthesized following General Procedure F.

Yield: (0.310 g, 97% over two steps).

ES-MS $[M-H]^{-}$: 447.5, Rt=6.931 min (Method-A1).

Intermediate 217

Tert-butyl (2-((2-fluorophenyl)amino)-6-(methyl (phenyl)carbamoyl)pyridin-4-yl)carbamate

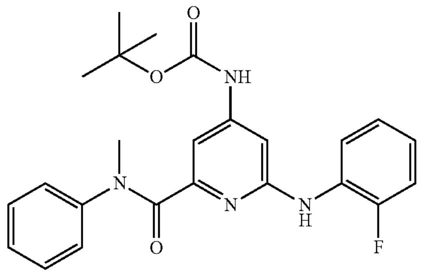 [SMILES: CN(C(=O)c1cc(NC(=O)OC(C)(C)C)cc(Nc2ccccc2F)n1)c1ccccc1]

Synthesized following General Procedure F.

Yield: (0.240 g, 77% over two steps).

ES-MS $[M-H]^{-}$: 435.4, Rt=6.863 min (Method-A1).

Intermediate 218

Tert-butyl (2-((3-fluorophenyl)amino)-6-(methyl (phenyl)carbamoyl)pyridin-4-yl)carbamate

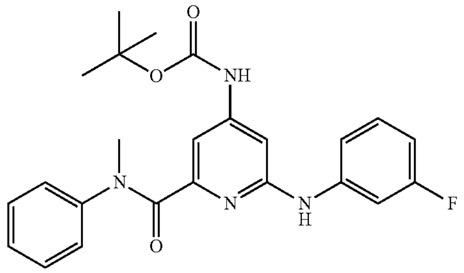 [SMILES: CN(C(=O)c1cc(NC(=O)OC(C)(C)C)cc(Nc2cccc(F)c2)n1)c1ccccc1]

Synthesized following General Procedure F.

Yield: (0.304 g, 98% over two steps).

ES-MS [M+H]+–: 437.2, Rt=6.917 min (Method-A1).

Intermediate 219

Tert-butyl (2-((3-fluorophenyl)amino)-6-(isoindoline-2-carbonyl)pyridin-4-yl)carbamate

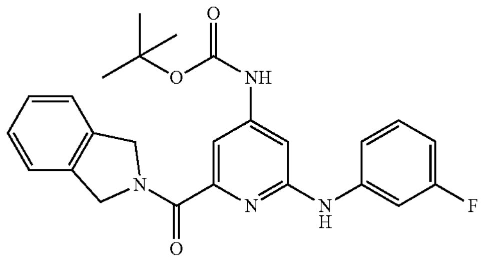 [SMILES: CC(C)(C)OC(=O)Nc1cc(Nc2cccc(F)c2)nc(C(=O)N2Cc3ccccc3C2)c1]

Synthesized following General Procedure F.

Yield: (0.132 g, 22% over two steps).

ES-MS [M+H]+–: 449.2, Rt=7.249 min (Method-A1).

Intermediate 220

Tert-butyl (2-((2,3-dihydro-1H-inden-2-yl)(methyl) carbamoyl)-6-((2-hydroxyphenyl)amino)-pyridin-4-yl)carbamate

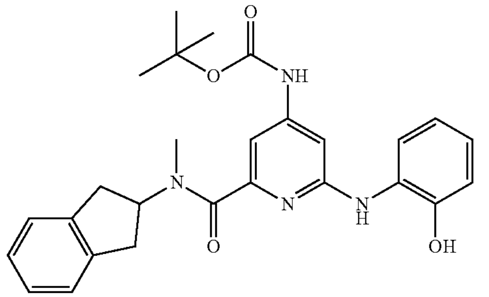 [SMILES: CN(C(=O)c1cc(NC(=O)OC(C)(C)C)cc(Nc2ccccc2O)n1)C1Cc2ccccc2C1]

Synthesized following General Procedure F.

Yield: (0.155 g, 61% over two steps).

ES-MS [M+H]+–: 475.3, Rt=7.045 min (Method-A1).

Intermediate 221

Tert-butyl (2-((2,3-dihydro-1H-inden-2-yl)(methyl) carbamoyl)-6-((2-fluorophenyl)amino)-pyridin-4-yl) carbamate

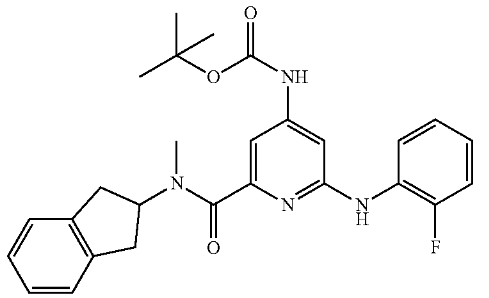 [SMILES: CN(C(=O)c1cc(NC(=O)OC(C)(C)C)cc(Nc2ccccc2F)n1)C1Cc2ccccc2C1]

Synthesized following General Procedure F.

Yield: (0.281 g, 95% over two steps).

ES-MS [M+H]+-: 477.3, Rt=7.250 min (Method-A1).

Intermediate 222

Tert-butyl (2-((2,3-dihydro-1H-inden-2-yl)carbamoyl)-6-((2-methoxyphenyl)amino)pyridin-4-yl)carbamate

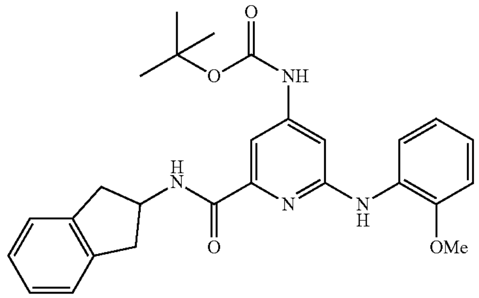

Synthesized following General Procedure F.

Yield: (0.041 g, 12% over two steps).

ES-MS [M+H]+-: 475.2, Rt=3.37 min (Method-D1).

Intermediate 223

Tert-butyl (2-((3-fluorophenyl)amino)-6-(phenylcarbamoyl)pyridin-4-yl)carbamate

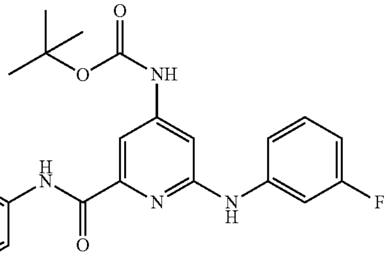

Synthesized following General Procedure F.

Yield: (0.146 g, 43% over two steps).

ES-MS [M+H]+-: 423.3, Rt=7.433 min (Method-A1).

Intermediate 224

Tert-butyl (2-((3-methoxyphenyl)amino)-6-(phenylcarbamoyl)pyridin-4-yl)carbamate

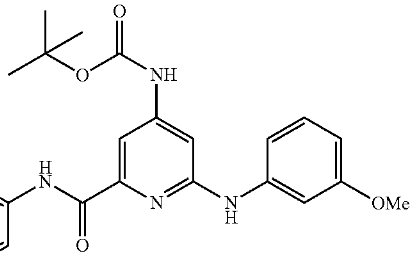

Synthesized following General Procedure F.

Yield: (0.261 g, 80% over two steps).

ES-MS [M+H]+-: 435.1, Rt=7.283 min (Method-A1).

Intermediate 225

Tert-butyl (2-((3-fluorophenyl)amino)-6-(m-tolylcarbamoyl)pyridin-4-yl)carbamate

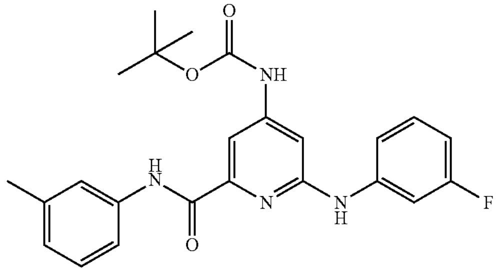 [SMILES: Cc1cccc(NC(=O)c2cc(NC(=O)OC(C)(C)C)cc(Nc3cccc(F)c3)n2)c1]

Synthesized following General Procedure F.

Yield: (0.147 g, 47% over two steps).

ES-MS [M+H]+-: 437.2, Rt=7.600 min (Method-A1).

Intermediate 226

Tert-butyl (2-((3,4-dimethylphenyl)carbamoyl)-6-((3-fluorophenyl)amino)pyridin-4-yl)carbamate

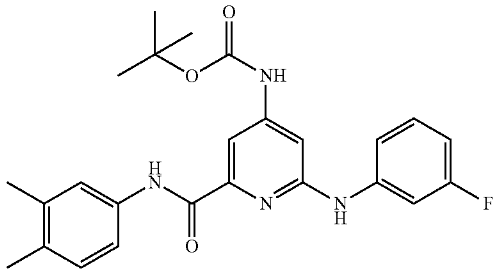 [SMILES: Cc1ccc(NC(=O)c2cc(NC(=O)OC(C)(C)C)cc(Nc3cccc(F)c3)n2)cc1C]

Synthesized following General Procedure F.

Yield: (0.220 g, 31% over two steps).

ES-MS [M+H]+-: 451.1, Rt=7.717 min (Method-A1).

Intermediate 227

Tert-butyl (2-((2,3-dihydro-1H-inden-2-yl)carbamoyl)-6-((2-fluorophenyl)amino)pyridin-4-yl)carbamate

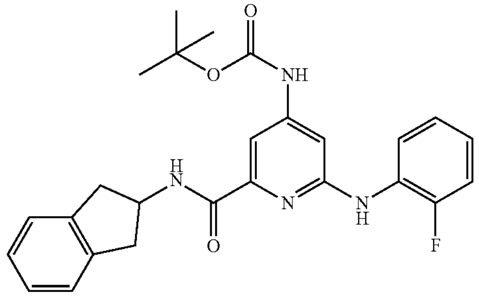 [SMILES: CC(C)(C)OC(=O)Nc1cc(Nc2ccccc2F)nc(C(=O)NC2Cc3ccccc3C2)c1]

Synthesized following General Procedure F.

Yield: (1.62 g, 36% over two steps).

ES-MS [M+H]+-: 463.2, Rt=7.319 min (Method-A1).

General Procedure G

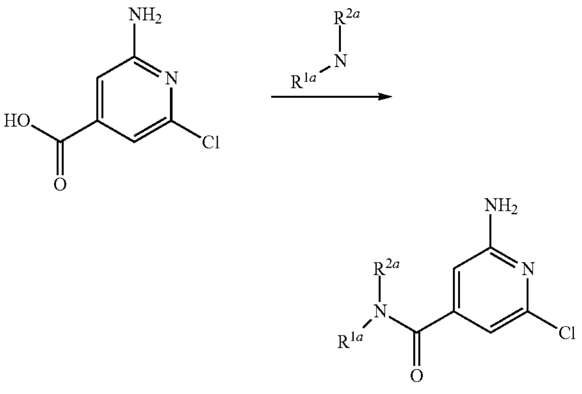

To a stirred solution of 2-amino-6-chloroisonicotinic acid (1.0 eq), the appropriate amine (ex: phenylanilina) (1.0 eq) and HATU (0.7 eq) in DMF (8 mL/mmol), was added DIPEA (1.3 eq). The resulting mixture was stirred at room temperature for 16 h. The reaction mixture was quenched with saturated sodium bicarbonate. The aqueous layer was extracted with ethyl acetate (x3), dried over anhydrous sodium sulphate, filtered and concentrated to dryness. The resultant crude was purified by flash column chromatography (EtOAc/Heptane 50-100) to obtain the desired product (ex: 2-amino-6-chloro-N-phenylisonicotinamide).

Intermediate 228

2-Amino-6-chloro-N-methyl-N-(1,2,3,4-tetrahydro-naphthalen-2-yl)isonicotinamide

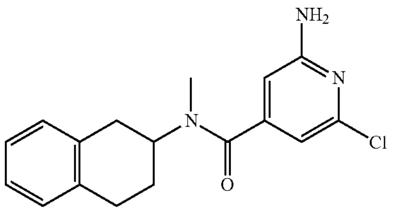 [SMILES: CN(C(=O)c1cc(N)nc(Cl)c1)C1CCc2ccccc2C1]

Synthesized following General Procedure G.

Yield: (0.16 g, 29%).

ES-MS $[M+H]^+$: 316.0, Rt=6.269 min (Method-A1).

Intermediate 229

2-Amino-6-chloro-N-methyl-N-phenylisonicotinamide

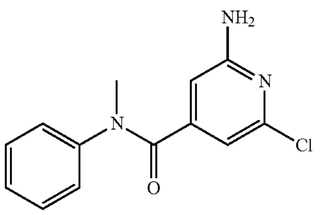 [SMILES: CN(C(=O)c1cc(N)nc(Cl)c1)c1ccccc1]

Synthesized following General Procedure G.

Yield: (0.090 g, 29%).

ES-MS $[M+H]^+$: 262.2, Rt=5.50 min (Method-A1).

Intermediate 230

2-Amino-6-chloro-N-(2,3-dihydro-1H-inden-2-yl)-N-methylisonicotinamide

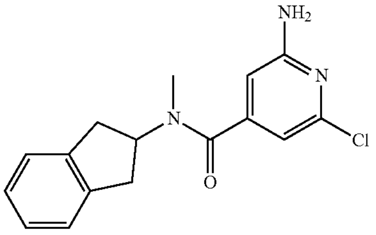 [SMILES: CN(C(=O)c1cc(N)nc(Cl)c1)C1Cc2ccccc2C1]

Synthesized following General Procedure G.

Yield: (0.290 g, 42%).

ES-MS $[M+H]^+$: 302.0, Rt=6.13 min (Method-A1).

Intermediate 231

2-Amino-6-chloro-N-(1,2,3,4-tetrahydronaphthalen-2-yl)isonicotinamide

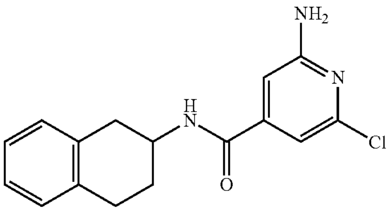 [SMILES: Nc1cc(C(=O)NC2CCc3ccccc3C2)cc(Cl)n1]

Synthesized following General Procedure G.

Yield: (0.135 g, 39%).

ES-MS $[M+H]^+$: 302.1, Rt=6.201 min (Method-A1).

Intermediate 232

2-Amino-6-chloro-N-phenylisonicotinamide

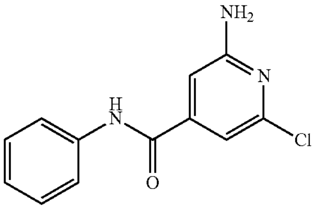 [SMILES: Nc1cc(C(=O)Nc2ccccc2)cc(Cl)n1]

Synthesized following General Procedure G.

Yield: (0.130 g, 33%).

ES-MS $[M+H]^+$: 248.1, Rt=5.66 min (Method-A1).

Intermediate 233

2-Amino-6-chloro-N-(2,3-dihydro-1H-inden-2-yl) isonicotinamide

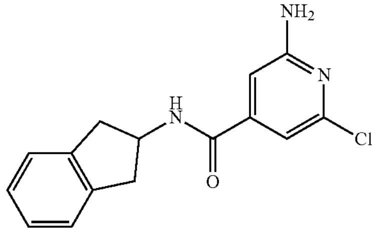 [SMILES: Nc1cc(C(=O)NC2Cc3ccccc3C2)cc(Cl)n1]

Synthesized following General Procedure G.
Yield: (0.124 g, 37%).
ES-MS $[M+H]^+$: 288.0, Rt=5.928 min (Method-A1).

General Procedure H

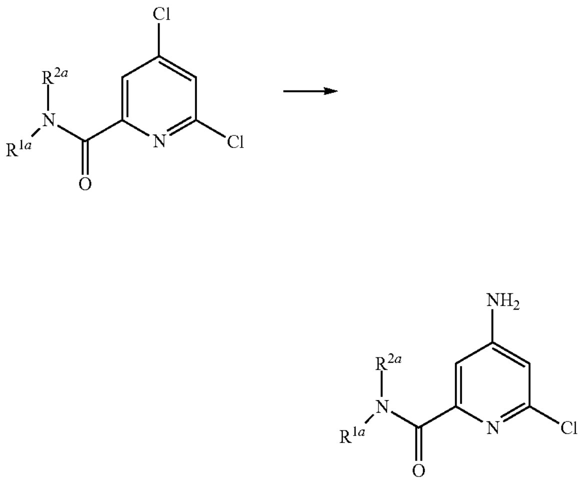

To a stirred solution of the appropriate 4,6-dichloropicolinamide (ex: (4,6-dichloropyridin-2-yl)(4-phenylpiperazin-1-yl)methanone) (1.0 eq) in dry DMF (5 mL/mmol) was added $NaN_3$ (3.0 eq) at 0° C. The mixture was stirred at 90° C. for 16 h. The mixture was then diluted with water and extracted with EtOAc (x3). Combined organic layers were washed with brine, dried over $MgSO_4$, filtered and concentrated. The crude residue was dissolved un MeOH (25 mL) and then $NaBH_4$ (2 eq) was added at 0° C. The resulting mixture was stirred at rt for 2 h. The solvent was then evaporated and the residue diluted with water, extracted with EtOAc (x3). Combined organic layers were washed with brine, dried over $MgSO_4$, filtered and concentrated. The resultant crude was purified by flash column chromatography (Hexane:EtOAc, from 80:20 to 0:100) to obtain the desired product (ex: (4-amino-6-chloropyridin-2-yl)(4-phenylpiperazin-1-yl)methanone).

Intermediate 234

(4-Amino-6-chloropyridin-2-yl)(4-phenylpiperazin-1-yl)methanone

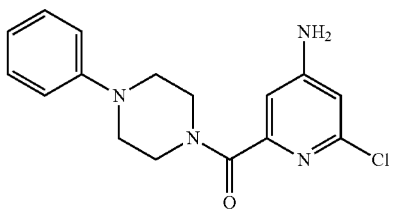 [SMILES: Nc1cc(Cl)nc(C(=O)N2CCN(c3ccccc3)CC2)c1]

Synthesized following General Procedure H.
Yield: (0.846 g, 84%).
ES-MS $[M-H]^-$: 315.2, Rt=5.863 min (Method-A1).

Intermediate 235

(4-Amino-6-chloropyridin-2-yl)(isoindolin-2-yl) methanone

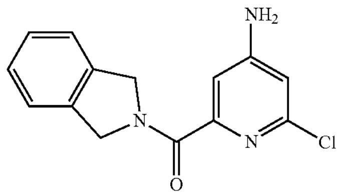 [SMILES: Nc1cc(Cl)nc(C(=O)N2Cc3ccccc3C2)c1]

Synthesized following General Procedure H.
Yield: (0.925 g, 76%).
ES-MS $[M+H]^+$: 274.9, Rt=2.29 min (Method-D1).

General Procedure I

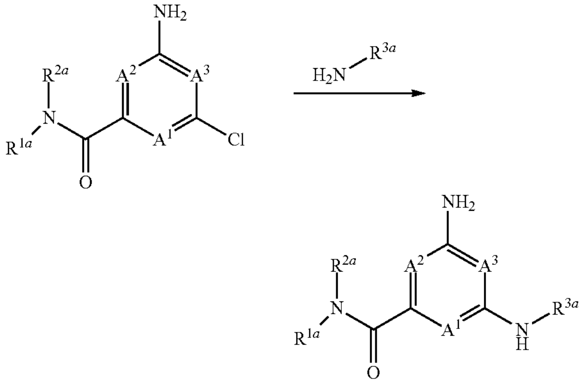

Method 1

BINAP (10 mol %) and Pd2(dba)$_3$ (6 mol %) were added over a degassed solution of the appropriate 2-amino-6-chloroisonicotinamide (ex: 2-amino-6-chloro-N-methyl-N-(1,2,3,4-tetrahydronaphthalen-2-yl)isonicotinamide) (1.0 eq), the appropriate aniline (ex: 2-aminophenol) (1.1 eq) and $Cs_2CO_3$ (2.8 eq) in dioxane (6 mL/mmol). The resulting mixture was stirred at 100° C. for 20 h. The reaction mixture was allowed to cool to room temperature and quenched with saturated sodium bicarbonate. The aqueous layer was extracted with ethyl acetate (3×), dried over anhydrous sodium sulphate, filtered and concentrated to dryness. The resultant crude was purified by flash column chromatography (EtOAc/Hexane 10-20%) to obtain the desired product (ex: 2-amino-6-((2-hydroxyphenyl)amino)-N-methyl-N-(1,2,3,4-tetrahydronaphthalen-2-yl)isonicotinamide).

Method 2

XantPhos (10 mol %) and $Pd(OAc)_2$ (5 mol %) were added over a degassed solution of the corresponding 4-amino-6-chloropicolinamide (ex: (4-amino-6-chloropyridin-2-yl)(4-phenylpiperazin-1-yl)methanone)(1.0 eq), the corresponding amine (ex: 2-fluoroaniline) (1.1 eq) and $Cs_2CO_3$ (2.5 eq) in dioxane (5 mL/mmol). The mixture was stirred at 100° C. for 18 h. The solvents were then evaporated under vacuo and the resulting crude residue was purified by column chromatography on silica gel (eluyent DCM:MeOH, from 100:0 to 0:100) to obtain the desired product (ex: (4-amino-6-((2-fluorophenyl)amino)pyridin-2-yl)(4-phenylpiperazin-1-yl)methanone).

Example 42

2-Amino-6-((2-hydroxyphenyl)amino)-N-methyl-N-(1,2,3,4-tetrahydronaphthalen-2-yl)isonicotinamide

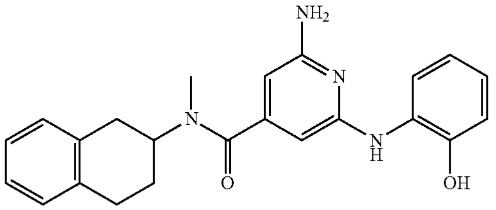 [SMILES: CN(C(=O)c1cc(N)nc(Nc2ccccc2O)c1)C1CCc2ccccc2C1]

Synthesized following General Procedure I, Method 1.

Yield: (0.030 g, 15%).

ES-MS [M−H]$^-$: 387.2, Rt=18.135 min (Method-B1).

$^1$H NMR (400 MHz, DMSO-$d_6$) δ 10.39 (d, J=49.1 Hz, 1H), 8.13-7.86 (m, 1H), 7.81-7.47 (m, 1H), 7.09 (d, J=19.4 Hz, 4H), 6.82 (d, J=4.8 Hz, 2H), 6.72 (s, 1H), 6.10-5.88 (m, 3H), 5.73 (d, J=2.2 Hz, 1H), 4.64 (s, 0.36H), 3.90 (s, 0.64H), 3.17-3.03 (m, 1H), 3.02-2.81 (m, 5H), 2.79-2.65 (m, 1H), 2.08-1.82 (m, 2H). Conformers present.

Example 43

2-Amino-6-((2-hydroxyphenyl)amino)-N-methyl-N-phenylisonicotinamide

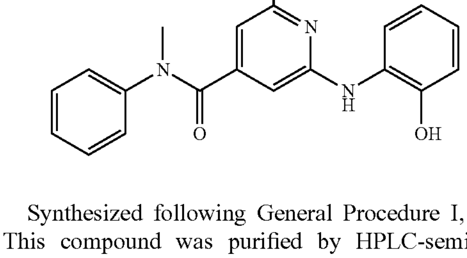

Synthesized following General Procedure I, Method 1. This compound was purified by HPLC-semipreparative (Method-E1).

Yield: (0.008 g, 26%).

ES-MS [M+H]+: 335.1, Rt=19.960 min (Method-B1).

$^1$H NMR (400 MHz, DMSO-$d_6$) δ 10.33 (brs, 1H), 7.73 (s, 1H), 7.32 (td, J=11.2, 9.8, 7.3 Hz, 3H), 7.21 (td, J=7.0, 1.5 Hz, 3H), 6.85-6.76 (m, 2H), 6.69 (ddd, J=7.9, 5.8, 3.1 Hz, 1H), 5.88 (d, J=8.0 Hz, 3H), 5.68 (d, J=1.1 Hz, 1H), 3.32 (d, J=7.2 Hz, 3H).

Example 44

2-Amino-N-(2,3-dihydro-1H-inden-2-yl)-6-((2-hydroxyphenyl)amino)-N-methyl-isonicotinamide

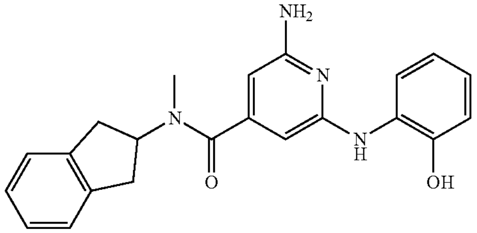 [SMILES: CN(C(=O)c1cc(N)nc(Nc2ccccc2O)c1)C1Cc2ccccc2C1]

Synthesized following General Procedure I, Method 1. This compound was purified by HPLC-semipreparative (Method-E1).

Yield: (0.101 g, 28%).

ES-MS [M+H]+: 375.1, Rt=17.825 min (Method-B1).

$^1$H NMR (400 MHz, DMSO-$d_6$) δ 10.36 (s, 1H), 8.06 (s, 1H), 7.58 (d, J=7.9 Hz, 2H), 7.41-7.07 (m, 9H), 6.89-6.79 (m, 4H), 6.74 (ddd, J=8.5, 5.6, 3.2 Hz, 2H), 6.13-5.88 (m, 7H), 5.75 (d, J=2.5 Hz, 2H), 5.34 (s, 1H), 4.65 (d, J=8.9 Hz, 2H), 3.04 (d, J=7.8 Hz, 7H), 2.78 (s, 4H), 2.72 (d, J=5.6 Hz, 2H).

Example 45

2-Amino-6-((2-hydroxyphenyl)amino)-N-(1,2,3,4-tetrahydronaphthalen-2-yl)isonicotinamide

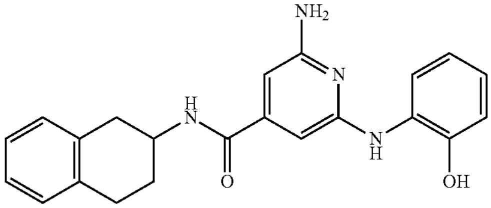 [SMILES: Nc1cc(C(=O)NC2CCc3ccccc3C2)cc(Nc2ccccc2O)n1]

Synthesized following General Procedure I, Method 1.

Yield: (0.019 g, 14%).

ES-MS [M+H]$^+$: 375.2, Rt=17.799 min (Method-B1).

$^1$H NMR (400 MHz, DMSO-$d_6$) δ 10.51 (s, 1H), 8.34 (d, J=7.6 Hz, 1H), 8.02 (s, 1H), 7.72-7.49 (m, 1H), 7.18-7.04 (m, 4H), 6.83 (dd, J=4.0, 1.3 Hz, 2H), 6.74 (ddd, J=7.9, 5.5, 3.4 Hz, 1H), 6.38 (d, J=1.2 Hz, 1H), 6.12 (d, J=1.1 Hz, 1H), 6.05 (s, 2H), 4.10 (ddd, J=10.3, 5.3, 2.6 Hz, 1H), 2.99 (ddd, J=16.3, 5.6, 1.6 Hz, 1H), 2.86 (dd, J=7.6, 4.0 Hz, 2H), 2.77 (dd, J=16.3, 10.3 Hz, 1H), 1.99 (ddt, J=9.6, 3.4, 1.7 Hz, 1H), 1.84-1.63 (m, 1H).

Example 46

2-Amino-6-((2-hydroxyphenyl)amino)-N-phenylisonicotinamide

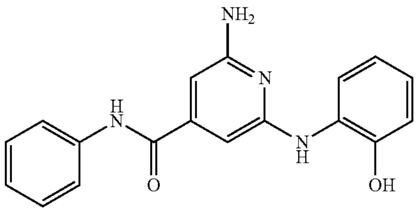 [SMILES: Nc1cc(C(=O)Nc2ccccc2)cc(Nc2ccccc2O)n1]

Synthesized following Procedure I, Method 1.

Yield: (0.011 g, 7%).

ES-MS $[M+H]^+$: 321.1, Rt=16.299 min (Method-B1).

$^1$H NMR (400 MHz, DMSO-$d_6$) δ 10.41 (brs, 1H), 10.22 (s, 1H), 8.07 (s, 1H), 7.85-7.70 (m, 2H), 7.66 (dt, J=7.9, 1.1 Hz, 1H), 7.45-7.27 (m, 2H), 7.21-6.98 (m, 1H), 6.84 (dd, J=3.9, 0.9 Hz, 2H), 6.80-6.64 (m, 1H), 6.45 (d, J=1.2 Hz, 1H), 6.18 (d, J=1.2 Hz, 1H), 6.12 (s, 2H).

Example 47

2-Amino-N-(2,3-dihydro-1H-inden-2-yl)-6-((2-hydroxyphenyl)amino)isonicotinamide

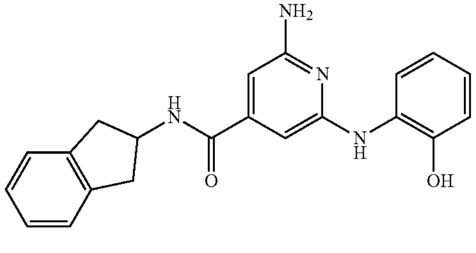 [SMILES: Nc1cc(C(=O)NC2Cc3ccccc3C2)cc(Nc2ccccc2O)n1]

Synthesized following General Procedure I, Method 1.

Yield: (0.009 g, 12%).

ES-MS [M+H]+: 361.1, Rt=17.214 min (Method-B1).

$^1$H NMR (400 MHz, DMSO-$d_6$) δ 10.52 (s, 1H), 8.57 (d, J=7.0 Hz, 1H), 8.00 (s, 1H), 7.68-7.47 (m, 1H), 7.22 (dd, J=5.4, 3.3 Hz, 2H), 7.18-7.07 (m, 2H), 6.88-6.80 (m, 2H), 6.73 (ddd, J=7.8, 5.3, 3.6 Hz, 1H), 6.37 (d, J=1.2 Hz, 1H), 6.11 (d, J=1.1 Hz, 1H), 6.03 (s, 2H), 4.63 (h, J=7.2 Hz, 1H), 3.21 (dd, J=15.9, 7.8 Hz, 2H), 2.92 (dd, J=15.9, 6.8 Hz, 2H).

Example 48

(4-Amino-6-((2-fluorophenyl)amino)pyridin-2-yl)(4-phenylpiperazin-1-yl)methanone

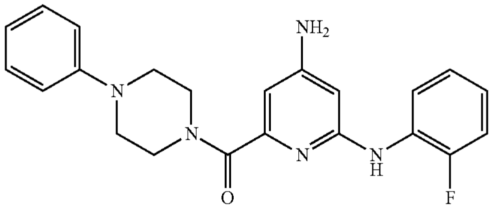 [SMILES: Nc1cc(Nc2ccccc2F)nc(C(=O)N2CCN(c3ccccc3)CC2)c1]

Synthesized following General Procedure L, Method 2.

Yield: (0.008 g, 2%).

ES-MS $[M-H]^-$: 390.3, Rt=19.100 min (Method-B1).

$^1$H NMR (400 MHz, DMSO-$d_6$) δ 8.28 (d, J=1.6 Hz, 1H), 7.91 (td, J=8.3, 1.7 Hz, 1H), 7.36-7.11 (m, 3H), 7.07 (td, J=7.7, 1.5 Hz, 1H), 7.02-6.87 (m, 3H), 6.81 (t, J=7.3 Hz, 1H), 6.24 (d, J=1.8 Hz, 1H), 6.05 (d, J=1.8 Hz, 1H), 6.00 (s, 2H), 3.67 (dt, J=24.1, 5.1 Hz, 4H), 3.11 (dt, J=40.0, 5.2 Hz, 4H).

General Procedure J-1

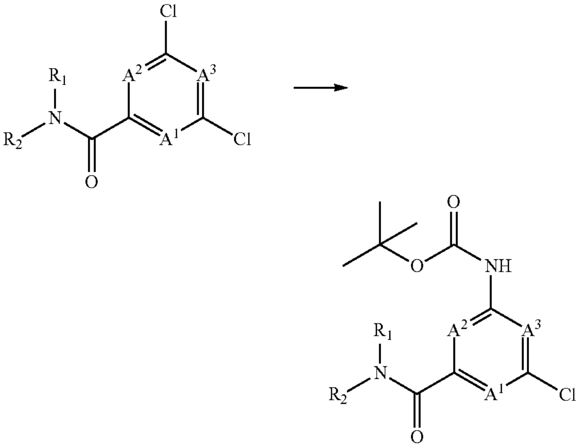

Method 1

To a stirred solution of (4-amino-6-chloropyridin-2-yl)(isoindolin-2-yl)methanone (0.925 g, 3.4 mmol, 1.0 eq) in dioxane (26 mL) were added di-tert-butyl dicarbonate (2.21 g, 10.1 mmol, 3.0 eq), DMAP (0.40 g, 3.3 mmol, 1.0 eq) and triethylamine (1.50 mL, 10.8 mmol, 3.2 eq). The resulting mixture was stirred at 100° C. for 16 h. The mixture was then cooled to rt and diluted with EtOAc and water. Layers were separated. Aqueous layer was extracted with EtOAc (×2). Combined organic layers were washed with water and brine, dried over $MgSO_4$, filtered and concentrated. The resultant crude was purified by flash column chromatography (Hexane:EtOAc 60:40) to obtain the desired product tert-butyl (2-chloro-6-(isoindoline-2-carbonyl)pyridin-4-yl)carbamate.

Method 2

Dppf (6 mol %) and $Pd(OAc)_2$ (2 mol %) were added over a degassed solution of the corresponding 4,6-dichloropicolinamide (ex: (4,6-dichloropyridin-2-yl)(3,4-dihydroisoquinolin-2(1H)-yl)methanone) (1.0 eq), tert-butyl carbamate (3.0 eq) and $K_2CO_3$ (2.0 eq) in dioxane (5 mL/mmol). The resulting mixture was stirred at 90° C. under nitrogen atmosphere for 16 h. The mixture was then diluted with EtOAc and water. Layers were separated. Aqueous layer was extracted with EtOAc (×2). Combined organic layers were washed with water and brine, dried over magnesium sulphate, filtered and concentrated. The resultant crude was purified by flash column chromatography (Hexane:EtOAc 60:40) to obtain the desired product (ex: tert-butyl (4-chloro-6-(1,2,3,4-tetrahydroisoquinoline-2-carbonyl)pyridin-2-yl) carbamate).

Intermediate 236

Tert-butyl (2-chloro-6-(isoindoline-2-carbonyl)pyridin-4-yl)carbamate

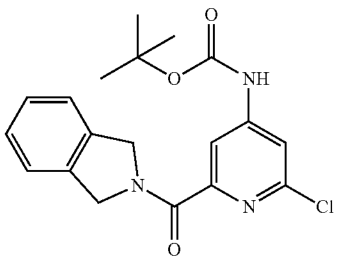 [SMILES: CC(C)(C)OC(=O)Nc1cc(Cl)nc(C(=O)N2Cc3ccccc3C2)c1]

Synthesized following General Procedure J-1, Method 1. Yield: (0.900 g, 71%).

ES-MS $[M+H]^+$: 374.9, Rt=3.17 min (Method-D1).

Intermediate 237

Tert-butyl (4-chloro-6-(1,2,3,4-tetrahydroisoquinoline-2-carbonyl)pyridin-2-yl)carbamate

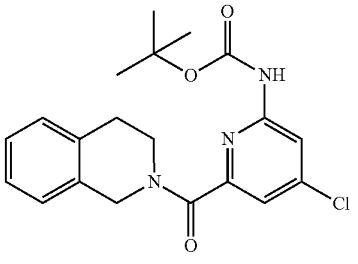 [SMILES: CC(C)(C)OC(=O)Nc1cc(Cl)cc(C(=O)N2CCc3ccccc3C2)n1]

Synthesized following General Procedure J-1, Method 2. Yield: (0.50 g, 75%).

ES-MS $[M+H]^+$: 388.1, Rt=7.21 min (Method-A1).

Intermediate 238

Tert-butyl (4-chloro-6-((2,3-dihydro-1H-inden-2-yl)carbamoyl)pyridin-2-yl)carbamate

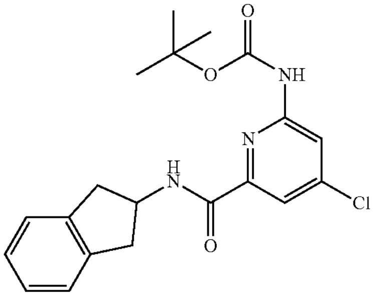 [SMILES: CC(C)(C)OC(=O)Nc1cc(Cl)cc(C(=O)NC2Cc3ccccc3C2)n1]

Synthesized following General Procedure J-1, Method 2. Yield: (0.370 g, 97%).

ES-MS $[M+H]^+$: 388.1, Rt=7.41 min (Method-A1).

General Procedure J-2

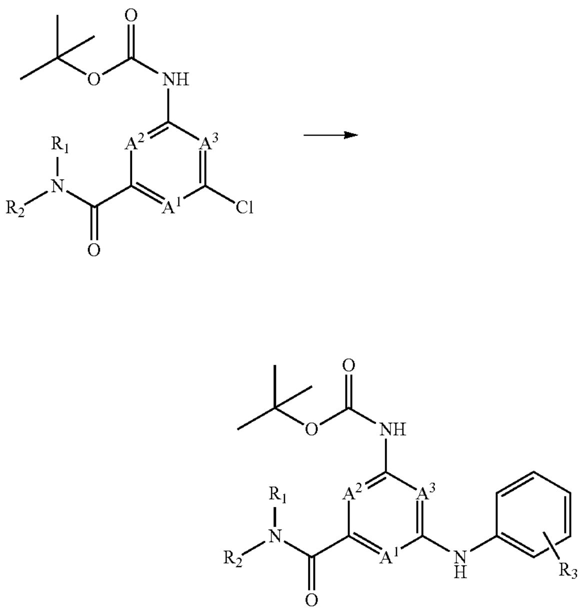

Method 1

Dppf (6 mol %) and $Pd(OAc)_2$ (2 mol %) were added over a degassed solution of the appropriate aryl chloride (ex: tert-butyl (2-chloro-6-(isoindoline-2-carbonyl)pyridin-4-yl)carbamate) (1.0 eq), the appropriate aniline (ex: 2-aminophenol) (3.0 eq) and $K_3PO_4$ (2.0 eq) in dioxane (6.4 mL/mmol). The resulting mixture was stirred at 90° C. under nitrogen atmosphere for 16 h. The mixture was then diluted with EtOAc and water. Layers were separated. Aqueous layer was extracted with EtOAc (×2). Combined organic layers were washed with water and brine, dried over $MgSO_4$, filtered and concentrated. The resultant crude was purified by flash column chromatography (Hexane:EtOAc 60:40) to obtain the desired product (ex: tert-butyl (2-((2-hydroxyphenyl)amino)-6-(isoindoline-2-carbonyl)pyridin-4-yl)carbamate).

Method 2

XPhos (5 mol %) and $Pd2(dba)_3$ (3 mol %) were added over a degassed solution of the corresponding (ex: tert-butyl (4-chloro-6-((2,3-dihydro-1H-inden-2-yl)carbamoyl)pyridin-2-yl)carbamate) (1.0 eq), the appropriate aniline (ex:3-methoxyaniline) (3.0 eq) and $Cs_2CO_3$ (3.0 eq) in dioxane (3 mL/mmol). The resulting mixture was stirred at 100° C. under nitrogen atmosphere for 18 h. The mixture was then diluted with EtOAc and water. Layers were separated. Aqueous layer was extracted with EtOAc (×2). Combined organic layers were washed with water and brine, dried over $MgSO_4$, filtered and concentrated. The resultant crude was purified by flash column chromatography (Hexane:EtOAc 60:40) to obtain the desired product (ex: tert-butyl (6-((2,3-dihydro-1H-inden-2-yl)carbamoyl)-4-((3-methoxyphenyl)amino)pyridin-2-yl)carbamate).

Intermediate 239

Tert-butyl (2-((2-fluorophenyl)amino)-6-(isoindoline-2-carbonyl)pyridin-4-yl)carbamate

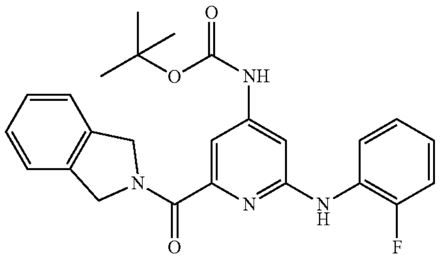 [SMILES: CC(C)(C)OC(=O)Nc1cc(Nc2ccccc2F)nc(C(=O)N2Cc3ccccc3C2)c1]

Synthesized following General Procedure J-2, Method 1. Yield: (0.110 g, 20%).

ES-MS $[M+H]^+$: 449.9, Rt=7.214 min (Method-A1).

Intermediate 240

Tert-butyl (2-((2-hydroxyphenyl)amino)-6-(isoindoline-2-carbonyl)pyridin-4-yl)carbamate

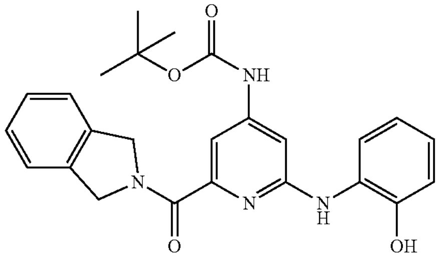 [SMILES: CC(C)(C)OC(=O)Nc1cc(Nc2ccccc2O)nc(C(=O)N2Cc3ccccc3C2)c1]

Synthesized following General Procedure J-2, Method 1. Yield: (0.250 g, 47%).

ES-MS $[M+H]^+$: 447.2, Rt=6.951 min (Method-A1).

Example 49

(6-Amino-4-((2-hydroxyphenyl)amino)pyridin-2-yl)(3,4-dihydroisoquinolin-2(1H)-yl)methanone

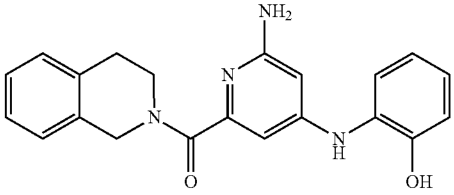 [SMILES: Nc1cc(Nc2ccccc2O)cc(C(=O)N2CCc3ccccc3C2)n1]

Synthesized following General Procedure J-2, Method 2. This compound was isolated directly after step 3, and it was purified by HPLC-semipreparative (Method-E1).

Yield: (0.130 g, 71%).

ES-MS $[M-H]^-$: 361.2, Rt=16.433 min (Method-B1).

$^1$H NMR (400 MHz, DMSO-$d_6$) δ 9.49 (d, J=4.8 Hz, 1H), 7.74 (d, J=7.5 Hz, 1H), 7.37-7.10 (m, 4H), 7.05 (d, J=6.9 Hz, 1H), 7.02-6.85 (m, 2H), 6.79 (ddt, J=11.4, 5.9, 2.9 Hz, 1H), 6.19 (dd, J=12.4, 1.9 Hz, 1H), 5.86 (dd, J=5.9, 1.9 Hz, 1H), 5.65 (d, J=4.8 Hz, 2H), 4.67 (d, J=18.8 Hz, 2H), 3.77 (t, J=5.9 Hz, 1H), 3.65 (t, J=5.8 Hz, 1H), 2.84 (q, J=6.6, 6.2 Hz, 2H).

Intermediate 241

Tert-butyl (4-(benzo[d][1,3]dioxol-4-ylamino)-6-((2,3-dihydro-1H-inden-2-yl)carbamoyl)-pyridin-2-yl)carbamate

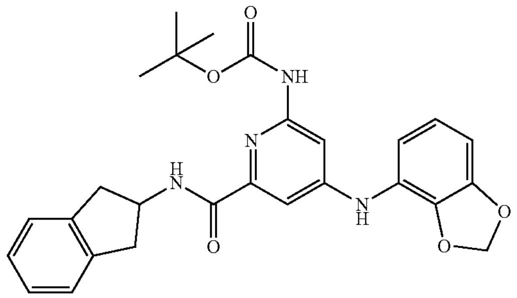

Synthesized following General Procedure J-2, Method 2. Yield: (0.240 g, 50%).

ES-MS $[M+H]^+$: 489.1, Rt=7.24 min (Method-A1).

Intermediate 242

Tert-butyl (6-((2,3-dihydro-1H-inden-2-yl)carbamoyl)-4-((3-methoxyphenyl)amino)pyridin-2-yl)carbamate

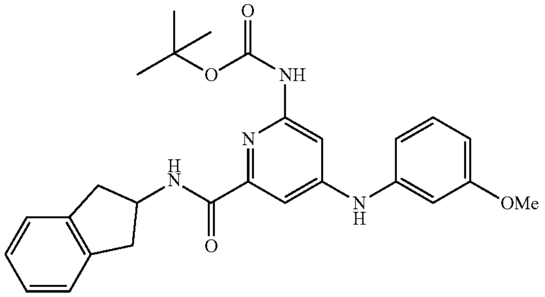 [SMILES: COc1cccc(Nc2cc(NC(=O)OC(C)(C)C)nc(C(=O)NC3Cc4ccccc4C3)c2)c1]

Synthesized following General Procedure J-2, Method 2. Yield: (0.130 g, 42%).

ES-MS $[M+H]^+$: 475.3, Rt=7.259 min (Method-A1).

General Procedure K

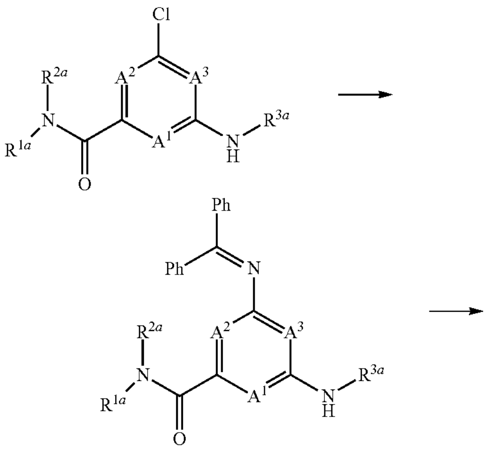

-continued

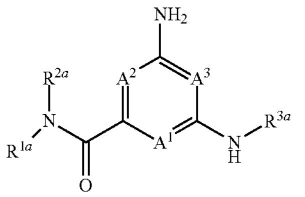

Step 1

BINAP (10 mol %) and Pd2(dba)$_2$ (5 mol %) were added over a degassed solution of the appropriate aryl chloride (ex: 6-chloro-4-((2-methoxyphenyl)amino)-N-methyl-N-phenylpicolinamide) (1.0 eq), diphenylmethanimine (1.2 eq) and NaOtBu (1.4 eq) in toluene (29 mL/mmol). The resulting mixture was stirred under reflux for 18 h. The mixture was then diluted with EtOAc and filtered through a pad of celite/$SiO_2$. The resulting filtrated were concentrated to dryness and used without further purification (ex: 6-((diphenylmethylene)amino)-4-((2-methoxyphenyl)amino)-N-methyl-N-phenylpicolinamide).

Step 2

To a stirred solution of the appropriate diphenylmethylene amine derivative (ex: 6-((diphenylmethylene)amino)-4-((2-methoxyphenyl)amino)-N-methyl-N-phenylpicolinamide) in THF (25 mL/mmol) was added HCl 1N (2 mL/mmol). The resulting mixture was stirred at room temperature for 5 h. The mixture was then diluted with EtOAc and sat. aq. $NaHCO_3$ solution. The organic layer was dried over $NaSO_4$, filtered and concentrated to dryness. The crude mixture was subjected to column chromatography on silica gel (Hexane:EtOAc, from 80:20 to 70:30) to obtain the desired amine product (ex: 6-amino-4-((2-methoxyphenyl)amino)-N-methyl-N-phenylpicolinamide).

Intermediate 243

6-((Diphenylmethylene)amino)-4-((2-methoxyphenyl)amino)-N-methyl-N-phenyl-picolinamide

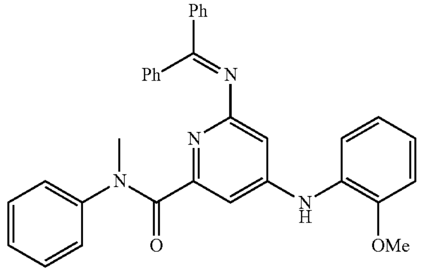 [SMILES: COc1ccccc1Nc1cc(N=C(c2ccccc2)c2ccccc2)nc(C(=O)N(C)c2ccccc2)c1]

Synthesized following General Procedure K, step 1. Yield: (0.194 g, used crude).

ES-MS $[M+H]^+$: 513.9, Rt=7.143 min (Method-A1).

Intermediate 244

(6-((Diphenylmethylene)amino)-4-((2-methoxyphenyl)amino)pyridin-2-yl)(4-phenyl-piperazin-1-yl)methanone

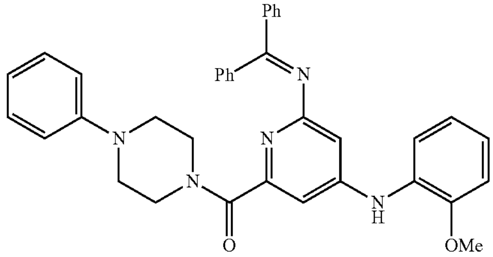 [SMILES: COc1ccccc1Nc1cc(N=C(c2ccccc2)c2ccccc2)nc(C(=O)N2CCN(c3ccccc3)CC2)c1]

Synthesized following General Procedure K, step 1. Yield: (0.682 g, used crude).

ES-MS $[M+H]^+$: 569.1, Rt=6.567 min (Method-A1).

Intermediate 245

6-Chloro-4-((2-methoxyphenyl)amino)-N-(1,2,3,4-tetrahydronaphthalen-2-yl)picolinamide

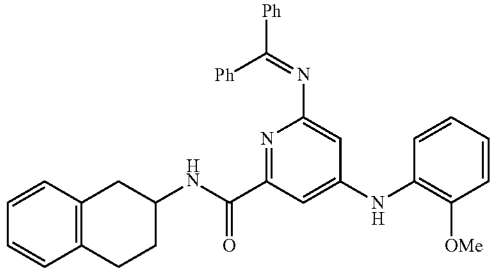 [SMILES: COc1ccccc1Nc1cc(N=C(c2ccccc2)c2ccccc2)nc(C(=O)NC2CCc3ccccc3C2)c1]

Synthesized following General Procedure K, step 1. Yield: (0.320 g, used crude).

ES-MS $[M+H]^+$: 553.1, Rt=7.553 min (Method-A1).

Intermediate 246

6-((Diphenylmethylene)amino)-4-((2-methoxyphenyl)amino)-N-phenylpicolinamide

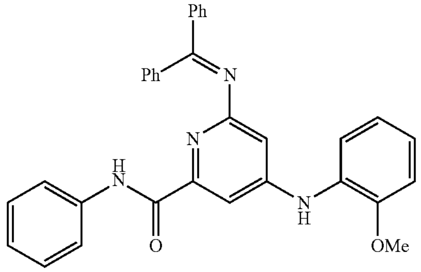 [SMILES: COc1ccccc1Nc1cc(N=C(c2ccccc2)c2ccccc2)nc(C(=O)Nc2ccccc2)c1]

Synthesized following General Procedure K, step 1. Yield: (0.135 g, quant.).

ES-MS $[M+H]^+$: 499.0, Rt=6.77 min (Method-A1).

Intermediate 247

N-(2,3-Dihydro-1H-inden-2-yl)-4-((diphenylmethylene)amino)-6-((2-methoxyphenyl)-amino)picolinamide

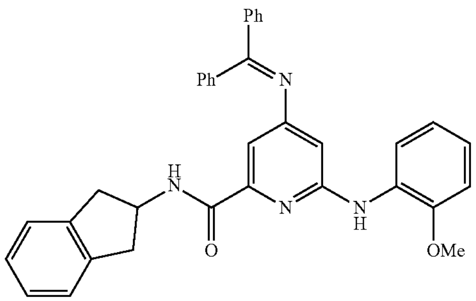 [SMILES: COc1ccccc1Nc1cc(N=C(c2ccccc2)c2ccccc2)cc(C(=O)NC2Cc3ccccc3C2)n1]

Synthesized following General Procedure K, step 1.
Yield: (0.381 g, used crude).
ES-MS $[M+H]^+$: 538.0, Rt=7.583 min (Method-A1).

Example 50

6-Amino-4-((2-methoxyphenyl)amino)-N-methyl-N-phenylpicolinamide

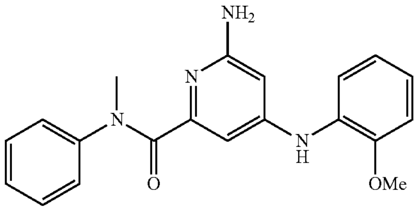

Synthesized following General Procedure K, step 2. Isolated as a white solid.

Yield: (0.067 g, 36% yield over 2 steps).

ES-MS $[M+H]^+$: 349.2, Rt=19.371 min (Method-B1).

$^1H$ NMR (400 MHz, DMSO-$d_6$) δ 10.40 (s, 1H), 8.54-8.19 (m, 1H), 7.59-7.41 (m, 2H), 7.38-7.19 (m, 3H), 7.16-7.01 (m, 2H), 6.94 (ddd, J=8.5, 6.0, 2.8 Hz, 1H), 6.78 (d, J=2.2 Hz, 1H), 5.98 (d, J=2.2 Hz, 1H), 5.70 (brs, 2H), 3.94 (s, 3H), 3.30 (s, 3H).

Example 51

(6-Amino-4-((2-methoxyphenyl)amino)pyridin-2-yl)(4-phenylpiperazin-1-yl)methanone

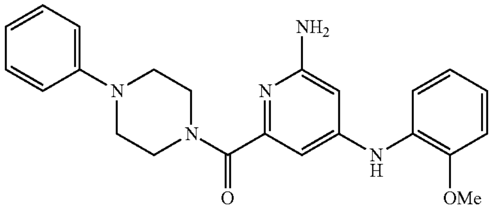 [SMILES: COc1ccccc1Nc1cc(N)nc(C(=O)N2CCN(c3ccccc3)CC2)c1]

Synthesized following General Procedure K, step 2. Isolated as a white solid.

Yield: (0.010 g, 2% over two steps).

ES-MS $[M+H]^+$: 404.2, Rt=17.765 min (Method-B1).

$^1H$ NMR (400 MHz, DMSO-$d_6$) δ 7.87 (s, 1H), 7.27-7.17 (m, 3H), 7.12-7.03 (m, 2H), 7.00-6.89 (m, 3H), 6.85-6.76 (m, 1H), 6.24 (s, 1H), 5.90 (s, 1H), 5.68 (brs, 2H), 3.79 (s, 3H), 3.74-3.63 (m, 2H), 3.62-3.51 (m, 2H), 3.21-3.06 (m, 4H).

Example 52

6-Amino-4-((2-methoxyphenyl)amino)-N-(1,2,3,4-tetrahydronaphthalen-2-yl)picolinamide

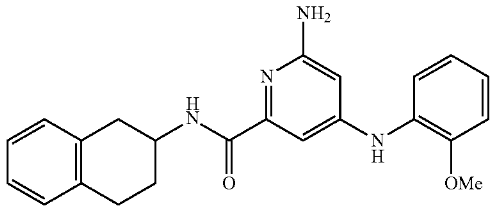 [SMILES: COc1ccccc1Nc1cc(N)nc(C(=O)NC2CCc3ccccc3C2)c1]

Synthesized following General Procedure K, step 2.

Yield: (0.146 g, 36% yield over 2 steps).

ES-MS $[M+H]^+$: 389.2, Rt=20.092 min (Method-B1).

$^1H$ NMR (400 MHz, DMSO-$d_6$) δ 8.08 (d, J=8.0 Hz, 1H), 7.71-7.41 (m, 2H), 7.67-7.57 (m, 4H), 7.03-6.84 (m, 2H), 6.83-6.67 (m, 2H), 6.13 (d, J=1.7 Hz, 1H), 6.06 (brs, 2H), 4.25-4.10 (m, 1H), 3.79 (s, 3H), 3.06 (dd, J=16.4, 5.1 Hz, 1H), 2.90-2.80 (m, 2H), 2.89-2.68 (m, 1H), 2.06-1.93 (m, 1H), 1.90-1.73 (m, 1H).

Example 53

6-Amino-4-((2-methoxyphenyl)amino)-N-phenylpicolinamide

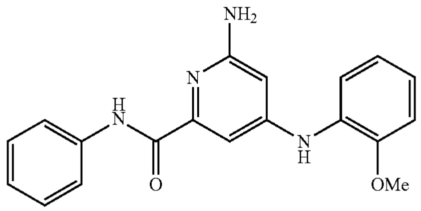

Synthesized following General Procedure K, step 2.

Yield: (0.020 g, 48% yield over 2 steps).

ES-MS $[M+H]^+$: 335.1, Rt=18.390 min (Method-B1).

$^1H$ NMR (400 MHz, DMSO-$d_6$) δ 10.18 (d, J=3.0 Hz, 1H), 8.11 (d, J=3.0 Hz, 1H), 7.75 (dd, J=8.2, 3.0 Hz, 2H), 7.36 (td, J=8.0, 2.9 Hz, 2H), 7.25 (d, J=7.9 Hz, 1H), 7.10 (q, J=6.7, 6.0 Hz, 3H), 7.03-6.90 (m, 2H), 6.18-5.92 (m, 1H), 5.83 (s, 2H), 3.80 (d, J=3.0 Hz, 3H).

Example 54

4-Amino-N-(2,3-dihydro-1H-inden-2-yl)-6-((2-methoxyphenyl)amino)picolinamide

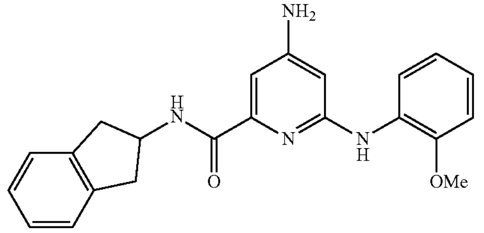 [SMILES: COc1ccccc1Nc1cc(N)cc(C(=O)NC2Cc3ccccc3C2)n1]

Synthesized following Procedure K, step 2. Isolated as a beige solid.

Yield: (0.258 g, 64%).

ES-MS [M+H]+: 375.2, Rt=19.512 min (Method-B1).

$^1$H NMR (400 MHz, DMSO-$d_6$) δ 8.20 (d, J=7.9 Hz, 1H), 7.78-7.51 (m, 2H), 7.36-7.22 (m, 2H), 7.17 (dd, J=6.2, 2.6 Hz, 2H), 6.93 (dq, J=15.3, 7.9, 7.3 Hz, 2H), 6.82-6.64 (m, 2H), 6.11 (d, J=1.8 Hz, 1H), 6.05 (s, 2H), 4.78-4.43 (m, 1H), 3.77 (s, 3H), 3.25 (dd, J=15.9, 7.0 Hz, 2H), 2.86 (dd, J=15.9, 5.2 Hz, 2H).

General Procedure L

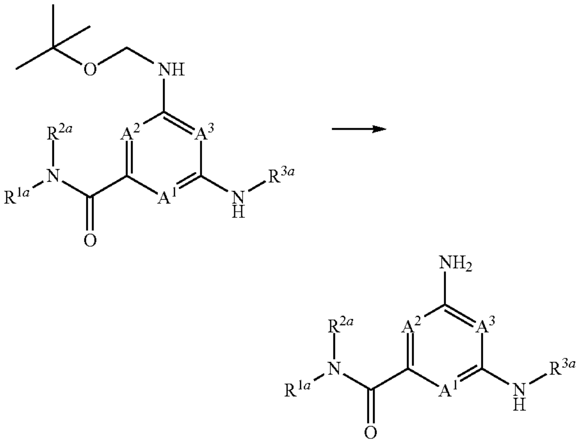

Method 1

To a stirred solution of the appropriate tert-butyl carbamate (ex: tert-butyl (6-((2-methoxyphenyl)amino)-2-(4-phenylpiperazine-1-carbonyl)pyrimidin-4-yl)carbamate) (1.0 eq.) in dioxane (3 mL/mmol) was added HCl (15 mL/mmol of a 4N solution in dioxane or 5 eq). The resulting mixture was stirred at room temperature for 16 h. The mixture was then diluted with sat. aq. $NaHCO_3$ and extracted with EtOAc (×3). Combined organic layers were washed with brine, dried over $MgSO_4$, filtered and concentrated. The crude was subjected to column chromatography on silica gel (DCM: MeOH, from 100:0 to 90:10) to produce the desired amine (ex: (4-amino-6-((2-methoxyphenyl)amino)pyrimidin-2-yl)(4-phenylpiperazin-1-yl)methanone).

Method 2

A solution of the appropriate tert-butyl carbamate (ex: tert-butyl (4-amino-6-(phenylcarbamoyl)pyridin-2-yl)carbamate) (1.0 eq) in TFA (4 mL/mmol) was stirred at rt for 2 h. The excess TFA was removed under vacuo and the residue was treated with sat. aq. $NaHCO_3$, extracted with EtOAc (×2). Combined organic layers were washed with brine, dried over $MgSO_4$, filtered and concentrated. The crude was subjected to column chromatography on silica gel (Hexane:EtOAc, from 95:05 to 50:50) to obtain the desired product (ex: 6-amino-N-phenyl-4-(pyridin-2-ylamino)pyridine-2-carboxamide).

Method 3

To a stirred solution of the appropriate tert-butyl carbamate (ex: tert-butyl (2-carbamoyl-6-((2-methoxyphenyl)amino)pyrimidin-4-yl)carbamate) (1.0 eq) in DCM (29.0 mL/mmol) was added $BBr_3$ (5.0 eq of a 1.0 M solution in DCM). The resulting solution was stirred at room temperature for 24 h. The reaction mixture was then diluted with water and extracted with EtOAc/MeOH (×3), dried over anhydrous sodium sulphate, filtered and concentrated to dryness. The resultant crude was purified by flash column chromatography (DCM:MeOH from 100:0 to 90:10) to obtain the desired amine product (ex: 4-amino-N-(2,3-dihydro-1H-inden-2-yl)-6-((2-hydroxyphenyl)amino)pyrimidine-2-carboxamide).

When $R^{3a}$ a methoxyphenyl, and demethylation occurs simultaneously resulting in the corresponding phenol.

Example 55

(4-Amino-6-((2-methoxyphenyl)amino)pyrimidin-2-yl)(4-phenylpiperazin-1-yl)methanone

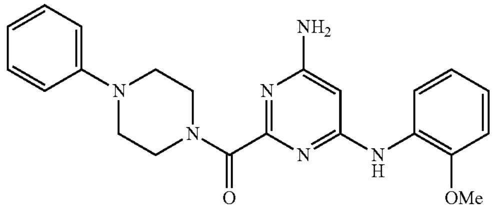 [SMILES: COc1ccccc1Nc1cc(N)nc(C(=O)N2CCN(c3ccccc3)CC2)n1]

Synthesized following General Procedure L, Method 1. Isolated as a yellow solid.

Yield: (0.059 g, 40%).

ES-MS [M+H]$^+$: 405.0, Rt=6.10 min (Method-A1).

Example 56

4-Amino-N-(2,3-dihydro-1H-inden-2-yl)-6-((2-hydroxyphenyl)amino)pyrimidine-2-carboxamide

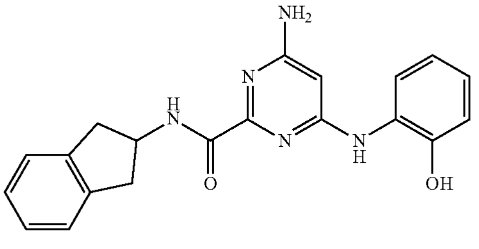

Synthesized following General Procedure L, Method 3. This product was purified by HPLC-semipreparative (Method-E1).

Yield: (0.010 g, 3%).

ES-MS [M+H]$^+$: 362.1, Rt=17.10 min (Method-B1).

$^1$H NMR (400 MHz, DMSO-$d_6$) δ 10.13 (s, 1H), 8.71-7.98 (m, 2H), 7.31 (dd, J=7.9, 1.6 Hz, 1H), 7.25 (dd, J=5.4, 3.3 Hz, 2H), 7.20-7.08 (m, 2H), 6.95 (ddd, J=8.1, 7.2, 1.6 Hz, 1H), 6.87 (dd, J=8.0, 1.6 Hz, 1H), 6.80-6.70 (m, 1H), 6.58 (s, 2H), 5.69 (s, 1H), 4.62 (qt, J=7.4, 5.8 Hz, 1H), 3.23 (dd, J=15.9, 7.4 Hz, 2H), 2.90 (dd, J=15.9, 5.8 Hz, 2H).

Example 57

4-Amino-6-((2-hydroxyphenyl)amino)-N-phenylpyrimidine-2-carboxamide

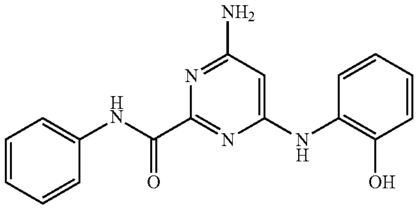 [SMILES: Nc1cc(Nc2ccccc2O)nc(C(=O)Nc2ccccc2)n1]

Synthesized following General Procedure L, Method 3. This product was purified by HPLC-semipreparative (Method-E1).

Yield: (0.008 g, 7%).

ES-MS $[M+H]^+$: 320.2, Rt=18.068 min (Method-B1).

$^1H$ NMR (400 MHz, $CD_3OD$) δ 7.90-7.59 (m, 2H), 7.46-7.26 (m, 3H), 7.25-7.11 (m, 1H), 7.04 (td, J=7.7, 1.6 Hz, 1H), 7.00-6.79 (m, 2H), 5.84 (s, 1H).

Example 58

(6-Amino-4-((2-hydroxyphenyl)amino)pyridin-2-yl)(isoindolin-2-yl)methanone

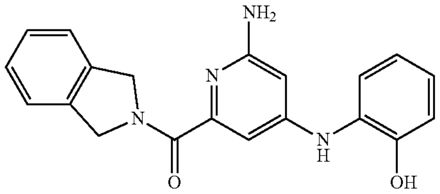 [SMILES: Nc1cc(Nc2ccccc2O)cc(C(=O)N2Cc3ccccc3C2)n1]

Synthesized following General Procedure L, Method 3. Purified first by flash column chromatography (DCM: MeOH 90:10) and then by HPLC-semipreparative (Method-E1).

Yield: (0.009 g, 10%).

ES-MS $[M-H]^-$: 345.2, Rt=23.379 min (Method-B1).

$^1H$ NMR (400 MHz, DMSO-$d_6$) δ 9.49 (s, 1H), 7.76 (s, 1H), 7.48-7.36 (m, 1H), 7.35-7.22 (m, 3H), 7.15 (dd, J=7.8, 1.6 Hz, 1H), 7.01-6.87 (m, 2H), 6.79 (td, J=7.5, 1.7 Hz, 1H), 6.47 (d, J=2.0 Hz, 1H), 5.90 (d, J=2.0 Hz, 1H), 5.67 (s, 2H), 5.06 (s, 2H), 4.79 (s, 2H).

Example 59

(6-Amino-4-((2-methoxyphenyl)amino)pyridin-2-yl)(isoindolin-2-yl)methanone

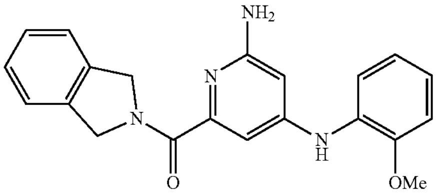 [SMILES: COc1ccccc1Nc1cc(N)nc(C(=O)N2Cc3ccccc3C2)c1]

Synthesized following Procedure L, Method 1.

Yield: (0.077 g, 33%).

ES-MS $[M-H]^-$: 361.2, Rt=19.895 min (Method-B1).

$^1H$ NMR (400 MHz, DMSO-$d_6$) δ 7.89 (s, 1H), 7.44-7.35 (m, 1H), 7.34-7.27 (m, 3H), 7.26-7.19 (m, 1H), 7.18-7.04 (m, 2H), 6.94 (ddd, J=7.8, 6.3, 2.5 Hz, 1H), 6.51 (d, J=1.9 Hz, 1H), 5.95 (d, J=2.0 Hz, 1H), 5.70 (brs, 2H), 5.06 (d, J=1.7 Hz, 2H), 4.79 (s, 2H), 3.80 (s, 3H).

Example 60

(4-(2-Fluorophenylamino)-6-aminopyrimidin-2-yl)(4-phenylpiperazin-1-yl)methanone

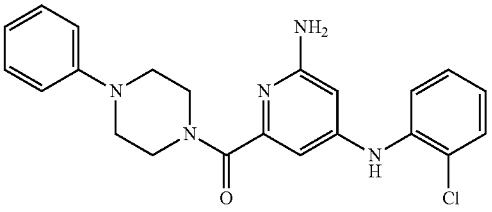

Synthesized following General Procedure L, Method 3. This product was obtained directly from (6-chloro-4-((2-chlorophenyl)amino)pyridin-2-yl)(4-phenylpiperazin-1-yl)methanone and it was purified by HPLC-semipreparative (Method-E1).

Yield: (0.026 g, 7%).

ES-MS $[M+H]^+$: 408.1, Rt=4.889 min (Method-B1).

$^1H$ NMR (400 MHz, DMSO-$d_6$) δ 8.25 (s, 1H), 7.53 (dd, J=8.0, 1.4 Hz, 1H), 7.45-7.29 (m, 2H), 7.23 (dd, J=8.7, 7.2 Hz, 2H), 7.16 (ddd, J=8.0, 7.2, 1.8 Hz, 1H), 7.03-6.93 (m, 2H), 6.86-6.74 (m, 1H), 6.24 (d, J=2.0 Hz, 1H), 5.85 (d, J=1.9 Hz, 1H), 5.80 (s, 2H), 3.70 (t, J=5.1 Hz, 2H), 3.59 (t, J=4.9 Hz, 2H), 3.17 (d, J=5.3 Hz, 2H), 3.12 (d, J=5.2 Hz, 2H).

Example 61

(6-Amino-4-((2-hydroxyphenyl)amino)pyridin-2-yl)(4-phenylpiperazin-1-yl)methanone

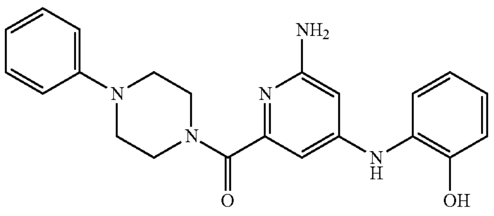 [SMILES: Nc1cc(Nc2ccccc2Cl)cc(C(=O)N2CCN(c3ccccc3)CC2)n1]

Synthesized following General Procedure L, Method 3. This product was purified by flash column chromatography (Hexane:EtOAc 60:40) followed by HPLC-semipreparative (Method-E1).

Yield: (0.013 g, 6%).

ES-MS $[M+H]^+$: 390.1, Rt=16.541 min (Method-B1).

$^1H$ NMR (400 MHz, DMSO-$d_6$) δ 9.51 (s, 1H), 7.74 (s, 1H), 7.23 (dd, J=8.7, 7.2 Hz, 2H), 7.15 (dd, J=7.8, 1.6 Hz, 1H), 6.96 (dt, J=8.0, 1.0 Hz, 3H), 6.91 (td, J=8.4, 8.0, 1.7 Hz, 1H), 6.85-6.74 (m, 2H), 6.21 (d, J=1.9 Hz, 1H), 5.85 (d, J=1.9 Hz, 1H), 5.64 (s, 2H), 3.64 (dt, J=43.9, 5.1 Hz, 4H), 3.23-3.00 (m, 4H).

Example 62

(4-(2-Fluorophenylamino)-6-aminopyrimidin-2-yl)(4-phenylpiperazin-1-yl)methanone

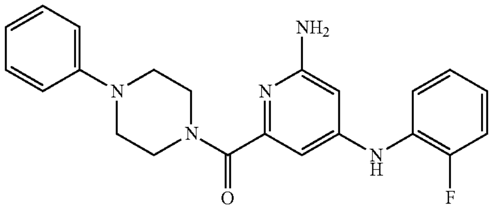 [SMILES: Nc1cc(Nc2ccccc2F)cc(C(=O)N2CCN(c3ccccc3)CC2)n1]

Synthesized following General Procedure L, Method 3.

Yield: (0.020 g, 29%).

ES-MS $[M+H]^+$: 392.1, Rt=17.693 min (Method-B1).

$^1H$ NMR (400 MHz, DMSO-$d_6$) δ 8.87 (Brs, 1H), 7.47-7.29 (m, 2H), 7.30-7.15 (m, 4H), 7.04-6.91 (m, 2H), 6.82 (tt, J=7.4, 1.1 Hz, 1H), 6.38-6.26 (m, 2H), 5.91 (t, J=1.7 Hz, 1H), 3.76-5.57 (m, 4H), 3.23-3.12 (m, 4H).

Example 63

(6-Amino-4-((2-methoxyphenyl)amino)pyridin-2-yl)(indolin-1-yl)methanone

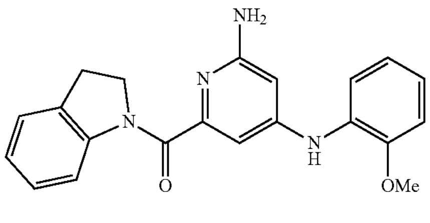 [SMILES: COc1ccccc1Nc1cc(N)nc(C(=O)N2CCc3ccccc32)c1]

Synthesized following General Procedure L, Method 3.

Yield: (0.218 g, 42%).

ES-MS $[M+H]^+$: 361.1, Rt=6.810 min (Method-A1).

Example 64

(6-Amino-4-((2-hydroxyphenyl)amino)pyridin-2-yl)(indolin-1-yl)methanone

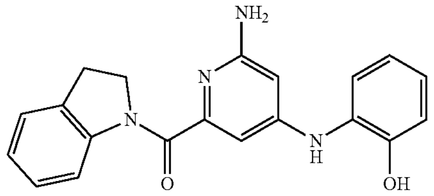 [SMILES: Nc1cc(Nc2ccccc2O)cc(C(=O)N2CCc3ccccc32)n1]

Synthesized following General Procedure L, Method 1. Isolated as a yellow powder. Purified by flash column chromatography (Hexane:EtOAc, from 95:05 to 50:50) followed by HPLC-semipreparative (Method-E1).

Yield: (0.025 g, 12%).

ES-MS $[M+H]^+$: 347.1, Rt=19.904 min (Method-B1).

$^1H$ NMR (400 MHz, DMSO-$d_6$) δ 10.33 (s, 1H), 10.20 (s, 1H), 8.37 (d, J=7.9 Hz, 1H), 7.37-7.22 (m, 3H), 7.18 (td, J=7.7, 1.4 Hz, 1H), 6.99-6.91 (m, 2H), 6.91-6.76 (m, 2H), 6.45 (d, J=2.1 Hz, 1H), 6.10 (s, 2H), 4.00 (t, J=8.5 Hz, 2H), 3.14 (t, J=8.4 Hz, 2H).

Example 65

6-Amino-4-((2-hydroxyphenyl)amino)-N-phenylpicolinamide

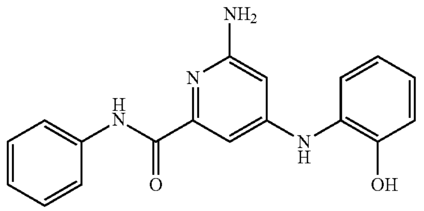 [SMILES: Nc1cc(Nc2ccccc2O)cc(C(=O)Nc2ccccc2)n1]

Synthesized following General Procedure L, Method 3.

Yield: (0.011 g, 6%).

ES-MS $[M+H]^+$: 321.1, Rt=16.794 min (Method-B1).

$^1H$ NMR (400 MHz, DMSO-$d_6$) δ 10.18 (s, 1H), 9.53 (brs, 1H), 7.98 (s, 1H), 7.81-7.69 (m, 2H), 7.44-7.30 (m, 2H), 7.16 (dd, J=7.8, 1.6 Hz, 1H), 7.13-7.05 (m, 1H), 7.00 (ddd, J=8.1, 7.2, 1.6 Hz, 1H), 6.96-6.88 (m, 2H), 6.82 (td, J=7.5, 1.6 Hz, 1H), 5.96 (d, J=2.0 Hz, 1H), 5.78 (s, 2H).

Example 66

6-Amino-4-((2-hydroxyphenyl)amino)-N-phenylpicolinamide

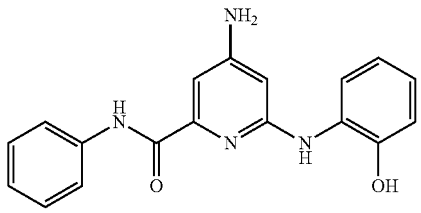 [SMILES: Nc1cc(Nc2ccccc2O)nc(C(=O)Nc2ccccc2)c1]

Synthesized following General Procedure L, Method 3. Yield: (0.030 g, 13%).

ES-MS $[M+H]^+$: 321.1, Rt=16.794 min (Method-B1).

$^1$H NMR (400 MHz, DMSO-$d_6$) δ 10.17 (s, 1H), 9.76 (s, 1H), 7.90-7.64 (m, 3H), 7.53 (s, 1H), 7.46-7.25 (m, 2H), 7.11 (t, J=7.3 Hz, 1H), 6.99-6.62 (m, 4H), 6.16 (s, 2H).

Example 67

6-Amino-N-(2,3-dihydro-1H-inden-2-yl)-4-((2-hydroxyphenyl)amino)picolinamide

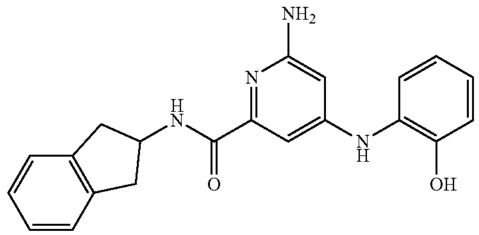 [SMILES: Nc1cc(Nc2ccccc2O)cc(C(=O)NC2Cc3ccccc3C2)n1]

Synthesized following General Procedure L, Method 3. Yield: (0.016 g, 8%).

ES-MS $[M-H]^-$: 361.1, Rt=17.259 min (Method-B1).

$^1$H NMR (400 MHz, DMSO-$d_6$) δ 9.46 (s, 1H), 8.22 (d, J=7.9 Hz, 1H), 7.85 (s, 1H), 7.25 (dd, J=5.4, 3.3 Hz, 2H), 7.20-7.14 (m, 2H), 7.12 (dd, J=7.8, 1.6 Hz, 1H), 6.97 (ddd, J=8.1, 7.2, 1.7 Hz, 1H), 6.90 (dd, J=8.0, 1.6 Hz, 1H), 6.86-6.75 (m, 2H), 5.89 (d, J=2.0 Hz, 1H), 5.64 (s, 2H), 4.63 (qt, J=7.5, 5.6 Hz, 1H), 3.23 (dd, J=16.0, 7.4 Hz, 2H), 2.88 (dd, J=15.9, 5.6 Hz, 2H).

Example 68

6-Amino-N-(2,3-dihydro-1H-inden-2-yl)-4-((2-hydroxy-4-methylphenyl)amino)picolinamide

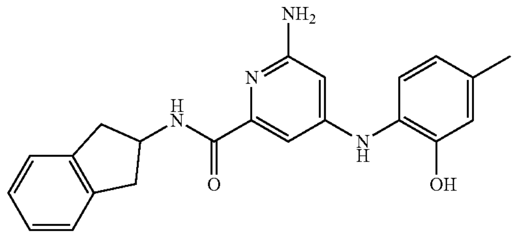 [SMILES: Cc1ccc(Nc2cc(N)nc(C(=O)NC3Cc4ccccc4C3)c2)c(O)c1]

Synthesized following General Procedure L, Method 3. This product was purified by HPLC-semipreparative (Method-E1).

Yield: (0.017 g, 23%).

ES-MS $[M+H]^+$: 375.2, Rt=17.864 min (Method-B1).

$^1$H NMR (400 MHz, DMSO-$d_6$) δ 9.34 (s, 1H), 8.22 (d, J=7.9 Hz, 1H), 7.75 (s, 1H), 7.25 (dd, J=5.4, 3.3 Hz, 2H), 7.19-7.09 (m, 2H), 6.97 (d, J=7.9 Hz, 1H), 6.77 (d, J=2.0 Hz, 1H), 6.72 (dd, J=2.0, 0.8 Hz, 1H), 6.61 (ddd, J=7.9, 2.0, 0.8 Hz, 1H), 5.80 (d, J=2.0 Hz, 1H), 5.59 (s, 2H), 4.63 (tdd, J=7.5, 5.6, 1.9 Hz, 1H), 3.23 (dd, J=16.0, 7.4 Hz, 2H), 2.87 (dd, J=15.9, 5.6 Hz, 2H), 2.22 (s, 3H).

Example 69

6-Amino-N-(2,3-dihydro-1H-inden-2-yl)-4-((4-fluoro-2-hydroxyphenyl)amino)picolinamide

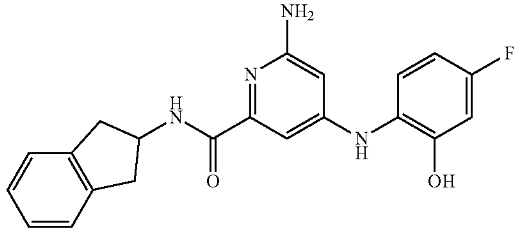 [SMILES: Nc1cc(Nc2ccc(F)cc2O)cc(C(=O)NC2Cc3ccccc3C2)n1]

Synthesized following General Procedure L, Method 3. This compound was purified by HPLC-semipreparative (Method-E1).

Yield: (0.008 g, 2%).

ES-MS [M+H]+: 379.2, Rt=17.543 min (Method-B1).

$^1$H NMR (400 MHz, DMSO-$d_6$) δ 9.97 (brs, 1H), 8.22 (d, J=7.9 Hz, 1H), 7.81 (s, 1H), 7.25 (dd, J=5.4, 3.3 Hz, 2H), 7.16 (dd, J=5.5, 3.2 Hz, 2H), 7.10 (dd, J=8.7, 6.4 Hz, 1H), 6.75 (d, J=2.0 Hz, 1H), 6.71 (dd, J=10.4, 2.9 Hz, 1H), 6.63 (td, J=8.5, 2.9 Hz, 1H), 5.75 (d, J=2.0 Hz, 1H), 5.62 (brs, 2H), 4.63 (tdd, J=7.5, 5.6, 1.9 Hz, 1H), 3.23 (dd, J=16.0, 7.3 Hz, 2H), 2.87 (dd, J=15.9, 5.6 Hz, 2H).

Example 70

6-Amino-N-(2,3-dihydro-1H-inden-2-yl)-4-((2-fluorophenyl)amino)picolinamide

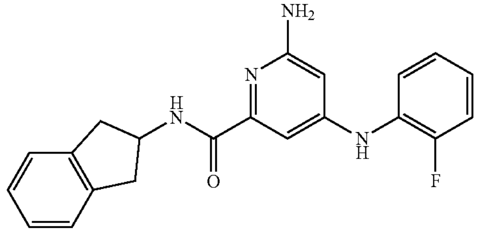 [SMILES: Nc1cc(Nc2ccccc2F)cc(C(=O)NC2Cc3ccccc3C2)n1]

Synthesized following General Procedure L, Method 3. Yield: (0.040 g, 16%).

ES-MS $[M+H]^+$: 363.1, Rt=18.261 min (Method-B1).

$^1$H NMR (400 MHz, DMSO-$d_6$) δ 8.44 (s, 1H), 8.23 (d, J=7.9 Hz, 1H), 7.39-7.28 (m, 2H), 7.27-7.21 (m, 2H), 7.18 (ddd, J=10.8, 6.5, 2.6 Hz, 4H), 6.85 (d, J=1.9 Hz, 1H), 5.95

(dd, J=2.0, 1.3 Hz, 1H), 5.78 (s, 2H), 4.64 (qt, J=7.4, 5.6 Hz, 1H), 3.29-3.16 (m, 2H), 2.89 (dd, J=16.0, 5.6 Hz, 2H).

Example 71

4-Amino-N-(2,3-dihydro-1H-inden-2-yl)-6-((2-fluorophenyl)amino)picolinamide

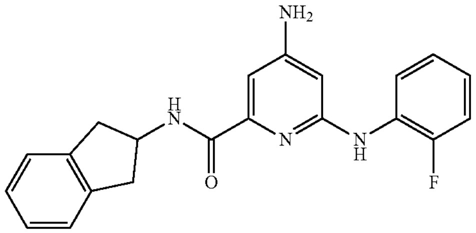

Synthesized following General Procedure L, Method 1.

Yield: (0.628 g, 50%).

ES-MS [M+H]+: 363.1, Rt=19.381 min (Method-B1).

$^{1}$H NMR (400 MHz, DMSO-$d_6$) δ 8.36 (d, J=1.5 Hz, 1H), 8.13 (d, J=7.9 Hz, 1H), 7.77-7.64 (m, 1H), 7.32 (dd, J=5.4, 3.3 Hz, 2H), 7.27-7.22 (m, 2H), 7.22-7.13 (m, 1H), 7.00 (ddd, J=7.2, 3.6, 1.4 Hz, 2H), 6.85 (dd, J=1.9, 0.6 Hz, 1H), 6.18 (s, 2H), 6.12 (d, J=1.8 Hz, 1H), 4.68 (qt, J=7.2, 4.7 Hz, 1H), 3.32 (dd, J=16.0, 7.0 Hz, 2H), 2.88 (dd, J=16.0, 4.7 Hz, 2H).

Example 72

6-Amino-4-((2-chlorophenyl)amino)-N-(2,3-dihydro-1H-inden-2-yl)picolinamide

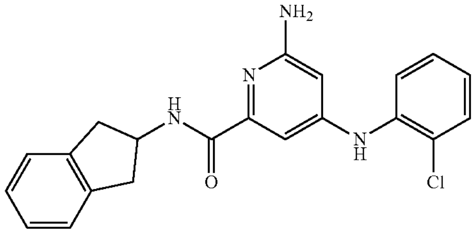 [SMILES: Nc1cc(Nc2ccccc2Cl)cc(C(=O)NC2Cc3ccccc3C2)n1]

Synthesized following General Procedure L, Method 3. This compound was purified by HPLC-semipreparative (Method-E1).

Yield: (0.019 g, 26%).

ES-MS $[M+H]^+$: 379.1, Rt=18.745 min (Method-B1).

$^{1}$H NMR (400 MHz, DMSO-$d_6$) δ 8.34 (s, 1H), 8.22 (d, J=7.9 Hz, 1H), 7.62-7.46 (m, 1H), 7.40-7.32 (m, 2H), 7.25 (dd, J=5.4, 3.3 Hz, 2H), 7.22-7.12 (m, 3H), 6.85 (d, J=2.0 Hz, 1H), 5.91 (d, J=2.0 Hz, 1H), 5.77 (s, 2H), 4.64 (qt, J=7.5, 5.6 Hz, 1H), 3.25 (d, J=7.3 Hz, 1H), 3.21 (d, J=7.3 Hz, 1H), 2.90 (d, J=5.6 Hz, 1H), 2.86 (d, J=5.6 Hz, 1H).

Example 73

6-Amino-4-(benzo[d][1,3]dioxol-4-ylamino)-N-phenylpicolinamide

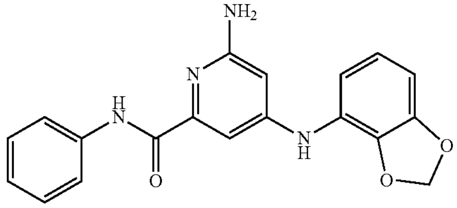

Synthesized following General Procedure L, Method 3. This product was purified by HPLC-semipreparative (Method-E1).

Yield: (0.021 g, 7%).

ES-MS $[M+H]^+$: 349.1, Rt=20.001 min (Method-B1).

$^{1}$H NMR (400 MHz, DMSO-$d_6$) δ 10.17 (s, 1H), 8.53 (s, 1H), 8.07-7.62 (m, 2H), 7.55-7.28 (m, 2H), 7.20-7.01 (m, 1H), 6.92 (d, J=2.0 Hz, 1H), 6.86 (t, J=8.0 Hz, 1H), 6.75 (ddd, J=8.1, 5.3, 1.2 Hz, 2H), 6.03 (s, 2H), 5.97 (d, J=2.0 Hz, 1H), 5.88 (s, 2H).

Example 74

6-Amino-4-((2-fluorophenyl)amino)-N-phenylpicolinamide

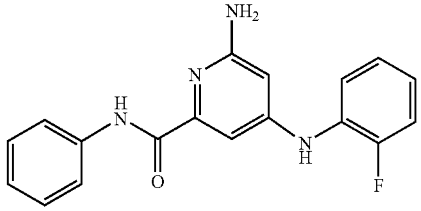 [SMILES: Nc1cc(Nc2ccccc2F)cc(C(=O)Nc2ccccc2)n1]

Synthesized following General Procedure L, Method 3.

Yield: (0.090 g, 80%).

ES-MS [M+H]+: 323.2, Rt=19.293 min (Method-B1).

$^{1}$H NMR (400 MHz, DMSO-$d_6$) δ 10.17 (s, 1H), 8.54 (s, 1H), 7.75 (dt, J=7.9, 1.2 Hz, 2H), 7.47-7.27 (m, 4H), 7.27-7.13 (m, 2H), 7.15-7.06 (m, 1H), 6.94 (dd, J=2.0, 0.6 Hz, 1H), 6.02 (dd, J=2.0, 1.3 Hz, 1H), 5.92 (s, 2H).

Example 75

4-Amino-6-((2-fluorophenyl)amino)-N-phenylpicolinamide

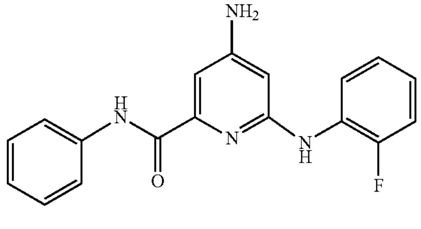 [SMILES: Nc1cc(Nc2ccccc2F)nc(C(=O)Nc2ccccc2)c1]

Synthesized following General Procedure L, Method 3. This compound was purified by HPLC-semipreparative (Method-E1).

Yield: (0.016 g, 35%).

ES-MS [M+H]+: 323.2, Rt=19.031 min (Method-B1).

$^{1}$H NMR (400 MHz, DMSO-$d_6$) δ 10.03 (s, 1H), 8.89-8.25 (m, 1H), 7.82 (td, J=8.2, 1.7 Hz, 1H), 7.71-7.54 (m, 2H), 7.37 (dd, J=8.5, 7.4 Hz, 2H), 7.32-7.17 (m, 2H), 7.14-7.00 (m, 2H), 6.89 (d, J=1.8 Hz, 1H), 6.23 (s, 2H), 6.15 (d, J=1.9 Hz, 1H).

Example 76

6-Amino-N-(2,3-dihydro-1H-inden-2-yl)-4-((2-methoxyphenyl)amino)picolinamide

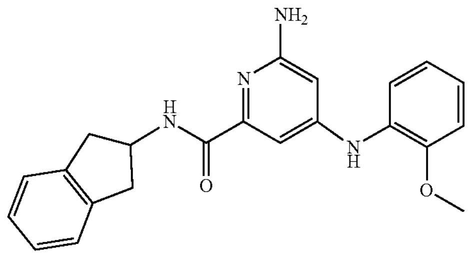 [SMILES: COc1ccccc1Nc1cc(N)nc(C(=O)NC2Cc3ccccc3C2)c1]

Synthesized following General Procedure L, Method 1.

Yield: (0.028 g, 11%).

ES-MS [M+H]$^+$: 375.2, Rt=20.194 min (Method-B1).

$^{1}$H NMR (400 MHz, DMSO-$d_6$) δ 8.22 (d, J=7.9 Hz, 1H), 7.98 (s, 1H), 7.30-7.14 (m, 4H), 7.14-7.02 (m, 2H), 6.94 (ddd, J=7.7, 6.9, 1.9 Hz, 1H), 6.87 (d, J=2.0 Hz, 1H), 5.95 (d, J=2.0 Hz, 1H), 5.67 (s, 2H), 4.63 (qt, J=7.5, 5.6 Hz, 1H), 3.78 (s, 3H), 3.23 (dd, J=16.0, 7.3 Hz, 2H), 2.88 (dd, J=16.0, 5.6 Hz, 2H). (d, J=5.6 Hz, 1H), 2.84 (d, J=5.6 Hz, 1H).

Example 77

6-Amino-4-((2-hydroxy-4-methylphenyl)amino)-N-phenylpicolinamide

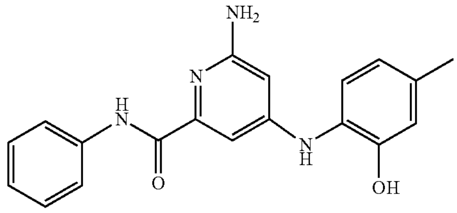 [SMILES: Cc1ccc(Nc2cc(N)nc(C(=O)Nc3ccccc3)c2)c(O)c1]

Synthesized following General Procedure L, Method 1.

Yield: (0.075 g, 36%).

ES-MS [M+H]$^+$: 335.2, Rt=17.430 min (Method-B1).

$^{1}$H NMR (400 MHz, DMSO-$d_6$) δ 10.18 (s, 1H), 9.36 (s, 1H), 7.87 (s, 1H), 7.81-7.58 (m, 2H), 7.36 (dd, J=8.5, 7.4 Hz, 2H), 7.18-7.05 (m, 1H), 7.01 (d, J=7.9 Hz, 1H), 6.87 (d, J=2.0 Hz, 1H), 6.82-6.69 (m, 1H), 6.63 (ddd, J=7.9, 2.0, 0.8 Hz, 1H), 5.87 (d, J=2.0 Hz, 1H), 5.74 (s, 2H), 2.24 (s, 3H).

Example 78

6-Amino-4-((4-fluoro-2-hydroxyphenyl)amino)-N-phenylpicolinamide

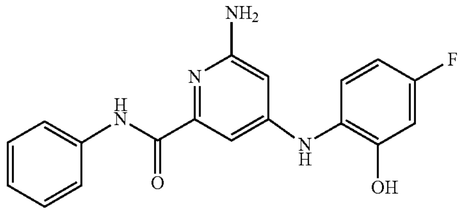 [SMILES: Nc1cc(Nc2ccc(F)cc2O)cc(C(=O)Nc2ccccc2)n1]

Synthesized following General Procedure L, Method 1.

Yield: (0.095 g, 57%).

ES-MS [M+H]$^+$: 339.2, Rt=17.149 min (Method-B1).

$^{1}$H NMR (400 MHz, DMSO-$d_6$) δ 10.18 (s, 1H), 10.02 (s, 1H), 7.93 (s, 1H), 7.86-7.65 (m, 2H), 7.36 (dd, J=8.5, 7.4 Hz, 2H), 7.22-7.00 (m, 2H), 6.85 (d, J=1.9 Hz, 1H), 6.73 (dd, J=10.4, 2.9 Hz, 1H), 6.65 (td, J=8.5, 2.9 Hz, 1H), 5.82 (d, J=2.0 Hz, 1H), 5.77 (s, 2H).

Example 79

6-Amino-N-phenyl-4-(pyridin-2-ylamino)pyridine-2-carboxamide

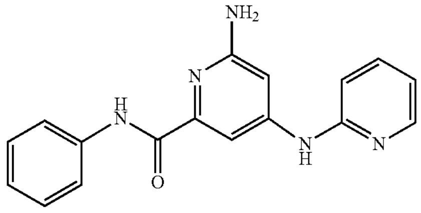 [SMILES: Nc1cc(Nc2ccccn2)cc(C(=O)Nc2ccccc2)n1]

Synthesized following General Procedure L, Method 2. This compound was purified by HPLC-semipreparative (Method-E1).

Yield: (0.033 g, 22%).

ES-MS [M+H]$^+$: 306.2, Rt=20.116 min (Method-B1).

$^{1}$H NMR (400 MHz, DMSO-$d_6$) δ 10.83 (brs, 1H), 10.35 (brs, 1H), 8.36 (dd, J=5.1, 1.9 Hz, 1H), 7.96-7.65 (m, 4H), 7.49 (d, J=1.9 Hz, 1H), 7.42 (dd, J=8.5, 7.4 Hz, 2H), 7.25-7.14 (m, 1H), 7.14-7.03 (m, 2H).

Example 80

6-Amino-N-phenyl-4-(pyridin-3-ylamino)picolinamide

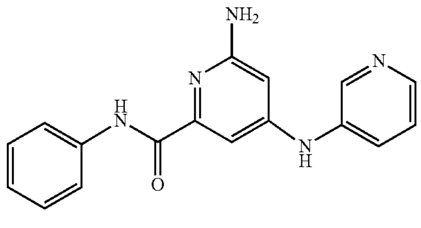 [SMILES: Nc1cc(Nc2cccnc2)cc(C(=O)Nc2ccccc2)n1]

Synthesized following General Procedure L, Method 2.

Yield: (0.042 g, 28%).

ES-MS $[M+H]^+$: 306.2, Rt=15.765 min (Method-B1).

$^1$H NMR (400 MHz, DMSO-$d_6$) δ 10.18 (s, 1H), 8.89 (s, 1H), 8.46 (d, J=2.7 Hz, 1H), 8.24 (dd, J=4.7, 1.4 Hz, 1H), 7.76 (dt, J=7.9, 1.1 Hz, 2H), 7.61 (ddd, J=8.3, 2.8, 1.5 Hz, 1H), 7.48-7.26 (m, 3H), 7.20-7.06 (m, 1H), 7.01 (d, J=2.0 Hz, 1H), 6.32 (d, J=2.0 Hz, 1H), 6.01 (s, 2H).

Example 81

2-amino-N-(2,3-dihydro-1H-inden-2-yl)-6-((2-hydroxyphenyl)amino)pyrimidine-4-carboxamide

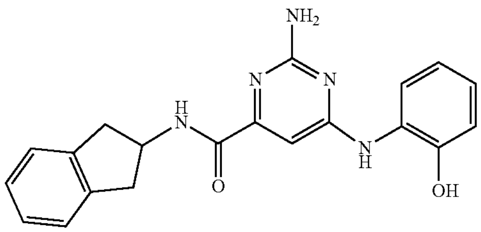 [SMILES: Nc1nc(Nc2ccccc2O)cc(C(=O)NC2Cc3ccccc3C2)n1]

Synthesized following General Procedure L, Method 3. This product was purified by HPLC-semipreparative (Method-E1).

Yield: (0.017 g, 15%).

ES-MS $[M+H]^+$: 362.1, Rt=17.549 min (Method-B1).

$^1$H NMR (400 MHz, DMSO-$d_6$) δ 10.02-9.70 (m, 1H), 8.74 (s, 1H), 8.24 (d, J=7.8 Hz, 1H), 7.78-7.53 (m, 1H), 7.25 (dd, J=5.4, 3.3 Hz, 2H), 7.21-7.10 (m, 2H), 6.95 (ddd, J=8.0, 7.2, 1.7 Hz, 1H), 6.87 (dd, J=8.0, 1.6 Hz, 1H), 6.78 (ddd, J=8.0, 7.3, 1.6 Hz, 1H), 6.70 (s, 1H), 6.40 (s, 2H), 4.64 (qt, J=7.5, 5.6 Hz, 1H), 3.24 (dd, J=16.0, 7.4 Hz, 2H), 2.90 (dd, J=16.0, 5.6 Hz, 2H).

Example 82

2-Amino-N-(2,3-dihydro-1H-inden-2-yl)-6-((2-hydroxyphenyl)amino)-N-methylpyrimidine-4-carboxamide

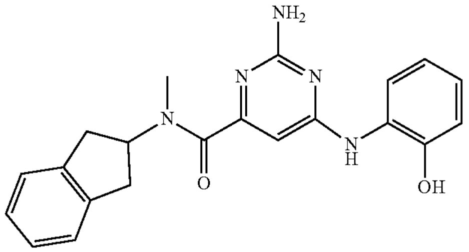 [SMILES: CN(C(=O)c1cc(Nc2ccccc2O)nc(N)n1)C1Cc2ccccc2C1]

Synthesized following General Procedure L, Method 3.

Yield: (0.030 g, 9%).

ES-MS $[M+H]^+$: 376.1, Rt=17.062 min (Method-B1).

$^1$H NMR (400 MHz, DMSO-$d_6$) δ 9.93 (brs, 1H), 8.56 (d, J=8.2 Hz, 1H), 7.73 (d, J=7.9 Hz, 1H), 7.42-7.06 (m, 4H), 6.96-6.89 (m, 1H), 6.86 (dd, J=8.0, 1.7 Hz, 1H), 6.83-6.71 (m, 1H), 6.44 (d, J=17.0 Hz, 2H), 6.10 (d, J=13.0 Hz, 1H), 5.32 (t, J=7.6 Hz, 0.36H), 4.67 (p, J=7.9 Hz, 0.64H), 3.20-2.94 (m, 4H), 2.76 (d, J=15.6 Hz, 3H). Conformers present.

Example 83

2-amino-6-((2-hydroxyphenyl)amino)-N-methyl-N-(1,2,3,4-tetrahydronaphthalen-2-yl)-pyrimidine-4-carboxamide

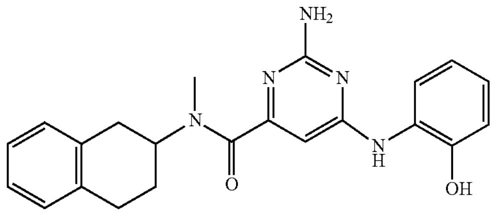 [SMILES: CN(C(=O)c1cc(Nc2ccccc2O)nc(N)n1)C1CCc2ccccc2C1]

Synthesized following General Procedure L, Method 3.

Yield: (0.013 g, 22%).

ES-MS $[M+H]^+$: 390.2, Rt=17.457 min (Method-B1).

$^1$H NMR (400 MHz, DMSO-$d_6$) δ 9.91 (d, J=21.7 Hz, 1H), 8.53 (d, J=16.5 Hz, 1H), 7.72 (t, J=6.1 Hz, 1H), 7.11 (s, 2H), 7.09-7.01 (m, 2H), 6.98-6.82 (m, 2H), 6.77 (dtd, J=14.9, 7.5, 1.7 Hz, 1H), 6.48 (s, 1H), 6.38 (s, 1H), 6.09 (d, J=4.9 Hz, 1H), 4.70-4.56 (m, 0.39H), 3.90 (dq, J=10.8, 5.3 Hz, 0.61H), 3.05 (d, J=11.2 Hz, 2H), 2.86 (d, J=4.1 Hz, 3H), 2.67 (t, J=1.9 Hz, 2H), 2.04-1.79 (m, 2H). Conformers present.

Example 84

2-Amino-6-((2-hydroxyphenyl)amino)-N-(1,2,3,4-tetrahydronaphthalen-2-yl)pyrimidine-4-carboxamide

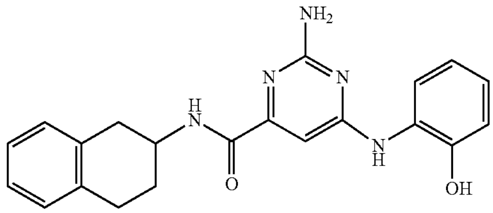 [SMILES: Nc1nc(Nc2ccccc2O)cc(C(=O)NC2CCc3ccccc3C2)n1]

Synthesized following General Procedure L, Method 3.

Yield: (0.018 g, 8%).

ES-MS $[M+H]^+$: 376.1, Rt=18.142 min (Method-B1).

$^1$H NMR (400 MHz, DMSO-$d_6$) δ 9.90 (s, 1H), 8.75 (s, 1H), 8.12 (d, J=8.1 Hz, 1H), 7.70 (d, J=7.9 Hz, 1H), 7.18-6.92 (m, 4H), 6.96 (ddd, J=8.0, 7.2, 1.6 Hz, 1H), 6.88 (dd, J=8.0, 1.6 Hz, 1H), 6.79 (ddd, J=8.0, 7.2, 1.6 Hz, 1H), 6.71 (s, 1H), 6.43 (brs, 2H), 4.12 (ddt, J=12.7, 8.8, 4.8 Hz, 1H), 3.03 (dd, J=16.1, 5.3 Hz, 1H), 2.90-2.73 (m, 3H), 2.06-1.94 (m, 1H), 1.89-1.73 (m, 1H).

Example 85

(2-Amino-6-((2-hydroxyphenyl)amino)pyrimidin-4-yl)(3,4-dihydroisoquinolin-2(1H)-yl)methanone

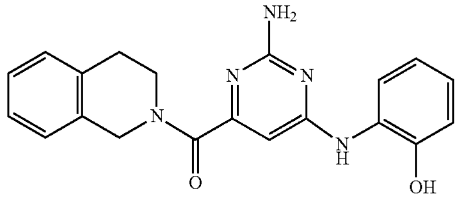 [SMILES: Nc1nc(Nc2ccccc2O)cc(C(=O)N2CCc3ccccc3C2)n1]

Synthesized following General Procedure L, Method 3.

Yield: (0.089 g, 27%).

ES-MS $[M+H]^+$: 362.1, Rt=16.410 min (Method-B1).

$^1$H NMR (400 MHz, DMSO-$d_6$) δ 9.94 (s, 1H), 8.59 (s, 1H), 7.76 (dd, J=14.0, 7.6 Hz, 1H), 7.29-7.02 (m, 4H), 6.97-6.90 (m, 1H), 6.87 (ddd, J=8.0, 2.6, 1.7 Hz, 1H), 6.78 (ddt, J=9.5, 7.4, 2.1 Hz, 1H), 6.46 (d, J=7.2 Hz, 2H), 6.14 (d, J=19.3 Hz, 1H), 4.70 (s, 1H), 4.61 (s, 1H), 3.78 (t, J=6.1 Hz, 1H), 3.63 (t, J=5.9 Hz, 1H), 2.85 (q, J=6.0 Hz, 2H). Conformers present.

Example 86

(2-Amino-6-((2-hydroxyphenyl)amino)pyrimidin-4-yl)(isoindolin-2-yl)methanone

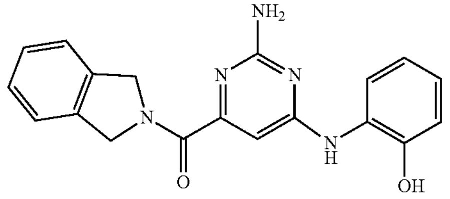 [SMILES: Nc1nc(Nc2ccccc2O)cc(C(=O)N2Cc3ccccc3C2)n1]

Synthesized following General Procedure L, Method 3. This product was purified by HPLC-semipreparative (Method-E1).

Yield: (0.010 g, 17%).

ES-MS $[M+H]^+$: 348.1, Rt=16.122 min (Method-B1).

$^1$H NMR (400 MHz, DMSO-$d_6$) δ 9.96 (brs, 1H), 8.63 (s, 1H), 7.73 (dd, J=8.0, 1.6 Hz, 1H), 7.53-7.36 (m, 1H), 7.35-7.19 (m, 3H), 7.00-6.91 (m, 1H), 6.88 (dd, J=8.0, 1.6 Hz, 1H), 6.79 (ddd, J=7.9, 7.2, 1.6 Hz, 1H), 6.47 (s, 2H), 6.35 (s, 1H), 5.01 (s, 2H), 4.80 (s, 2H).

Example 87

4-Amino-N-(2,3-dihydro-1H-inden-2-yl)-6-(o-tolylamino)picolinamide

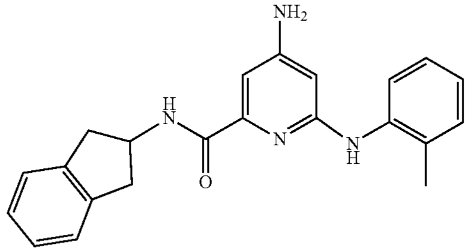 [SMILES: Cc1ccccc1Nc1cc(N)cc(C(=O)NC2Cc3ccccc3C2)n1]

Synthesized following General Procedure L, Method 1.

Yield: (0.016 g, 36%).

ES-MS $[M-H]^-$: 359.2, Rt=21.867 min (Method-B1).

$^1$H NMR (400 MHz, DMSO-$d_6$) δ 8.12 (d, J=7.8 Hz, 1H), 7.76 (s, 1H), 7.35-7.21 (m, 3H), 7.21-7.11 (m, 3H), 7.03 (td, J=7.6, 1.5 Hz, 1H), 6.94 (td, J=7.4, 1.4 Hz, 1H), 6.72 (d, J=1.9 Hz, 1H), 6.01 (brs, 2H), 5.83 (d, J=1.9 Hz, 1H), 4.61 (qt, J=7.3, 4.9 Hz, 1H), 3.31-3.14 (m, 2H), 2.81 (dd, J=16.0, 4.9 Hz, 2H), 2.14 (s, 3H).

Example 88

(4-Amino-6-((2-hydroxyphenyl)amino)pyridin-2-yl)(4-phenylpiperazin-1-yl)methanone

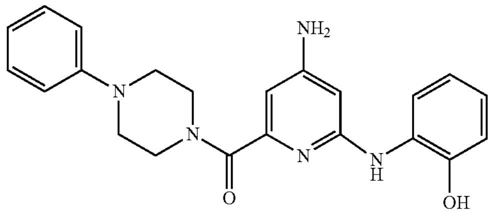 [SMILES: Nc1cc(Nc2ccccc2O)nc(C(=O)N2CCN(c3ccccc3)CC2)c1]

Synthesized following General Procedure L, Method 1. This compound was purified by HPLC-semipreparative (Method-E1).

Yield: (0.032 g, 35%).

ES-MS $[M-H]^-$: 390.2, Rt=17.224 min (Method-B1).

$^1$H NMR (400 MHz, DMSO-$d_6$) δ 10.95 (s, 1H), 8.08 (s, 1H), 7.34 (dd, J=7.9, 1.6 Hz, 1H), 7.23 (dd, J=8.8, 7.3 Hz, 2H), 7.03-6.90 (m, 2H), 6.89-6.75 (m, 3H), 6.71 (ddd, J=7.9, 7.0, 1.8 Hz, 1H), 6.25-6.09 (m, 3H), 6.04 (d, J=1.8 Hz, 1H), 3.71 (s, 2H), 3.55 (s, 2H), 3.18 (s, 2H), 3.08 (s, 2H).

Example 89

4-Amino-6-(benzo[d][1,3]dioxol-4-ylamino)-N-(2,3-dihydro-1H-inden-2-yl)picolinamide

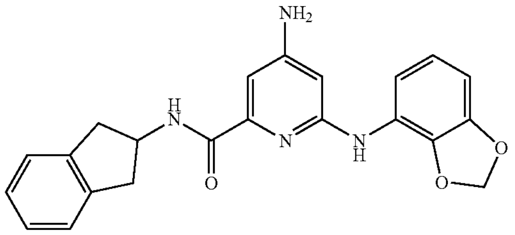 [SMILES: Nc1cc(Nc2cccc3c2OCO3)nc(C(=O)NC2Cc3ccccc3C2)c1]

Synthesized following General Procedure L, Method 1.

Yield: (0.056 g, 36%).

ES-MS $[M-H]^-$: 389.3, Rt=5.152 min (Method-F1).

$^1$H NMR (400 MHz, DMSO-$d_6$) δ 8.23 (s, 1H), 8.12 (d, J=7.8 Hz, 1H), 7.26 (dd, J=5.4, 3.3 Hz, 2H), 7.21-7.10 (m, 2H), 6.93 (dd, J=8.3, 1.2 Hz, 1H), 6.76 (d, J=1.9 Hz, 1H), 6.70-6.61 (m, 1H), 6.58 (dd, J=7.8, 1.2 Hz, 1H), 6.06 (s, 2H), 5.98 (d, J=1.9 Hz, 1H), 5.88 (s, 2H), 4.62 (qt, J=7.2, 4.9 Hz, 1H), 3.28 (d, J=7.1 Hz, 1H), 3.24 (d, J=7.1 Hz, 1H), 2.83 (d, J=4.9 Hz, 1H), 2.79 (d, J=4.8 Hz, 1H).

Example 90

4-Amino-N-(2,3-dihydro-1H-inden-2-yl)-6-((2-fluoro-3-methylphenyl)amino)picolinamide

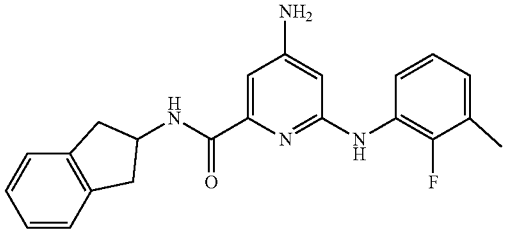 [SMILES: Cc1cccc(Nc2cc(N)cc(C(=O)NC3Cc4ccccc4C3)n2)c1F]

Synthesized following General Procedure L, Method 1.

Yield: (0.089 g, 37%).

ES-MS $[M-H]^-$: 377.2, Rt=5.771 min (Method-F1).

$^1$H NMR (400 MHz, DMSO-$d_6$) δ 8.20 (d, J=1.4 Hz, 1H), 8.08 (d, J=7.8 Hz, 1H), 7.44 (ddd, J=7.8, 6.4, 3.4 Hz, 1H), 7.26 (dd, J=5.4, 3.3 Hz, 2H), 7.21-7.09 (m, 2H), 6.89-6.80 (m, 2H), 6.78 (d, J=1.8 Hz, 1H), 6.10 (s, 2H), 6.05 (d, J=1.9 Hz, 1H), 4.62 (qt, J=7.3, 4.9 Hz, 1H), 3.26 (dd, J=16.0, 7.1 Hz, 2H), 2.81 (dd, J=16.0, 4.8 Hz, 2H), 2.20 (d, J=2.1 Hz, 3H).

Example 91

4-Amino-N-(2,3-dihydro-1H-inden-2-yl)-6-((2-hydroxy-3-methylphenyl)amino)picolinamide

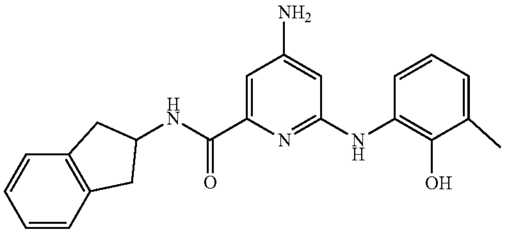 [SMILES: Cc1cccc(Nc2cc(N)cc(C(=O)NC3Cc4ccccc4C3)n2)c1O]

Synthesized following General Procedure L, Method 1.

Yield: (0.070 g, 35%).

ES-MS $[M-H]^-$: 375.3, Rt=19.087 min (Method-B1).

$^1$H NMR (400 MHz, DMSO-$d_6$) δ 9.74 (s, 1H), 8.31-7.85 (m, 2H), 7.24 (dd, J=5.4, 3.3 Hz, 2H), 7.20-7.11 (m, 2H), 7.01 (dd, J=8.0, 1.7 Hz, 1H), 6.78 (ddd, J=7.4, 1.7, 0.8 Hz, 1H), 6.72 (d, J=1.9 Hz, 1H), 6.61 (t, J=7.7 Hz, 1H), 6.20 (s, 2H), 5.99 (d, J=1.9 Hz, 1H), 4.64 (qt, J=7.4, 5.3 Hz, 1H), 3.29 (d, J=7.4 Hz, 1H), 3.25 (d, J=7.3 Hz, 1H), 2.88 (d, J=5.4 Hz, 1H), 2.84 (d, J=5.3 Hz, 1H), 2.13 (s, 3H).

Example 92

4-Amino-N-(2,3-dihydro-1H-inden-2-yl)-6-((3-fluorophenyl)amino)picolinamide

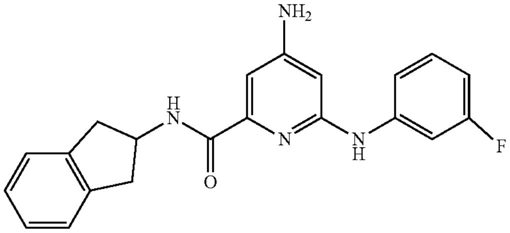 [SMILES: Nc1cc(Nc2cccc(F)c2)nc(C(=O)NC2Cc3ccccc3C2)c1]

Synthesized following General Procedure L, Method 1.

Yield: (0.074 g, 30%).

ES-MS $[M-H]^-$: 363.2, Rt=21.911 min (Method-B1).

$^1$H NMR (400 MHz, DMSO-$d_6$) δ 8.99-8.84 (m, 1H), 8.07 (d, J=7.7 Hz, 1H), 7.48-7.31 (m, 1H), 7.26 (dd, J=5.4, 3.3 Hz, 2H), 7.21-7.08 (m, 4H), 6.83 (d, J=1.9 Hz, 1H), 6.69-6.50 (m, 1H), 6.19 (s, 2H), 6.07 (d, J=1.9 Hz, 1H), 4.65 (qt, J=7.3, 5.2 Hz, 1H), 3.28 (dd, J=16.0, 7.2 Hz, 2H), 2.88 (dd, J=15.9, 5.2 Hz, 2H).

Example 93

4-Amino-6-((2-methoxyphenyl)amino)-N-phenylpicolinamide

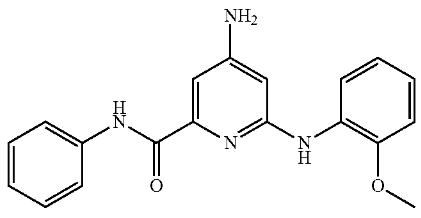

Synthesized following General Procedure L, Method 1.
Yield: (0.058 g, 58%).
ES-MS [M+H]+: 335.2, Rt=21.067 min (Method-B1).
$^1$H NMR (400 MHz, DMSO-$d_6$) δ 10.17 (s, 1H), 7.76-7.67 (m, 4H), 7.42-7.33 (m, 2H), 7.15-6.94 (m, 4H), 6.86 (d, J=1.8 Hz, 1H), 6.21 (d, J=1.8 Hz, 1H), 6.17 (s, 2H), 3.84 (s, 3H).

Example 94

4-Amino-6-(benzo[d][1,3]dioxol-4-ylamino)-N-phenylpicolinamide

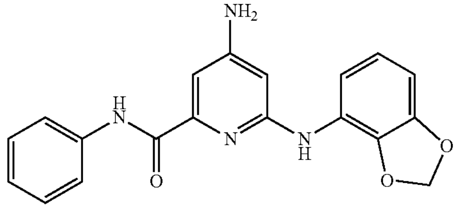 [SMILES: Nc1cc(Nc2cccc3c2OCO3)nc(C(=O)Nc2ccccc2)c1]

Synthesized following General Procedure L, Method 1. This product was purified by HPLC-semipreparative (Method-E1).
Yield: (0.058 g, 15%).
ES-MS [M−H]$^-$: 347.2, Rt=20.706 min (Method-B1).
$^1$H NMR (400 MHz, DMSO-$d_6$) δ 10.13 (s, 1H), 8.40 (s, 1H), 7.81-7.55 (m, 2H), 7.56-7.24 (m, 2H), 7.23-7.00 (m, 2H), 6.95-6.77 (m, 2H), 6.69 (dd, J=7.8, 1.1 Hz, 1H), 6.19 (s, 2H), 6.07 (d, J=1.9 Hz, 1H), 5.99 (s, 2H).

Example 95

(4-Amino-6-(benzo[d][1,3]dioxol-4-ylamino)pyridin-2-yl)(isoindolin-2-yl)methanone

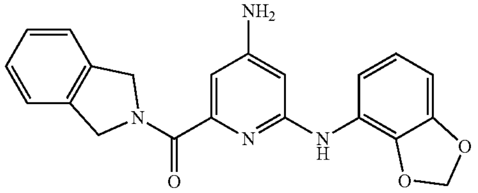 [SMILES: Nc1cc(Nc2cccc3c2OCO3)nc(C(=O)N2Cc3ccccc3C2)c1]

Synthesized following General Procedure L, Method 1.
Yield: (0.104 g, 52%).
ES-MS [M−H]$^-$: 375.2, Rt=4.599 min (Method-F1).
$^1$H NMR (400 MHz, DMSO-$d_6$) δ 8.19 (s, 1H), 7.48-7.33 (m, 1H), 7.32-7.18 (m, 3H), 7.06 (dd, J=8.3, 1.1 Hz, 1H), 6.78 (t, J=8.0 Hz, 1H), 6.64 (dd, J=7.8, 1.1 Hz, 1H), 6.52 (d, J=1.8 Hz, 1H), 6.04-5.97 (m, 3H), 5.96 (s, 2H), 5.02 (s, 2H), 4.80 (s, 2H).

Example 96

(6-(2-Methoxyphenylamino)-4-aminopyridin-2-yl)(isoindolin-2-yl)methanone

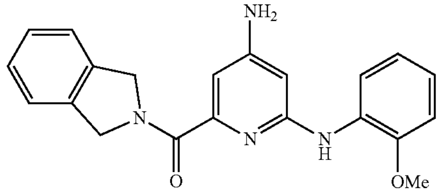 [SMILES: COc1ccccc1Nc1cc(N)cc(C(=O)N2Cc3ccccc3C2)n1]

Synthesized following General Procedure L, Method 1.
Yield: (0.011 g, 6%).
ES-MS [M+H]+: 361.1, Rt=18.324 min (Method-B1).
$^1$H NMR (400 MHz, DMSO-$d_6$) δ 7.76 (dd, J=7.8, 1.7 Hz, 1H), 7.61 (s, 1H), 7.45-7.34 (m, 1H), 7.33-7.19 (m, 3H), 7.01 (dd, J=8.1, 1.6 Hz, 1H), 6.95 (td, J=7.7, 1.7 Hz, 1H), 6.88 (td, J=7.6, 1.6 Hz, 1H), 6.50 (d, J=1.8 Hz, 1H), 6.11 (d, J=1.9 Hz, 1H), 5.95 (s, 2H), 5.00 (s, 2H), 4.92-4.60 (m, 2H), 3.82 (s, 3H).

Example 97

4-Amino-N-(2,3-dihydro-1H-inden-2-yl)-6-(m-tolylamino)picolinamide

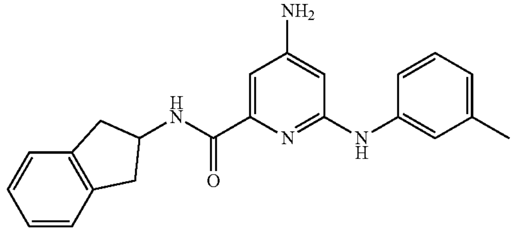 [SMILES: Cc1cccc(Nc2cc(N)cc(C(=O)NC3Cc4ccccc4C3)n2)c1]

Synthesized following General Procedure L, Method 1.
Yield: (0.011 g, 53%).
ES-MS [M+H]+: 359.2, Rt=19.922 min (Method-B1).
$^1$H NMR (400 MHz, DMSO-$d_6$) δ 8.56 (s, 1H), 8.08 (d, J=7.8 Hz, 1H), 7.41-7.22 (m, 3H), 7.22-7.13 (m, 2H), 7.10 (ddt, J=8.1, 1.7, 0.8 Hz, 1H), 6.99 (t, J=7.8 Hz, 1H), 6.79 (d, J=1.8 Hz, 1H), 6.64 (ddt, J=7.3, 1.8, 0.9 Hz, 1H), 6.09 (s, 2H), 6.04 (d, J=2.0 Hz, 1H), 4.66 (qt, J=7.3, 4.9 Hz, 1H), 3.32 (dd, J=16.0, 4.9 Hz, 2H), 2.87 (dd, J=16.0, 4.9 Hz, 2H), 2.18 (s, 3H).

Example 98

4-Amino-N-(2,3-dihydro-1H-inden-2-yl)-6-((4-fluorophenyl)amino)picolinamide

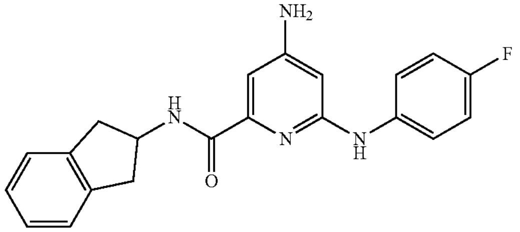 [SMILES: Nc1cc(Nc2ccc(F)cc2)nc(C(=O)NC2Cc3ccccc3C2)c1]

Synthesized following General Procedure L, Method 1.

Yield: (0.081 g, 33%).

ES-MS [M+H]+: 363.2, Rt=19.327 min (Method-B1).

$^{1}$H NMR (400 MHz, DMSO-$d_6$) δ 8.62 (s, 1H), 8.06 (d, J=8.0 Hz, 1H), 7.43-7.25 (m, 4H), 7.23-7.10 (m, 2H), 6.92 (t, J=8.9 Hz, 2H), 6.78 (d, J=1.8 Hz, 1H), 6.10 (s, 2H), 5.98 (d, J=1.9 Hz, 1H), 4.74-4.57 (m, 1H), 3.26 (dd, J=16.0, 7.0 Hz, 2H), 2.86 (dd, J=16.0, 4.6 Hz, 2H).

Example 99

4-Amino-6-((2-cyanophenyl)amino)-N-(2,3-dihydro-1H-inden-2-yl)picolinamide

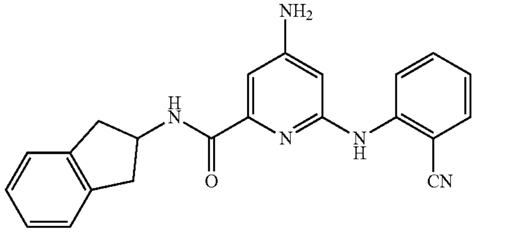 [SMILES: N#Cc1ccccc1Nc1cc(N)cc(C(=O)NC2Cc3ccccc3C2)n1]

Synthesized following General Procedure L, Method 1.

Yield: (0.042 g, 92%).

ES-MS [M+H]+: 370.2, Rt=18.511 min (Method-B1).

$^{1}$H NMR (400 MHz, DMSO-$d_6$) δ 8.81 (s, 1H), 8.01 (d, J=8.0 Hz, 1H), 7.61-7.55 (m, 1H), 7.50 (dd, J=8.5, 1.2 Hz, 1H), 7.47-7.38 (m, 1H), 7.24 (dd, J=5.4, 3.3 Hz, 2H), 7.17 (dt, J=5.2, 3.7 Hz, 2H), 7.06 (t, J=7.3 Hz, 1H), 6.84 (d, J=1.9 Hz, 1H), 6.22 (s, 2H), 6.10 (d, J=1.9 Hz, 1H), 4.61 (dtd, J=11.9, 7.1, 4.8 Hz, 1H), 3.23 (dd, J=16.0, 7.0 Hz, 2H), 2.79 (dd, J=15.9, 4.8 Hz, 2H).

Example 100

4-Amino-N-(2,3-dihydro-1H-inden-2-yl)-6-((3-methoxyphenyl)amino)picolinamide

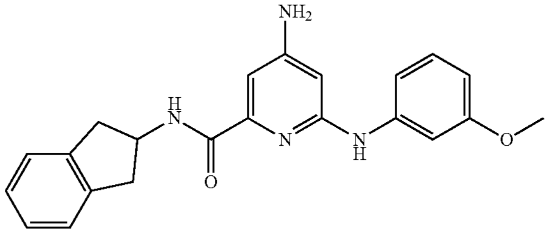

Synthesized following General Procedure L, Method 1.

Yield: (0.092 g, 69%).

ES-MS [M+H]+: 375.2, Rt=19.138 min (Method-B1).

$^{1}$H NMR (400 MHz, DMSO-$d_6$) δ 8.61 (s, 1H), 8.09 (d, J=7.7 Hz, 1H), 7.24 (dd, J=5.4, 3.3 Hz, 2H), 7.19-7.11 (m, 2H), 7.05 (t, J=2.2 Hz, 1H), 7.00 (t, J=8.1 Hz, 1H), 6.89 (ddd, J=8.1, 2.0, 1.0 Hz, 1H), 6.78 (d, J=1.9 Hz, 1H), 6.39 (ddd, J=8.2, 2.5, 0.9 Hz, 1H), 6.10 (s, 2H), 6.05 (d, J=1.9 Hz, 1H), 4.63 (qt, J=7.4, 5.1 Hz, 1H), 3.65 (s, 3H), 3.30-3.19 (m, 2H), 2.85 (dd, J=16.0, 5.1 Hz, 2H).

Example 101

4-Amino-6-((2-chlorophenyl)amino)-N-(2,3-dihydro-1H-inden-2-yl)picolinamide

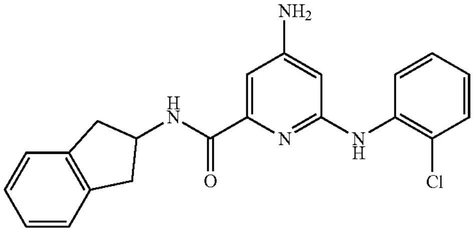 [SMILES: Nc1cc(Nc2ccccc2Cl)nc(C(=O)NC2Cc3ccccc3C2)c1]

Synthesized following General Procedure L, Method 1.

Yield: (0.088 g, 34%).

ES-MS [M−H]$^{-}$: 379.3, Rt=21.979 min (Method-B1).

$^{1}$H NMR (400 MHz, DMSO-$d_6$) δ 8.10 (d, J=7.9 Hz, 1H), 8.00 (s, 1H), 7.60 (dd, J=8.2, 1.6 Hz, 1H), 7.39 (dd, J=8.0, 1.5 Hz, 1H), 7.25 (dd, J=5.4, 3.3 Hz, 2H), 7.21-7.14 (m, 2H), 7.11 (ddd, J=8.1, 7.3, 1.6 Hz, 1H), 6.97 (ddd, J=8.0, 7.3, 1.6 Hz, 1H), 6.80 (d, J=1.9 Hz, 1H), 6.13 (brs, 2H), 6.07 (d, J=1.9 Hz, 1H), 4.61 (qt, J=7.2, 5.0 Hz, 1H), 3.24 (dd, J=16.0, 7.2 Hz, 2H), 2.82 (dd, J=16.0, 5.0 Hz, 2H).

Example 102

4-Amino-N-(2,3-dihydro-1H-inden-2-yl)-6-(pyridin-3-ylamino)picolinamide

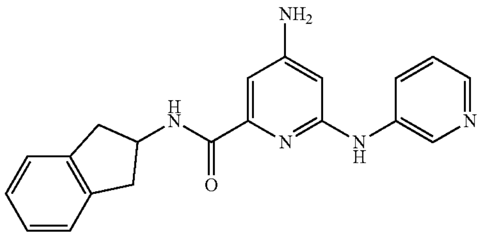 [SMILES: Nc1cc(Nc2cccnc2)nc(C(=O)NC2Cc3ccccc3C2)c1]

Synthesized following Procedure L, Method 1.

Yield: (0.040 g, 52%).

ES-MS [M−H]$^-$: 346.2, Rt=19.567 min (Method-B1).

$^1$H NMR (400 MHz, DMSO-$d_6$) δ 8.86 (s, 1H), 8.52 (dd, J=2.6, 0.7 Hz, 1H), 8.06 (d, J=7.9 Hz, 1H), 8.02 (dd, J=4.6, 1.4 Hz, 1H), 7.89 (ddd, J=8.4, 2.7, 1.5 Hz, 1H), 7.27 (dd, J=5.4, 3.3 Hz, 2H), 7.22-7.14 (m, 2H), 7.08 (ddd, J=8.4, 4.6, 0.7 Hz, 1H), 6.82 (d, J=1.9 Hz, 1H), 6.19 (brs, 2H), 6.07 (d, J=1.9 Hz, 1H), 4.65 (qt, J=7.3, 5.3 Hz, 1H), 3.26 (dd, J=16.0, 7.1 Hz, 2H), 2.88 (dd, J=15.9, 5.3 Hz, 2H).

Example 103

(6-(2-Fluorophenylamino)-4-aminopyridin-2-yl)(isoindolin-2-yl)methanone

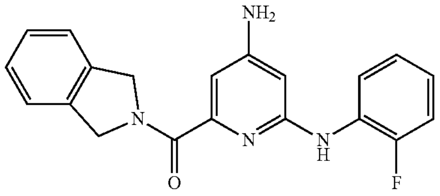 [SMILES: Nc1cc(Nc2ccccc2F)nc(C(=O)N2Cc3ccccc3C2)c1]

Synthesized following Procedure L, Method 1.

Yield: (0.046 g, 55%).

ES-MS [M−H]$^-$: 349.2, Rt=20.907 min (Method-B1).

$^1$H NMR (400 MHz, DMSO-$d_6$) δ 8.28 (d, J=1.2 Hz, 1H), 7.75 (td, J=8.2, 1.7 Hz, 1H), 7.43-7.34 (m, 1H), 7.33-7.16 (m, 4H), 7.12 (td, J=7.7, 1.5 Hz, 1H), 7.01 (dddd, J=8.1, 7.4, 4.9, 1.8 Hz, 1H), 6.56 (d, J=1.9 Hz, 1H), 6.08 (d, J=1.9 Hz, 1H), 6.01 (brs, 2H), 5.09-4.90 (m, 2H), 4.87-4.61 (m, 2H).

Example 104

(4-Amino-6-((2-hydroxyphenyl)amino)pyridin-2-yl)(isoindolin-2-yl)methanone

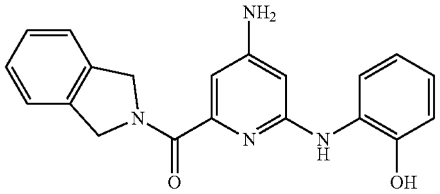 [SMILES: Nc1cc(Nc2ccccc2O)nc(C(=O)N2Cc3ccccc3C2)c1]

Synthesized following General Procedure L, Method 1. This compound was purified by HPLC-semipreparative (Method-E1).

Yield: (0.013 g, 7%).

ES-MS [M−H]$^-$: 347.3, Rt=16.775 min (Method-B1).

$^1$H NMR (400 MHz, DMSO-$d_6$) δ 10.57 (brs, 1H), 7.95 (s, 1H), 7.37 (dd, J=7.9, 1.6 Hz, 2H), 7.34-7.25 (m, 2H), 7.23 (td, J=7.6, 6.9, 1.8 Hz, 1H), 6.91-6.78 (m, 2H), 6.74 (ddd, J=7.8, 6.9, 1.9 Hz, 1H), 6.41 (d, J=1.8 Hz, 1H), 6.11 (s, 2H), 6.07 (d, J=1.9 Hz, 1H), 4.91 (s, 2H), 4.81 (s, 2H).

Example 105

(4-Amino-6-((3-fluorophenyl)amino)pyridin-2-yl)(4-phenylpiperazin-1-yl)methanone

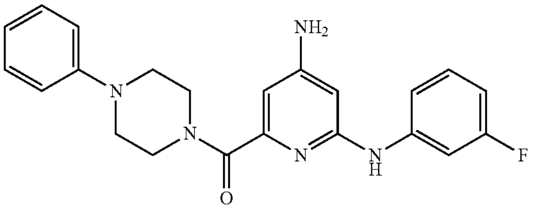 [SMILES: Nc1cc(Nc2cccc(F)c2)nc(C(=O)N2CCN(c3ccccc3)CC2)c1]

Synthesized following General Procedure L, Method 1.

Yield: (0.085 g, 40%).

ES-MS [M−H]$^-$: 392.1, Rt=18.637 min (Method-B1).

$^1$H NMR (400 MHz, DMSO-$d_6$) δ 9.19-8.63 (m, 1H), 8.13-7.59 (m, 1H), 7.46-7.11 (m, 4H), 7.07-6.90 (m, 2H), 6.81 (tt, J=7.2, 1.0 Hz, 1H), 6.58 (ddt, J=8.9, 5.5, 2.7 Hz, 1H), 6.27 (d, J=1.9 Hz, 1H), 6.08 (s, 2H), 6.02 (d, J=1.8 Hz, 1H), 3.70 (d, J=30.2 Hz, 4H), 3.28-3.03 (m, 4H).

Example 106

4-Amino-N-(2,3-dihydro-1H-inden-2-yl)-6-((2-methoxyphenyl)amino)-N-methyl-picolinamide

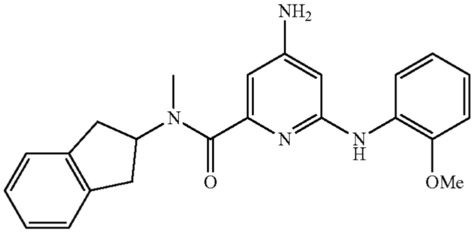 [SMILES: COc1ccccc1Nc1cc(N)cc(C(=O)N(C)C2Cc3ccccc3C2)n1]

Synthesized following General Procedure L, Method 1.

Yield: (0.127 g, 55%).

ES-MS [M−H]$^-$: 389.2, Rt=18.885 min (Method-B1).

$^1$H NMR (400 MHz, DMSO-$d_6$) δ 7.99-7.77 (m, 1H), 7.50 (s, 1H), 7.25 (s, 1H), 7.14 (dt, J=13.1, 4.8 Hz, 3H), 6.93 (dtd, J=22.2, 7.9, 4.1 Hz, 3H), 6.14 (d, J=1.9 Hz, 1H), 6.04 (d, J=1.8 Hz, 1H), 5.92 (s, 2H), 5.41-4.72 (m, 1H), 3.79 (d, J=15.7 Hz, 3H), 3.08-2.86 (m, 3H), 2.78 (d, J=13.6 Hz, 3H). Conformers present.

Example 107

4-Amino-N-(2,3-dihydro-1H-inden-2-yl)-6-((3-fluorophenyl)amino)-N-methylpicolinamide

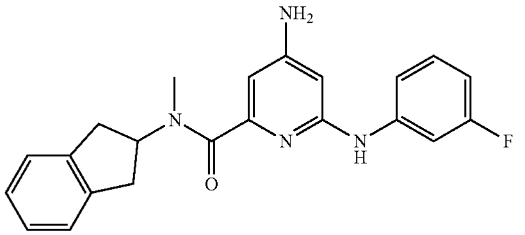 [SMILES: CN(C(=O)c1cc(N)cc(Nc2cccc(F)c2)n1)C1Cc2ccccc2C1]

Synthesized following General Procedure L, Method 1.

Yield: (0.111 g, 53%).

ES-MS $[M-H]^-$: 377.2, Rt=19.101 min (Method-B1).

$^1$H NMR (400 MHz, DMSO-$d_6$) δ 8.91 (s, 1H), 7.89-7.60 (m, 1H), 7.35-6.97 (m, 6H), 6.74-6.55 (m, 1H), 6.19 (d, J=1.8 Hz, 1H), 6.06 (s, 2H), 6.03-5.89 (m, 1H), 5.45-4.74 (m, 1H), 3.23-2.94 (m, 4H), 2.79 (d, J=21.0 Hz, 3H). Conformers present Example 108

4-Amino-N-(2,3-dihydro-1H-inden-2-yl)-6-((3-fluoro-2-methylphenyl)amino)picolinamide

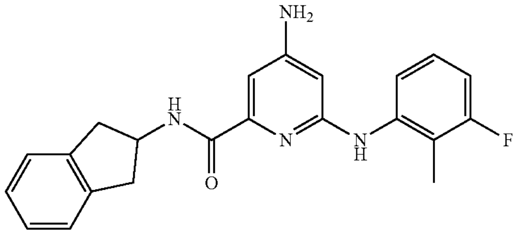 [SMILES: Cc1c(F)cccc1Nc1cc(N)cc(C(=O)NC2Cc3ccccc3C2)n1]

Synthesized following General Procedure L, Method 1.

Yield: (0.052 g, 38%).

ES-MS $[M-H]^-$: 377.2, Rt=19.896 min (Method-B1).

$^1$H NMR (400 MHz, DMSO-$d_6$) δ 8.08 (s, 1H), 8.00 (s, 1H), 7.25 (dd, J=5.4, 3.3 Hz, 2H), 7.21-7.11 (m, 3H), 7.03 (q, J=7.5 Hz, 1H), 6.82 (t, J=8.8 Hz, 1H), 6.76 (d, J=1.8 Hz, 1H), 6.08 (brs, 2H), 5.90 (d, J=1.9 Hz, 1H), 4.61 (qt, J=7.3, 4.9 Hz, 1H), 3.25 (dd, J=16.0, 7.1 Hz, 2H), 2.81 (dd, J=16.0, 4.9 Hz, 2H), 2.05 (d, J=2.1 Hz, 3H).

Example 109

4-Amino-6-((3,5-difluorophenyl)amino)-N-(2,3-dihydro-1H-inden-2-yl)picolinamide

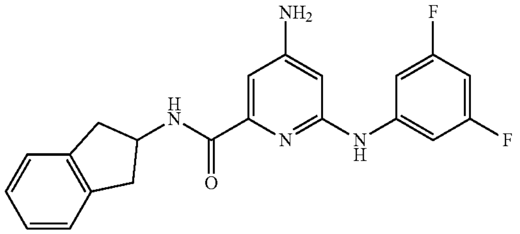

Synthesized following General Procedure L, Method 1. This product was purified by HPLC-semipreparative (Method-E1).

Yield: (0.179 g, 14%).

ES-MS $[M-H]^-$: 381.2, Rt=20.079 min (Method-B1).

$^1$H NMR (400 MHz, DMSO-$d_6$) δ 9.14 (s, 1H), 8.06 (d, J=7.6 Hz, 1H), 7.24 (dd, J=5.4, 3.3 Hz, 2H), 7.18-7.05 (m, 4H), 6.85 (d, J=1.8 Hz, 1H), 6.58 (tt, J=9.3, 2.3 Hz, 1H), 6.26 (s, 2H), 6.08 (d, J=1.9 Hz, 1H), 4.65 (tdd, J=7.4, 5.6, 1.6 Hz, 1H), 3.31-3.22 (m, 2H), 2.89 (dd, J=15.9, 5.7 Hz, 2H).

Example 110

4-Amino-6-((2-hydroxyphenyl)amino)-N-methyl-N-phenylpicolinamide

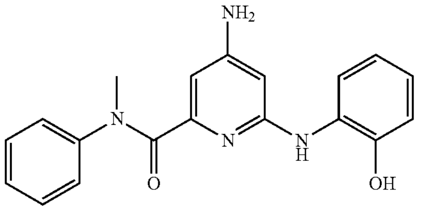

Synthesized following General Procedure L, Method 1.

Yield: (0.048 g, 33%).

ES-MS $[M-H]^-$: 335.2, Rt=16.027 min (Method-B1).

$^1$H NMR (400 MHz, DMSO-$d_6$) δ 11.02 (brs, 1H), 7.92 (brs, 1H), 7.52-7.00 (m, 6H), 6.91-6.72 (m, 2H), 6.67 (ddd, J=8.5, 6.7, 2.1 Hz, 1H), 6.19-5.95 (m, 3H), 5.86 (d, J=1.8 Hz, 1H), 3.32 (s, 3H).

Example 111

4-Amino-N-(2,3-dihydrobenzo[b][1,4]dioxin-6-yl)-6-((2-fluorophenyl)amino)picolinamide

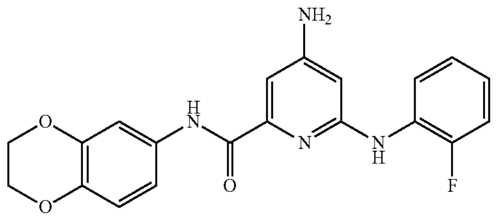 [SMILES: Nc1cc(Nc2ccccc2F)nc(C(=O)Nc2ccc3c(c2)OCCO3)c1]

Synthesized following General Procedure L, Method 1.

Yield: (0.063 g, 45%).

ES-MS $[M-H]^-$: 381.1, Rt=18.684 min (Method-B1).

$^1$H NMR (400 MHz, DMSO-$d_6$) δ 9.87 (s, 1H), 8.40 (d, J=1.3 Hz, 1H), 7.79 (td, J=8.2, 1.7 Hz, 1H), 7.32 (d, J=2.4 Hz, 1H), 7.26 (ddd, J=11.4, 8.1, 1.5 Hz, 1H), 7.18 (td, J=7.7, 1.5 Hz, 1H), 7.06 (dddd, J=8.1, 7.4, 4.9, 1.7 Hz, 1H), 6.99 (dd, J=8.7, 2.5 Hz, 1H), 6.89-6.77 (m, 2H), 6.21 (s, 2H), 6.13 (d, J=1.8 Hz, 1H), 4.38-4.05 (m, 4H).

Example 112

4-Amino-N-(2,3-dihydro-1H-inden-2-yl)-6-((3-hydroxyphenyl)amino)picolinamide

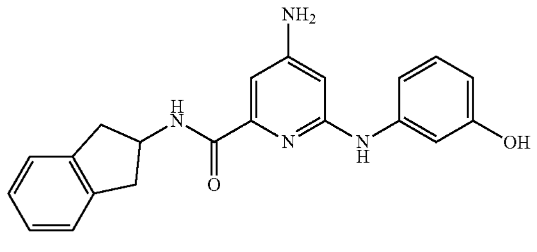 [SMILES: Nc1cc(Nc2cccc(O)c2)nc(C(=O)NC2Cc3ccccc3C2)c1]

Synthesized following General Procedure L, Method 1.

Yield: (0.048 g, 46%).

ES-MS $[M-H]^-$: 361.2, Rt=17.097 min (Method-B1).

$^1$H NMR (400 MHz, DMSO-$d_6$) δ 9.16 (s, 1H), 8.48 (s, 1H), 8.12 (d, J=7.7 Hz, 1H), 7.26 (dd, J=5.4, 3.3 Hz, 2H), 7.20-7.10 (m, 2H), 6.89 (t, J=8.0 Hz, 1H), 6.82 (t, J=2.2 Hz, 1H), 6.81-6.72 (m, 2H), 6.26 (ddd, J=8.0, 2.3, 1.0 Hz, 1H), 6.18-5.96 (m, 3H), 4.63 (qt, J=7.3, 5.4 Hz, 1H), 3.28 (dd, J=16.0, 7.3 Hz, 2H), 2.88 (dd, J=15.9, 5.3 Hz, 2H).

Example 113

6-(2-Methoxyphenylamino)-4-amino-N-methyl-N-phenylpyridine-2-carboxamide

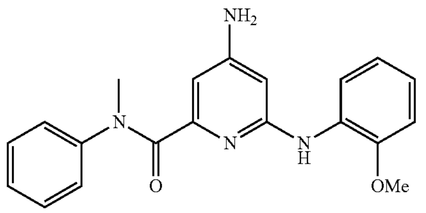 [SMILES: COc1ccccc1Nc1cc(N)cc(C(=O)N(C)c2ccccc2)n1]

Synthesized following General Procedure L, Method 1. Yield: (0.046 g, 19%).

ES-MS $[M-H]^-$: 349.2, Rt=16.953 min (Method-B1).

$^1$H NMR (400 MHz, DMSO-$d_6$) δ 7.39-7.24 (m, 4H), 7.21-7.04 (m, 3H), 6.89 (dd, J=8.0, 1.6 Hz, 1H), 6.78 (dtd, J=21.9, 7.4, 1.7 Hz, 2H), 6.23 (d, J=1.8 Hz, 1H), 5.95 (d, J=1.8 Hz, 1H), 5.83 (brs, 2H), 3.77 (s, 3H), 3.34 (s, 3H).

Example 114

4-Amino-6-((2-fluorophenyl)amino)-N-methyl-N-phenylpicolinamide

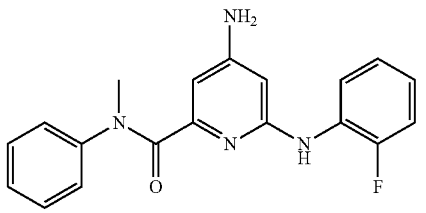 [SMILES: CN(C(=O)c1cc(N)cc(Nc2ccccc2F)n1)c1ccccc1]

Synthesized following General Procedure L, Method 1. Yield: (0.045 g, 28%).

ES-MS $[M-H]^-$: 337.2, Rt=16.184 min (Method-B1).

$^1$H NMR (400 MHz, DMSO-$d_6$) δ 8.05 (s, 1H), 7.48-7.23 (m, 3H), 7.21-7.00 (m, 4H), 7.01-6.88 (m, 1H), 6.88-6.74 (m, 1H), 6.26 (d, J=1.8 Hz, 1H), 5.95 (d, J=1.9 Hz, 1H), 5.90 (brs, 2H), 3.34 (s, 3H).

Example 115

6-(3-Fluorophenylamino)-4-amino-N-methyl-N-phenylpyridine-2-carboxamide

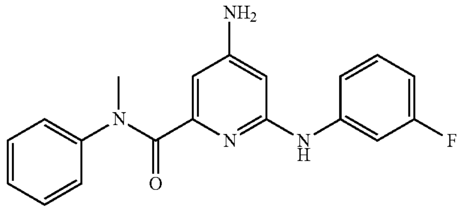 [SMILES: CN(C(=O)c1cc(N)cc(Nc2cccc(F)c2)n1)c1ccccc1]

Synthesized following General Procedure L, Method 1. Yield: (0.141 g, 61%).

ES-MS $[M-H]^-$: 337.1, Rt=17.228 min (Method-B1).

$^1$H NMR (400 MHz, DMSO-$d_6$) δ 8.67 (s, 1H), 7.34 (d, J=12.8 Hz, 1H), 7.27-7.18 (m, 2H), 7.18-6.99 (m, 4H), 6.87 (d, J=8.2 Hz, 1H), 6.71-6.34 (m, 1H), 6.28 (d, J=1.8 Hz, 1H), 5.94 (s, 2H), 5.81 (d, J=1.9 Hz, 1H), 3.36 (s, 3H).

Example 116

(6-(3-Fluorophenylamino)-4-aminopyridin-2-yl)(isoindolin-2-yl)methanone

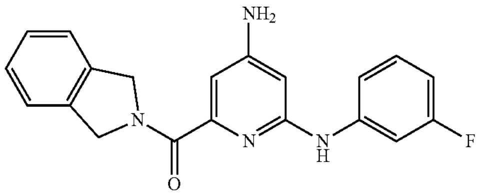 [SMILES: Nc1cc(Nc2cccc(F)c2)nc(C(=O)N2Cc3ccccc3C2)c1]

Synthesized following Procedure L, Method 1.
Yield: (0.011 g, 10%).
ES-MS [M−H]$^-$: 349.2, Rt=18.481 min (Method-B1).
$^1$H NMR (400 MHz, DMSO-$d_6$) δ 8.93 (s, 1H), 7.57 (ddd, J=12.7, 2.9, 1.5 Hz, 1H), 7.46-7.35 (m, 1H), 7.35-7.14 (m, 5H), 6.61 (tq, J=7.3, 2.5 Hz, 1H), 6.52 (d, J=1.8 Hz, 1H), 6.10 (brs, 2H), 6.09 (d, J=1.9 Hz, 1H), 5.03 (s, 2H), 4.85 (s, 2H).

Example 117

4-Amino-N-(2,3-dihydro-1H-inden-2-yl)-6-((2-hydroxyphenyl)amino)-N-methyl-picolinamide

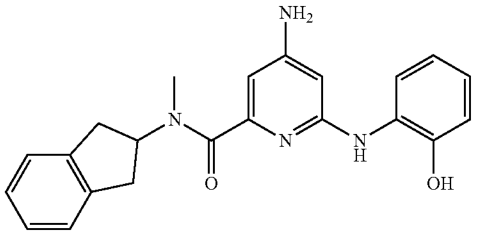 [SMILES: CN(C(=O)c1cc(N)cc(Nc2ccccc2O)n1)C1Cc2ccccc2C1]

Synthesized following General Procedure L, Method 1.
Yield: (0.079 g, 53%).
ES-MS [M+H]+−: 375.2, Rt=17.994 min (Method-B1).

Example 118

4-Amino-N-(2,3-dihydro-1H-inden-2-yl)-6-((2-fluorophenyl)amino)-N-methylpicolinamide

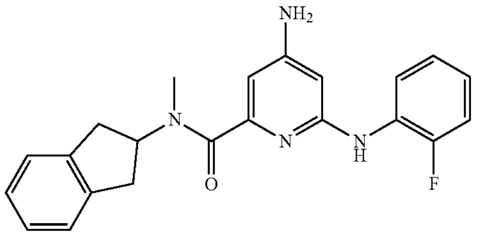 [SMILES: CN(C(=O)c1cc(N)cc(Nc2ccccc2F)n1)C1Cc2ccccc2C1]

Synthesized following General Procedure L, Method 1.
Yield: (0.105 g, 47%).
ES-MS [M+H]+−: 377.2, Rt=6.500 min (Method-A1).

Example 119

4-Amino-6-((3-fluorophenyl)amino)-N-phenylpicolinamide

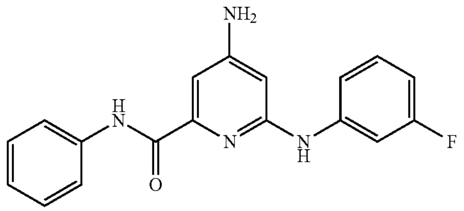

Synthesized following General Procedure L, Method 1.
Yield: (0.094 g, 91%).
ES-MS [M+H]+−: 323.1, Rt=6.720 min (Method-A1).

Example 120

4-Amino-6-((3-methoxyphenyl)amino)-N-phenylpicolinamide

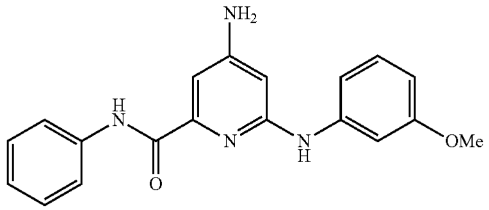

Synthesized following General Procedure L, Method 1.
Yield: (0.023 g, 11%).
ES-MS [M+H]+−: 335.2, Rt=6.584 min (Method-A1).

Example 121

4-Amino-6-((3-fluorophenyl)amino)-N-(m-tolyl)picolinamide

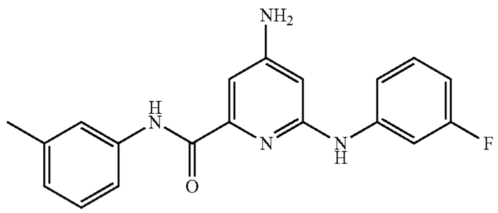 [SMILES: Cc1cccc(NC(=O)c2cc(N)cc(Nc3cccc(F)c3)n2)c1]

Synthesized following General Procedure L, Method 1.
Yield: (0.064 g, 56%).
ES-MS [M+H]+−: 337.1, Rt=20.314 min (Method-B1).

Example 122

4-Amino-N-(3,4-dimethylphenyl)-6-((3-fluorophenyl)amino)picolinamide

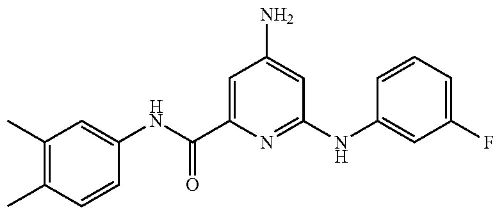 [SMILES: Cc1ccc(NC(=O)c2cc(N)cc(Nc3cccc(F)c3)n2)cc1C]

Synthesized following General Procedure L, Method 1. Yield: (0.085 g, 50%).

ES-MS [M+H]+–: 351.1, Rt=20.873 min (Method-B1).

Example 123

6-Amino-4-(benzo[d][1,3]dioxol-4-ylamino)-N-(2,3-dihydro-1H-inden-2-yl)picolinamide

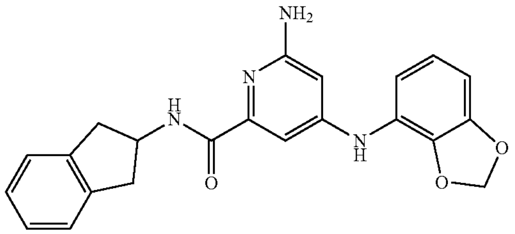 [SMILES: Nc1cc(Nc2cccc3c2OCO3)cc(C(=O)NC2Cc3ccccc3C2)n1]

Synthesized following General Procedure L, Method 1. Yield: (0.179 g, 89%).

ES-MS $[M-H]^-$: 389.2, Rt=18.082 min (Method-B1).

$^1$H NMR (400 MHz, DMSO-$d_6$) δ 8.46 (s, 1H), 8.23 (d, J=7.9 Hz, 1H), 7.25 (dd, J=5.4, 3.3 Hz, 2H), 7.20-7.08 (m, 2H), 6.92-6.77 (m, 2H), 6.72 (td, J=7.8, 1.2 Hz, 2H), 6.01 (s, 2H), 5.90 (d, J=2.0 Hz, 1H), 5.74 (s, 2H), 4.64 (qt, J=7.5, 5.6 Hz, 1H), 3.23 (dd, J=16.0, 7.3 Hz, 2H), 2.88 (dd, J=16.0, 5.6 Hz, 2H).

Example 124

6-Amino-N-(2,3-dihydro-1H-inden-2-yl)-4-((3-methoxyphenyl)amino)picolinamide

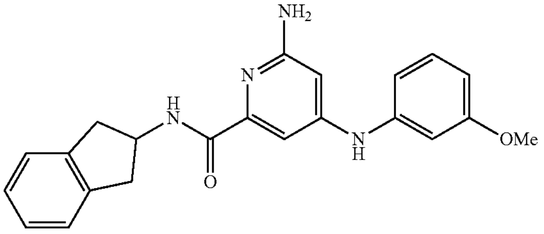 [SMILES: COc1cccc(Nc2cc(N)nc(C(=O)NC3Cc4ccccc4C3)c2)c1]

Synthesized following General Procedure L, Method 1. Yield: (0.065 g, 63%).

ES-MS $[M+H]^+$: 375.2, Rt=6.396 min (Method-A1).

General Procedure M

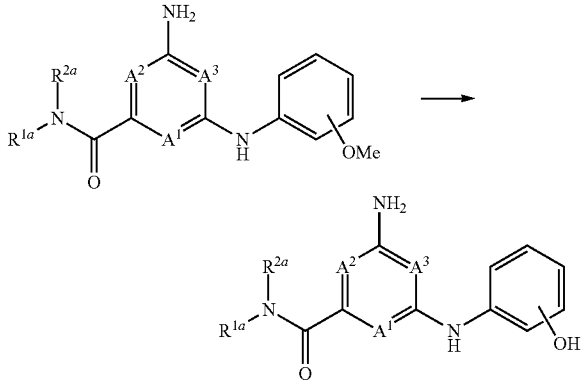

To a stirred solution of the appropriate methoxy compound (ex: (4-amino-6-((2-methoxyphenyl)amino)pyrimidin-2-yl)(4-phenylpiperazin-1-yl)methanone) (1.0 eq) in DCM (20 mL/mmol) at 0° C. (ice-bath) was added $BBr_3$ (1.0 M solution in DCM, from 2.0 to 5.0 eq). The resulting solution was stirred at room temperature for 24 h. The reaction mixture was then diluted with water and extracted with EtOAc/MeOH ((×3), dried over anhydrous sodium sulphate, filtered, and concentrated to dryness. The resultant crude was purified by flash column chromatography (DCM:MeOH from 100:0 to 90:10 or Hexane:EtOAc, from 80:20 to 70:30) to obtain the desired alcohol compound (ex: (4-amino-6-((2-hydroxyphenyl)amino)pyrimidin-2-yl)(4-phenylpiperazin-1-yl)methanone).

Example 125

(4-Amino-6-((2-hydroxyphenyl)amino)pyrimidin-2-yl)(4-phenylpiperazin-1-yl)methanone

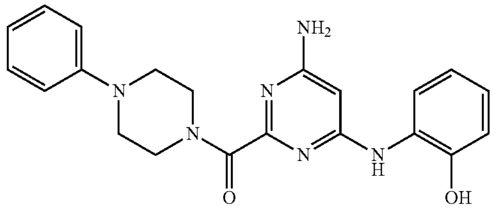 [SMILES: Nc1cc(Nc2ccccc2O)nc(C(=O)N2CCN(c3ccccc3)CC2)n1]

Synthesized following General Procedure M. Isolated as a yellow solid. This product was purified by HPLC-semipreparative (Method-E1).

Yield: (0.005 g, 5%).

ES-MS $[M+H]^+$: 391.3, Rt=15.507 min (Method-B1).

$^1$H NMR (400 MHz, $CDCl_3$-$d_6$) δ 7.67 (s, 1H), 7.23 (d, J=7.9 Hz, 2H), 7.14 (d, J=7.8 Hz, 1H), 7.06-6.96 (m, 3H), 6.91-6.81 (m, 4H), 6.79 (d, J=7.7 Hz, 1H), 5.71 (brs, 2H), 3.77 (s, 2H), 3.64 (s, 2H), 3.14 (s, 2H), 3.06 (s, 2H).

Example 126

4-Amino-6-((2-hydroxyphenyl)amino)-N-(1,2,3,4-tetrahydronaphthalen-2-yl)-1,3,5-triazine-2-carboxamide

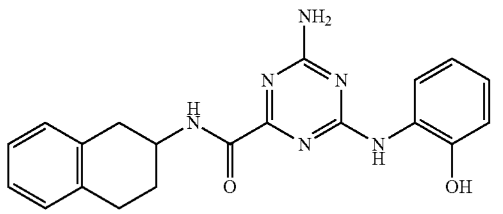

Synthesized following General Procedure M. Isolated as a beige solid. This product was purified by HPLC-semi-preparative (Method-E1) as a beige solid.

Yield: (0.014 g, 7%).

ES-MS $[M-H]^-$: 375.2, Rt=17.628 min (Method-B1).

$^1$H NMR (400 MHz, DMSO-$d_6$) δ 9.95 (brs, 1H), 8.48 (s, 1H), 8.41 (d, J=7.8 Hz, 1H), 7.86 (d, J=7.8 Hz, 1H), 7.43 (d, J=20.8 Hz, 2H), 7.19-7.03 (m, 4H), 6.94 (td, J=7.6, 1.6 Hz, 1H), 6.87 (dd, J=8.0, 1.6 Hz, 1H), 6.78 (td, J=7.6, 1.6 Hz, 1H), 4.12 (ddd, J=10.6, 5.3, 2.4 Hz, 1H), 3.00 (dd, J=15.9, 5.0 Hz, 1H), 2.92-2.71 (m, 3H), 2.07-1.90 (m, 1H), 1.91-1.67 (m, 1H).

Example 127

6-Amino-4-((2-hydroxyphenyl)amino)-N-(1,2,3,4-tetrahydronaphthalen-2-yl)picolinamide

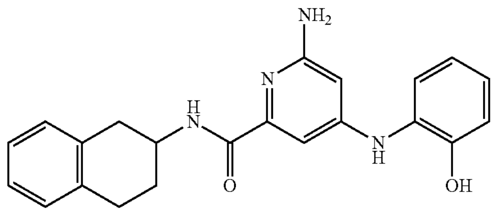 [SMILES: Nc1cc(Nc2ccccc2O)cc(C(=O)NC2CCc3ccccc3C2)n1]

Synthesized following General Procedure M.

Yield: (0.011 g, 18%).

ES-MS [M+H]+: 375.2, Rt=18.793 min (Method-B1).

$^1$H NMR (400 MHz, DMSO-$d_6$) δ 9.77 (s, 1H), 8.03 (d, J=8.0 Hz, 1H), 7.64 (s, 1H), 7.44 (d, J=8.0 Hz, 1H), 7.21-7.03 (m, 4H), 6.88-6.71 (m, 3H), 6.71-6.60 (m, 1H), 6.20-6.00 (m, 3H), 4.17 (s, 1H), 3.05 (d, J=16.0 Hz, 1H), 2.92-2.66 (m, 3H), 2.07-1.94 (s, 1H), 1.88-1.73 (m, 1H).

Example 128

6-Amino-4-((2-hydroxyphenyl)amino)-N-methyl-N-phenylpicolinamide

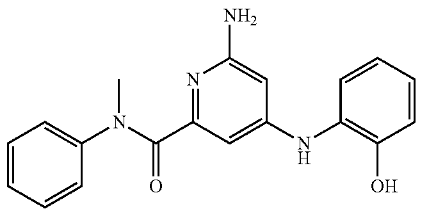 [SMILES: CN(C(=O)c1cc(Nc2ccccc2O)cc(N)n1)c1ccccc1]

Synthesized following General Procedure M. Isolated as a beige solid.

Yield: (0.018 g, 27%).

ES-MS $[M+H]^+$: 335.2, Rt=18.202 min (Method-B1).

$^1$H NMR (400 MHz, DMSO-$d_6$) δ 10.30 (s, 1H), 10.11 (s, 1H), 8.35-8.23 (m, 1H), 7.55-7.39 (m, 2H), 7.37-7.20 (m, 3H), 6.97-6.84 (m, 2H), 6.84-6.68 (m, 2H), 5.99-5.78 (m, 3H), 3.27 (s, 3H).

Example 129

4-Amino-N-(2,3-dihydro-1H-inden-2-yl)-6-((2-hydroxyphenyl)amino)picolinamide

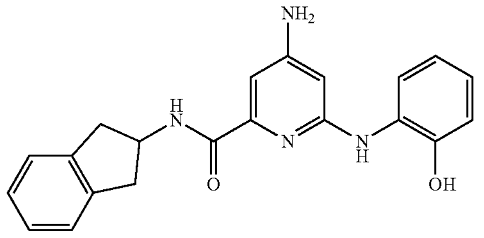

Synthesized following General Procedure M. Isolated as a white powder. Purified by flash column chromatography (DCM:MeOH from 100:0 to 90:10) followed by HPLC-semipreparative (Method-E1).

Yield: (0.012 g, 55%).

ES-MS $[M+H]^+$: 361.1, Rt=18.106 min (Method-B1).

$^1$H NMR (400 MHz, DMSO-$d_6$) δ 9.77 (brs, 1H), 8.18 (d, J=7.8 Hz, 1H), 7.60 (s, 1H), 7.39 (dd, J=7.6, 1.3 Hz, 1H), 7.25 (dt, J=7.3, 3.6 Hz, 2H), 7.20-7.14 (m, 2H), 6.84-6.76 (m, 2H), 6.73 (d, J=1.8 Hz, 1H), 6.63 (ddd, J=7.9, 6.2, 2.6 Hz, 1H), 6.08 (s, 1H), 6.06 (d, J=1.9 Hz, 1H), 4.64 (qt, J=7.4, 5.4 Hz, 1H), 3.29-3.17 (m, 2H), 2.86 (dd, J=15.9, 5.4 Hz, 2H).

Example 130

(2-Amino-6-((2-hydroxyphenyl)amino)pyrimidin-4-yl)(4-phenylpiperazin-1-yl)methanone

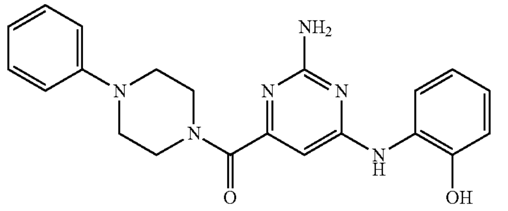

Synthesized following General Procedure M. Isolated as a white solid.

Yield: (0.002 g, 6%).

ES-MS $[M-H]^-$: 389.3, Rt=16.586 min (Method-B1).

$^1$H NMR (400 MHz, MeOD) δ 7.58 (dd, J=8.0, 1.6 Hz, 1H), 7.34-7.20 (m, 2H), 7.08-6.97 (m, 3H), 6.95-6.80 (m, 3H), 6.18 (s, 1H), 3.85 (t, J=5.3 Hz, 2H), 3.66 (t, J=5.2 Hz, 2H), 3.21 (dt, J=22.5, 5.3 Hz, 4H).

General Procedure N

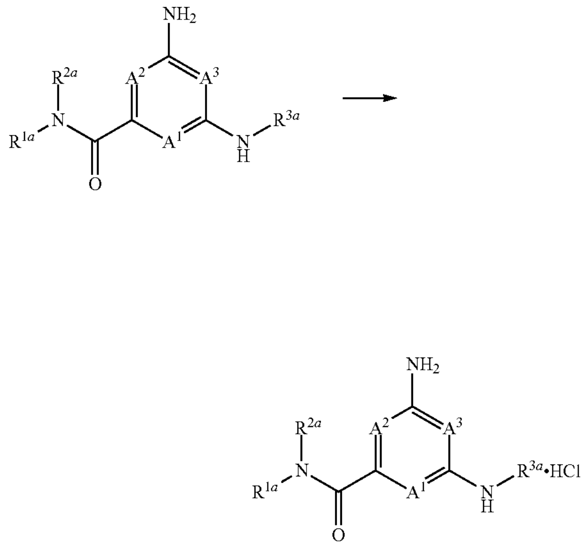

To a stirred solution of the corresponding 4,6-diaminopicolinamide in the minimal amount of dioxane was added HCl (1.1 eq. of a 4N solution in dioxane). The resulting mixture was stirred at rt for 16 h. Then $Et_2O$ (25 mL) was added and the suspension was cooled using an ice-bath. The resulting suspension was filtered and washed with $Et_2O$ to obtain the desired product.

Example 131

4-Amino-N-(2,3-dihydro-1H-inden-2-yl)-6-((2-hydroxyphenyl)amino)-N-methyl-picolinamide hydrochloride

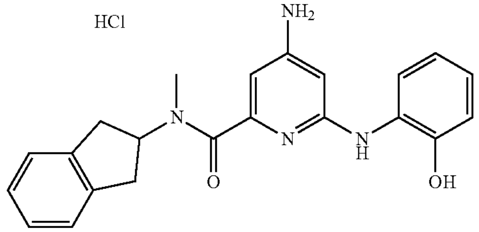 [SMILES: CN(C(=O)c1cc(N)cc(Nc2ccccc2O)n1)C1Cc2ccccc2C1 ; Cl]

Synthesized following General Procedure N.

Yield: (0.046 g, 74%).

ES-MS $[M-H]^-$: 375.2, Rt=17.953 min (Method-B1).

$^1$H NMR (400 MHz, DMSO-$d_6$) δ 12.48 (brs, 1H), 10.13 (brs, 1H), 8.74 (brs, 1H), 7.46 (brs, 2H), 7.27-7.19 (m, 2H), 7.20-7.07 (m, 2H), 6.99 (d, J=8.0 Hz, 1H), 6.85 (t, J=7.5 Hz, 1H), 6.34 (s, 1H), 5.93-5.82 (m, 1H), 5.29, 5.30-4.50 (m, 1H), 3.21-3.01 (m, 4H), 2.83 (s, 3H). Mixture of conformers.

Example 132

4-Amino-N-(2,3-dihydro-1H-inden-2-yl)-6-((2-fluorophenyl)amino)-N-methylpicolinamide hydrochloride

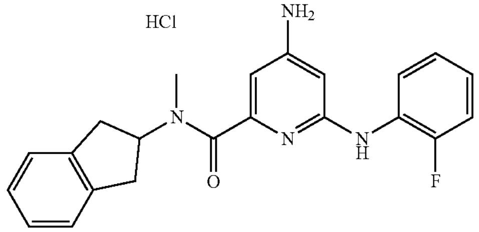 [SMILES: CN(C(=O)c1cc(N)cc(Nc2ccccc2F)n1)C1Cc2ccccc2C1 ; Cl]

Synthesized following General Procedure N.

Yield: (0.100 g, 87%).

ES-MS $[M-H]^-$: 377.2, Rt=5.088 min (Method-F1).

$^1$H NMR (400 MHz, DMSO-$d_6$) δ 9.38 (brs, 1H), 7.68 (brs, 2H), 7.53-7.44 (m, 1H), 7.39 (qd, J=8.3, 4.0 Hz, 2H), 7.29 (td, J=7.4, 1.8 Hz, 1H), 7.24 (s, 2H), 7.17 (dd, J=5.6, 3.2 Hz, 2H), 6.43 (s, 1H), 5.90 (dd, J=2.0, 1.1 Hz, 1H), 5.37-4.60 (m, 1H), 3.54-3.32 (m, 2H), 3.20-3.00 (m, 2H), 2.83 (s, 3H). Conformers present.

Example 133

4-amino-N-(2,3-dihydro-1H-inden-2-yl)-6-((2-methoxyphenyl)amino)picolinamide hydrochloride

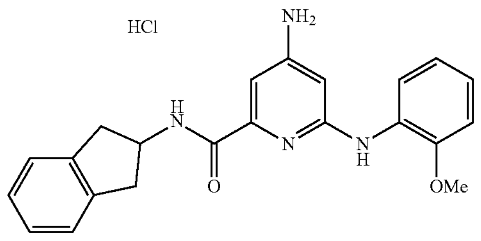 [SMILES: COc1ccccc1Nc1cc(N)cc(C(=O)NC2Cc3ccccc3C2)n1 ; Cl]

Synthesized following General Procedure N.

Yield: (0.0055 g, 48%).

ES-MS [M−H]$^-$: 375.2, Rt=19.567 min (Method-B1).

$^1$H NMR (400 MHz, DMSO-$d_6$) δ 12.01 (s, 1H), 9.46 (s, 1H), 8.94 (s, 1H), 7.62 (s, 1H), 7.48-7.23 (m, 4H), 7.18 (td, J=6.0, 5.6, 2.6 Hz, 3H), 7.04 (t, J=7.7 Hz, 1H), 6.86 (d, J=2.0 Hz, 1H), 5.99 (d, J=2.0 Hz, 1H), 4.69 (h, J=6.8 Hz, 1H), 3.84 (s, 3H), 3.29 (dd, J=16.1, 7.7 Hz, 2H), 2.98 (dd, J=16.1, 6.0 Hz, 2H).

Example 134

4-Amino-6-((3-fluorophenyl)amino)-N-phenylpicolinamide hydrochloride

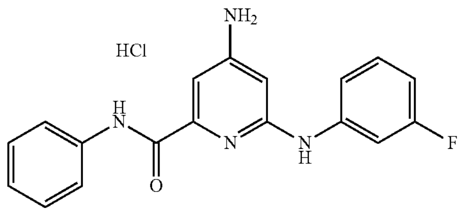 [SMILES: Nc1cc(Nc2cccc(F)c2)nc(C(=O)Nc2ccccc2)c1 ; Cl]

Synthesized following General Procedure N.

Yield: (0.027 g, 25%).

ES-MS [M−H]$^-$: 323.2, Rt=19.501 min (Method-B1).

$^1$H NMR (400 MHz, DMSO-$d_6$) δ 10.79 (brs, 1H), 9.59 (brs, 1H), 7.76 (d, J=8.0 Hz, 2H), 7.43 (dt, J=15.9, 7.7 Hz, 3H), 7.37-7.25 (m, 1H), 7.18 (td, J=5.3, 2.5 Hz, 2H), 7.03 (d, J=21.1 Hz, 2H), 6.39-6.21 (m, 1H).

Example 135

4-Amino-6-((3-methoxyphenyl)amino)-N-phenylpicolinamide hydrochloride

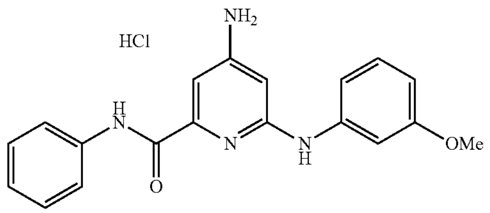 [SMILES: COc1cccc(Nc2cc(N)cc(C(=O)Nc3ccccc3)n2)c1 ; Cl]

Synthesized following General Procedure N.

Yield: (0.017 g, 68%).

ES-MS [M−H]$^-$: 335.2, Rt=19.000 min (Method-B1).

$^1$H NMR (400 MHz, DMSO-$d_6$) δ 10.96 (brs, 1H), 9.51 (brs, 1H), 7.76 (d, J=8.0 Hz, 2H), 7.39 (dt, J=19.6, 8.0 Hz, 3H), 7.18 (t, J=7.4 Hz, 1H), 7.06 (s, 1H), 7.00-6.86 (m, 2H), 6.84-6.67 (m, 1H), 6.26 (d, J=1.9 Hz, 1H), 3.79 (s, 3H).

Example 136

4-Amino-6-((3-fluorophenyl)amino)-N-(m-tolyl)picolinamide hydrochloride

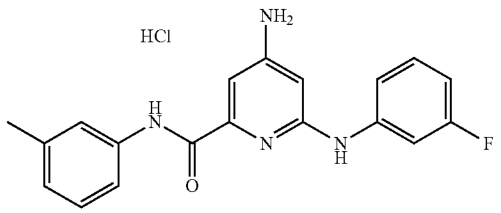 [SMILES: Cc1cccc(NC(=O)c2cc(N)cc(Nc3cccc(F)c3)n2)c1 ; Cl]

Synthesized following General Procedure N.

Yield: (0.057 g, 81%).

ES-MS [M−H]$^-$: 337.1, Rt=20.325 min (Method-B1).

$^1$H NMR (400 MHz, DMSO-$d_6$) δ 10.67 (brs, 1H), 9.61 (brs, 1H), 7.69-7.50 (m, 2H), 7.51-7.38 (m, 1H), 7.30 (q, J=11.6, 7.8 Hz, 2H), 7.17 (dd, J=8.1, 2.0 Hz, 1H), 7.09-6.92 (m, 3H), 6.28 (s, 1H), 2.33 (s, 3H).

Example 137

6-(3-Fluorophenylamino)-4-amino-N-(3,4-dimethylphenyl)pyridine-2-carboxamide hydrochloride

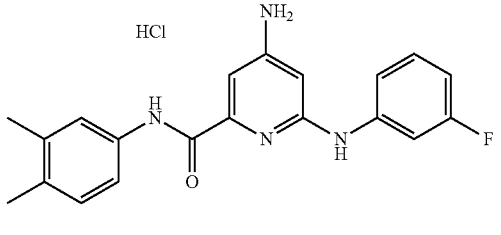 [SMILES: Cc1ccc(NC(=O)c2cc(N)cc(Nc3cccc(F)c3)n2)cc1C ; Cl]

Synthesized following General Procedure N.

Yield: (0.018 g, 19%).

ES-MS [M−H]$^-$: 351.1, Rt=20.868 min (Method-B1).

$^1$H NMR (400 MHz, DMSO-$d_6$) δ 10.61 (brs, 1H), 9.51 (brs, 1H), 7.73-7.39 (m, 4H), 7.34 (s, 1H), 7.27-7.13 (m, 2H), 7.03 (s, 2H), 6.26 (brs, 2H), 2.23 (s, 3H), 2.21 (s, 3H).

Example 138

4-Amino-N-(2,3-dihydro-1H-inden-2-yl)-6-((3-fluorophenyl)amino)picolinamide hydrochloride

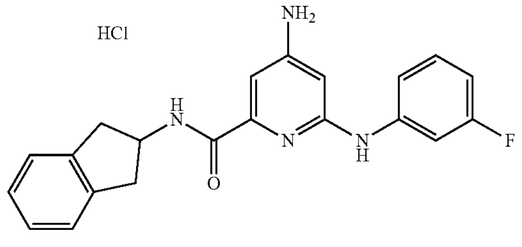 [SMILES: Nc1cc(Nc2cccc(F)c2)nc(C(=O)NC2Cc3ccccc3C2)c1 ; Cl]

Synthesized following General Procedure N.

Yield: (13.216 g, 92%).

ES-MS $[M-H]^-$: 363.1, Rt=19.640 min (Method-B1).

$^1$H NMR (400 MHz, DMSO-$d_6$) δ 12.04 (s, 1H), 9.67 (s, 1H), 9.40 (s, 1H), 7.68 (s, 2H), 7.46 (d, J=7.6 Hz, 1H), 7.34-7.06 (m, 6H), 7.04 (s, 1H), 6.92 (d, J=2.0 Hz, 1H), 6.27 (s, 1H), 4.69 (q, J=6.9 Hz, 1H), 3.28 (dd, J=16.1, 7.6 Hz, 2H), 2.98 (dd, J=16.0, 6.0 Hz, 2H).

Example 139

4-Amino-N-(2,3-dihydro-1H-inden-2-yl)-6-((2-fluorophenyl)amino)picolinamide hydrochloride

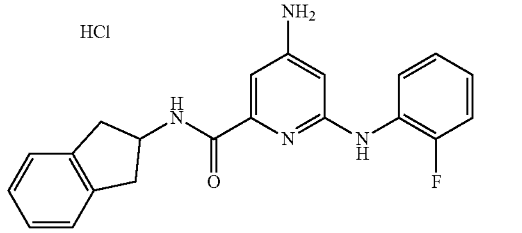 [SMILES: Nc1cc(Nc2ccccc2F)nc(C(=O)NC2Cc3ccccc3C2)c1 ; Cl]

Synthesized following General Procedure N.

Yield: (1.11 g, 94%).

ES-MS $[M-H]^-$: 363.1, Rt=19.356 min (Method-B1).

$^1$H NMR (400 MHz, DMSO-$d_6$) δ 12.17 (s, 1H), 9.36 (s, 2H), 7.71 (s, 2H), 7.50 (td, J=8.0, 1.8 Hz, 1H), 7.26 (dd, J=5.4, 3.3 Hz, 2H), 7.17 (dd, J=5.5, 3.2 Hz, 2H), 6.90 (d, J=1.9 Hz, 1H), 5.95 (s, 1H), 4.69 (h, J=6.8 Hz, 1H), 3.28 (dd, J=16.1, 7.7 Hz, 2H), 2.98 (dd, J=16.0, 6.0 Hz, 2H).

Example 140

4-Amino-6-((3,5-difluorophenyl)amino)-N-(2,3-dihydro-1H-inden-2-yl)picolinamide hydrochloride

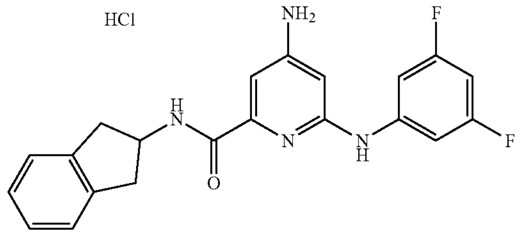 [SMILES: Nc1cc(Nc2cc(F)cc(F)c2)nc(C(=O)NC2Cc3ccccc3C2)c1 ; Cl]

Synthesized following General Procedure N.

Yield: (0.013 g, 42%).

ES-MS $[M-H]^-$: 381.1, Rt=20.290 min (Method-B1).

$^1$H NMR (400 MHz, DMSO-$d_6$) δ 9.57 (brs, 1H), 7.25 (dd, J=5.4, 3.3 Hz, 2H), 7.20-7.14 (m, 2H), 7.10 (d, J=8.7 Hz, 2H), 6.92 (t, J=2.6 Hz, 2H), 6.30 (s, 1H), 4.73-4.63 (m, 1H), 3.28 (dd, J=16.0, 7.6 Hz, 2H), 2.95 (dd, J=16.3, 5.5 Hz, 2H).

Example 141

6-Amino-N-(2,3-dihydro-1H-inden-2-yl)-4-((3-methoxyphenyl)amino)picolinamide hydrochloride

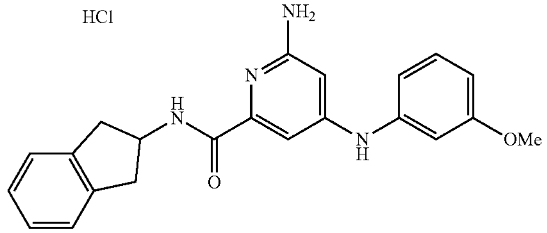 [SMILES: COc1cccc(Nc2cc(N)nc(C(=O)NC3Cc4ccccc4C3)c2)c1 ; Cl]

Synthesized following General Procedure N.

Yield: (0.043 g, 69%).

ES-MS $[M-H]^-$: 375.2, Rt=18.223 min (Method-B1).

$^1$H NMR (400 MHz, DMSO-$d_6$) δ 12.07 (s, 1H), 9.69 (s, 1H), 9.44 (s, 1H), 7.32 (brs, 1H), 7.25 (dd, J=5.4, 3.3 Hz, 2H), 7.22-7.13 (m, 4H), 7.07-6.98 (m, 2H), 6.93 (d, J=2.1 Hz, 1H), 6.06 (d, J=2.0 Hz, 1H), 4.68 (ddt, J=14.2, 7.7, 6.3 Hz, 1H), 3.77 (s, 3H), 3.27 (dd, J=16.1, 7.8 Hz, 2H), 2.97 (dd, J=16.0, 6.2 Hz, 2H).

Biological Assays

Compounds of the Disclosure are capable of binding allosterically to $-glucocerebrosidase enzyme (either mutated or not) thereby stabilizing the enzyme against denaturation and enhancing its catalytic activity.

Enhancement of β-Glucocerebrosidase Activity Measured in Gaucher Disease Fibroblasts Materials Human fibroblasts from a patient with Gaucher disease homozygous for p.L444P mutation (GM08760A) were purchased from Coriell Institute for Medical Research (Camden, NJ, USA).

Cell Culture and Compound Treatment

Fibroblasts were seeded at $5\times10^3$ cells per well in 96-well cell culture plates (Corning, NY, USA) in Dulbecco's Modified Eagle's Media (DMEM) supplemented with 10% of fetal bovine serum (FBS), 1% penicillin/streptomycin (P/S) (Thermo Fisher Scientific, Waltham, MA, USA) and grown at 37° C., 5% $CO_2$ overnight for cell attachment. Subsequently, cells were incubated in the absence or presence of the compounds at the desired concentration for 4 days. After incubation, cells were washed twice with phosphate-buffered saline (PBS) and enzyme activity assay was performed.

Enzyme Activity Assay

β-glucocerebrosidase activity in intact cultured cells was measured by using 4-methylumbelliferyl-β-D-glucopyranoside substrate (Apollo Scientific, UK). Briefly, cells were incubated with 4-MU-β-D-glucopyranoside in 0.1 M acetate buffer pH=4 at 37° C. for 1 hour. The reaction was stopped by adding 200 μL at 100 mM glycine-NaOH pH=10.7. The liberated 4-MU was measured on a GloMax Discover plate reader (Promega, Madison, WI, USA) with and excitation at 340 nm and emission at 460 nm. Enzyme activities were expressed in treated cells as X-fold increase in comparison with non-treated cells (X=1 represents no enhancement).

The capacity of the compounds of the disclosure to produce an increase in enzyme activity in GBA fibroblasts bearing L444P at concentrations between 6 and 50 μM is denoted as follows:

Increase in comparison with non-treated of >2.0 fold is shown as A

Increase in comparison with non-treated of >1.7-2.0 fold is shown as B

Increase in comparison with non-treated of 1.2-1.7 fold is shown as C

D means that no increase compared with non-treated cells was detected in this method ND means "not determined"

TABLE 1

Enzyme activity assay for exemplified compounds

| Example # | Range |
|---|---|
| Example 1 | C |
| Example 2 | C |
| Example 3 | C |
| Example 4 | C |
| Example 5 | C |
| Example 6 | D |
| Example 7 | D |
| Example 8 | C |
| Example 9 | C |
| Example 10 | C |
| Example 11 | B |
| Example 12 | B |
| Example 13 | C |
| Example 14 | D |
| Example 15 | D |
| Example 16 | C |
| Example 17 | D |
| Example 18 | D |
| Example 19 | C |
| Example 20 | C |
| Example 21 | C |
| Example 22 | A |
| Example 23 | C |
| Example 27 | A |
| Example 28 | C |
| Example 29 | B |
| Example 30 | C |
| Example 31 | B |
| Example 24 | C |
| Example 25 | B |
| Example 26 | C |
| Example 32 | B |

TABLE 2

Enzyme activity assay for compounds of Examples 33-141

| Example # | Range |
|---|---|
| Example 33 | D |
| Example 34 | D |
| Example 35 | C |
| Example 36 | C |
| Example 37 | D |
| Example 38 | D |
| Example 39 | C |
| Example 40 | C |
| Example 41 | D |
| Example 42 | C |
| Example 43 | C |
| Example 44 | C |
| Example 45 | C |
| Example 46 | B |
| Example 47 | C |
| Example 48 | C |
| Example 49 | B |
| Example 50 | D |
| Example 51 | C |
| Example 52 | B |
| Example 53 | C |
| Example 54 | C |
| Example 55 | ND |
| Example 56 | B |
| Example 57 | B |
| Example 58 | B |
| Example 59 | C |
| Example 60 | C |
| Example 61 | C |
| Example 62 | D |
| Example 63 | ND |
| Example 64 | C |
| Example 65 | A |
| Example 66 | B |
| Example 67 | B |
| Example 68 | C |
| Example 69 | B |
| Example 70 | D |
| Example 71 | B |
| Example 72 | D |
| Example 73 | C |
| Example 74 | C |
| Example 75 | C |
| Example 76 | D |
| Example 77 | C |
| Example 78 | B |
| Example 79 | C |
| Example 80 | C |
| Example 81 | B |
| Example 82 | C |
| Example 83 | D |
| Example 84 | C |
| Example 85 | C |
| Example 86 | C |
| Example 87 | B |
| Example 88 | C |
| Example 89 | C |
| Example 90 | C |
| Example 91 | B |
| Example 92 | A |
| Example 93 | B |
| Example 94 | B |
| Example 95 | C |
| Example 96 | C |
| Example 97 | A |
| Example 98 | B |
| Example 99 | D |
| Example 100 | A |
| Example 101 | B |
| Example 102 | C |
| Example 103 | C |
| Example 104 | C |
| Example 105 | B |
| Example 106 | C |
| Example 107 | C |
| Example 108 | B |
| Example 109 | A |
| Example 110 | C |
| Example 111 | A |
| Example 112 | A |
| Example 113 | C |
| Example 114 | D |
| Example 115 | C |
| Example 116 | C |
| Example 117 | ND |
| Example 118 | ND |
| Example 119 | ND |
| Example 120 | ND |
| Example 121 | ND |

TABLE 2-continued

| Enzyme activity assay for compounds of Examples 33-141 | |
|---|---|
| Example # | Range |
| Example 122 | ND |
| Example 123 | C |
| Example 124 | ND |
| Example 125 | C |
| Example 126 | C |
| Example 127 | B |
| Example 128 | C |
| Example 129 | C |
| Example 130 | C |
| Example 131 | C |
| Example 132 | C |
| Example 133 | C |
| Example 134 | A |
| Example 135 | A |
| Example 136 | A |
| Example 137 | ND |
| Example 138 | A |
| Example 139 | C |
| Example 140 | A |
| Example 141 | C |

All publications cited in this specification are incorporated herein by reference. While the disclosure has been described with reference to particular embodiments, it will be appreciated that modifications can be made without departing from the spirit of the disclosure. Such modifications are intended to fall within the scope of the appended claims.

The disclosure also relates to the following particular embodiments designated as [1] for the first embodiment, [2] for the second embodiment, and so on:

[1] A compound of formula (IA):

(IA)

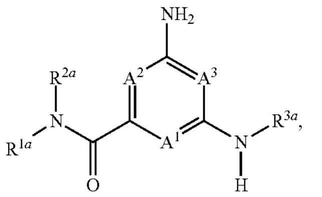

or a pharmaceutically acceptable salt or solvate thereof, wherein $A^1$, $A^2$, and $A^3$ are each independently selected from the group consisting of N, CH and $C(R^{4a})$, provided that at least one of $A^1$, $A^2$, or $A^3$ is N;

each $R^{4a}$ is independently selected from the group consisting of halogen, —$C_{1-4}$ alkyl, —$C_{1-4}$ alkoxy, and —CN;

$R^{1a}$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(═O)$Ra^a$, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, -(5- to 10-membered)-$C_{2-9}$ heterocyclyl, and optionally substituted —O—($C_{6-10}$ aryl); and wherein said cycloalkyl, alkylcycloalkyl, aryl, alkylaryl, heteroaryl, alkylheteroaryl, heterocyclyl and alkylheterocyclyl is optionally fused to a further (second) ring; and $R^{2a}$ is selected from the group consisting of hydrogen, —$C_{1-4}$ alkyl, and $C_{3-6}$ cycloalkyl, wherein said —$C_{1-4}$ alkyl is optionally substituted; or $R^{1a}$ and $R^{2a}$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

$Ra^a$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each $Rb^a$ is independently hydrogen, —$C_{1-4}$ alkyl, —$C_{3-10}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms; and $R^{3a}$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —$ORb^a$, —$SRb^a$, —$N(Rb^a)_2$, —$C_{1-4}$alkyl optionally substituted with 1, 2, or 3 substituents each independently selected from the group consisting of halogen, —CN, —$ORb^a$, and —$N(Rb^a)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[2] The compound of [1], or a pharmaceutically acceptable salt or solvate thereof, wherein $A^1$ is N and $A^2$ and $A^3$ are each independently selected from the group consisting of CH and $C(R^{4a})$.

[3] The compound of [1], or a pharmaceutically acceptable salt or solvate thereof, wherein $A^2$ is N and $A^1$ and $A^3$ are each independently selected from the group consisting of CH and $C(R^{4a})$.

[4] The compound of [1], or a pharmaceutically acceptable salt or solvate thereof, wherein $A^3$ is N and $A^1$ and $A^2$ are each independently selected from the group consisting of CH and $C(R^{4a})$.

[5] The compound of [1], or a pharmaceutically acceptable salt or solvate thereof, wherein $A^1$ and $A^2$ are both N and $A^3$ is CH or $C(R^{4a})$.

[6] The compound of [1], or a pharmaceutically acceptable salt or solvate thereof, wherein $A^1$ and $A^3$ are both N and $A^2$ is CH or $C(R^{4a})$.

[7] The compound of [1], or a pharmaceutically acceptable salt or solvate thereof, wherein $A^2$ and $A^3$ are both N and $A^1$ is CH or $C(R^{4a})$.

[8] The compound of [1], or a pharmaceutically acceptable salt or solvate thereof, wherein $A^1$, $A^2$, and $A^3$ are N.

[9] The compound of any one of [1] to [8], or a pharmaceutically acceptable salt or solvate thereof, wherein $R^3$ is unsubstituted —$C_{6-10}$ aryl or —$C_{6-10}$ aryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, —CN, —$O(C_{1-4})$alkyl, —$N(C_{1-4}$ alkyl$)_2$, and —$NH(C_{1-4}$ alkyl).

[10] The compound of any one of [1] to [8], or a pharmaceutically acceptable salt or solvate thereof, wherein $R^3$ is unsubstituted -(5- to 10-membered)-$C_{6-9}$ heteroaryl or -(5- to 10-membered)-$C_{6-9}$ heteroaryl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, —CN, —$O(C_{1-4})$alkyl, —$N(C_{1-4}$ alkyl$)_2$, and —$NH(C_{1-4}$ alkyl).

[11] The compound of any one of [1] to [8], or a pharmaceutically acceptable salt or solvate thereof, wherein $R^{3a}$ is unsubstituted —$C_{3-10}$ cycloalkyl or —$C_{3-10}$ cycloalkyl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, —CN, —$O(C_{1-4})$alkyl, —$N(C_{1-4}$ alkyl$)_2$, and —$NH(C_{1-4}$ alkyl).

[12] The compound of any one of [1] to [8], or a pharmaceutically acceptable salt or solvate thereof, wherein $R^{3a}$ is -(5- to 10-membered)-$C_{2-9}$ heterocyclyl optionally substituted with 1, 2 or 3 substituents each independently selected from the group consisting of halogen, hydroxy, —CN, —$ORb^a$, —$SRb^a$, —$N(Rb^a)_2$, —$C_{1-4}$alkyl optionally substituted with 1, 2, or 3 substituents each independently selected from the group consisting of halogen, —CN, —$ORb^a$, and —$N(Rb^a)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[13] The compound of any one of [1] to [12], or a pharmaceutically acceptable salt or solvate thereof, wherein $R^{2a}$ is H.

[14] The compound of any one of [1] to [12], or a pharmaceutically acceptable salt or solvate thereof, wherein $R^{2a}$ is —$C_{1-4}$ alkyl.

[15] The compound of any one of [1] to [14], or a pharmaceutically acceptable salt or solvate thereof, wherein $R^{1a}$ is —$C_{6-10}$ aryl or —$C_{1-4}$ alkyl-$C_{6-10}$ aryl, wherein said aryl or alkylaryl is optionally substituted with 1, 2 or 3 groups each independently selected from the group consisting of halogen, hydroxy, —CN, —$ORb^a$, —$SRb^a$, —$N(Rb^a)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein $Rb^a$ is as defined in [1].

The compound of any one of [1] to [15], or a pharmaceutically acceptable salt or solvate thereof, wherein $R^{1a}$ is unsubstituted phenyl or unsubstituted benzyl.

[17] The compound of any one of [1] to [14], or a pharmaceutically acceptable salt or solvate thereof, wherein $R^{1a}$ is —$C_{3-10}$ cycloalkyl or —$C_{1-4}$ alkyl-$C_{3-10}$ cycloalkyl, wherein said cycloalkyl or alkylcycloalkyl is optionally substituted with 1, 2 or 3 substituents each independently selected from the group consisting of halogen, hydroxy, —CN, —$ORb^a$, —$SRb^a$, —$N(Rb^a)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein $Rb^a$ is as defined in claim 1; and wherein said cycloalkyl is optionally fused to a further (second) ring.

[18] The compound of any one of [1] to [14] and [17], or a pharmaceutically acceptable salt or solvate thereof, wherein $R^{1a}$ is unsubstituted —$C_{3-10}$ cycloalkyl fused to a phenyl ring.

[19] The compound of any one of [1] to [18], or a pharmaceutically acceptable salt or solvate thereof, wherein $Rb^a$ is hydrogen or —$C_{1-4}$ alkyl.

[20] The compound of any one of [1] to [12], or a pharmaceutically acceptable salt or solvate thereof, wherein $R^{1a}$ and $R^{2a}$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring.

[21] The compound of [20], or a pharmaceutically acceptable salt or solvate thereof, wherein $R^{1a}$ and $R^{2a}$ together with the nitrogen atom to which they are attached form a 5- or 6-membered ring optionally fused to a phenyl ring.

[22] The compound of [1], which is selected from the group consisting of

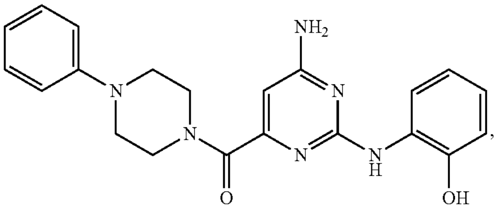
,

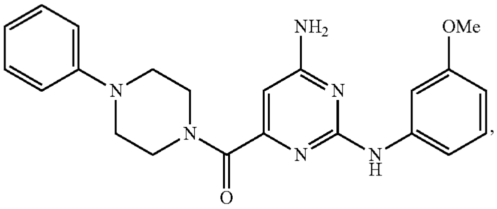
,

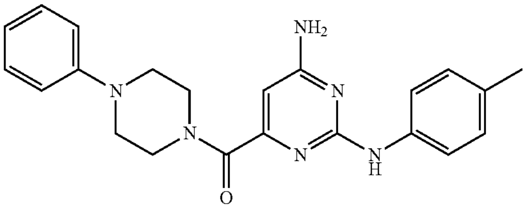
,

-continued
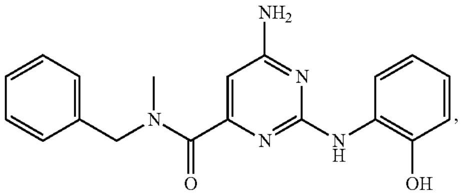,
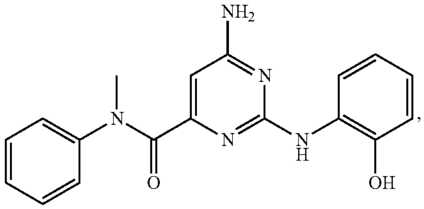,
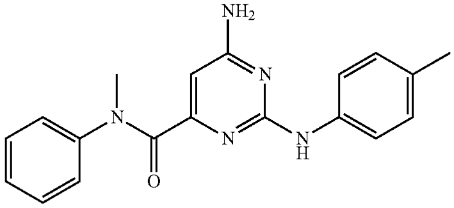,
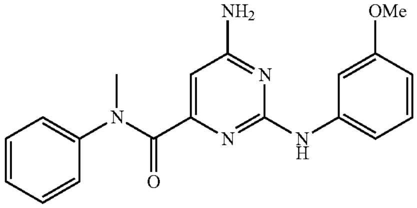,
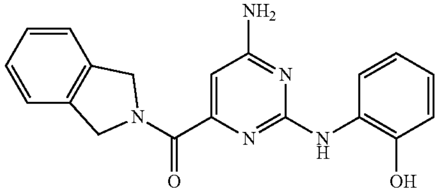,
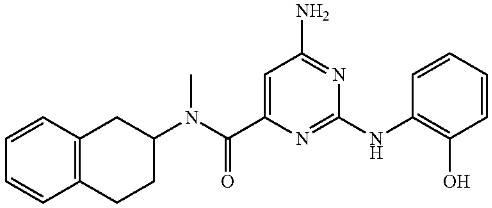,
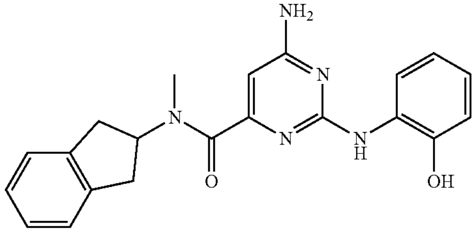,
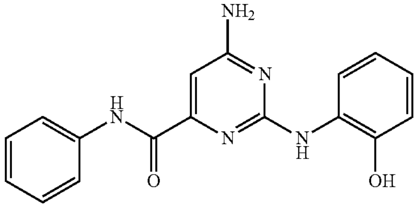,
-continued
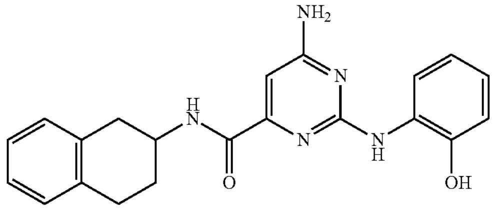,
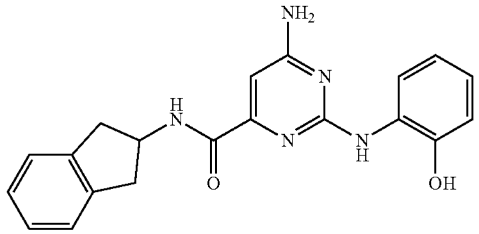,
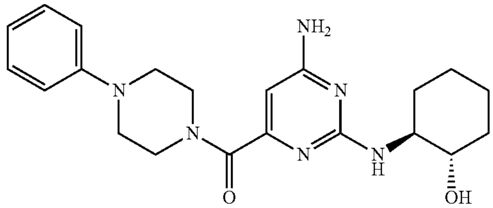,
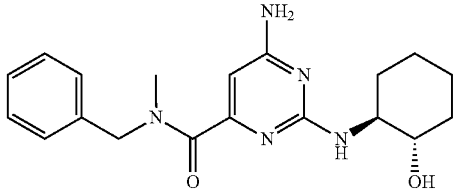,
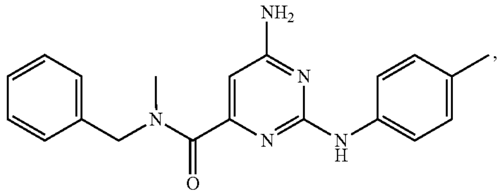,
and
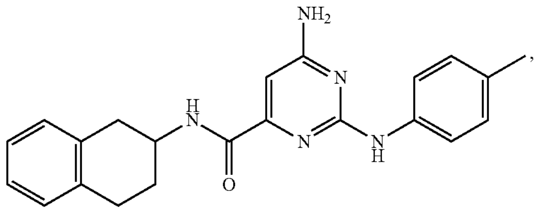,
or a pharmaceutically acceptable salt or solvate thereof.
[23] The compound of [1], which is selected from the group consisting of
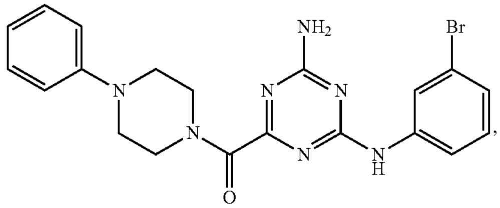, -continued

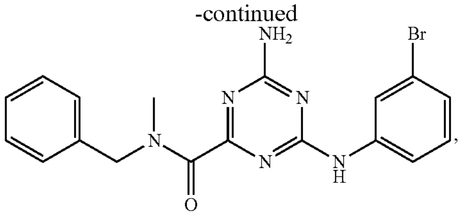

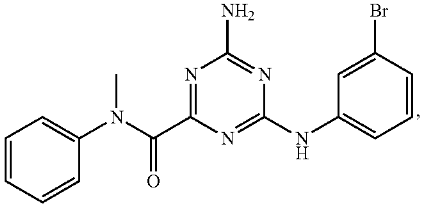

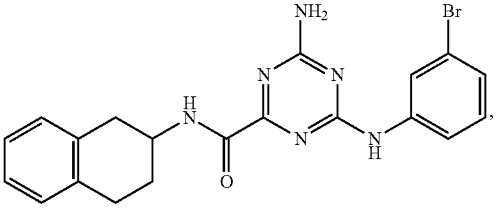

and

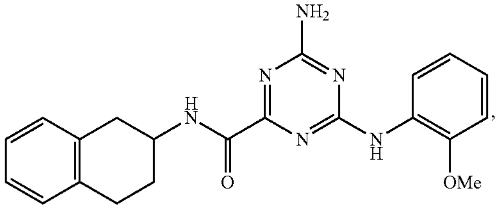

or a pharmaceutically acceptable salt or solvate thereof.

[24] A compound of formula (IB):

(IB)

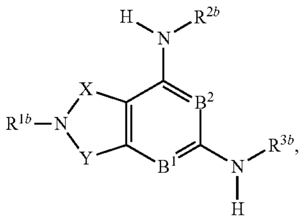

or a pharmaceutically acceptable salt or solvate thereof, wherein $B^1$ and $B^2$ are each independently selected from the group consisting of N, CH and $C(R^{4b})$, provided that at least one of $B^1$ or $B^2$ is N;

each $R^{4b}$ is independently selected from the group consisting of halogen, —$C_{1-4}$ alkyl, —$C_{1-4}$ alkoxy, and —CN;

X and Y are independently selected from the group consisting of a bond (i.e. is absent), $C_{1-4}$ alkylene, C(═O), C(═O)—$C_{1-2}$ alkylene, and $C_{1-2}$ alkylene-C(═O);

$R^{1b}$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, —$C_{1-4}$ alkyl-(5- to 10-membered)-$C_{2-9}$ heterocyclyl, and —C(═O)$Ra^b$, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^b$, —$SRb^b$, —$N(Rb^b)_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, -(5- to 10-membered)-$C_{2-9}$ heterocyclyl, and optionally substituted —O—($C_{6-10}$ aryl); and wherein said cycloalkyl, alkylcycloalkyl, aryl, alkylaryl, heteroaryl, alkylheteroaryl, heterocyclyl and alkylheterocyclyl is optionally fused to a further (second) ring; and $Ra^b$ is selected from the group consisting of —$C_{1-4}$ alkyl, —$C_{3-10}$ cycloalkyl, —$C_{1-4}$ alkyl-$C_{3-10}$ cycloalkyl, —$C_{6-10}$ aryl, —$C_{1-4}$ alkyl-$C_{6-10}$ aryl, -(5- to 10-membered)-$C_{1-9}$ heteroaryl, —$C_{1-4}$ alkyl-(5- to 10-membered)-$C_{1-9}$ heteroaryl, -(5- to 10-membered)-$C_{2-9}$ heterocyclyl, and —$C_{1-4}$ alkyl-(5- to 10-membered)-$C_{2-9}$ heterocyclyl, wherein said alkyl, cycloalkyl, alkylcycloalkyl, aryl, alkylaryl, heteroaryl, alkylheteroaryl, heterocyclyl and alkylheterocyclyl groups are optionally substituted with 1, 2 or 3 substituents each independently selected from the group consisting of halogen, hydroxy, —CN, —$ORb^b$, —$SRb^b$, —$N(Rb^b)_2$, —$C_{1-4}$alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl; and wherein said cycloalkyl, alkylcycloalkyl, aryl, alkylaryl, heteroaryl, alkylheteroaryl, heterocyclyl and alkylheterocyclyl is optionally fused to a further (second) ring;

each $Rb^b$ is independently hydrogen, —$C_{1-4}$ alkyl, —$C_{3-10}$ cycloalkyl, or -(5- to 10-membered)-$C_{2-9}$ heterocyclyl, wherein said alkyl, cycloalkyl or heterocyclyl group is optionally substituted by 1, 2 or 3 fluorine atoms; and $R^{2b}$ and $R^{3b}$ are each independently selected from the group consisting of hydrogen, —$C_{1-4}$ alkyl, —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —$ORb^b$, —$SRb^b$, —$N(Rb^b)_2$, —$C_{1-4}$alkyl optionally substituted with 1, 2, or 3 substituents each independently selected from the group consisting of halogen, —CN, —$ORb^b$, and —$N(Rb^b)_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[25] The compound of [24], or a pharmaceutically acceptable salt or solvate thereof, wherein $B^1$ and $B^2$ are N.

[26] The compound of [24], or a pharmaceutically acceptable salt or solvate thereof, wherein $B^1$ is N and $B^2$ is selected from the group consisting of CH and $C(R^{4b})$.

[27] The compound of [24], or a pharmaceutically acceptable salt or solvate thereof, wherein $B^2$ is N and $B^1$ is selected from the group consisting of CH and $C(R^{4b})$.

[28] The compound of any one of [24] to [27], or a pharmaceutically acceptable salt or solvate thereof, wherein $R^{2b}$ is hydrogen or —$C_{1-4}$ alkyl and $R^{3b}$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —ORb$^b$, —SRb$^b$, —N(Rb$^b$)$_2$, —$C_{1-4}$alkyl optionally substituted with 1, 2, or 3 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[29] The compound of any one of [24] to [27], or a pharmaceutically acceptable salt or solvate thereof, wherein $R^{3b}$ is hydrogen or —$C_{1-4}$ alkyl and $R^{2b}$ is selected from the group consisting of —$C_{6-10}$ aryl, -(5- to 10-membered)-$C_{1-9}$ heteroaryl, —$C_{3-10}$ cycloalkyl, and -(5- to 10-membered)-$C_{2-9}$ heterocyclyl, wherein said aryl, heteroaryl, cycloalkyl, and heterocyclyl groups are optionally substituted with 1, 2 or 3 substituents each independently selected from the group consisting of halogen, hydroxy, —CN, —ORb$^b$, —SRb$^b$, —N(Rb$^b$)$_2$, —$C_{1-4}$alkyl optionally substituted with 1, 2, or 3 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[30] The compound of any one of [24] to [27], or a pharmaceutically acceptable salt or solvate thereof, wherein $R^{2b}$ is hydrogen or —$C_{1-4}$ alkyl and $R^{3b}$ is unsubstituted —$C_{6-10}$ aryl or —$C_{6-10}$ aryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH ($C_{1-4}$ alkyl).

[31] The compound of any one of [24] to [27], or a pharmaceutically acceptable salt or solvate thereof, wherein $R^{3b}$ is hydrogen or —$C_{1-4}$ alkyl and $R^{2b}$ is unsubstituted —$C_{6-10}$ aryl or —$C_{6-10}$ aryl substituted with 1 or 2 substituents each independently selected from the group consisting of halogen, hydroxy, —CN, —O($C_{1-4}$)alkyl, —S($C_{1-4}$alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH ($C_{1-4}$ alkyl).

[32] The compound of any one of [24] to [27], or a pharmaceutically acceptable salt or solvate thereof, wherein $R^{2b}$ is hydrogen or —$C_{1-4}$ alkyl and $R^{3b}$ is unsubstituted -(5- to 10-membered)-$C_{6-9}$ heteroaryl or -(5- to 10-membered)-$C_{6-9}$ heteroaryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH ($C_{1-4}$ alkyl).

[33] The compound of any one of [24] to [27], or a pharmaceutically acceptable salt or solvate thereof, wherein $R^{3b}$ is hydrogen or —$C_{1-4}$ alkyl and $R^{2b}$ is unsubstituted -(5- to 10-membered)-$C_{6-9}$ heteroaryl or -(5- to 10-membered)-$C_{6-9}$ heteroaryl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH ($C_{1-4}$ alkyl).

[34] The compound of any one of [24] to [27], or a pharmaceutically acceptable salt or solvate thereof, wherein $R^{2b}$ is hydrogen or —$C_{1-4}$ alkyl and $R^{3b}$ is —$C_{3-10}$ cycloalkyl or -(5- to 10-membered)-$C_{2\_}$ heterocyclyl, wherein said cycloalkyl or heterocyclyl groups are optionally substituted with 1, 2 or 3 substituents each independently selected from the group consisting of halogen, hydroxy, —CN, —ORb$^b$, —SRb$^b$, —N(Rb$^b$)$_2$, —$C_{1-4}$alkyl optionally substituted with 1, 2, or 3 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[35] The compound of any one of [24] to [27], or a pharmaceutically acceptable salt or solvate thereof, wherein $R^{3b}$ is hydrogen or —$C_{1-4}$ alkyl and $R^{2b}$ is —$C_{3-10}$ cycloalkyl or -(5- to 10-membered)-$C_{2\_}$ heterocyclyl, wherein said cycloalkyl or heterocyclyl groups are optionally substituted with 1, 2 or 3 substituents each independently selected from the group consisting of halogen, hydroxy, —CN, —ORb$^b$, —SRb$^b$, —N(Rb$^b$)$_2$, —$C_{1-4}$alkyl optionally substituted with 1, 2, or 3 substituents each independently selected from the group consisting of halogen, —CN, —ORb$^b$, and —N(Rb$^b$)$_2$, optionally substituted —$C_{6-10}$ aryl, optionally substituted -(5- to 10-membered)-$C_{1-9}$ heteroaryl and -(5- to 10-membered)-$C_{2-9}$ heterocyclyl.

[36] The compound of any one of [24] to [28], [30], [32], or [34], or a pharmaceutically acceptable salt or solvate thereof, wherein $R^{2b}$ is hydrogen.

[37] The compound of any one of [24] to [27], [29], [31], [33], or [35], or a pharmaceutically acceptable salt or solvate thereof, wherein $R^{3b}$ is hydrogen.

[38] The compound of any one of [24] to [37], or a pharmaceutically acceptable salt or solvate thereof, wherein $R^{1b}$ is —$C_{6-10}$ aryl or —$C_{1-4}$ alkyl-$C_{6-10}$ aryl, wherein said aryl or alkylaryl is optionally substituted with 1, 2 or 3 groups each independently selected from the group consisting of halogen, hydroxy, —CN, —ORb$^b$, —SRb$^b$, —N(Rb$^b$)$_2$, —$C_{1-4}$ alkyl optionally substituted with 1, 2, or 3 halogen atoms, optionally substituted —$C_{6-10}$ aryl, optionally substituted -(5- to 10-membered)-$C_{1-9}$ heteroaryl, and -(5- to 10-membered)-$C_{2-9}$ heterocyclyl, wherein Rb$^a$ is as defined in [24].

[39] The compound of any one of [24] to [38], or a pharmaceutically acceptable salt or solvate thereof, wherein $R^{1b}$ is unsubstituted phenyl.

[40] The compound of any one of [24] to [38], or a pharmaceutically acceptable salt or solvate thereof, wherein $R^{1b}$ is unsubstituted benzyl or unsubstituted phenethyl.

[41] The compound of any one of [24] to [40], or a pharmaceutically acceptable salt or solvate thereof, wherein Rb$^b$ is hydrogen or —$C_{1-4}$ alkyl.

[42] The compound of any one of [24] to [41], or a pharmaceutically acceptable salt or solvate thereof, wherein X is absent and Y is selected from the group consisting of a bond (i.e. is absent), $C_{1-4}$ alkylene, C(═O), C(═O)—$C_{1-2}$ alkylene, and $C_{1-2}$ alkylene-C(═O).

[43] The compound of any one of [24] to [41], or a pharmaceutically acceptable salt or solvate thereof, wherein X is $C_{1-4}$ alkylene and Y is selected from the group consisting of a bond (i.e. is absent), $C_{1-4}$ alkylene, C(═O), C(═O)—$C_{1-2}$ alkylene, and $C_{1-2}$ alkylene-C(═O).

[44] The compound of any one of [24] to [41], or a pharmaceutically acceptable salt or solvate thereof, wherein X is C(═O) and Y is selected from the group consisting of a bond (i.e. is absent), $C_{1-4}$ alkylene, C(═O), C(═O)—$C_{1-2}$ alkylene, and $C_{1-2}$ alkylene-C(═O).

[45] The compound of any one of [24] to [41], or a pharmaceutically acceptable salt or solvate thereof, wherein X is C(═O)—$C_{1-2}$ alkylene and Y is selected from the group consisting of a bond (i.e. is absent), $C_{1-4}$ alkylene, C(═O), C(═O)—$C_{1-2}$ alkylene, and $C_{1-2}$ alkylene-C(═O).

[46] The compound of any one of [24] to [41], or a pharmaceutically acceptable salt or solvate thereof, wherein X is $C_{1-2}$ alkylene-C(═O) and Y is selected from the group consisting of a bond (i.e. is absent), $C_{1-4}$ alkylene, C(═O), C(═O)—$C_{1-2}$ alkylene, and $C_{1-2}$ alkylene-C(═O).

[47] The compound of any one of [24] to [41], or a pharmaceutically acceptable salt or solvate thereof, wherein Y is a bond (i.e., is absent) and X is selected from the group consisting of a bond (i.e. is absent), $C_{1-4}$ alkylene, C(═O), C(═O)—$C_{1-2}$ alkylene, and $C_{1-2}$ alkylene-C(═O).

[48] The compound of any one of [24] to [41], or a pharmaceutically acceptable salt or solvate thereof, wherein Y is $C_{1-4}$ alkylene and X is selected from the group consisting of a bond (i.e. is absent), $C_{1-4}$ alkylene, C(═O), C(═O)—$C_{1-2}$ alkylene, and $C_{1-2}$ alkylene-C(═O).

[49] The compound of any one of [24] to [41], or a pharmaceutically acceptable salt or solvate thereof, wherein Y is C(═O) and X is selected from the group consisting of a bond (i.e. is absent), $C_{1-4}$ alkylene, C(═O), C(═O)—$C_{1-2}$ alkylene, and $C_{1-2}$ alkylene-C(═O).

[50] The compound of any one of [24] to [41], or a pharmaceutically acceptable salt or solvate thereof, wherein Y is C(═O)—$C_{1-2}$ alkylene and X is selected from the group consisting of a bond (i.e. is absent), $C_{1-4}$ alkylene, C(═O), C(═O)—$C_{1-2}$ alkylene, and $C_{1-2}$ alkylene-C(═O).

[51] The compound of any one of [24] to [41], or a pharmaceutically acceptable salt or solvate thereof, wherein Y is $C_{1-2}$ alkylene-C(═O) and X is selected from the group consisting of a bond (i.e. is absent), $C_{1-4}$ alkylene, C(═O), C(═O)—$C_{1-2}$ alkylene, and $C_{1-2}$ alkylene-C(═O).

[52] The compound of any one of [24] to [41], or a pharmaceutically acceptable salt or solvate thereof, wherein X and Y are each independently $C_{1-4}$ alkylene.

[53] The compound of any one of [24] to [41] and [52], or a pharmaceutically acceptable salt or solvate thereof, wherein X is a methylene group and Y is an ethylene group.

[54] The compound of any one of [24] to [41] and [52], or a pharmaceutically acceptable salt or solvate thereof, wherein X is an ethylene group and Y is a methylene group.

[55] The compound of [24], which is selected from the group consisting of

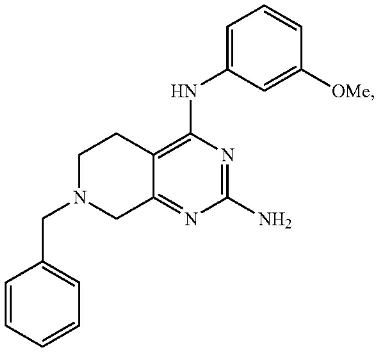

,

-continued

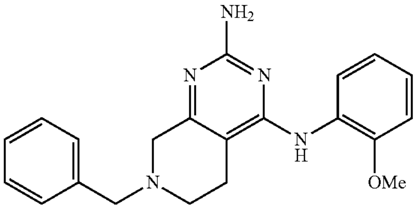

,

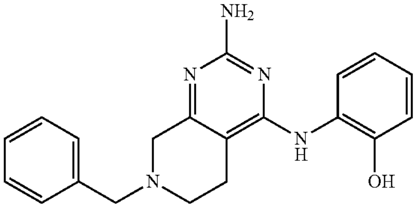

.

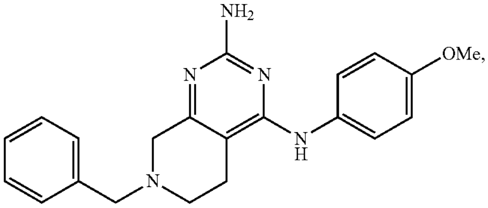

,

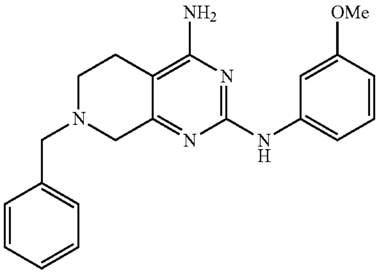

,

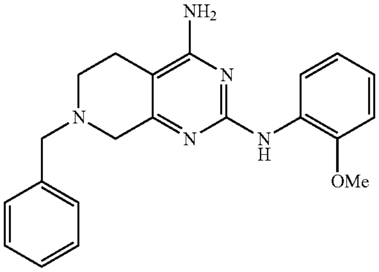

,

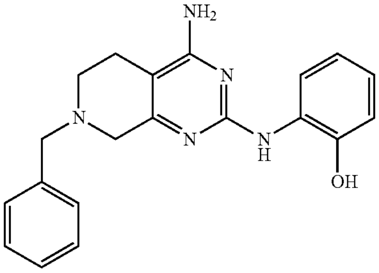

,

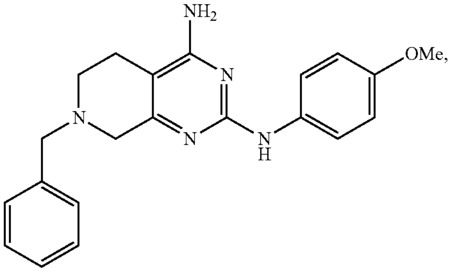

,

-continued

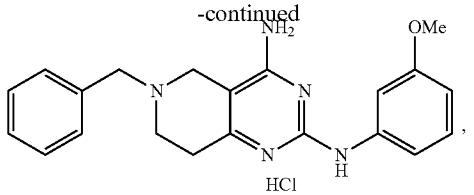

, and

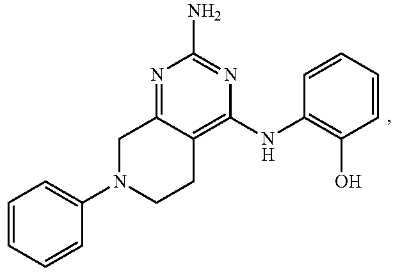

, or a pharmaceutically acceptable salt or solvate thereof.

[56] A pharmaceutical composition, comprising an effective amount of a compound of any one of [1] to [23], or a pharmaceutically acceptable salt or solvate thereof, and at least one pharmaceutically acceptable excipient.

[57] A pharmaceutical composition, comprising an effective amount of a compound of any one of [24] to [55], or a pharmaceutically acceptable salt or solvate thereof, and at least one pharmaceutically acceptable excipient.

[58] A method of treating or preventing a condition associated with the alteration of the activity of β-glucocerebrosidase in a patient in need thereof, comprising administering to the patient an effective amount of a compound as in any one of [1] to [55], or a pharmaceutically acceptable salt or solvate thereof.

[59] A method of treating or preventing a lysosomal storage disease, comprising administering to a patient in need thereof an effective amount of a compound as in any one of [1] to [55], or a pharmaceutically acceptable salt or solvate thereof.

[60] The method of [59], wherein the lysosomal storage disease is Gaucher's disease.

[61] A method of treating or preventing an α-synucleinopathy, comprising administering to a patient in need thereof an effective amount of a compound as in any one of [1] to [55], or a pharmaceutically acceptable salt or solvate thereof.

[62] A method of treating or preventing a disease or disorder, comprising administering to a patient in need thereof an effective amount of a compound as in any one of [1] to [55], or a pharmaceutically acceptable salt or solvate thereof, wherein said disease or disorder is selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging.

[63] The method of any one of [58] to [62], further comprising administering to the patient at least one other therapeutic agent.

[64] The method of [63], wherein the therapeutic agent is an effective amount of an enzyme for enzyme replacement therapy.

[65] The method of [64], wherein the enzyme is β-glucocerebrosidase or an analog thereof.

[66] The method of [64], wherein the enzyme is imiglucerase.

[67] The method of [63], wherein the therapeutic agent is an effective amount of a small molecule chaperone.

[68] The method of [67], wherein the small molecule chaperone binds competitively to an enzyme.

[69] The method of [67] or [68], wherein the small molecule chaperone is selected from the group consisting of iminoalditols, iminosugars, aminosugars, thiophenylglycosides, glycosidase, sulfatase, glycosyl transferase, phosphatase, and peptidase inhibitors.

[70] The method of [69], wherein the small molecule chaperone is selected from the group consisting of isofagomine, N-nonyl-1-deoxynojirimycin (NN-DNJ), ambroxol, and miglustat.

[71] A compound as defined in any one of [1] to [55], or a pharmaceutically acceptable salt or solvate thereof, for use as a medicament.

[72] A compound as defined in any one of [1] to [55], or a pharmaceutically acceptable salt or solvate thereof, for use in the treatment or prevention of a condition associated with the alteration of the activity of β-glucocerebrosidase in a patient.

[73] A compound as defined in any one of [1] to [55], or a pharmaceutically acceptable salt or solvate thereof, for use in the treatment or prevention of a lysosomal storage disease.

[74] The compound for use as in [73], wherein said use is for the treatment or prevention of Gaucher's disease.

[75] A compound as defined in any one of [1] to [55], or a pharmaceutically acceptable salt or solvate thereof, for use in the treatment or prevention of an α-synucleinopathy.

[76] A compound as defined in any one of [1] to [55], or a pharmaceutically acceptable salt or solvate thereof, for use in the treatment or prevention of a disease or disorder, wherein said disease or disorder is selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging.

[77] Use of a compound as defined in any one of [1] to [55], or a pharmaceutically acceptable salt or solvate thereof, for the manufacture of a medicament for the treatment or prevention of a condition associated with the alteration of the activity of β-glucocerebrosidase in a patient.

[78] Use of a compound as defined in any one of [1] to [55], or a pharmaceutically acceptable salt or solvate thereof, for the manufacture of a medicament for the treatment or prevention of a lysosomal storage disease.

[79] Use as in [78], wherein the manufacture is for a treatment or prevention of Gaucher's disease.

[80] Use of a compound as defined in any one of [1] to [55], or a pharmaceutically acceptable salt or solvate thereof, for the manufacture of a medicament for the treatment or prevention of an α-synucleinopathy.

[81] Use of a compound as defined in any one of [1] to [55], or a pharmaceutically acceptable salt or solvate thereof, for the manufacture of a medicament for the treatment or prevention of a disease or disorder selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging.

[82] A pharmaceutical composition as defined in [56] or [57] for use as a medicament.

[83] A pharmaceutical composition as defined in [56] or [57] for use in the treatment or prevention of a condition associated with the alteration of the activity of β-glucocerebrosidase in a patient.

[84] A pharmaceutical composition as defined in [56] or [57] for use in the treatment or prevention of a lysosomal storage disease.

[85] The pharmaceutical composition of [84], wherein said use is for the treatment or prevention of Gaucher's disease.

[86] A pharmaceutical composition as defined in [56] or [57] for use in the treatment or prevention of an α-synucleinopathy.

[87] A pharmaceutical composition as defined in [56] or [57] for use in the treatment or prevention of a disease or disorder, wherein said disease or disorder is selected from the group consisting of: Gaucher's disease, Parkinson's disease, dementia with Lewy bodies, diffuse Lewy body disease, multiple system atrophy (MSA), epilepsy, bipolar disorder, schizophrenia, an anxiety disorder, major depression, polycystic kidney disease, type 2 diabetes, open angle glaucoma, multiple sclerosis (MS), multiple myeloma, Alzheimer's disease, amyothophic lateral sclerosis (ALS), corticobasal degeneration, frontotemporal lobe dementia, GBA1 Parkinson, neuronopathic Gaucher's disease, neuroaxonal dystrophy, neurodegenerative diseases with parkinsonism, progressive supranuclear palsy, pure autonomic failure, sporadic Creuzfeldt-Jakob disease, and unimpaired aging.

What is claimed is:

1. A compound of formula (IA):

(IA)

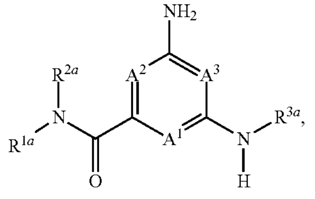

or a pharmaceutically acceptable salt or solvate thereof, wherein $A^1$, $A^2$, and $A^3$ are each independently selected from the group consisting of N, CH and $C(R^{4a})$, provided that at least one of $A^1$, $A^2$, or $A^3$ is N and no more than two of $A^1$, $A^2$, or $A^3$ are N;

each $R^{4a}$ is independently selected from the group consisting of halogen, —$C_{1-4}$ alkyl, —$C_{1-4}$ alkoxy, and —CN;

$R^{1a}$ is selected from the group consisting of $C_{5-7}$ cycloalkyl, phenyl, and —$C_{1-3}$ alkyl-phenyl, wherein said $C_{5-7}$ cycloalkyl, phenyl and —$C_{1-3}$ alkyl-phenyl groups are optionally substituted with 1, 2 or 3 substituents each independently selected from the group consisting of halogen, hydroxy, —CN, —$ORb^a$, —$SRb^a$, —$N(Rb^a)$ 2, and —$C_{1-4}$ alkyl optionally substituted with 1, 2, or 3 halogen atoms; and wherein said $C_{5-7}$ cycloalkyl, phenyl, and —$C_{1-3}$ alkyl-phenyl is optionally fused to a further (second) ring; and $R^{2a}$ is selected from the group consisting of hydrogen and —$C_{1-4}$ alkyl; or $R^{1a}$ and $R^{2a}$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

each $Rb^a$ is independently hydrogen or —$C_{1-4}$ alkyl, wherein said alkyl group is optionally substituted by 1, 2 or 3 fluorine atoms; and $R^{3a}$ is selected from the group consisting of cyclohexyl, phenyl, and pyridinyl, wherein said cyclohexyl, phenyl, and pyridinyl groups are optionally substituted with 1, 2 or 3 substituents each independently selected from the group consisting of halogen, hydroxy, —CN, —$ORb^a$, —$SRb^a$, —$N(Rb^a)_2$, and $C_{1-4}$ alkyl optionally substituted with 1, 2, or 3 substituents each independently selected from the group consisting of halogen, —CN, —$ORb^a$, and —$N(Rb^a)_2$, and wherein said phenyl is optionally fused to a 5- or 6-membered heterocyclic.

2. The compound of claim 1, or a pharmaceutically acceptable salt or solvate thereof, wherein $A^1$ is N and $A^2$ and $A^3$ are each independently selected from the group consisting of CH and $C(R^{4a})$.

3. The compound of claim 1, or a pharmaceutically acceptable salt or solvate thereof, wherein $A^2$ is N and $A^1$ and $A^3$ are each independently selected from the group consisting of CH and $C(R^{4a})$; or $A^3$ is N and $A^1$ and $A^2$ are each independently selected from the group consisting of CH and $C(R^{4a})$; or $A^1$ and $A^2$ are both N and $A^3$ is CH or $C(R^{4a})$; or $A^1$ and $A^3$ are both N and $A^2$ is CH or $C(R^{4a})$; or $A^2$ and $A^3$ are both N and $A^1$ is CH or $C(R^{4a})$.

4. The compound of claim 1, or a pharmaceutically acceptable salt or solvate thereof, wherein $R^{3a}$ is unsubstituted phenyl or phenyl substituted with 1 or 2 substituents each independently selected from the group consisting of halogen, hydroxy, —CN, —$O(C_{1-4})$alkyl, —$S(C_{1-4})$alkyl, —$N(C_{1-4}$ alkyl$)_2$, —$NH(C_{1-4}$ alkyl), and —$C_{1-4}$ alkyl optionally substituted with 1, 2, or 3 substituents each independently selected from the group consisting of halogen, —CN, —$O(C_{1-4})$alkyl, —$N(C_{1-4}$ alkyl$)_2$, and —NH ($C_{1-4}$ alkyl).

5. The compound of claim 4, or a pharmaceutically acceptable salt or solvate thereof, wherein $R^{3a}$ is phenyl substituted with 1 or 2 substituents each independently selected from the group consisting of F, Cl, Br, I, hydroxy, methyl, methoxy, and —CN.

6. The compound of claim 5, or a pharmaceutically acceptable salt or solvate thereof, wherein $R^{3a}$ is phenyl substituted with F or hydroxy at the ortho- or meta-position of the phenyl ring.

7. The compound of claim 1, or a pharmaceutically acceptable salt or solvate thereof, wherein $R^{3a}$ is unsubstituted phenyl fused to a 5- or 6-membered heterocyclic ring.

8. The compound of claim 1, or a pharmaceutically acceptable salt or solvate thereof, wherein $R^{3a}$ is unsubstituted pyridinyl or pyridinyl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl)$_2$, and —NH ($C_{1-4}$ alkyl).

9. The compound of claim 1, or a pharmaceutically acceptable salt or solvate thereof, wherein $R^{3a}$ is unsubstituted cyclohexyl or cyclohexyl substituted with 1 or 2 substituents each independently selected from the group consisting of halogen, hydroxy, —CN, —O($C_{1-4}$)alkyl, —S($C_{1-4}$)alkyl, —N($C_{1-4}$ alkyl)$_2$, —NH($C_{1-4}$ alkyl), and —$C_{1-4}$ alkyl optionally substituted with 1, 2, or 3 substituents each independently selected from the group consisting of halogen, —CN, —O($C_{1-4}$)alkyl, —N($C_{1-4}$ alkyl) 2, and —NH($C_{1-4}$ alkyl).

10. The compound of claim 1, or a pharmaceutically acceptable salt or solvate thereof, wherein $R^{2a}$ is H.

11. The compound of claim 1, or a pharmaceutically acceptable salt or solvate thereof, wherein $R^{2a}$ is —$C_{1-4}$ alkyl.

12. The compound of claim 1, or a pharmaceutically acceptable salt or solvate thereof, wherein $R^{1a}$ is phenyl or —$C_{1-3}$ alkyl-phenyl, wherein said phenyl or —$C_{1-3}$ alkyl-phenyl is optionally substituted with 1, 2 or 3 groups each independently selected from the group consisting of halogen, hydroxy, —CN, —ORb$^a$, —SRb$^a$, —N(Rb$^a$)$_2$, and —$C_{1-4}$ alkyl optionally substituted with 1, 2, or 3 halogen atoms; and wherein said phenyl is optionally fused to a further (second) ring.

13. The compound of claim 12, or a pharmaceutically acceptable salt or solvate thereof, wherein $R^{1a}$ is unsubstituted phenyl or unsubstituted benzyl.

14. The compound of claim 12, or a pharmaceutically acceptable salt or solvate thereof, wherein $R^{1a}$ is phenyl fused to a 5- or 6-membered heterocyclic ring.

15. The compound of claim 1, or a pharmaceutically acceptable salt or solvate thereof, wherein $R^{1a}$ is $C_{5-7}$ cycloalkyl, wherein said $C_{5-7}$ cycloalkyl is optionally substituted with 1, 2 or 3 substituents each independently selected from the group consisting of halogen, hydroxy, —CN, —ORb$^a$, —SRb$^a$, —N(Rb$^a$)$_2$, and —$C_{1-4}$ alkyl optionally substituted with 1, 2, or 3 halogen atoms; and wherein said $C_{5-7}$ cycloalkyl is optionally fused to a further (second) ring.

16. The compound of claim 15, or a pharmaceutically acceptable salt or solvate thereof, wherein $R^{1a}$ is unsubstituted $C_{5-7}$ cycloalkyl fused to a phenyl ring.

17. A pharmaceutical composition, comprising a compound of claim 16, or a pharmaceutically acceptable salt or solvate thereof, and at least one pharmaceutically acceptable excipient.

18. The compound of claim 16, or a pharmaceutically acceptable salt or solvate thereof, wherein $R^{1a}$ is cyclopentyl fused to a phenyl ring.

19. The compound of claim 1, or a pharmaceutically acceptable salt or solvate thereof, wherein Rb$^a$ is hydrogen or unsubstituted-$C_{1-4}$ alkyl.

20. The compound of claim 1, or a pharmaceutically acceptable salt or solvate thereof, wherein $R^{1a}$ and $R^{2a}$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring.

21. The compound of claim 20, or a pharmaceutically acceptable salt or solvate thereof, wherein $R^{1a}$ and $R^{2a}$ together with the nitrogen atom to which they are attached form a 5- or 6-membered ring optionally fused to a phenyl ring.

22. The compound of claim 1, which is selected from the group consisting of

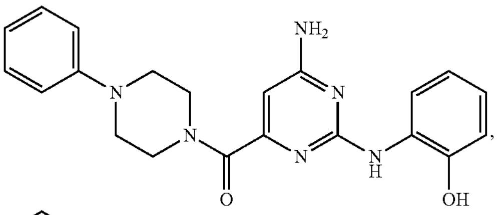
,

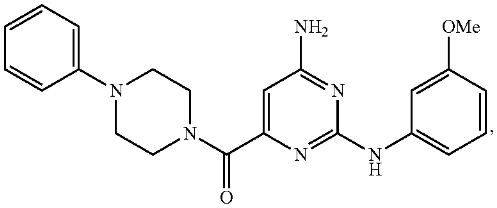
,

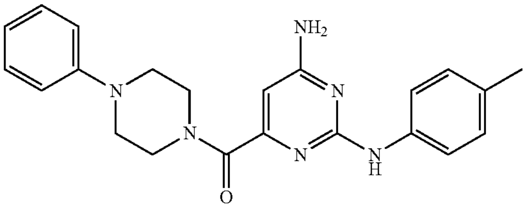
,

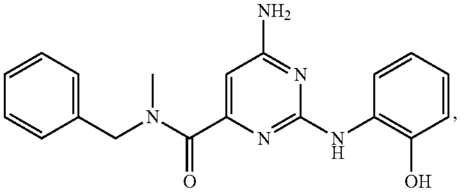
,

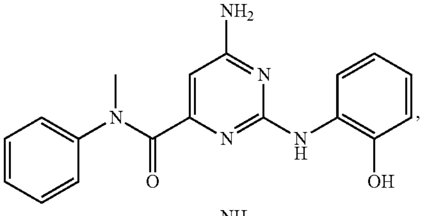
,

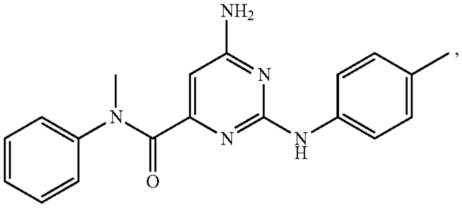
,

-continued
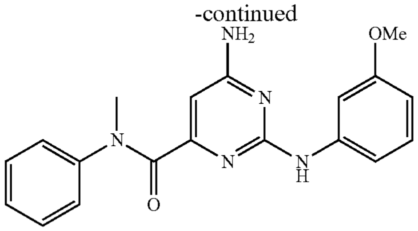
,
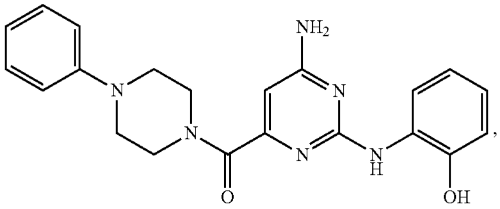
,
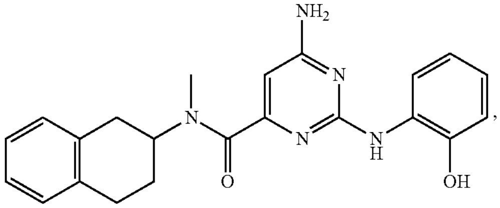
,
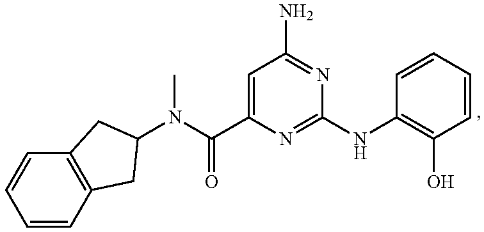
,
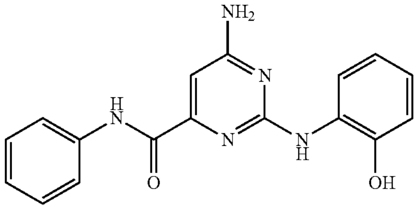
,
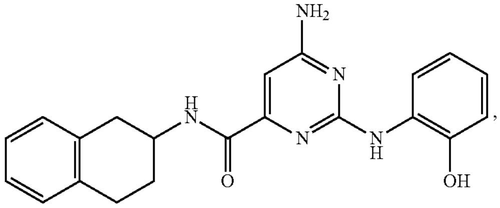
,
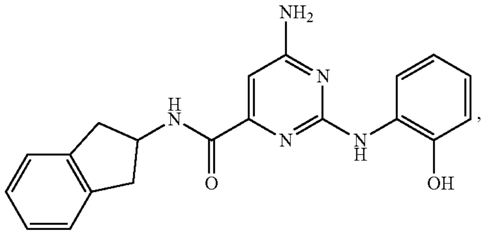
,
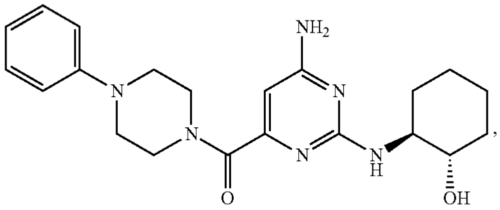
,
-continued
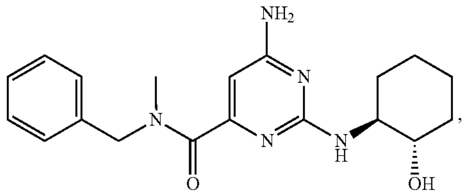
,
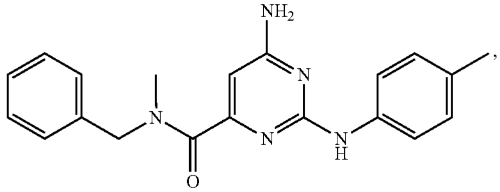
,
and
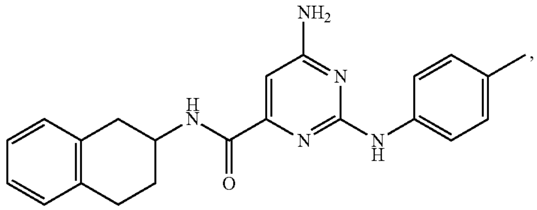
,
or a pharmaceutically acceptable salt or solvate thereof.
23. The compound of claim 1, which is selected from the group consisting of
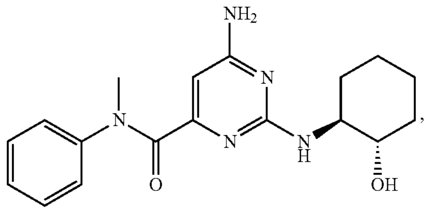
,
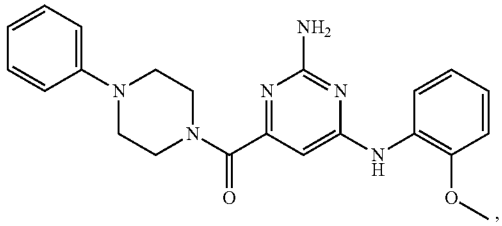
,
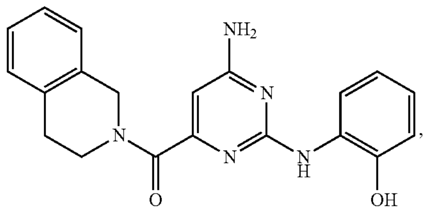
,
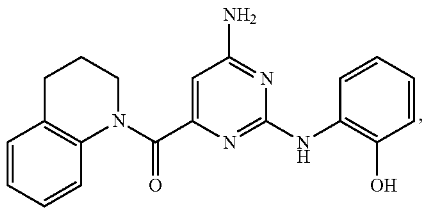
, -continued
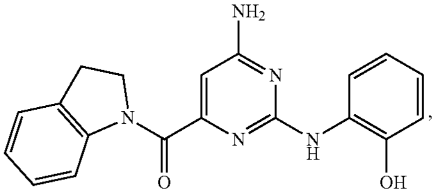,
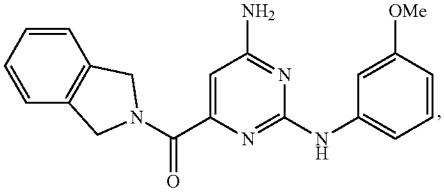,
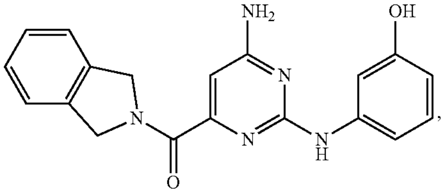,
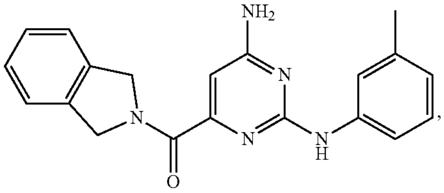,
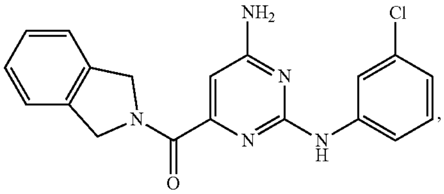,
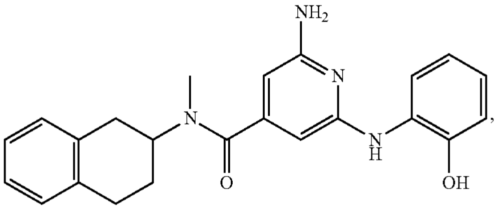,
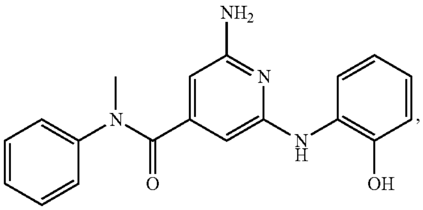,
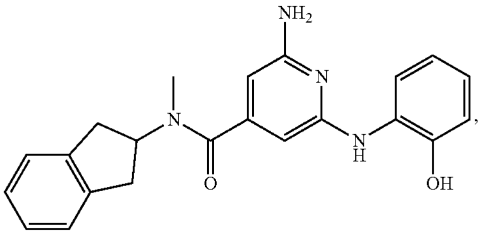,
-continued
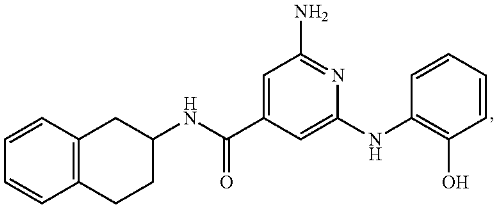,
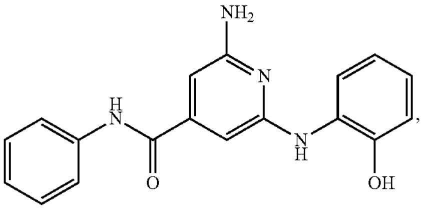,
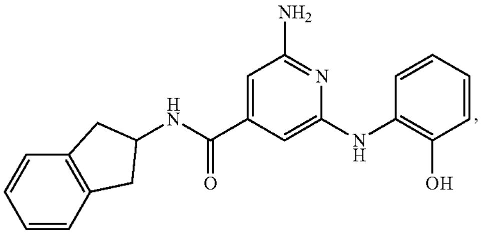,
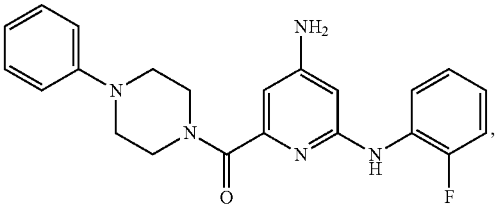,
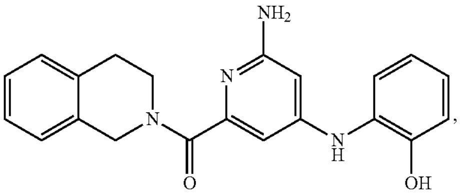,
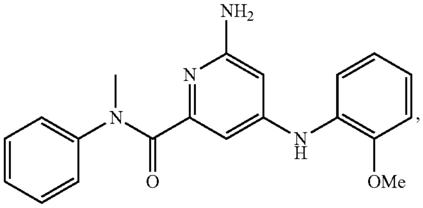,
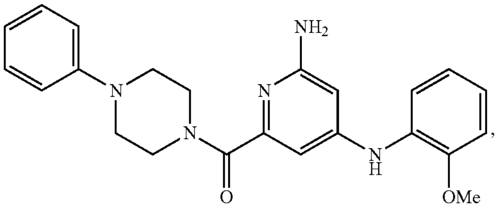,
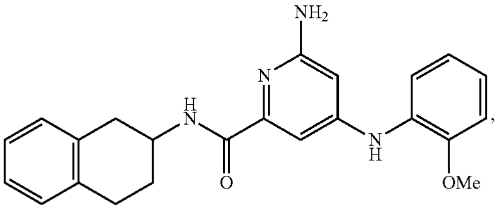, -continued
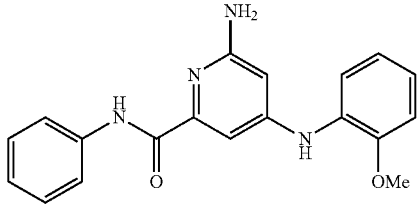
,
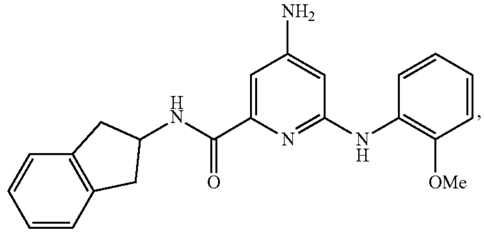
,
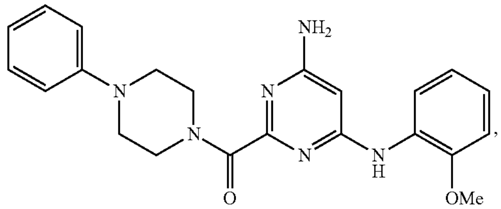
,
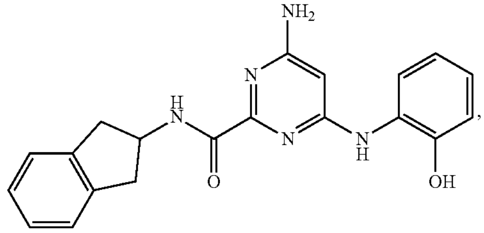
,
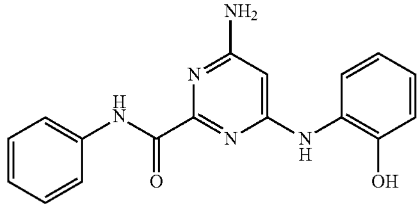
,
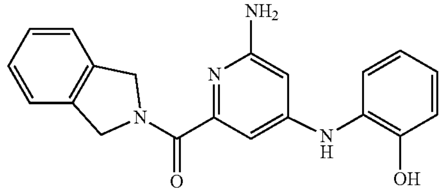
,
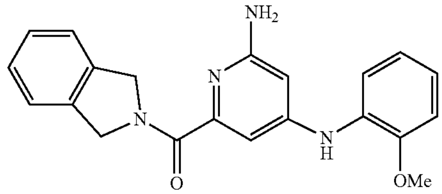
,
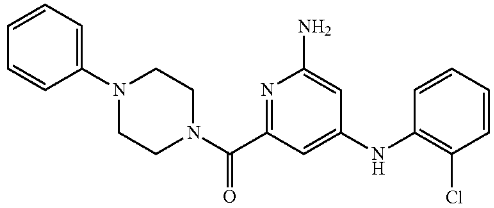
,
-continued
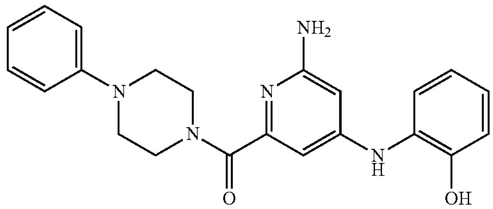
,
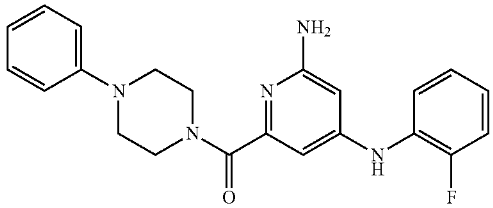
,
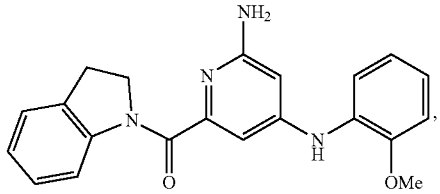
,
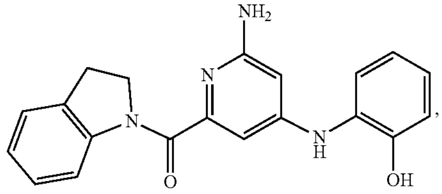
,
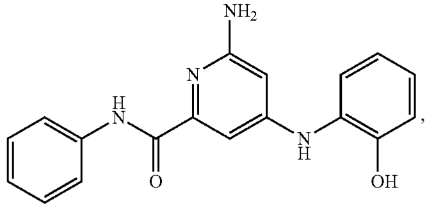
,
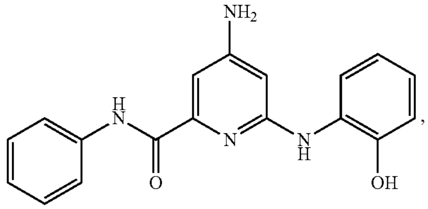
,
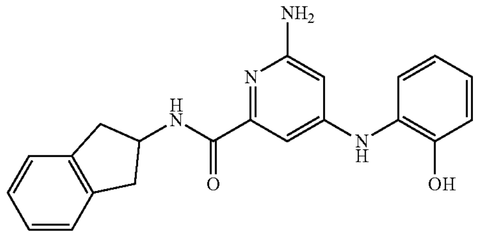
,
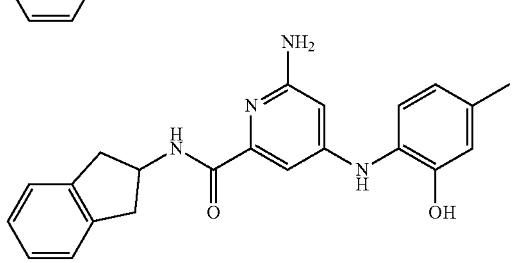
, -continued
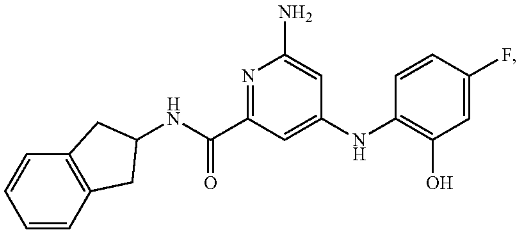
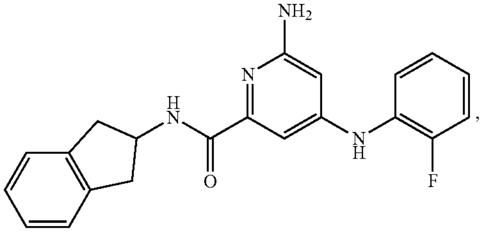
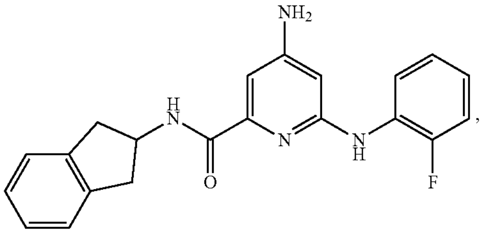
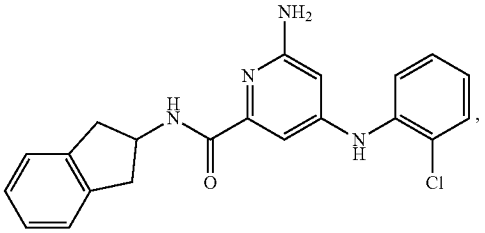
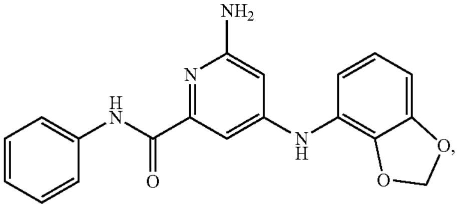
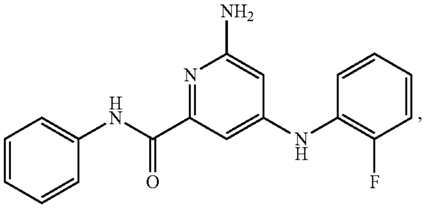
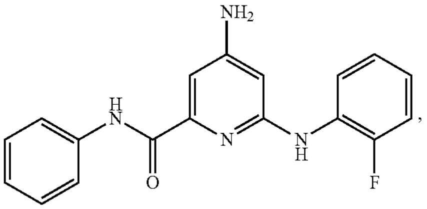
-continued
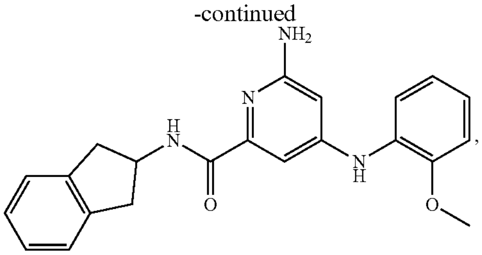
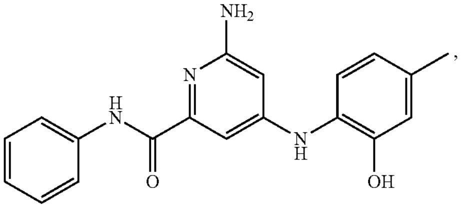
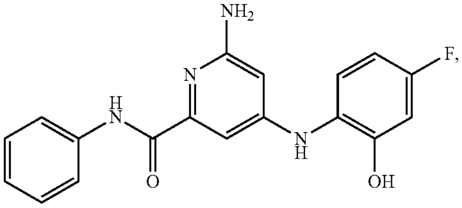
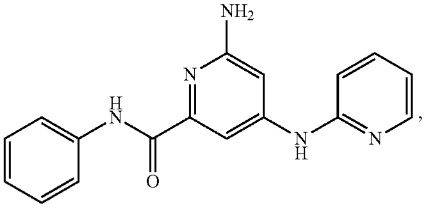
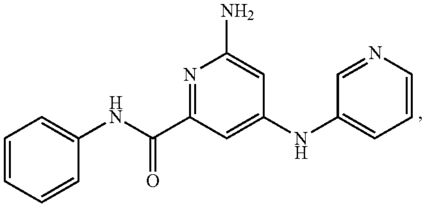
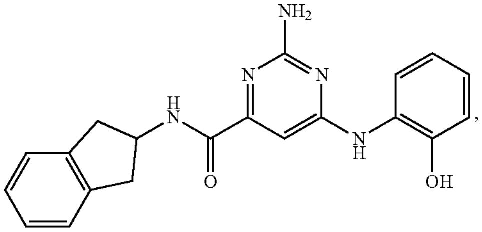
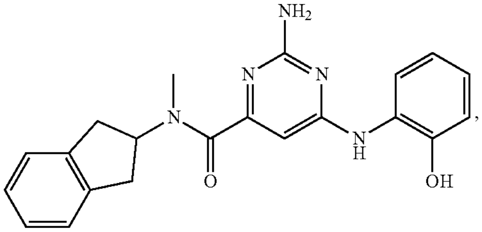
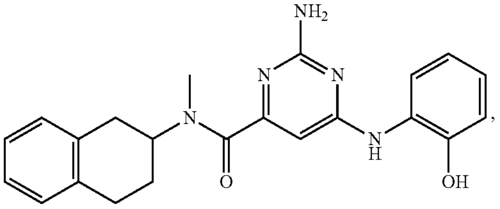

-continued
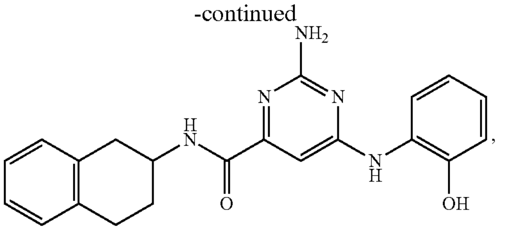
,
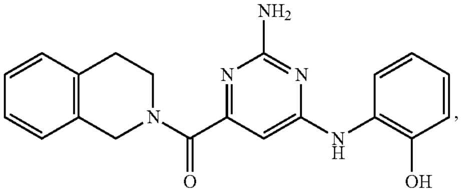
,
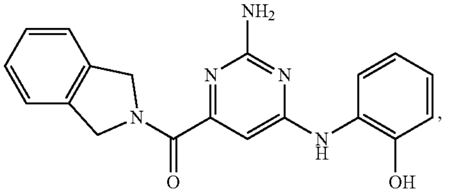
,
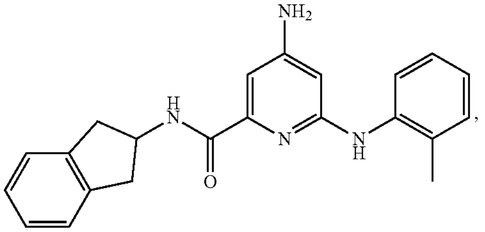
,
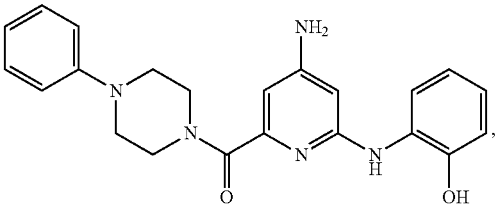
,
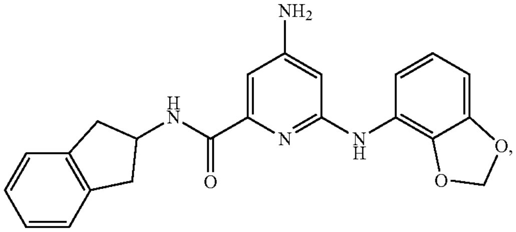
,
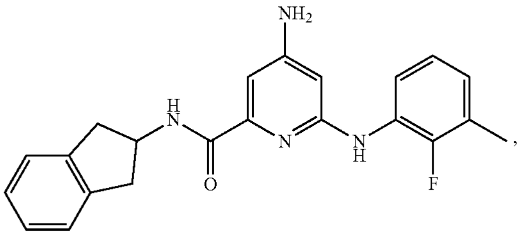
,
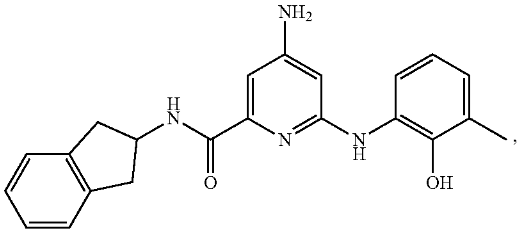
,
-continued
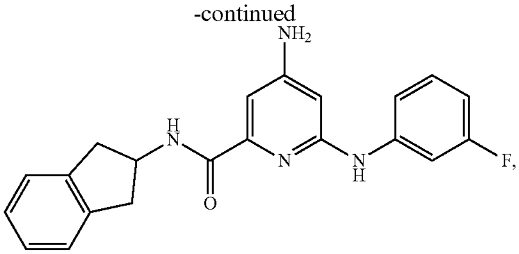
,
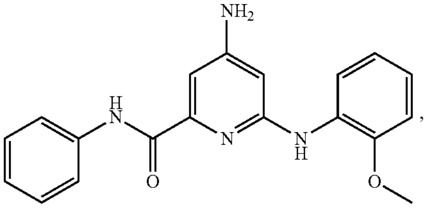
,
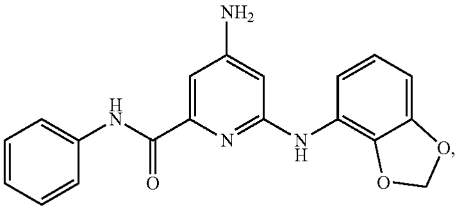
,
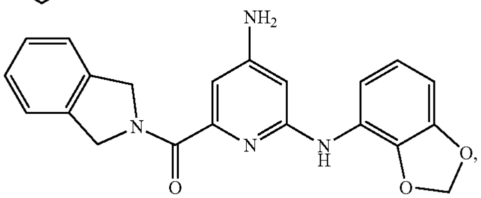
,
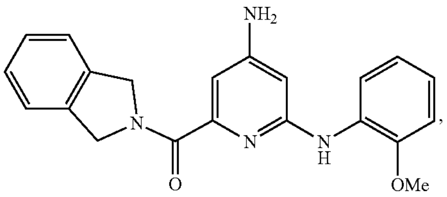
,
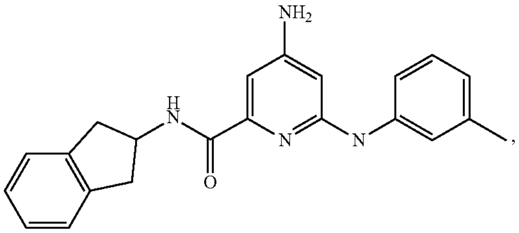
,
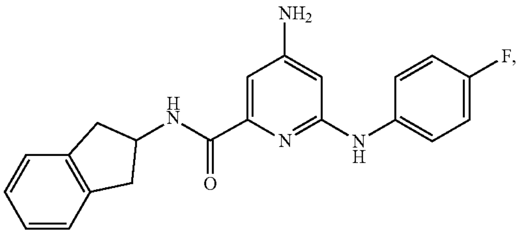
,
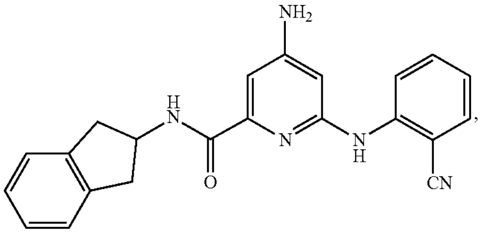
, -continued
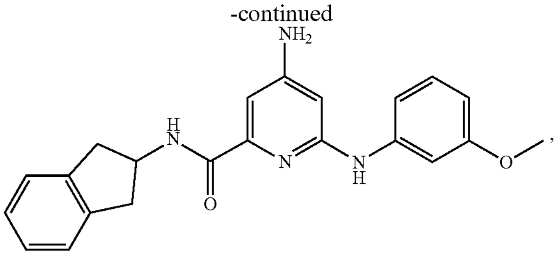
,
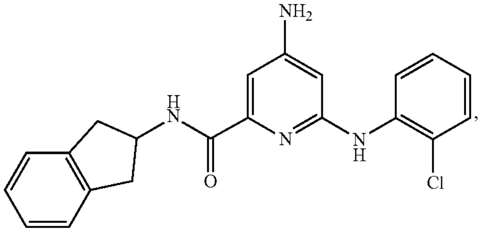
,
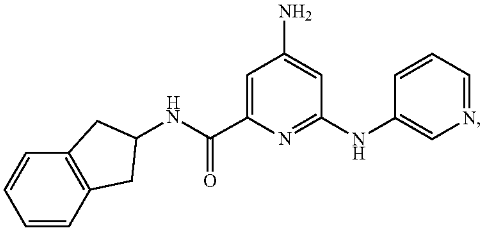 [SMILES: Nc1cc(Nc2ccccc2F)nc(C(=O)NC2Cc3ccccc3C2)c1]
,
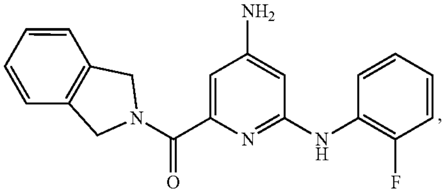
,
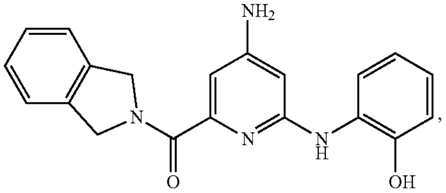
,
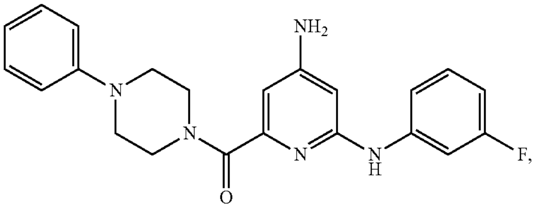
,
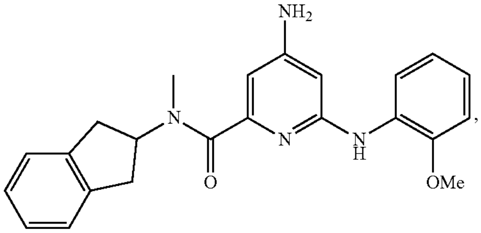
,
-continued
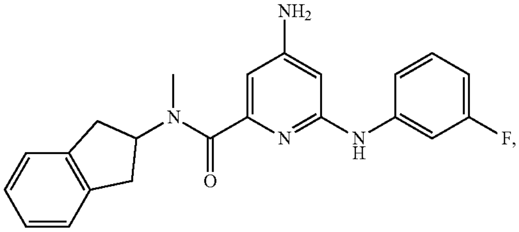
,
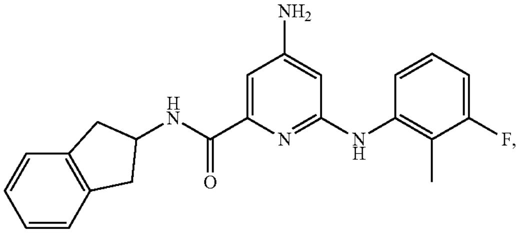
,
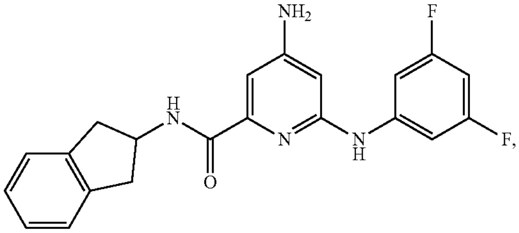
,
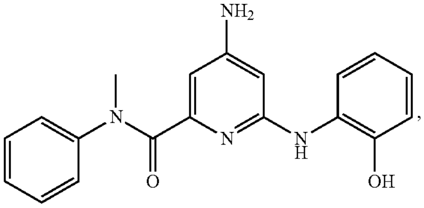
,
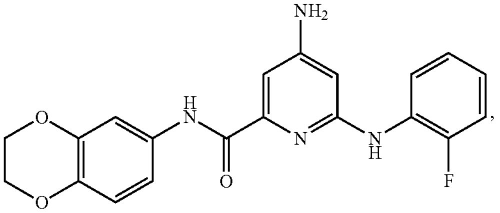
,
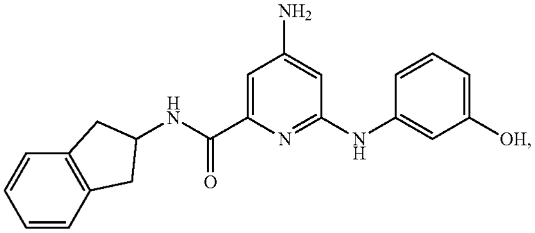
,
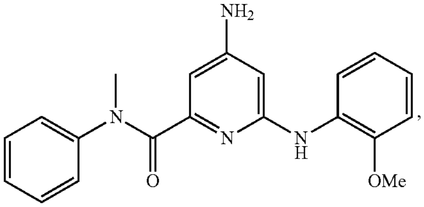
, -continued
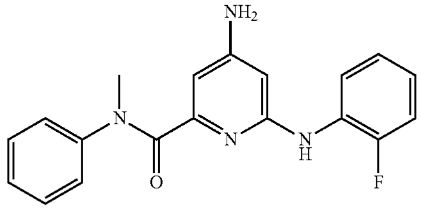,
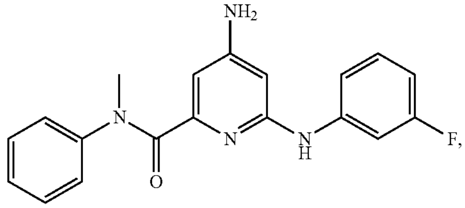,
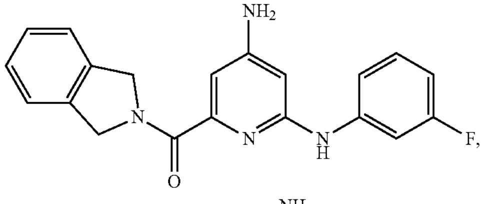,
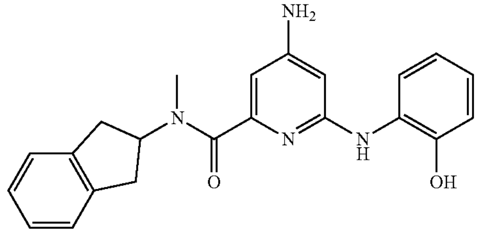,
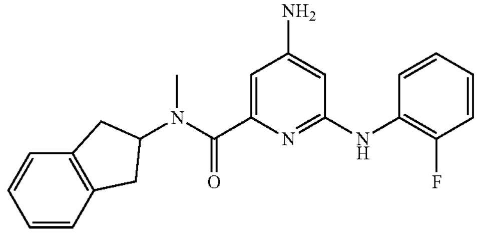,
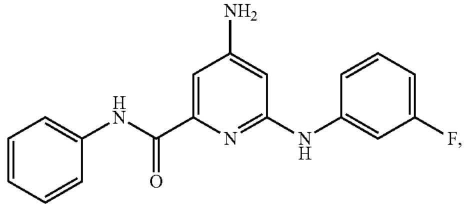,
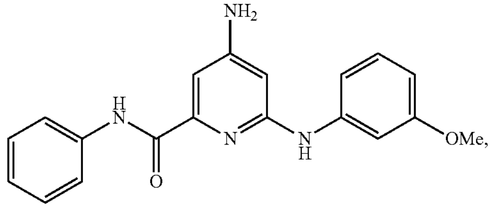,
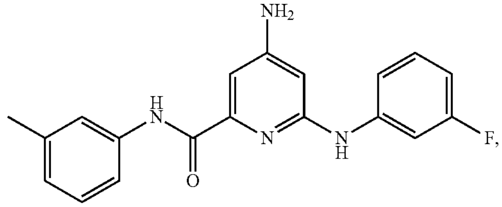,
-continued
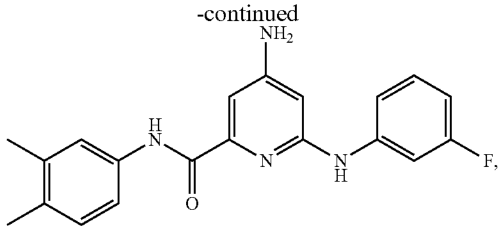,
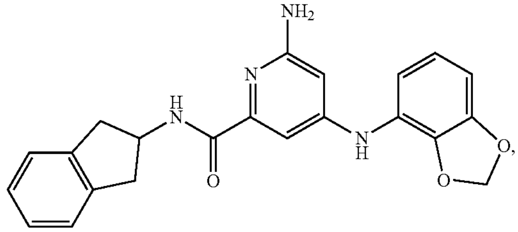,
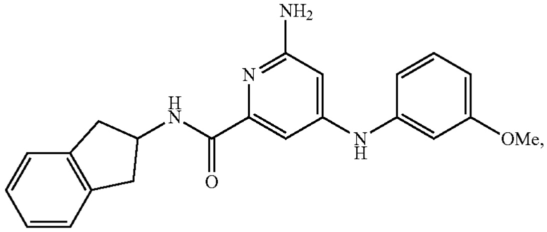,
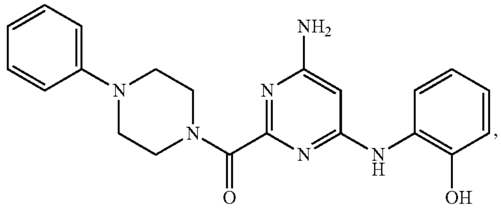,
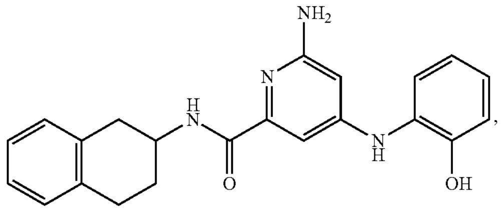,
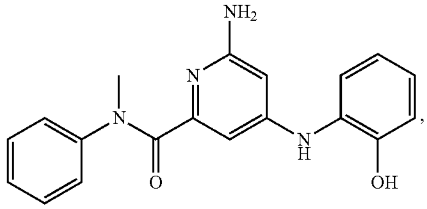,
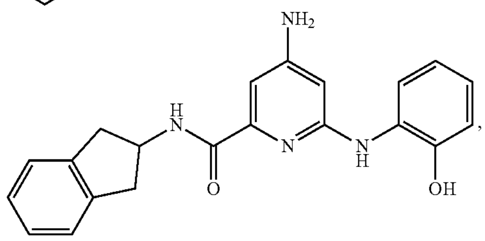,
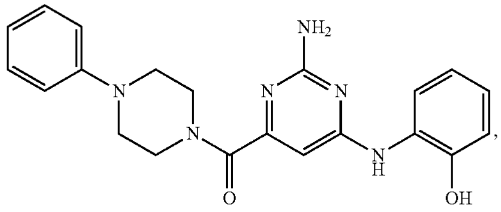, -continued and

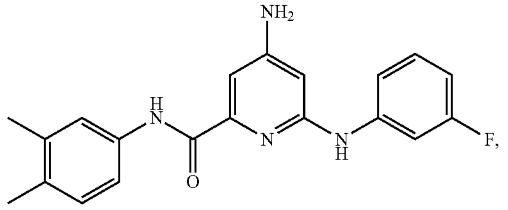

or a pharmaceutically acceptable salt or solvate thereof.

24. The compound of claim 23, wherein the compound is:

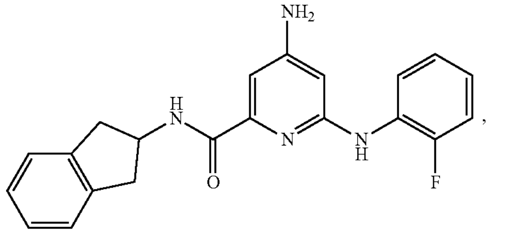 [SMILES: Nc1cc(Nc2ccccc2F)nc(C(=O)NC2Cc3ccccc3C2)c1]

or a pharmaceutically acceptable salt thereof.

25. A pharmaceutically acceptable salt of the compound of claim 1, selected from the group consisting of

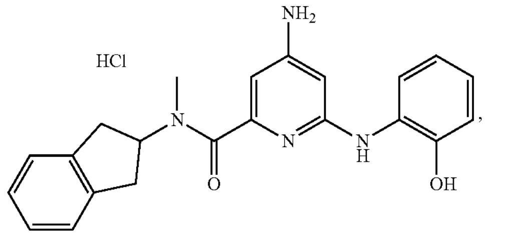

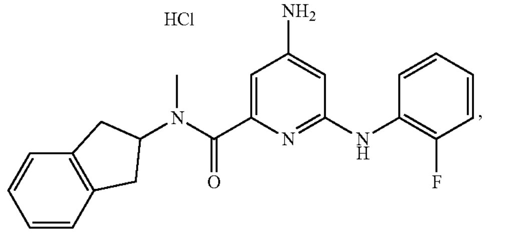

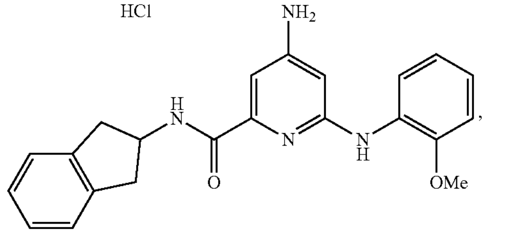

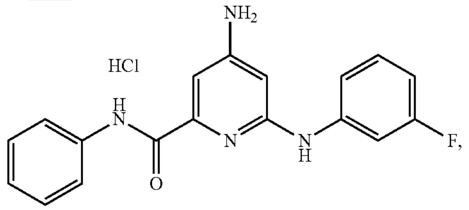

-continued

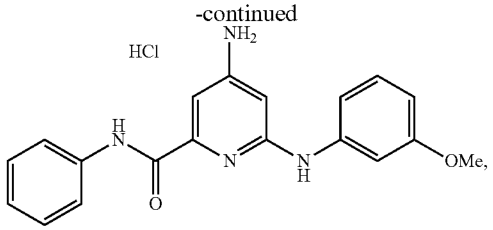

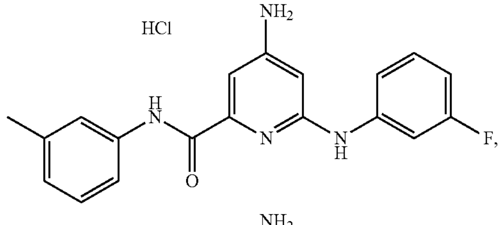

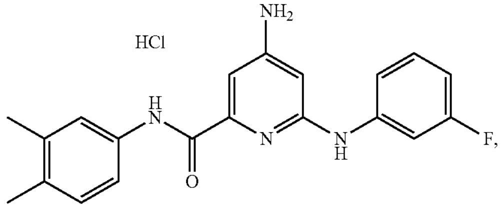

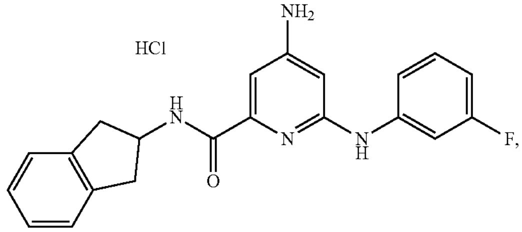

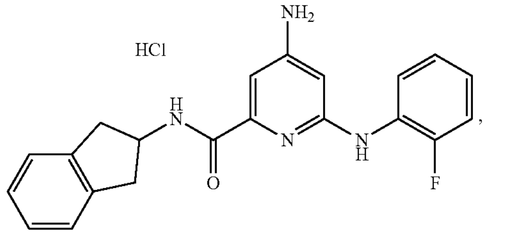

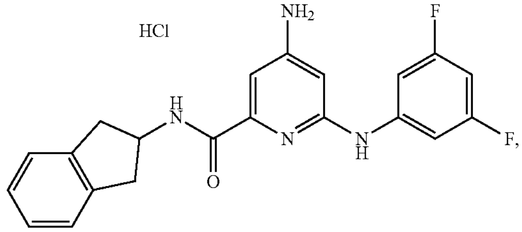

and

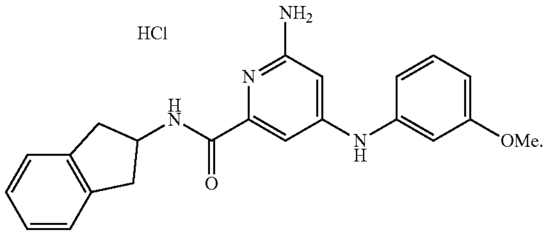

26. A pharmaceutical composition, comprising a compound of claim 24, or a pharmaceutically acceptable salt thereof, and at least one pharmaceutically acceptable excipient.

27. A pharmaceutical composition, comprising a compound of claim 1, or a pharmaceutically acceptable salt or solvate thereof, and at least one pharmaceutically acceptable excipient.

28. A method of treating Gaucher's disease, comprising administering to a patient in need thereof an effective amount of a compound of formula (IA):

(IA)

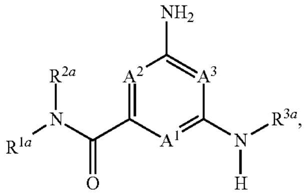

or a pharmaceutically acceptable salt or solvate thereof, wherein $A^1$, $A^2$, and $A^3$ are each independently selected from the group consisting of N, CH and $C(R^{4a})$, provided that at least one of $A^1$, $A^2$, or $A^3$ is N and no more than two of $A^1$, $A^2$, or $A^3$ are N;

each $R^{4a}$ is independently selected from the group consisting of halogen, $-C_{1-4}$ alkyl, $-C_{1-4}$ alkoxy, and —CN;

$R^{1a}$ is selected from the group consisting of $C_{5-7}$ cycloalkyl, phenyl, and $-C_{1-3}$ alkyl-phenyl, wherein said $C_{5-7}$ cycloalkyl, phenyl and $-C_{1-3}$ alkyl-phenyl groups are optionally substituted with 1, 2 or 3 substituents each independently selected from the group consisting of halogen, hydroxy, —CN, $-ORb^a$, $-SRb^a$, $-N(Rb^a)_2$, and $-C_{1-4}$ alkyl optionally substituted with 1, 2, or 3 halogen atoms; and wherein said $C_{5-7}$ cycloalkyl, phenyl, and $-C_{1-3}$ alkyl-phenyl is optionally fused to a further (second) ring; and $R^{2a}$ is selected from the group consisting of hydrogen and $-C_{1-4}$ alkyl; or $R^{1a}$ and $R^{2a}$ together with the nitrogen atom to which they are attached form an optionally substituted 5- to 10-membered heterocyclic ring, wherein said heterocyclic ring optionally contains 1, 2, or 3 additional heteroatoms selected from the group consisting of N, S, or O, and wherein said heterocyclic ring is optionally fused to a phenyl ring;

each $Rb^a$ is independently hydrogen or $-C_{1-4}$ alkyl, wherein said alkyl group is optionally substituted by 1, 2 or 3 fluorine atoms; and $R^{3a}$ is selected from the group consisting of cyclohexyl, phenyl, and pyridinyl, wherein said cyclohexyl, phenyl, and pyridinyl groups are optionally substituted with 1, 2 or 3 substituents each independently selected from the group consisting of halogen, hydroxy, —CN, $-ORb^a$, $-SRb^a$, $-N(Rb^a)_2$, and $C_{1-4}$ alkyl optionally substituted with 1, 2, or 3 substituents each independently selected from the group consisting of halogen, —CN, $-ORb^a$, and $-N(Rb^a)_2$, and wherein said phenyl is optionally fused to a 5- or 6-membered heterocyclic ring.

29. The method of claim 28, further comprising administering to the patient at least one other therapeutic agent.

30. The method of claim 28, wherein the compound is:

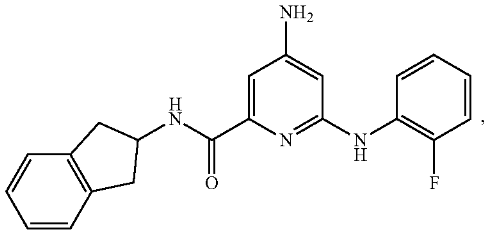

or a pharmaceutically acceptable salt thereof.

31. A pharmaceutically acceptable salt of the compound of claim 24, wherein the pharmaceutically acceptable salt is the hydrochloride salt.

* * * * *